(12) United States Patent
Fayadat-Dilman et al.

(10) Patent No.: US 11,072,658 B2
(45) Date of Patent: Jul. 27, 2021

(54) ANTI-PD-1/LAG3 BISPECIFIC ANTIBODIES

(71) Applicants: MERCK SHARP & DOHME CORP., Rahway, NJ (US); ZYMEWORKS INC., Vancouver (CA)

(72) Inventors: Laurence Fayadat-Dilman, Palo Alto, CA (US); Veronica Juan, Palo Alto, CA (US); Shireen Khan, Castro Valley, CA (US); Shaopeng Huang, Shanghai (CN); Hua Ying, Shanghai (CN); Eric Escobar Cabrera, Burnaby (CA); Genevieve Desjardins, Vancouver (CA)

(73) Assignees: MERCK SHARP & DOHME CORP., Rahway, NJ (US); ZYMEWORKS, INC., Vancouver (CA)

( * ) Notice: Subject to any disclaimer, the term of this patent is extended or adjusted under 35 U.S.C. 154(b) by 59 days.

(21) Appl. No.: 16/264,201

(22) Filed: Jan. 31, 2019

(65) Prior Publication Data
US 2019/0233518 A1 Aug. 1, 2019

(30) Foreign Application Priority Data
Feb. 1, 2018 (WO) .................. PCT/CN18/074918

(51) Int. Cl.
A61K 39/00 (2006.01)
C07K 16/28 (2006.01)
C07K 16/46 (2006.01)

(52) U.S. Cl.
CPC ...... C07K 16/2818 (2013.01); C07K 16/2803 (2013.01); C07K 16/468 (2013.01); C07K 2317/24 (2013.01); C07K 2317/31 (2013.01); C07K 2317/41 (2013.01); C07K 2317/55 (2013.01); C07K 2317/565 (2013.01); C07K 2317/76 (2013.01); C07K 2317/92 (2013.01)

(58) Field of Classification Search
CPC ............ C07K 16/2818; C07K 16/2803; C07K 16/468; C07K 2317/24; C07K 2317/31
See application file for complete search history.

(56) References Cited

U.S. PATENT DOCUMENTS

| | | | |
|---|---|---|---|
| 5,624,821 A | 4/1997 | Winter et al. | |
| 5,648,260 A | 7/1997 | Winter et al. | |
| 5,677,425 A | 10/1997 | Bodmer et al. | |
| 5,714,350 A | 2/1998 | Co et al. | |
| 5,731,168 A | 3/1998 | Carter et al. | |
| 5,869,046 A | 2/1999 | Presta et al. | |
| 6,121,022 A | 9/2000 | Presta et al. | |
| 6,165,745 A | 12/2000 | Ward et al. | |
| 6,194,551 B1 | 2/2001 | Idusogie et al. | |
| 6,277,375 B1 | 8/2001 | Ward | |
| 6,350,861 B1 | 2/2002 | Co et al. | |
| 7,029,872 B2 | 4/2006 | Gerngross | |
| 7,449,308 B2 | 11/2008 | Gerngross et al. | |
| 8,354,509 B2 | 1/2013 | Carven et al. | |
| 8,592,562 B2 | 11/2013 | Kannan et al. | |
| 9,248,181 B2 | 2/2016 | de Kruif et al. | |
| 10,188,730 B2 | 1/2019 | Liang et al. | |
| 2006/0057702 A1 | 3/2006 | Rosenthal et al. | |
| 2014/0154254 A1 | 6/2014 | Kannan et al. | |
| 2014/0370020 A1 | 12/2014 | Kuramochi et al. | |
| 2016/0039947 A1 | 2/2016 | Demarest et al. | |
| 2016/0222121 A1 | 8/2016 | Johnson et al. | |
| 2017/0097333 A1 | 4/2017 | Bhagwat et al. | |
| 2021/0032342 A1 | 2/2021 | Fayadat-Dilman et al. | |

FOREIGN PATENT DOCUMENTS

| | | | |
|---|---|---|---|
| WO | WO 1994029351 A2 | 12/1994 |
| WO | WO 1994029351 A3 | 12/1994 |
| WO | WO 2000042072 A2 | 7/2000 |
| WO | WO 2000042072 A3 | 7/2000 |
| WO | WO 2003086310 A2 | 10/2003 |
| WO | WO 2003086310 A3 | 10/2003 |
| WO | WO 2005120571 A2 | 12/2005 |
| WO | WO 2005120571 A3 | 12/2005 |
| WO | WO 2008156712 A1 | 12/2008 |
| WO | WO 2012058768 A1 | 5/2012 |
| WO | WO 2012131555 A2 | 10/2012 |
| WO | WO 2012131555 A3 | 10/2012 |
| WO | WO 2013063702 A1 | 5/2013 |
| WO | WO 2014124326 A1 | 8/2014 |
| WO | WO 2015173756 A2 | 11/2015 |
| WO | WO 2015173756 A3 | 11/2015 |
| WO | WO 2015181805 A1 | 12/2015 |
| WO | WO 2015181805 A9 | 12/2015 |
| WO | WO 2016028672 A1 | 2/2016 |
| WO | WO 2016172485 A2 | 10/2016 |
| WO | WO 2016172485 A3 | 10/2016 |
| WO | WO 2017011580 A2 | 1/2017 |
| WO | WO 2017011580 A3 | 1/2017 |

(Continued)

OTHER PUBLICATIONS

Ahmadzadeh et al., 2009, "Tumor Antigen-Specific CD8 T Cells Infiltrating the Tumor Express High Levels of PD-1 and Are Functionally Impaired," Blood, 114(8):1537-1544.

Andreae et al., 2002, "Maturation and Activation of Dendritic Cells Induced by Lymphocyte Activation gene-3 (CD223)," J Immunol., 168(8):3874-3880.

Blackburn et al., 2009, "Coregulation of CD8+ T Cell Exhaustion by Multiple Inhibitory Receptors During Chronic Viral Infection," Nat Immunol., 10(1):29-37.

Choi et al., 2003, "Use of Combinatorial Genetic Libraries to Humanize N-linked Glycosylation in the Yeast Pichia Pastoris," Proc Natl Acad Sci USA, 100(9):5022-5027.

Dong et al., 2002, "Tumor-associated B7-H1 Promotes T-cell Apoptosis: A Potential Mechanism of Immune Evasion," Nat Med., 8(8):793-800.

(Continued)

Primary Examiner — Sheela J. Huff
(74) Attorney, Agent, or Firm — Jones Day

(57) ABSTRACT

Provided herein are anti-PD-1/LAG3 bispecific antibodies and antigen-binding fragments. Also provided here are methods and uses of these antibodies and antigen-binding fragments in the treatment of cancer or infectious disease.

19 Claims, 6 Drawing Sheets

Specification includes a Sequence Listing.

(56) References Cited

FOREIGN PATENT DOCUMENTS

| WO | WO 2017019846 A1 | 2/2017 |
|---|---|---|
| WO | WO 2017019846 A8 | 2/2017 |

OTHER PUBLICATIONS

Gala et al., 2004, "V Region Carbohydrate and Antibody Expression," J Immunol., 172(9):5489-5494.
Gao et al., 2009, "Overexpression of PD-L1 Significantly Associates With Tumor Aggressiveness and Postoperative Recurrence in Human Hepatocellular Carcinoma," Clin Cancer Res., 15(3):971-979.
Ghebeh et al., 2006, "The B7-H1 (PD-L1) T Lymphocyte-Inhibitory Molecule Is Expressed in Breast Cancer Patients With Infiltrating Ductal Carcinoma: Correlation With Important High-Risk Prognostic Factors," Neoplasia, 8(3):190-198.
Ghebeh et al., 2008, "FOXP3+ Tregs and B7-H1+/PD-1+ T Lymphocytes Co-Infiltrate the Tumor Tissues of High-Risk Breast Cancer Patients: Implication for Immunotherapy," BMC Cancer, 8:57 (12 pages).
Hamanishi et al., 2007, "Programmed Cell Death 1 Ligand 1 and Tumor-Infiltrating CD8+ T Lymphocytes Are Prognostic Factors of Human Ovarian Cancer," Proc Natl Acad Sci USA, 104(9):3360-3365.
Hamilton et al., 2003, "Production of Complex Human Glycoproteins in Yeast," Science, 301(5637):1244-1246.
Hamilton et al., 2006, "Humanization of Yeast to Produce Complex Terminally Sialylated Glycoproteins," Science, 313(5792):1441-1443.
Hino et al., 2010, "Tumor Cell Expression of Programmed Cell death-1 Ligand 1 Is a Prognostic Factor for Malignant Melanoma," Cancer, 116(7):1757-1766.
Huard et al., 1994, "Cellular Expression and Tissue Distribution of the Human LAG-3-encoded Protein, an MHC Class II Ligand," Immunogenetics, 39(3):213-217.
Inman et al., 2007, "PD-L1 (B7-H1) Expression by Urothelial Carcinoma of the Bladder and BCG-induced Granulomata: Associations With Localized Stage Progression," Cancer, 109(8):1499-1505.
International Search Report and Written Opinion of International Patent Application No. PCT/CN2018/074918 (Pub. No. WO 2019148412) dated Apr. 12, 2019 (13 pages).
International Search Report and Written Opinion of International Patent Application No. PCT/US2019/016038 (Pub. No. WO 2019152642) dated Apr. 12, 2019 (9 pages).
Kisielow et al., 2005, "Expression of Lymphocyte Activation Gene 3 (LAG-3) on B Cells Is Induced by T Cells," Eur J Immunol., 35(7):2081-2088.

La Motte-Mohs et al., 2016, "MGD013, a Bispecific PD-1 x LAG-3 Dual-Affinity Re-Targeting (DART®) Protein with T-cell Immunomodulatory Activity for Cancer Treatment," Retrieved from the Internet: URL:http://files.shareholder.com/downloads/AMDA-278VRP/5641768791x0x886238/9181C658-BC8D-4410-88B2-BD08E68ABDEE/MacroGenics_AACR_2016-MGD013 pd-1XLAG-3 DART.PDF [retrieved on May 4, 2017].
Li et al., 2006, "Optimization of Humanized IgGs in Glycoengineered Pichia Pastoris," Nat. Biotechnol., 24(2):210-215.
Marshall, 1972, "Glycoproteins," Annu Rev Biochem.,41:673-702.
Murray et al., 2002, "Epitope Affinity Chromatography and Biophysical Studies of Monoclonal Antibodies and Recombinant Antibody Fragments," J Chromatogr Sci., 40(6):343-349.
Nett et al., 2011, "A Combinatorial Genetic Library Approach to Target Heterologous Glycosylation Enzymes to the Endoplasmic Reticulum or the Golgi Apparatus of Pichia Pastoris," Yeast, 28(3):237-252.
Nomi et al., 2007, "Clinical Significance and Therapeutic Potential of the Programmed death-1 Ligand/Programmed death-1 Pathway in Human Pancreatic Cancer," Clin Cancer Res., 13(7):2151-2157.
Ohigashi et al., 2005, "Clinical Significance of Programmed death-1 ligand-1 and Programmed death-1 ligand-2 Expression in Human Esophageal Cancer," Clin Cancer Res., 11(8):2947-2953.
Presta, 2005, "Selection, Design, and Engineering of Therapeutic Antibodies," J Allergy Clin Immunol., 116(4):731-736.
Sharpe et al., 2007, "The Function of Programmed Cell Death 1 and Its Ligands in Regulating Autoimmunity and Infection," Nat Immunol., 8(3):239-245.
Shields et al., 2001, "High Resolution Mapping of the Binding Site on Human IgG1 for Fc Gamma RI, Fc Gamma RII, Fc Gamma RIII, and FcRn and Design of IgG1 Variants With Improved Binding to the Fc Gamma R," J Biol Chem.,276(9):6591-6604 (Epub 2000).
Shimauchi et al., 2007, "Augmented Expression of Programmed death-1 in Both Neoplastic and Non-Neoplastic CD4+ T-cells in Adult T-cell Leukemia/Lymphoma," Int J Cancer, 121(12):2585-2590.
Spiro, 2002, "Protein Glycosylation: Nature, Distribution, Enzymatic Formation, and Disease Implications of Glycopeptide Bonds," Glycobiology, 12(4):43R-56R.
Thompson et al., 2007, "PD-1 Is Expressed by Tumor-Infiltrating Immune Cells and Is Associated With Poor Outcome for Patients With Renal Cell Carcinoma," Clin Cancer Res., 13(6):1757-1761.
Triebel et al., 1990, "LAG-3, a Novel Lymphocyte Activation Gene Closely Related to CD4," J Exp Med., 171(5):1393-1405.
Wallick et al., 1988, "Glycosylation of a VH Residue of a Monoclonal Antibody Against Alpha (1-6) Dextran Increases Its Affinity for Antigen," J Exp Med., 168(3):1099-1109.
Workman et al., 2009, "LAG-3 Regulates Plasmacytoid Dendritic Cell Homeostasis," J Immunol., 182(4):1885-1891.
Yang et al., 2008, "PD-L1: PD-1 Interaction Contributes to the Functional Suppression of T-cell Responses to Human Uveal Melanoma Cells in Vitro," Invest Ophthalmol Vis Sci., 49(6):2518-2525.

ial Serial No. PCT/CN2018/074918 filed Feb. 1, 2018,

SEQUENCE LISTING

<160> NUMBER OF SEQ ID NOS: 152

<210> SEQ ID NO 1
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val

```
                115                 120                 125
Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 2
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 2

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 3
<211> LENGTH: 15
<212> TYPE: PRT
<213> ORGANISM: Artificial Sequence
<220> FEATURE:
```

<223> OTHER INFORMATION: Description of Artificial Sequence: Synthetic
    peptide

<400> SEQUENCE: 3

Arg Ala Ser Lys Ser Val Ser Thr Ser Gly Phe Ser Tyr Leu His
1               5                   10                  15

<210> SEQ ID NO 4
<211> LENGTH: 7
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 4

Leu Ala Ser Asn Leu Glu Ser
1               5

<210> SEQ ID NO 5
<211> LENGTH: 9
<212> TYPE: PRT
<213> ORGANISM: Artificial Sequence
<220> FEATURE:
<223> OTHER INFORMATION: Description of Artificial Sequence: Synthetic
    peptide

<400> SEQUENCE: 5

Gln His Ser Trp Glu Leu Pro Leu Thr
1               5

<210> SEQ ID NO 6
<211> LENGTH: 219
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 6

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 7
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100                 105                 110

Gly Thr Thr Val Thr Val Ser Ser
        115                 120

<210> SEQ ID NO 8
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 8

Ser Tyr Tyr Leu Tyr
1               5

<210> SEQ ID NO 9
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 9

Gly Val Asn Pro Ser Asn Gly Gly Thr Asn Phe Asn Glu Lys Phe Lys
1               5                   10                  15

Ser

<210> SEQ ID NO 10
<211> LENGTH: 11
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 10

Arg Leu Ser His Tyr Asp Gly Gly Phe Asp Tyr
1               5                   10

<210> SEQ ID NO 11
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly or Ser
<220> FEATURE:
<221> NAME/KEY: MOD_RES
<222> LOCATION: (3)..(3)
<223> OTHER INFORMATION: Lys, Thr, His or Arg
<220> FEATURE:
<221> NAME/KEY: MOD_RES
<222> LOCATION: (4)..(4)
<223> OTHER INFORMATION: Phe, His or Tyr
<220> FEATURE:
<221> NAME/KEY: MOD_RES
<222> LOCATION: (5)..(5)
<223> OTHER INFORMATION: Arg, Gly, Ala, Leu or Ser
<220> FEATURE:
<221> NAME/KEY: MOD_RES
<222> LOCATION: (6)..(6)
<223> OTHER INFORMATION: Glu, Ala, Ser, Gln or Val

<400> SEQUENCE: 11

Leu Xaa Xaa Xaa Xaa Xaa Ser
1               5

<210> SEQ ID NO 12
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ser or Ala
<220> FEATURE:
<221> NAME/KEY: MOD_RES
<222> LOCATION: (2)..(2)
<223> OTHER INFORMATION: His or Gln
<220> FEATURE:
<221> NAME/KEY: MOD_RES
<222> LOCATION: (3)..(3)
<223> OTHER INFORMATION: Ser or Ala
<220> FEATURE:
<221> NAME/KEY: MOD_RES
<222> LOCATION: (4)..(4)
<223> OTHER INFORMATION: Trp, Tyr or Thr
<220> FEATURE:
<221> NAME/KEY: MOD_RES
<222> LOCATION: (5)..(5)
<223> OTHER INFORMATION: Glu, His or Gln

<400> SEQUENCE: 12

Xaa Xaa Xaa Xaa Xaa Leu Pro Leu Thr
1               5

```
<210> SEQ ID NO 13
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Lys Phe Arg Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 14
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Lys Phe Arg Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95
```

```
                85                  90                  95
Glu Leu Pro Leu Thr Phe Gly Gln Gly Thr Lys Leu Glu Ile Lys
            100                 105                 110

<210> SEQ ID NO 15
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Leu Gly Lys Phe Arg Glu Ser
1               5

<210> SEQ ID NO 16
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 16

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Thr His Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 17
<211> LENGTH: 111
<212> TYPE: PRT
<213> ORGANISM: Artificial Sequence
<220> FEATURE:
<223> OTHER INFORMATION: Description of Artificial Sequence: Synthetic
``` polypeptide

<400> SEQUENCE: 17

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Thr His Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110
```

<210> SEQ ID NO 18
<211> LENGTH: 7
<212> TYPE: PRT
<213> ORGANISM: Artificial Sequence
<220> FEATURE:
<223> OTHER INFORMATION: Description of Artificial Sequence: Synthetic peptide

<400> SEQUENCE: 18

```
Leu Gly Thr His Arg Ala Ser
1               5
```

<210> SEQ ID NO 19
<211> LENGTH: 218
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 19

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ser Lys Tyr Arg Ser Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ser Gln Ala Tyr
                85                  90                  95

His Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

```
Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 20
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 20

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ser Lys Tyr Arg Ser Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ser Gln Ala Tyr
                85                  90                  95

His Leu Pro Leu Thr Phe Gly Gln Gly Thr Lys Leu Glu Ile Lys
            100                 105                 110

<210> SEQ ID NO 21
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 21

Leu Ser Lys Tyr Arg Ser Ser
1               5

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 22

Ser Gln Ala Tyr His Leu Pro Leu Thr
1               5

<210> SEQ ID NO 23
<211> LENGTH: 218
<212> TYPE: PRT
<213> ORGANISM: Artificial Sequence
<220> FEATURE:
```

<223> OTHER INFORMATION: Description of Artificial Sequence: Synthetic
      polypeptide

<400> SEQUENCE: 23

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Lys Tyr Gly Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ala Gln Ala Thr
                85                  90                  95

Gln Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 24
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Lys Tyr Gly Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ala Gln Ala Thr
                85                  90                  95

Gln Leu Pro Leu Thr Phe Gly Gln Gly Thr Lys Leu Glu Ile Lys
            100                 105                 110

<210> SEQ ID NO 25
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Leu Gly Lys Tyr Gly Ala Ser
1               5

<210> SEQ ID NO 26
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ala Gln Ala Thr Gln Leu Pro Leu Thr
1               5

<210> SEQ ID NO 27
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 27

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
                20                  25                  30

Gly Phe Ser Tyr Leu His Trp Tyr Leu Gln Lys Pro Gly Gln Pro Pro
            35                  40                  45

Gln Leu Leu Ile Phe Leu Gly His Phe Ala Ser Ser Gly Val Pro Asp
        50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gly Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys

<210> SEQ ID NO 28
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly His Phe Ala Ser Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110

<210> SEQ ID NO 29
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Leu Gly His Phe Ala Ser Ser
1               5

<210> SEQ ID NO 30
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 30

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Arg Tyr Leu Gln Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

```
Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215
```

<210> SEQ ID NO 31
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 31

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Arg Tyr Leu Gln Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110
```

<210> SEQ ID NO 32
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 32

```
Leu Gly Arg Tyr Leu Gln Ser
1               5
```

<210> SEQ ID NO 33
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 33

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Thr His Ser Val Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 34
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 34

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Thr His Ser Val Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110

<210> SEQ ID NO 35
<211> LENGTH: 7
<212> TYPE: PRT
<213> ORGANISM: Artificial Sequence
```

```
<220> FEATURE:
<223> OTHER INFORMATION: Description of Artificial Sequence: Synthetic
      peptide

<400> SEQUENCE: 35

Leu Gly Thr His Ser Val Ser
1               5

<210> SEQ ID NO 36
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 36

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ser Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 37
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 37

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30
```

```
Tyr Tyr Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Asp Asp Thr Ser Val Tyr Tyr Cys
                 85                  90                  95

Thr Arg Arg Asp Ser Asn Tyr Asp Gly Gly Phe Asp Tyr Trp Gly Gln
                100                 105                 110

Gly Thr Thr Val Thr Val Ser Ser
            115                 120
```

<210> SEQ ID NO 38
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 38

```
Asp Ile Val Met Thr Gln Thr Pro Leu Ser Leu Ser Val Thr Pro Gly
 1               5                  10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Arg His Arg Ala Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Trp
                 85                  90                  95

Glu Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
210                 215
```

<210> SEQ ID NO 39
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 39

```
Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Arg His Arg Ala Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110
```

<210> SEQ ID NO 40
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

```
Gln Tyr Tyr Tyr Tyr
1               5
```

<210> SEQ ID NO 41
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 41

```
Arg Asp Ser Asn Tyr Asp Gly Gly Phe Asp Tyr
1               5                   10
```

<210> SEQ ID NO 42
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 42

```
Leu Gly Arg His Arg Ala Ser
1               5
```

<210> SEQ ID NO 43
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

```
Glu Val Gln Leu Val Gln Ser Gly Ala Glu Val Lys Lys Pro Gly Ala
1               5                   10                  15
```

```
Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ser Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215
```

<210> SEQ ID NO 44
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ser Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120
```

<210> SEQ ID NO 45
<211> LENGTH: 218
<212> TYPE: PRT

<213> ORGANISM: Artificial Sequence
<220> FEATURE:
<223> OTHER INFORMATION: Description of Artificial Sequence: Synthetic
      polypeptide

<400> SEQUENCE: 45

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Phe Tyr Arg Thr Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ser Gln Met Ala
                85                  90                  95

Asp Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 46
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 46

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Gly Phe Tyr Arg Thr Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ser Gln Met Ala
                85                  90                  95

Asp Leu Pro Leu Thr Phe Gly Gln Gly Thr Lys Leu Glu Ile Lys
            100                 105

<210> SEQ ID NO 47
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 47

Leu Gly Phe Tyr Arg Thr Ser
1               5

<210> SEQ ID NO 48
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 48

Ser Gln Met Ala Asp Leu Pro Leu Thr
1               5

<210> SEQ ID NO 49
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 49

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Thr Tyr Trp Val Arg Gln Ala Pro Gly Gln Gly Leu Glu Trp Ile
        35                  40                  45

Gly Gly Ile Glu Pro Asn Arg Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

```
Pro Ser Asn Thr Lys Val Asp Lys Arg Val Glu
    210                 215

<210> SEQ ID NO 50
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 50

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Thr Tyr Trp Val Arg Gln Ala Pro Gly Gln Gly Leu Glu Trp Ile
        35                  40                  45

Gly Gly Ile Glu Pro Asn Arg Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 51
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 51

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ala Gln Thr Phe
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160
```

Gly Asn Ser Gln Glu Ser Val Thr Glu Gln Asp Ser Lys Asp Ser Thr
            165                 170                 175

Tyr Ser Leu Ser Ser Thr Leu Thr Leu Ser Lys Ala Asp Tyr Glu Lys
        180                 185                 190

His Lys Val Tyr Ala Cys Glu Val Thr His Gln Gly Leu Ser Ser Pro
    195                 200                 205

Val Thr Lys Ser Phe Asn Arg Gly Glu Cys
    210                 215

<210> SEQ ID NO 52
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 52

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ala Gln Thr Phe
                85                  90                  95

Glu Leu Pro Leu Thr Phe Gly Gln Gly Thr Lys Leu Glu Ile Lys
            100                 105                 110

<210> SEQ ID NO 53
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 53

Gln Tyr Tyr Thr Tyr
1               5

<210> SEQ ID NO 54
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 54

Gly Ile Glu Pro Asn Arg Gly Gly Thr Asn Phe Asn Glu Lys Phe Lys
1               5                   10                  15

Ser

<210> SEQ ID NO 55
<211> LENGTH: 9
<212> TYPE: PRT

<213> ORGANISM: Artificial Sequence
<220> FEATURE:
<223> OTHER INFORMATION: Description of Artificial Sequence: Synthetic
      peptide

<400> SEQUENCE: 55

Ala Gln Thr Phe Glu Leu Pro Leu Thr
1               5

<210> SEQ ID NO 56
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 56

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ser Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 57
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 57

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Asp Thr Ser Val Tyr Tyr Cys
                85                  90                  95

Thr Arg Arg Asp Ser Asn Tyr Asp Gly Gly Phe Asp Tyr Trp Gly Gln
                100                 105                 110

Gly Thr Thr Val Thr Val Ser Ser
            115                 120

<210> SEQ ID NO 58
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 58

Asp Ile Val Met Thr Gln Thr Pro Leu Ser Leu Ser Val Thr Pro Gly
 1               5                  10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
            35                  40                  45

Gln Leu Leu Ile Phe Leu Ser Lys Phe Arg Arg Ser Gly Val Pro Asp
 50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
                100                 105                 110

Thr Val Ala Ala Pro Ser Val Phe Ile Phe Pro Pro Ser Asp Glu Gln
            115                 120                 125

Leu Lys Ser Gly Thr Ala Ser Val Val Cys Leu Leu Asn Asn Phe Tyr
130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
                180                 185                 190

His Lys Val Tyr Ala Cys Glu Val Thr His Gln Gly Leu Ser Ser Pro
            195                 200                 205

Val Thr Lys Ser Phe Asn Arg Gly Glu Cys
    210                 215

<210> SEQ ID NO 59
<211> LENGTH: 111
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 59

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ser Lys Phe Arg Arg Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110

<210> SEQ ID NO 60
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Leu Ser Lys Phe Arg Arg Ser
1               5

<210> SEQ ID NO 61
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (4)..(4)
<223> OTHER INFORMATION: Thr or Tyr

<400> SEQUENCE: 61

Gln Tyr Tyr Xaa Tyr
1               5

<210> SEQ ID NO 62
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Val or Ile
<220> FEATURE:
<221> NAME/KEY: MOD_RES
<222> LOCATION: (3)..(3)
<223> OTHER INFORMATION: Glu or Asn
<220> FEATURE:
<221> NAME/KEY: MOD_RES
<222> LOCATION: (5)..(5)
<223> OTHER INFORMATION: Asn or Ser
<220> FEATURE:
<221> NAME/KEY: MOD_RES

```
<222> LOCATION: (6)..(6)
<223> OTHER INFORMATION: Arg or Asn
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (12)..(12)
<223> OTHER INFORMATION: Ser or Asn

<400> SEQUENCE: 62

Gly Xaa Xaa Pro Xaa Xaa Xaa Gly Thr Asn Phe Xaa Glu Lys Phe Lys
1               5                   10                  15

Ser

<210> SEQ ID NO 63
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (2)..(2)
<223> OTHER INFORMATION: Gly, Ala or Ser
<220> FEATURE:
<221> NAME/KEY: MOD_RES
<222> LOCATION: (3)..(3)
<223> OTHER INFORMATION: Arg, Phe, Ser or Lys
<220> FEATURE:
<221> NAME/KEY: MOD_RES
<222> LOCATION: (4)..(4)
<223> OTHER INFORMATION: His, Tyr, Asn or Phe
<220> FEATURE:
<221> NAME/KEY: MOD_RES
<222> LOCATION: (5)..(5)
<223> OTHER INFORMATION: Arg or Leu
<220> FEATURE:
<221> NAME/KEY: MOD_RES
<222> LOCATION: (6)..(6)
<223> OTHER INFORMATION: Ala, Thr, Glu or Arg

<400> SEQUENCE: 63

Leu Xaa Xaa Xaa Xaa Xaa Ser
1               5

<210> SEQ ID NO 64
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (1)..(1)
<223> OTHER INFORMATION: Gln, Ser or Ala
<220> FEATURE:
<221> NAME/KEY: MOD_RES
<222> LOCATION: (2)..(2)
<223> OTHER INFORMATION: Gln or His
<220> FEATURE:
<221> NAME/KEY: MOD_RES
<222> LOCATION: (3)..(3)
<223> OTHER INFORMATION: Ser, Met or Thr
<220> FEATURE:
<221> NAME/KEY: MOD_RES
<222> LOCATION: (4)..(4)
<223> OTHER INFORMATION: Trp, Ala or Phe
<220> FEATURE:
<221> NAME/KEY: MOD_RES
<222> LOCATION: (5)..(5)
```

<223> OTHER INFORMATION: Glu or Asp

<400> SEQUENCE: 64

Xaa Xaa Xaa Xaa Xaa Leu Pro Leu Thr
1               5

<210> SEQ ID NO 65
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 65

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Leu Tyr Trp Met Lys Gln Arg Pro Gly Gln Gly Leu Glu Trp Ile
            35                  40                  45

Gly Gly Val Asn Pro Ser Asn Gly Gly Thr Asn Phe Ser Glu Lys Phe
        50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr

```
              325                 330                 335
Lys Gly Arg Pro Lys Ala Pro Gln Val Tyr Thr Ile Pro Pro Lys
            340                 345                 350
Glu Gln Met Ala Lys Asp Lys Val Ser Leu Thr Cys Met Ile Thr Asp
            355                 360                 365
Phe Phe Pro Glu Asp Ile Thr Val Glu Trp Gln Trp Asn Gly Gln Pro
370                 375                 380
Ala Glu Asn Tyr Lys Asn Thr Gln Pro Ile Met Asp Thr Asp Gly Ser
385                 390                 395                 400
Tyr Phe Val Tyr Ser Lys Leu Asn Val Gln Lys Ser Asn Trp Glu Ala
                405                 410                 415
Gly Asn Thr Phe Thr Cys Ser Val Leu His Glu Gly Leu His Asn His
                420                 425                 430
His Thr Glu Lys Ser Leu Ser His Ser Pro Gly Lys
                435                 440
```

<210> SEQ ID NO 66
<211> LENGTH: 218
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 66

```
Asp Ile Val Leu Thr Gln Ser Pro Thr Ser Leu Ala Val Ser Leu Gly
1               5                   10                  15
Gln Arg Ala Thr Ile Ser Cys Arg Ala Ser Lys Ser Val Ser Thr Ser
            20                  25                  30
Gly Phe Ser Tyr Leu His Trp Tyr Gln Gln Lys Pro Gly Gln Pro Pro
        35                  40                  45
Lys Leu Leu Ile Phe Leu Ala Ser Asn Leu Glu Ser Gly Val Pro Ala
    50                  55                  60
Arg Phe Ser Gly Ser Gly Ser Gly Thr Asp Phe Thr Leu Asn Ile His
65                  70                  75                  80
Pro Val Glu Glu Glu Asp Ala Ala Thr Tyr Tyr Cys Gln His Ser Trp
                85                  90                  95
Glu Leu Pro Leu Thr Phe Gly Ala Gly Thr Lys Leu Glu Leu Lys Arg
            100                 105                 110
Ala Asp Ala Ala Pro Thr Val Ser Ile Phe Pro Pro Ser Ser Glu Gln
        115                 120                 125
Leu Thr Ser Gly Gly Ala Ser Val Val Cys Phe Leu Asn Asn Phe Tyr
    130                 135                 140
Pro Lys Asp Ile Asn Val Lys Trp Lys Ile Asp Gly Ser Glu Arg Gln
145                 150                 155                 160
Asn Gly Val Leu Asn Ser Trp Thr Asp Gln Asp Ser Lys Asp Ser Thr
                165                 170                 175
Tyr Ser Met Ser Ser Thr Leu Thr Leu Thr Lys Asp Glu Tyr Glu Arg
            180                 185                 190
His Asn Ser Tyr Thr Cys Glu Ala Thr His Lys Thr Ser Thr Ser Pro
        195                 200                 205
Ile Val Lys Ser Phe Asn Arg Asn Glu Cys
    210                 215
```

<210> SEQ ID NO 67
<211> LENGTH: 444

<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 67

Gln Val Gln Leu Gln Gln Pro Gly Ala Glu Leu Val Lys Pro Gly Thr
1               5                   10                  15

Ser Val Lys Leu Ser Cys Lys Ala Ser Gly Tyr Thr Phe Thr Asn Tyr
            20                  25                  30

Tyr Met Tyr Trp Val Lys Gln Arg Pro Gly Gln Gly Leu Glu Trp Ile
        35                  40                  45

Gly Gly Ile Asn Pro Ser Asn Gly Gly Thr Asn Phe Asn Glu Lys Phe
    50                  55                  60

Lys Asn Lys Ala Thr Leu Thr Val Asp Ser Ser Ser Thr Thr Tyr
65                  70                  75                  80

Met Gln Leu Ser Ser Leu Thr Ser Glu Asp Ser Ala Val Tyr Tyr Cys
                85                  90                  95

Thr Arg Arg Asp Tyr Arg Phe Asp Met Gly Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Asp Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
            405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 68
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 68

Asp Ile Val Leu Thr Gln Ser Pro Ala Ser Leu Ala Val Ser Leu Gly
1               5                   10                  15

Gln Arg Ala Ala Ile Ser Cys Arg Ala Ser Lys Gly Val Ser Thr Ser
            20                  25                  30

Gly Tyr Ser Tyr Leu His Trp Tyr Gln Gln Lys Pro Gly Gln Ser Pro
        35                  40                  45

Lys Leu Leu Ile Tyr Leu Ala Ser Tyr Leu Glu Ser Gly Val Pro Ala
    50                  55                  60

Arg Phe Ser Gly Ser Gly Ser Gly Thr Asp Phe Thr Leu Asn Ile His
65                  70                  75                  80

Pro Val Glu Glu Glu Asp Ala Ala Thr Tyr Tyr Cys Gln His Ser Arg
                85                  90                  95

Asp Leu Pro Leu Thr Phe Gly Thr Gly Thr Lys Leu Glu Leu Lys Arg
            100                 105                 110

Ala Asp Ala Ala Pro Thr Val Ser Ile Phe Pro Pro Ser Ser Glu Gln
        115                 120                 125

Leu Thr Ser Gly Gly Ala Ser Val Val Cys Phe Leu Asn Asn Phe Tyr
    130                 135                 140

Pro Lys Asp Ile Asn Val Lys Trp Lys Ile Asp Gly Ser Glu Arg Gln
145                 150                 155                 160

Asn Gly Val Leu Asn Ser Trp Thr Asp Gln Asp Ser Lys Asp Ser Thr
                165                 170                 175

Tyr Ser Met Ser Ser Thr Leu Thr Leu Thr Lys Asp Glu Tyr Glu Arg
            180                 185                 190

His Asn Ser Tyr Thr Cys Glu Ala Thr His Lys Thr Ser Thr Ser Pro
        195                 200                 205

Ile Val Lys Ser Phe Asn Arg Asn Glu Cys
    210                 215

<210> SEQ ID NO 69
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 69

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
             20                  25                  30

Tyr Leu Tyr Trp Met Lys Gln Arg Pro Gly Gln Gly Leu Glu Trp Ile
         35                  40                  45

Gly Val Asn Pro Ser Asn Gly Gly Thr Gln Phe Ser Glu Lys Phe
 50                  55                  60

Lys Ser Lys Ala Thr Leu Thr Val Asp Lys Ser Ser Thr Ala Tyr
 65                  70                  75                  80

Met Gln Leu Ser Ser Leu Thr Ser Glu Asp Ser Ala Val Tyr Tyr Cys
             85                  90                  95

Thr Arg Arg Asp Ser Asn Tyr Asp Gly Gly Phe Asp Tyr Trp Gly Gln
         100                 105                 110

Gly Thr Thr Leu Thr Val Ser Ser Ala Lys Thr Thr Pro Pro Ser Val
         115                 120                 125

Tyr Pro Leu Ala Pro Gly Ser Ala Ala Gln Thr Asn Ser Met Val Thr
         130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                 165                 170                 175

Leu Gln Ser Asp Leu Tyr Thr Leu Ser Ser Ser Val Thr Val Pro Ser
             180                 185                 190

Ser Thr Trp Pro Ser Glu Thr Val Thr Cys Asn Val Ala His Pro Ala
         195                 200                 205

Ser Ser Thr Lys Val Asp Lys Lys Ile Val Pro Arg Asp Cys Gly Cys
 210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                 245                 250                 255

Thr Cys Val Val Val Ala Ile Ser Lys Asp Asp Pro Glu Val Gln Phe
             260                 265                 270

Ser Trp Phe Val Asp Asp Val Glu Val His Thr Ala Gln Thr Gln Pro
         275                 280                 285

Arg Glu Glu Gln Phe Asn Ser Thr Phe Arg Ser Val Ser Glu Leu Pro
 290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                 325                 330                 335

Lys Gly Arg Pro Lys Ala Pro Gln Val Tyr Thr Ile Pro Pro Pro Lys
             340                 345                 350

Glu Gln Met Ala Lys Asp Lys Val Ser Leu Thr Cys Met Ile Thr Asp
         355                 360                 365

Phe Phe Pro Glu Asp Ile Thr Val Glu Trp Gln Trp Asn Gly Gln Pro
 370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                 405                 410                 415

Gly Asn Thr Phe Thr Cys Ser Val Leu His Glu Gly Leu His Asn His
             420                 425                 430

His Thr Glu Lys Ser Leu Ser His Ser Pro Gly Lys
            435                 440

<210> SEQ ID NO 70
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 70

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
            20                  25                  30

Tyr Leu Tyr Trp Met Lys Gln Arg Pro Gly Gln Gly Leu Glu Trp Ile
        35                  40                  45

Gly Gly Val Asn Pro Ser Asn Gly Gly Thr Glu Phe Ser Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Leu Thr Val Ser Ser Ala Lys Thr Thr Pro Pro Ser Val
        115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
            180                 185                 190

Ser Thr Trp Pro Ser Glu Thr Val Thr Cys Asn Val Ala His Pro Ala
        195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe
            260                 265                 270

Ser Trp Phe Val Asp Asp Val Glu Val His Thr Ala Gln Thr Gln Pro
        275                 280                 285

Arg Glu Glu Gln Phe Asn Ser Thr Phe Arg Ser Val Ser Glu Leu Pro
    290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
                355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
                420                 425                 430

His Thr Glu Lys Ser Leu Ser His Ser Pro Gly Lys
                435                 440

<210> SEQ ID NO 71
<211> LENGTH: 444
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 71

Gln Val Gln Leu Gln Gln Pro Gly Ala Glu Leu Val Lys Pro Gly Ala
1               5                   10                  15

Ser Val Lys Leu Ser Cys Lys Ala Ser Gly Tyr Thr Phe Thr Ser Tyr
                20                  25                  30

Tyr Leu Tyr Trp Met Lys Gln Arg Pro Gly Gln Gly Leu Glu Trp Ile
            35                  40                  45

Gly Gly Val Asn Pro Ser Asn Gly Gly Thr Ala Phe Ser Glu Lys Phe
    50                  55                  60

Lys Ser Lys Ala Thr Leu Thr Val Asp Lys Ser Ser Ser Thr Ala Tyr
65                  70                  75                  80

Met Gln Leu Ser Ser Leu Thr Ser Glu Asp Ser Ala Val Tyr Tyr Cys
                85                  90                  95

Thr Arg Arg Asp Ser Asn Tyr Asp Gly Gly Phe Asp Tyr Trp Gly Gln
                100                 105                 110

Gly Thr Thr Leu Thr Val Ser Ser Ala Lys Thr Thr Pro Pro Ser Val
            115                 120                 125

Tyr Pro Leu Ala Pro Gly Ser Ala Ala Gln Thr Asn Ser Met Val Thr
    130                 135                 140

Leu Gly Cys Leu Val Lys Gly Tyr Phe Pro Glu Pro Val Thr Val Thr
145                 150                 155                 160

Trp Asn Ser Gly Ser Leu Ser Ser Gly Val His Thr Phe Pro Ala Val
                165                 170                 175

Leu Gln Ser Asp Leu Tyr Thr Leu Ser Ser Ser Val Thr Val Pro Ser
                180                 185                 190

Ser Thr Trp Pro Ser Glu Thr Val Thr Cys Asn Val Ala His Pro Ala
            195                 200                 205

Ser Ser Thr Lys Val Asp Lys Lys Ile Val Pro Arg Asp Cys Gly Cys
    210                 215                 220

Lys Pro Cys Ile Cys Thr Val Pro Glu Val Ser Ser Val Phe Ile Phe
225                 230                 235                 240

Pro Pro Lys Pro Lys Asp Val Leu Thr Ile Thr Leu Thr Pro Lys Val
                245                 250                 255

Thr Cys Val Val Val Ala Ile Ser Lys Asp Asp Pro Glu Val Gln Phe

```
                    260                 265                 270
Ser Trp Phe Val Asp Val Glu Val His Thr Ala Gln Thr Gln Pro
            275                 280                 285

Arg Glu Glu Gln Phe Asn Ser Thr Phe Arg Ser Val Ser Glu Leu Pro
        290                 295                 300

Ile Met His Gln Asp Trp Leu Asn Gly Lys Glu Phe Lys Cys Arg Val
305                 310                 315                 320

Asn Ser Ala Ala Phe Pro Ala Pro Ile Glu Lys Thr Ile Ser Lys Thr
                325                 330                 335

Lys Gly Arg Pro Lys Ala Pro Gln Val Tyr Thr Ile Pro Pro Pro Lys
            340                 345                 350

Glu Gln Met Ala Lys Asp Lys Val Ser Leu Thr Cys Met Ile Thr Asp
        355                 360                 365

Phe Phe Pro Glu Asp Ile Thr Val Glu Trp Gln Trp Asn Gly Gln Pro
    370                 375                 380

Ala Glu Asn Tyr Lys Asn Thr Gln Pro Ile Met Asp Thr Asp Gly Ser
385                 390                 395                 400

Tyr Phe Val Tyr Ser Lys Leu Asn Val Gln Lys Ser Asn Trp Glu Ala
                405                 410                 415

Gly Asn Thr Phe Thr Cys Ser Val Leu His Glu Gly Leu His Asn His
            420                 425                 430

His Thr Glu Lys Ser Leu Ser His Ser Pro Gly Lys
        435                 440

<210> SEQ ID NO 72
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 72

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Glu Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175
```

```
Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 73
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Ser Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95
```

Thr Arg Arg Asp Ser Asn Tyr Asp Gly Gly Phe Asp Tyr Trp Gly Gln
            100                 105                 110

Gly Thr Thr Val Thr Val Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
            435                 440                 445

<210> SEQ ID NO 74
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

Glu Val Gln Leu Val Gln Ser Gly Ala Glu Val Lys Lys Pro Gly Ala

```
1               5                   10                  15
Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
            50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
            85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
            165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
            245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
            290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
            325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
            355                 360                 365

Val Lys Gly Phe Tyr Pro Ser Asp Ile Ala Val Glu Trp Glu Ser Asn
            370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430
```

His Asn His Tyr Thr Gln Lys Ser Leu Ser Leu Ser Leu Gly Lys
            435                 440                 445

<210> SEQ ID NO 75
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 76
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110

<210> SEQ ID NO 77
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 77

| | | | | | | | | | | | | | | |
|---|---|---|---|---|---|---|---|---|---|---|---|---|---|---|
| Glu | Val | Gln | Leu | Val | Gln | Ser | Gly | Ala | Glu | Val | Lys | Lys | Pro | Gly | Ala |
| 1 | | | | 5 | | | | | 10 | | | | | 15 | |
| Ser | Val | Lys | Val | Ser | Cys | Lys | Ala | Ser | Gly | Tyr | Thr | Phe | Thr | Ser | Tyr |
| | | | 20 | | | | | 25 | | | | | 30 | | |
| Tyr | Leu | Tyr | Trp | Val | Arg | Gln | Ala | Pro | Gly | Gln | Gly | Leu | Glu | Trp | Ile |
| | | 35 | | | | | 40 | | | | | 45 | | | |
| Gly | Gly | Val | Asn | Pro | Ser | Asn | Ala | Gly | Thr | Asn | Phe | Ser | Glu | Lys | Phe |
| | 50 | | | | | 55 | | | | | 60 | | | | |
| Lys | Ser | Arg | Val | Thr | Leu | Thr | Val | Asp | Thr | Ser | Ile | Ser | Thr | Ala | Tyr |
| 65 | | | | | 70 | | | | | 75 | | | | | 80 |
| Met | Glu | Leu | Ser | Arg | Leu | Arg | Ser | Asp | Asp | Thr | Ala | Val | Tyr | Tyr | Cys |
| | | | | 85 | | | | | 90 | | | | | 95 | |
| Thr | Arg | Arg | Asp | Ser | Asn | Tyr | Asp | Gly | Gly | Phe | Asp | Tyr | Trp | Gly | Gln |
| | | | 100 | | | | | 105 | | | | | 110 | | |
| Gly | Thr | Thr | Val | Thr | Val | Ser | Ser | Ala | Ser | Thr | Lys | Gly | Pro | Ser | Val |
| | | 115 | | | | | 120 | | | | | 125 | | | |
| Phe | Pro | Leu | Ala | Pro | Cys | Ser | Arg | Ser | Thr | Ser | Glu | Ser | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Lys | Thr | Tyr | Thr | Cys | Asn | Val | Asp | His | Lys |
| | | 195 | | | | | 200 | | | | | 205 | | | |
| Pro | Ser | Asn | Thr | Lys | Val | Asp | Lys | Arg | Val | Glu | Ser | Lys | Tyr | Gly | Pro |
| | 210 | | | | | 215 | | | | | 220 | | | | |
| Pro | Cys | Pro | Pro | Cys | Pro | Ala | Pro | Glu | Phe | Leu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Val | Asp | Val | Ser | Gln | Glu | Asp | Pro | Glu |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | 275 | | | | | 280 | | | | | 285 | | | |
| Thr | Lys | Pro | Arg | Glu | Glu | Gln | Phe | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Gln | Glu | Glu | Met | Thr | Lys | Asn | Gln | Val | Ser | Leu | Thr | Cys | Leu |
| | | 355 | | | | | 360 | | | | | 365 | | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |
| Asp | Gly | Ser | Phe | Phe | Leu | Tyr | Ser | Arg | Leu | Thr | Val | Asp | Lys | Ser | Arg |

```
                    405                 410                 415
Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445
```

<210> SEQ ID NO 78
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 78

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Ser Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120
```

<210> SEQ ID NO 79
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 79

```
Gly Val Asn Pro Ser Asn Ala Gly Thr Asn Phe Ser Glu Lys Phe Lys
1               5                   10                  15

Ser
```

<210> SEQ ID NO 80
<211> LENGTH: 225
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 80

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45
```

```
Gly Gly Val Asn Pro Ser Asn Gly Gly Thr Asn Phe Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Arg Asp Ser Asn Tyr Asp Gly Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
210                 215                 220

Pro
225

<210> SEQ ID NO 81
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 81

Glu Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
                 20                  25                  30

Tyr Leu Tyr Trp Val Arg Gln Ala Pro Gly Gln Gly Leu Glu Trp Ile
             35                  40                  45

Gly Gly Val Asn Pro Ser Asn Gly Gly Thr Asn Phe Asn Glu Lys Phe
 50                  55                  60

Lys Ser Arg Val Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Arg Asp Ser Asn Tyr Asp Gly Gly Phe Asp Tyr Trp Gly Gln
                100                 105                 110

Gly Thr Thr Leu Thr Val Ser Ser
            115                 120

<210> SEQ ID NO 82
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide
```

<400> SEQUENCE: 82

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Leu Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
    370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
```

-continued

```
                405                 410                 415
Trp Gln Glu Gly Asn Val Phe Ser Cys Ser Val Met His Glu Ala Leu
        420                 425                 430
His Asn His Tyr Thr Gln Lys Ser Leu Ser Leu Ser Leu Gly Lys
        435                 440                 445
```

<210> SEQ ID NO 83
<211> LENGTH: 447
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 83

```
Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
        275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320
```

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Ser Leu Ser Leu Gly Lys
        435                 440                 445

<210> SEQ ID NO 84
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 84

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 85
```

<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 85

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Leu Tyr Trp Val Arg Gln Ala Pro Gly Gln Gly Leu Glu Trp Ile
            35                  40                  45

Gly Gly Val Asn Pro Ser Asn Ala Gly Thr Asn Phe Asn Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100                 105                 110

Gly Thr Thr Val Thr Val Ser Ser
        115                 120

<210> SEQ ID NO 86
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 86

Gly Val Asn Pro Ser Asn Ala Gly Thr Asn Phe Asn Glu Lys Phe Lys
1               5                   10                  15

Ser

<210> SEQ ID NO 87
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 87

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Leu Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln

```
                100             105             110
Gly Thr Thr Val Thr Val Ser Ser Ala Ser Thr Lys Gly Pro Ser Val
            115             120             125

Phe Pro Leu Ala Pro Cys Ser Arg Ser Thr Ser Glu Ser Thr Ala Ala
130             135             140

Leu Gly Cys Leu Val Lys Asp Tyr Phe Pro Glu Pro Val Thr Val Ser
145             150             155             160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Lys Thr Tyr Thr Cys Asn Val Asp His Lys
            195             200             205

Pro Ser Asn Thr Lys Val Asp Lys Arg Val Glu
            210             215

<210> SEQ ID NO 88
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 88

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Ser Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100             105             110

Gly Thr Thr Val Thr Val Ser Ser
            115             120

<210> SEQ ID NO 89
<211> LENGTH: 447
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 89

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Ser Glu Lys Phe
```

```
            50                  55                  60
Lys Ser Arg Val Thr Leu Thr Val Asp Thr Ser Ile Ser Thr Ala Tyr
 65                  70                  75                  80

Met Glu Leu Ser Arg Leu Arg Ser Asp Thr Ala Val Tyr Tyr Cys
                 85                  90                  95

Thr Arg Arg Leu Ser His Tyr Asp Gly Phe Asp Tyr Trp Gly Gln
                100                 105                 110

Gly Thr Thr Val Thr Val Ser Ser Ala Ser Thr Lys Gly Pro Ser Val
                115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu Ser Lys Tyr Gly Pro
210                 215                 220

Pro Cys Pro Pro Cys Pro Ala Pro Glu Phe Leu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
                260                 265                 270

Val Gln Phe Asn Trp Tyr Val Asp Gly Val Glu Val His Asn Ala Lys
                275                 280                 285

Thr Lys Pro Arg Glu Glu Gln Phe Asn Ser Thr Tyr Arg Val Val Ser
290                 295                 300

Val Leu Thr Val Leu His Gln Asp Trp Leu Asn Gly Lys Glu Tyr Lys
305                 310                 315                 320

Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
                340                 345                 350

Pro Ser Gln Glu Glu Met Thr Lys Asn Gln Val Ser Leu Thr Cys Leu
                355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
                420                 425                 430

His Asn His Tyr Thr Gln Lys Ser Leu Ser Leu Ser Leu Gly Lys
                435                 440                 445

<210> SEQ ID NO 90
<211> LENGTH: 450
<212> TYPE: PRT
<213> ORGANISM: Artificial Sequence
```

<220> FEATURE:
<223> OTHER INFORMATION: Description of Artificial Sequence: Synthetic
      polypeptide

<400> SEQUENCE: 90

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Phe Asp Tyr Trp Gly Gln
            100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val

```
385                 390                 395                 400
Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
                420                 425                 430

Glu Ala Leu His Asn His Tyr Thr Gln Lys Ser Leu Ser Leu Ser Pro
            435                 440                 445

Gly Lys
    450

<210> SEQ ID NO 91
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide
<220> FEATURE:
<221> NAME/KEY: MOD_RES
<222> LOCATION: (7)..(7)
<223> OTHER INFORMATION: Gly or Ala
<220> FEATURE:
<221> NAME/KEY: MOD_RES
<222> LOCATION: (12)..(12)
<223> OTHER INFORMATION: Ser or Asn

<400> SEQUENCE: 91

Gly Val Asn Pro Ser Asn Xaa Gly Thr Asn Phe Xaa Glu Lys Phe Lys
1               5                   10                  15

Ser

<210> SEQ ID NO 92
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (56)..(56)
<223> OTHER INFORMATION: Gly or Ala
<220> FEATURE:
<221> NAME/KEY: MOD_RES
<222> LOCATION: (61)..(61)
<223> OTHER INFORMATION: Ser or Asn

<400> SEQUENCE: 92

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Tyr Leu Tyr Trp Val Arg Gln Ala Pro Gly Gln Gly Leu Glu Trp Ile
            35                  40                  45

Gly Gly Val Asn Pro Ser Asn Xaa Gly Thr Asn Phe Xaa Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
            100                 105                 110

Gly Thr Thr Val Thr Val Ser Ser
```

```
                115                 120

<210> SEQ ID NO 93
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide
<220> FEATURE:
<221> NAME/KEY: MOD_RES
<222> LOCATION: (56)..(56)
<223> OTHER INFORMATION: Gly or Ala
<220> FEATURE:
<221> NAME/KEY: MOD_RES
<222> LOCATION: (61)..(61)
<223> OTHER INFORMATION: Ser or Asn

<400> SEQUENCE: 93

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Xaa Gly Thr Asn Phe Xaa Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 94
<211> LENGTH: 450
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 94

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125
```

```
Phe Pro Leu Ala Pro Ser Ser Lys Ser Thr Ser Gly Gly Thr Ala Ala
            130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 95
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 95

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
```

```
                        20                  25                  30
Tyr Leu Tyr Trp Val Arg Gln Ala Pro Gly Gln Gly Leu Glu Trp Ile
                35                  40                  45

Gly Gly Val Asn Pro Ser Asn Ala Gly Thr Asn Phe Asn Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Arg Arg Asp Ser Asn Tyr Asp Gly Gly Phe Asp Tyr Trp Gly Gln
                100                 105                 110

Gly Thr Thr Val Thr Val Ser Ser
                115                 120

<210> SEQ ID NO 96
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 96

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
                20                  25                  30

Asn Val Asp Trp Val Arg Gln Ala Arg Gly Gln Arg Leu Glu Trp Ile
                35                  40                  45

Gly Asp Ile Asn Pro Asn Asp Gly Gly Thr Ile Tyr Ala Gln Lys Phe
        50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
                100                 105                 110

Thr Thr Val Thr Val Ser Ser Ala Ser Thr Lys Gly Pro Ser Val Phe
                115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Lys Leu Ser Ser Val Val Thr Val Pro Ser
                180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255
```

Arg Thr Pro Glu Val Thr Cys Val Val Val Ser Val Ser His Glu Asp
                260                 265                 270

Pro Glu Val Lys Phe Asn Trp Tyr Val Asp Gly Val Glu Val His Asn
            275                 280                 285

Ala Lys Thr Lys Pro Arg Glu Glu Gln Tyr Asn Ser Thr Tyr Arg Val
        290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Leu Pro Pro Ser Arg Asp Glu Leu Thr Lys Asn Gln Val Ser Leu Leu
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Leu Thr Trp Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 97
<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 97

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Gln Ala Arg Gly Gln Arg Leu Glu Trp Ile
        35                  40                  45

Gly Asp Ile Asn Pro Asn Asp Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 98
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 98

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Glu
        115                 120                 125

Leu Lys Ser Gly Thr Ala Thr Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Tyr Leu Glu Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 99
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 99

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Gln Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys
            100                 105                 110

<210> SEQ ID NO 100

<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 100

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Arg
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Arg Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 101
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 101

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
        35                  40                  45

Gly Gly Val Asn Pro Ser Asn Ala Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ala Ser Thr Lys Gly Pro Ser Val
        115                 120                 125

Phe Pro Leu Ala Pro Ser Ser Lys Ser Thr Ser Gly Gly Thr Ala Ala
130                 135                 140

Leu Gly Cys Glu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Glu Ser Ser Gly Leu Tyr Ser Leu Leu Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 102
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 102

```
Glu Val Gln Leu Val Gln Ser Gly Ala Glu Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Gln Ala Pro Gly Gln Gly Leu Glu Trp Ile
            35                  40                  45

Gly Gly Val Asn Pro Ser Asn Ala Gly Thr Asn Phe Asn Glu Lys Phe
        50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Leu Ser His Tyr Asp Gly Gly Phe Asp Tyr Trp Gly Gln
                100                 105                 110

Gly Thr Thr Val Thr Val Ser Ser Ala Ser Thr Lys Gly Pro Ser Val
            115                 120                 125

Phe Pro Leu Ala Pro Ser Ser Lys Ser Thr Ser Gly Gly Thr Ala Ala
130                 135                 140

Leu Gly Cys Glu Val Thr Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Glu Ser Ser Gly Leu Tyr Ser Leu Leu Ser Val Val Thr Val Pro
                180                 185                 190

Ser Ser Ser Leu Gly Thr Gln Thr Tyr Ile Cys Asn Val Asn His Lys
                195                 200                 205

Pro Ser Asn Thr Lys Val Asp Lys Lys Val Glu Pro Lys Ser Cys Asp
210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
                260                 265                 270

Asp Pro Glu Val Lys Phe Asn Trp Tyr Val Asp Gly Val Glu Val His
            275                 280                 285

Asn Ala Lys Thr Lys Pro Arg Glu Glu Gln Tyr Asn Ser Thr Tyr Arg
        290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Tyr Pro Pro Ser Arg Asp Glu Leu Thr Lys Asn Gln Val Ser Leu
                355                 360                 365

Thr Cys Leu Val Lys Gly Phe Tyr Pro Ser Asp Ile Ala Val Glu Trp
370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Ala Leu Val Ser Lys Leu Thr Val Asp
                405                 410                 415
```

```
Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 103
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 103

Asp Ile Val Met Thr Gln Thr Pro Leu Ser Leu Ser Val Thr Pro Gly
1               5                   10                  15

Gln Pro Ala Ser Ile Ser Cys Arg Ala Ser Lys Ser Val Ser Thr Ser
            20                  25                  30

Gly Phe Ser Tyr Leu His Trp Tyr Leu Gln Lys Pro Gly Gln Pro Pro
        35                  40                  45

Gln Leu Leu Ile Phe Leu Ser Lys Tyr Arg Ser Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Ser Gln Ala Tyr
                85                  90                  95

His Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Arg
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Arg Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 104
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 104

Gln Met Gln Leu Val Gln Ser Gly Pro Glu Val Lys Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Arg Ala Arg Gly Gln Arg Leu Glu Trp Ile
```

```
            35                  40                  45
Gly Asp Ile Asn Pro Asn Asp Gly Gly Thr Ile Tyr Ala Gln Lys Phe
 50                  55                  60

Gln Glu Arg Val Thr Ile Thr Val Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Asn Tyr Arg Trp Phe Gly Ala Met Asp His Trp Gly Gln Gly
                100                 105                 110

Thr Thr Val Thr Val Ser Ser Ala Ser Thr Lys Gly Pro Ser Val Phe
            115                 120                 125

Pro Leu Ala Pro Ser Ser Lys Ser Thr Ser Gly Gly Thr Ala Ala Leu
        130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val Arg Thr Phe Pro Ala Val Leu
                165                 170                 175

Lys Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Ser Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Val
            340                 345                 350

Tyr Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Ala Leu Val Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

<210> SEQ ID NO 105
```

<211> LENGTH: 119
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 105

Gln Met Gln Leu Val Gln Ser Gly Pro Glu Val Lys Pro Gly Thr
1               5                   10                  15

Ser Val Lys Val Ser Cys Lys Ala Ser Gly Tyr Thr Phe Thr Asp Tyr
            20                  25                  30

Asn Val Asp Trp Val Arg Arg Ala Arg Gly Gln Arg Leu Glu Trp Ile
        35                  40                  45

Gly Asp Ile Asn Pro Asn Asp Gly Gly Thr Ile Tyr Ala Gln Lys Phe
    50                  55                  60

Gln Glu Arg Val Thr Ile Thr Val Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asn Tyr Arg Trp Phe Gly Ala Met Asp His Trp Gly Gln Gly
            100                 105                 110

Thr Thr Val Thr Val Ser Ser
        115

<210> SEQ ID NO 106
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 106

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Glu Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys Arg
            100                 105                 110

Thr Val Ala Ala Pro Ser Val Phe Ile Phe Pro Pro Ser Asp Glu Glu
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Glu Glu Ser Val Thr Glu Gln Asp Ser Lys Asp Ser Thr
                165                 170                 175

Tyr Ser Leu Ser Ser Thr Leu Glu Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 107
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 107

Asp Ile Val Met Thr Gln Thr Pro Leu Ser Leu Ser Val Thr Pro Gly
1               5                   10                  15

Gln Pro Ala Ser Ile Ser Cys Lys Ala Ser Gln Ser Leu Asp Tyr Glu
            20                  25                  30

Gly Asp Ser Asp Met Asn Trp Tyr Leu Glu Lys Pro Gly Gln Pro Pro
        35                  40                  45

Gln Leu Leu Ile Tyr Gly Ala Ser Asn Leu Glu Ser Gly Val Pro Asp
    50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln Gln Ser Thr
                85                  90                  95

Glu Asp Pro Arg Thr Phe Gly Gly Gly Thr Lys Val Glu Ile Lys
            100                 105                 110

<210> SEQ ID NO 108
<211> LENGTH: 449
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 108

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Glu Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Glu Val Thr Asp Tyr Phe Pro Glu Pro Val Thr Val Ser
145                 150                 155                 160

```
Trp Asn Ser Gly Ala Leu Thr Ser Gly Val His Thr Phe Pro Ala Val
                165                 170                 175

Leu Glu Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Ser Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Val Leu Pro Pro Ser Arg Asp Glu Leu Thr Lys Asn Gln Val Ser Leu
        355                 360                 365

Leu Cys Leu Val Lys Gly Phe Tyr Pro Ser Asp Ile Ala Val Glu Trp
    370                 375                 380

Glu Ser Asn Gly Gln Pro Glu Asn Asn Tyr Leu Thr Trp Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly

<210> SEQ ID NO 109
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 109

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Tyr Leu Tyr Trp Val Arg Glu Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60
```

```
Lys Ser Arg Val Thr Leu Thr Val Asp Thr Ser Ile Ser Thr Ala Tyr
 65                  70                  75                  80

Met Glu Leu Ser Arg Leu Arg Ser Asp Asp Thr Ala Val Tyr Tyr Cys
                 85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 110
<211> LENGTH: 218
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 110

Asp Ile Val Met Thr Gln Thr Pro Leu Ser Leu Ser Val Thr Pro Gly
 1               5                  10                  15

Gln Pro Ala Ser Ile Ser Cys Arg Ala Ser Lys Ser Val Ser Thr Ser
             20                  25                  30

Gly Phe Ser Tyr Leu His Trp Tyr Leu Arg Lys Pro Gly Gln Pro Pro
         35                  40                  45

Gln Leu Leu Ile Phe Leu Ala Ser Asn Leu Glu Ser Gly Val Pro Asp
     50                  55                  60

Arg Phe Ser Gly Ser Gly Ser Gly Thr Asp Phe Thr Leu Lys Ile Ser
 65                  70                  75                  80

Arg Val Glu Ala Glu Asp Val Gly Val Tyr Tyr Cys Gln His Ser Trp
                 85                  90                  95

Glu Leu Pro Leu Thr Phe Gly Gln Gly Thr Lys Leu Glu Ile Lys Arg
            100                 105                 110

Thr Val Ala Ala Pro Ser Val Phe Ile Phe Pro Pro Ser Asp Glu Arg
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Lys Glu Ser Val Thr Glu Gln Asp Ser Lys Asp Ser Thr
                165                 170                 175

Tyr Ser Leu Ser Ser Arg Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 111
<211> LENGTH: 111
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 111

Asp Ile Val Met Thr Gln Thr Pro Leu Ser Leu Ser Val Thr Pro Gly
 1               5                  10                  15
```

```
Gln Pro Ala Ser Ile Ser Cys Arg Ala Ser Lys Ser Val Ser Thr Ser
            20                  25                  30

Gly Phe Ser Tyr Leu His Trp Tyr Leu Arg Lys Pro Gly Gln Pro Pro
        35                  40                  45

Gln Leu Leu Ile Phe Leu Ala Ser Asn Leu Glu Ser Gly Val Pro Asp
50                  55                  60

Arg Phe Ser Gly Ser Gly Ser Gly Thr Asp Phe Thr Leu Lys Ile Ser
65                  70                  75                  80

Arg Val Glu Ala Glu Asp Val Gly Val Tyr Tyr Cys Gln His Ser Trp
                85                  90                  95

Glu Leu Pro Leu Thr Phe Gly Gln Gly Thr Lys Leu Glu Ile Lys
            100                 105                 110

<210> SEQ ID NO 112
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 112

Asp Tyr Asn Val Asp
1               5

<210> SEQ ID NO 113
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 113

Asp Ile Asn Pro Asn Asp Gly Gly Thr Ile Tyr Ala Gln Lys Phe Gln
1               5                   10                  15

Glu

<210> SEQ ID NO 114
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 114

Asn Tyr Arg Trp Phe Gly Ala Met Asp His
1               5                   10

<210> SEQ ID NO 115
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 115

Lys Ala Ser Gln Ser Leu Asp Tyr Glu Gly Asp Ser Asp Met Asn
1               5                   10                  15

<210> SEQ ID NO 116
```

```
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 116

Gly Ala Ser Asn Leu Glu Ser
1               5

<210> SEQ ID NO 117
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 117

Gln Gln Ser Thr Glu Asp Pro Arg Thr
1               5

<210> SEQ ID NO 118
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 118

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215
```

<210> SEQ ID NO 119
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 119

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Tyr Tyr Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 120
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 120

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Tyr Tyr Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

-continued

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu
    210                 215

<210> SEQ ID NO 121
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 121

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser
        115                 120

<210> SEQ ID NO 122
<211> LENGTH: 219
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 122

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
            20                  25                  30

Tyr Tyr Tyr Trp Val Arg Gln Ala Pro Gly Gln Gly Leu Glu Trp Ile
        35                  40                  45

Gly Gly Val Asn Pro Ser Asn Gly Gly Thr Asn Phe Asn Glu Lys Phe
    50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Cys Ser Arg Ser Thr Ser Glu Ser Thr Ala Ala
130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
                195                 200                 205

Pro Ser Asn Thr Lys Val Asp Lys Arg Val Glu
210                 215

<210> SEQ ID NO 123
<211> LENGTH: 120
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 123

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Gln Tyr
                20                  25                  30

Tyr Tyr Tyr Trp Val Arg Gln Ala Pro Gly Gln Gly Leu Glu Trp Ile
            35                  40                  45

Gly Gly Val Asn Pro Ser Asn Gly Gly Thr Asn Phe Asn Glu Lys Phe
50                  55                  60

Lys Ser Arg Val Thr Leu Thr Val Asp Thr Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Thr Arg Arg Asp Ser Asn Tyr Asp Gly Gly Phe Asp Tyr Trp Gly Gln
                100                 105                 110

Gly Thr Thr Val Thr Val Ser Ser
            115                 120

<210> SEQ ID NO 124
<211> LENGTH: 329
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 124

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
50                  55                  60

Leu Ser Ser Val Val Thr Val Pro Ser Ser Ser Leu Gly Thr Gln Thr
65                  70                  75                  80

```
Tyr Ile Cys Asn Val Asn His Lys Pro Ser Asn Thr Lys Val Asp Lys
                85                  90                  95

Lys Val Glu Pro Lys Ser Cys Asp Lys Thr His Thr Cys Pro Pro Cys
            100                 105                 110

Pro Ala Pro Glu Leu Leu Gly Gly Pro Ser Val Phe Leu Phe Pro Pro
        115                 120                 125

Lys Pro Lys Asp Thr Leu Met Ile Ser Arg Thr Pro Glu Val Thr Cys
    130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                165                 170                 175

Glu Gln Tyr Asn Ser Thr Tyr Arg Val Val Ser Val Leu Thr Val Leu
            180                 185                 190

His Gln Asp Trp Leu Asn Gly Lys Glu Tyr Lys Cys Lys Val Ser Asn
        195                 200                 205

Lys Ala Leu Pro Ala Pro Ile Glu Lys Thr Ile Ser Lys Ala Lys Gly
    210                 215                 220

Gln Pro Arg Glu Pro Gln Val Tyr Thr Leu Pro Pro Ser Arg Asp Glu
225                 230                 235                 240

Leu Thr Lys Asn Gln Val Ser Leu Thr Cys Leu Val Lys Gly Phe Tyr
                245                 250                 255

Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly
                325

<210> SEQ ID NO 125
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 125

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 126
<211> LENGTH: 449
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 126

```
Val Thr Leu Arg Glu Ser Gly Pro Ala Leu Val Lys Pro Thr Gln Thr
 1               5                  10                  15

Leu Thr Leu Thr Cys Thr Phe Ser Gly Phe Ser Leu Ser Thr Ser Gly
            20                  25                  30

Met Ser Val Gly Trp Ile Arg Gln Pro Pro Gly Lys Ala Leu Glu Trp
        35                  40                  45

Leu Ala Asp Ile Trp Trp Asp Asp Lys Lys Asp Tyr Asn Pro Ser Leu
    50                  55                  60

Lys Ser Arg Leu Thr Ile Ser Lys Asp Thr Ser Lys Asn Gln Val Val
65                  70                  75                  80

Leu Lys Val Thr Asn Met Asp Pro Ala Asp Thr Ala Thr Tyr Tyr Cys
                85                  90                  95

Ala Arg Ser Met Ile Thr Asn Trp Tyr Phe Asp Val Trp Gly Ala Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Ala Ala Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Ser Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
```

```
                355                 360                 365
Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
                420                 425                 430

Ala Leu His Asn His Tyr Thr Gln Lys Ser Leu Ser Leu Ser Pro Gly
                435                 440                 445

Lys

<210> SEQ ID NO 127
<211> LENGTH: 213
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 127

Asp Ile Gln Met Thr Gln Ser Pro Ser Thr Leu Ser Ala Ser Val Gly
1               5                   10                  15

Asp Arg Val Thr Ile Thr Cys Lys Cys Gln Leu Ser Val Gly Tyr Met
                20                  25                  30

His Trp Tyr Gln Gln Lys Pro Gly Lys Ala Pro Lys Leu Leu Ile Tyr
            35                  40                  45

Asp Thr Ser Lys Leu Ala Ser Gly Val Pro Ser Arg Phe Ser Gly Ser
    50                  55                  60

Gly Ser Gly Thr Glu Phe Thr Leu Thr Ile Ser Ser Leu Gln Pro Asp
65                  70                  75                  80

Asp Phe Ala Thr Tyr Tyr Cys Phe Gln Gly Ser Gly Tyr Pro Phe Thr
                85                  90                  95

Phe Gly Gly Gly Thr Lys Leu Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys
    210

<210> SEQ ID NO 128
<211> LENGTH: 5
<212> TYPE: PRT
<213> ORGANISM: Artificial Sequence
<220> FEATURE:
<223> OTHER INFORMATION: Description of Artificial Sequence: Synthetic
``` peptide

<400> SEQUENCE: 128

Val Val Val Pro Pro
1               5

<210> SEQ ID NO 129
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 129

Ser Tyr Tyr Leu Tyr
1               5

<210> SEQ ID NO 130
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 130

Val Asn Pro Ser Asn Gly Gly Thr Asn Phe Asn Glu Lys Phe Lys
1               5                   10                  15

<210> SEQ ID NO 131
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 131

Asp Ser Asn Tyr Asp Gly Gly Phe Asp Tyr
1               5                   10

<210> SEQ ID NO 132
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 132

Arg Ala Ser Lys Ser Val Ser Thr Ser Gly Phe Ser Tyr Leu His
1               5                   10                  15

<210> SEQ ID NO 133
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 133

Ala Ser Asn Leu Glu
1               5

<210> SEQ ID NO 134

```
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 134

Gln His Ser Trp Glu Leu Pro Leu Thr
1               5

<210> SEQ ID NO 135
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 135

Leu Ser His Tyr Asp
1               5

<210> SEQ ID NO 136
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 136

Gly Lys Phe Arg Glu
1               5

<210> SEQ ID NO 137
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 137

Gly Thr His Arg Ala
1               5

<210> SEQ ID NO 138
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 138

Ser Lys Tyr Arg Ser
1               5

<210> SEQ ID NO 139
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 139
```

```
Ser Gln Ala Tyr His Leu Pro Leu Thr
1               5
```

<210> SEQ ID NO 140
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 140

```
Gly Lys Tyr Gly Ala
1               5
```

<210> SEQ ID NO 141
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 141

```
Ala Gln Ala Thr Gln Leu Pro Leu Thr
1               5
```

<210> SEQ ID NO 142
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 142

```
Gly His Phe Ala Ser
1               5
```

<210> SEQ ID NO 143
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 143

```
Gly Arg Tyr Leu Gln
1               5
```

<210> SEQ ID NO 144
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 144

```
Gly Thr His Ser Val
1               5
```

<210> SEQ ID NO 145
<211> LENGTH: 5
<212> TYPE: PRT
<213> ORGANISM: Artificial Sequence
<220> FEATURE:

<223> OTHER INFORMATION: Description of Artificial Sequence: Synthetic
      peptide

<400> SEQUENCE: 145

Gln Tyr Tyr Tyr Tyr
1               5

<210> SEQ ID NO 146
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 146

Gly Arg His Arg Ala
1               5

<210> SEQ ID NO 147
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 147

Gly Phe Tyr Arg Thr
1               5

<210> SEQ ID NO 148
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 148

Ser Gln Met Ala Asp Leu Pro Leu Thr
1               5

<210> SEQ ID NO 149
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 149

Gln Tyr Tyr Thr Tyr
1               5

<210> SEQ ID NO 150
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 150

Ile Glu Pro Asn Arg Gly Gly Thr Asn Phe Asn Glu Lys Phe Lys
1               5                   10                  15

```
<210> SEQ ID NO 151
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 151

Ala Gln Thr Phe Glu Leu Pro Leu Thr
1               5

<210> SEQ ID NO 152
<211> LENGTH: 5
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 152

Ser Lys Phe Arg Arg
1               5
```

ANTI-PD-1/LAG3 BISPECIFIC ANTIBODIES

CROSS-REFERENCE TO RELATED APPLICATIONS

This application claims the benefit of priority to International Serial No. PCT/CN2018/074918 filed Feb. 1, 2018, the disclosure of which is incorporated by reference herein in its entirety.

SEQUENCE LISTING

This application incorporates by reference in its entirety the Computer Readable Form (CRF) of a Sequence Listing in ASCII text format submitted via EFS-Web. The Sequence Listing text file submitted via EFS-Web, entitled 14463-001-999_SEQ_LISTING.txt, was created on Jan. 3, 2019, and is 203,053 bytes in size.

1. FIELD

Provided herein are treatments of conditions ameliorated by counteracting tumor mediated immune suppression. More specifically provided herein are anti-PD-1/LAG3 bispecific antibodies, as well as use of these antibodies in the treatment of diseases such as cancer and infectious disease.

2. BACKGROUND

PD-1 is recognized as an important molecule in immune regulation and the maintenance of peripheral tolerance. PD-1 is moderately expressed on naive T, B and NKT cells and up-regulated by TB cell receptor signaling on lymphocytes, monocytes and myeloid cells (1).

Two known ligands for PD-1, PD-L1 (B7-H1) and PD-L2 (B7-DC), are expressed in human cancers arising in various tissues. In large sample sets of e.g. ovarian, renal, colorectal, pancreatic, liver cancers and melanoma, it was shown that PD-L1 expression correlated with poor prognosis and reduced overall survival irrespective of subsequent treatment (2-13). Similarly, PD-1 expression on tumor infiltrating lymphocytes was found to mark dysfunctional T cells in breast cancer and melanoma (14-15) and to correlate with poor prognosis in renal cancer (16). Thus, it has been proposed that PD-L1 expressing tumor cells interact with PD-1 expressing T cells to attenuate T cell activation and evasion of immune surveillance, thereby contributing to an impaired immune response against the tumor.

Several monoclonal antibodies (mAb) that inhibit the interaction between PD-1 and one or both of its ligands PD-L1 and PD-L2 are in clinical development for treating cancer. It has been proposed that the efficacy of such antibodies might be enhanced if administered in combination with other approved or experimental cancer therapies, e.g., radiation, surgery, chemotherapeutic agents, targeted therapies, agents that inhibit other signaling pathways that are dysregulated in tumors, and other immune enhancing agents.

LAG3 (CD223) is a cell surface molecule expressed on activated T cells (Huard et al. Immunogenetics 39:213-217, 1994), NK cells (Triebel et al. J Exp Med 171:1393-1405, 1990), B cells (Kisielow et al. Eur J Immunol 35:2081-2088, 2005), and plasmacytoid dendritic cells (Workman et al. J Immunol 182:1885-1891, 2009) that plays an important role in the function of these lymphocyte subsets. In addition, the interaction between LAG3 and its major ligand, Class II MHC, is thought to play a role in modulating dendritic cell function (Andreae et al. J Immunol 168:3874-3880, 2002). Recent preclinical studies have documented a role for LAG-3 in CD8 T-cell exhaustion (Blackburn et al. Nat Immunol 10:29-37, 2009). As with chronic viral infection, tumor antigen-specific $CD4^+$ and $CD8^+$ T cells display impaired effector function and an exhausted phenotype characterized by decreased production of pro-inflammatory cytokines and hyporesponsiveness to antigenic re-stimulation. This is mediated by cell extrinsic mechanisms, such as regulatory T-cells (Treg), and cell intrinsic mechanisms, such as inhibitory molecules that are upregulated on exhausted, tumor-infiltrating lymphocytes (TIL). These inhibitory mechanisms represent a formidable barrier to effective antitumor immunity.

LAG3 is expressed on tolerized TILs suggesting that they contribute to tumor-mediated immune suppression. Inhibition of LAG3 may lead to enhanced activation of antigen-specific T cells from which a therapeutic benefit may be gained. There is a need in the art for high efficacy therapeutic antibodies which antagonize the activity of LAG3 and PD-1 which can be used to generate a robust immune response to tumors.

3. SUMMARY

Provided herein is an anti-PD-1/LAG-3 bispecific antibody comprising: an anti-PD-1 antigen-binding fragment comprising humanized 08A affinity matured Fab98, 99, 100, 101, 102, 103 or 104 heavy and light chain complementarity determining regions (CDRs) with or without a S61N glycosylation site correction and/or G56A deamidation site correction (sequential numbering) in the CDRH2 region, and an anti-LAG3 antigen-binding fragment comprising the heavy and light chain CDR regions of anti-LAG3 humanized antibody 22D2 Ab6.

Also provided herein is an anti-PD-1/LAG-3 bispecific antibody comprising: an anti-PD-1 antigen-binding fragment comprising humanized 08A affinity matured Fab98, 99, 100, 101, 102, 103 or 104 heavy and light chain variable regions with or without a S61N glycosylation site correction and/or G56A deamidation site correction (sequential numbering) in the CDRH2 region, and an anti-LAG3 antigen-binding fragment comprising the heavy and light chain variable regions of anti-LAG3 humanized antibody 22D2 Ab6.

Also provided is an anti-PD-1/LAG-3 bispecific antibody comprising: an anti-PD-1 antigen-binding fragment comprising humanized 08A heavy and light chain CDR regions with or without a S61N glycosylation site correction and/or G56A deamidation site correction in the CDRH2 region and an anti-LAG3 antigen-binding fragment comprising the heavy and light chain CDR regions of the anti-LAG3 antibody 22D2 Ab6. Also provided herein is an anti-PD-1/LAG-3 bispecific antibody comprising: an anti-PD-1 antigen-binding fragment comprising humanized 08A heavy and light chain variable regions with or without a S61N glycosylation site correction and/or G56A deamidation site correction in the CDRH2 region and an anti-LAG3 antigen-binding fragment comprising the heavy and light chain variable regions of the anti-LAG3 antibody 22D2 Ab6.

Also provided herein is an anti-PD-1/LAG-3 bispecific antibody comprising: an anti-PD-1 antigen-binding fragment comprising humanized 08A affinity matured Fab128, 133, 138 or 139 heavy and light chain CDR regions with or without an S61N glycosylation site correction and/or G56A deamidation site correction in the CDRH2 region and an anti-LAG3 antigen-binding fragment comprising the heavy and light chain CDR regions of anti-LAG3 antibody 22D2 Ab6. Also provided herein is an anti-PD-1/LAG-3 bispecific antibody comprising: an anti-PD-1 antigen-binding fragment comprising humanized 08A affinity matured Fab128, 133, 138 or 139 heavy and light chain variable regions with or without an S61N glycosylation site correction and/or G56A deamidation site correction in the CDRH2 region and an anti-LAG3 antigen-binding fragment comprising the heavy and light chain variable regions of anti-LAG3 antibody 22D2 Ab6.

In certain embodiments, the anti-PD-1 antigen-binding fragment comprises a heavy chain comprising an IgG1 constant region comprising CH1 mutations at L145E, K147T, Q175E, and S183L (EU numbering), and a light chain kappa constant region comprising mutations at Q124R, T178R (EU numbering); and the anti-LAG3 antigen-binding fragment comprises an anti-LAG3 heavy chain comprising an IgG1 constant region comprising CH1 mutations at S181K (EU numbering), and an anti-LAG3 light chain kappa constant region comprising mutations at Q124E, S131T, T178Y, and T180E, wherein the mutations are in EU numbering.

In other embodiments, the IgG1 heavy chain constant regions of the anti-PD-1 and anti-LAG3 antigen-binding fragments further comprise pairs of CH3 mutations selected from the group consisting of: L351Y/F405A/Y407V and T366I/K392M/T394W; T350V/L351Y/F405A/Y407V and T350V/T366L/K392M/T394W; and T350V/L351Y/F405A/Y407V and T350V/T366L/K392M/T394W, wherein the mutations are in EU numbering.

In certain embodiments, the anti-LAG3 and anti-PD-1 heavy chains each comprises one or more of L234A or L234D; L235A or L235D; D265S or D265A; G237A; and N297A, N297Q, or N297D mutations in the CH2 region, wherein the mutations are in EU numbering.

Also provided herein are isolated nucleic acids encoding anyone of the anti-PD-1/LAG3 bispecific antibodies, or antigen-binding fragments provided herein. Also provided herein are expression vectors comprising such nucleic acid (wherein said polypeptides can optionally comprise a leader sequence). These isolated nucleic acids and the expression vectors comprising them can be used to express the antibodies or antigen-binding fragments thereof in recombinant host cells. Thus, Also provided herein are host cells comprising such isolated nucleic acids. In one embodiment, the host cell is Chinese hamster ovary cell. In one embodiment, the host cell is a yeast cell, for example a *Pichia* cell or a *Pichia pastoris* host cell.

4. BRIEF DESCRIPTION OF THE FIGURES

FIG. 1 depicts the testing of the Fab and the bispecific antibodies provided herein in the engineered Jurkat.hPD-1.IL2luc+ THP-1.PD-L1 Assay. Bispecific antibodies and Fabs were able to reverse the immune suppression produced by the PD1-PDL1 interactions. This was measured as an increase in IL2 mediated luciferase levels when antibodies/Fab was incubated with Jurkat cells (PD1+ve) and THP1PDL1 cells (+LPS, IFNg, aCD3).

5. DETAILED DESCRIPTION

5.1 Terminology

Figure 1:
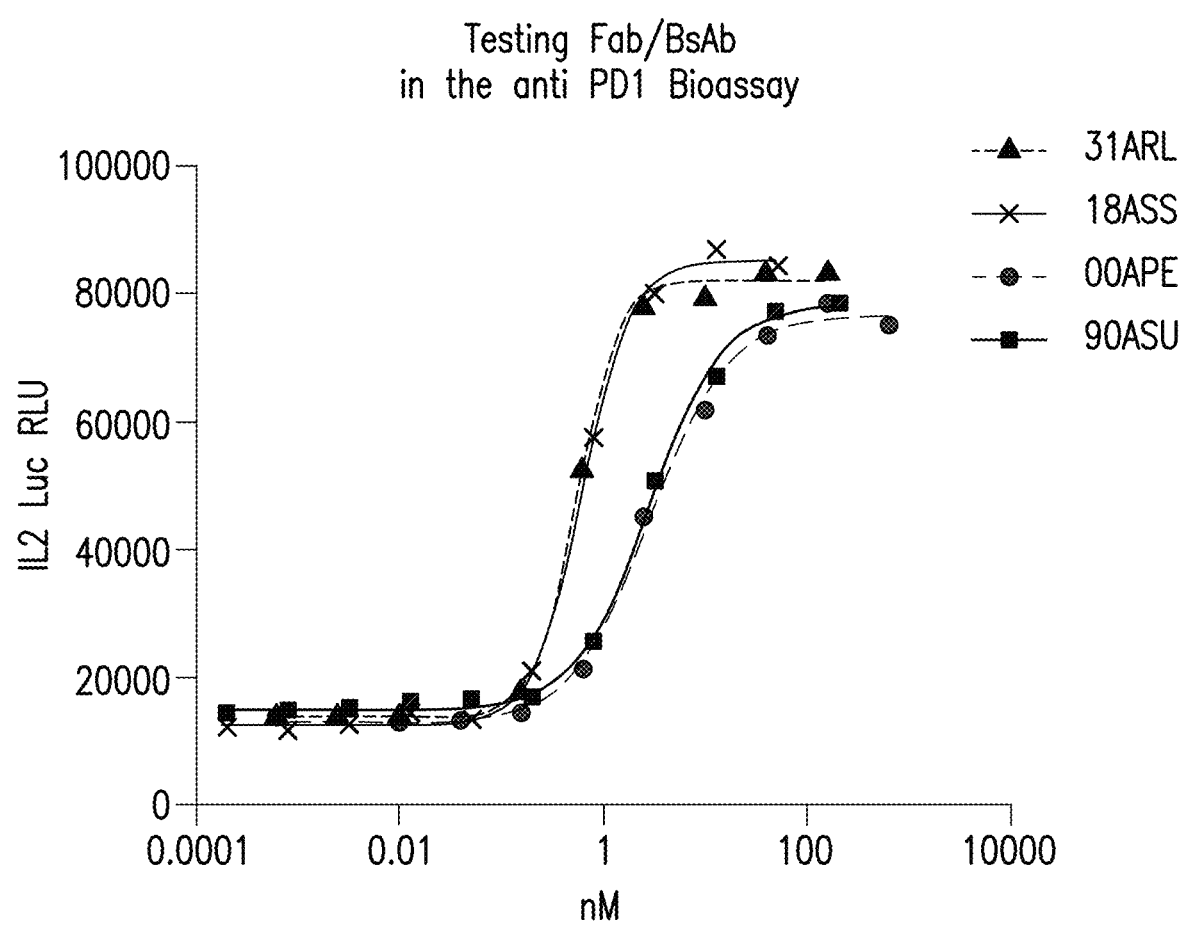

So that the invention can be more readily understood, certain technical and scientific terms are specifically defined below. Unless specifically defined elsewhere in this document, all other technical and scientific terms used herein have the meaning commonly understood by one of ordinary skill in the art to which this invention belongs.

As used herein, including the appended claims, the singular forms of words such as "a," "an," and "the," include their corresponding plural references unless the context clearly dictates otherwise.

"Administration" and "treatment," as it applies to an animal, human, experimental subject, cell, tissue, organ, or biological fluid, refers to contact of an exogenous pharmaceutical, therapeutic, diagnostic agent, or composition to the animal, human, subject, cell, tissue, organ, or biological fluid. Treatment of a cell encompasses contact of a reagent to the cell, as well as contact of a reagent to a fluid, where the fluid is in contact with the cell. "Administration" and "treatment" also means in vitro and ex vivo treatments, e.g., of a cell, by a reagent, diagnostic, binding compound, or by another cell.

"Treat" or "treating" means to administer a therapeutic agent, such as a composition containing any of the antibodies or antigen-binding fragments provided herein, internally or externally to a subject or patient having one or more disease symptoms, or being suspected of having a disease, for which the agent has therapeutic activity. Typically, the agent is administered in an amount effective to alleviate one or more disease symptoms in the treated subject or population, whether by inducing the regression of or inhibiting the progression of such symptom(s) by any clinically measurable degree. The amount of a therapeutic agent that is effective to alleviate any particular disease symptom can vary according to factors such as the disease state, age, and weight of the patient, and the ability of the drug to elicit a desired response in the subject. Whether a disease symptom has been alleviated can be assessed by any clinical measurement typically used by physicians or other skilled healthcare providers to assess the severity or progression status of that symptom.

As used herein, the term "antibody" refers to any form of antibody that exhibits the desired biological activity. Thus, it is used in the broadest sense and specifically covers, but is not limited to, monoclonal antibodies (including full length monoclonal antibodies comprising two light chains and two heavy chains), polyclonal antibodies, multispecific antibodies (e.g., bispecific antibodies), humanized antibodies, fully human antibodies, and chimeric antibodies.

In general, the basic antibody structural unit comprises a tetramer. Each tetramer includes two identical pairs of polypeptide chains, each pair having one "light" (about 25 kDa) and one "heavy" chain (about 50-70 kDa). The amino-terminal portion of each chain includes a variable region of about 100 to 110 or more amino acids primarily responsible for antigen recognition. The carboxy-terminal portion of the heavy chain can define a constant region primarily responsible for effector function.

The term "light chain" when used in reference to an antibody refers to a polypeptide chain of about 25 kDa, wherein the amino-terminal portion includes a variable region of about 100 to about 110 or more amino acids, and a carboxy-terminal portion includes a constant region. The approximate length of a light chain is 211 to 217 amino acids. Typically, human light chains are classified as kappa (κ) and lambda (λ) light chains based on the amino acid sequence of the constant domains. Light chain amino acid sequences are well known in the art. A light chain can be a human light chain.

The term "heavy chain" when used in reference to an antibody refers to a polypeptide chain of about 50-70 kDa, wherein the amino-terminal portion includes a variable region of about 120 to 130 or more amino acids, and a carboxy-terminal portion includes a constant region. The constant region can be one of five distinct types, (e.g., isotypes) referred to as alpha (α), delta (δ), epsilon (ε), gamma (γ), and mu (μ), based on the amino acid sequence of the heavy chain constant region. The distinct heavy chains differ in size: α, δ, and γ contain approximately 450 amino acids, while μ and ε contain approximately 550 amino acids. When combined with a light chain, these distinct types of heavy chains give rise to five well known classes (e.g., isotypes) of immunoglobulin (Ig), IgA, IgD, IgE, IgG, and IgM, respectively, including four subclasses of IgG, namely IgG1, IgG2, IgG3, and IgG4. A heavy chain can be a human heavy chain.

Within light and heavy chains, the variable and constant regions are joined by a "J" region of about 12 or more amino acids, with the heavy chain also including a "D" region of about 10 more amino acids. See generally, *Fundamental Immunology*, Ch. 7 (Paul, W., ed., 2nd ed. Raven Press, N.Y. (1989)).

The variable regions of each light/heavy chain pair form the antibody binding site. Thus, in general, an intact antibody has two binding sites. Except in bifunctional or bispecific antibodies, the two binding sites are, in general, the same.

The term "variable region," "variable domain," "V region," or "V domain" refers to a portion of the light or heavy chains of an antibody that is generally located at the amino-terminal of the light or heavy chain and has a length of about 120 to 130 amino acids in the heavy chain and about 100 to 110 amino acids in the light chain, and are used in the binding and specificity of each particular antibody for its particular antigen. The segment of Ig chains which is variable in sequence between different antibodies. In some instances, it extends to Kabat residue 109 in the light chain and 113 in the heavy chain. The variable region of the heavy chain may be referred to as "VH." The variable region of the light chain may be referred to as "VL." The term "variable" refers to the fact that certain segments of the variable regions differ extensively in sequence among antibodies. The V region mediates antigen binding and defines specificity of a particular antibody for its particular antigen. However, the variability is not evenly distributed across the 110-amino acid span of the variable regions. Instead, the V regions consist of less variable (e.g., relatively invariant) stretches called framework regions (FRs) of about 15-30 amino acids separated by shorter regions of greater variability (e.g., extreme variability) called "hypervariable regions" that are each about 9-12 amino acids long. The variable regions of heavy and light chains each comprise four FRs, largely adopting a β sheet configuration, connected by three hypervariable regions, which form loops connecting, and in some cases form part of, the β sheet structure. The hypervariable regions in each chain are held together in close proximity by the FRs and, with the hypervariable regions from the other chain, contribute to the formation of the antigen-binding site of antibodies (see, e.g., Kabat et al., *Sequences of Proteins of Immunological Interest* (5th ed. 1991)). The constant regions are not involved directly in binding an antibody to an antigen, but exhibit various effector functions, such as participation of the antibody in antibody dependent cellular cytotoxicity (ADCC) and complement dependent cytotoxicity (CDC). The variable regions differ extensively in sequence between different antibodies. In specific embodiments, the variable region is a human variable region.

The term "variable region residue numbering as in Kabat" or "amino acid position numbering as in Kabat", and variations thereof, refer to the numbering system used for heavy chain variable regions or light chain variable regions of the compilation of antibodies in Kabat et al., supra. Using this numbering system, the actual linear amino acid sequence may contain fewer or additional amino acids corresponding to a shortening of, or insertion into, an FR or CDR of the variable domain. For example, a heavy chain variable domain may include a single amino acid insert (residue 52a according to Kabat) after residue 52 and three inserted residues (e.g., residues 82a, 82b, and 82c, etc. according to Kabat) after residue 82. The Kabat numbering of residues may be determined for a given antibody by alignment at regions of homology of the sequence of the antibody with a "standard" Kabat numbered sequence. The Kabat numbering system is generally used when referring to a residue in the variable domain (approximately residues 1-107 of the light chain and residues 1-113 of the heavy chain) (e.g., Kabat et al., supra). The "EU numbering system" or "EU index" is generally used when referring to a residue in an immunoglobulin heavy chain constant region (e.g., the EU index reported in Kabat et al., supra). The "EU index as in Kabat" refers to the residue numbering of the human IgG 1 EU antibody. Other numbering systems have been described, for example, by AbM, Chothia, Contact, IMGT, and AHon.

Typically, the variable domains of both the heavy and light chains comprise three hypervariable regions, also called complementarity determining regions (CDRs), located within relatively conserved framework regions (FR). The CDRs are usually aligned by the framework regions, enabling binding to a specific epitope. In general, from N-terminal to C-terminal, both light and heavy chains variable domains comprise FR1, CDR1, FR2, CDR2, FR3, CDR3 and FR4. The assignment of amino acids to each domain is, generally, in accordance with the definitions of *Sequences of Proteins of Immunological Interest*, Kabat, et al.; National Institutes of Health, Bethesda, Md.; 5$^{th}$ ed.; NIH Publ. No. 91-3242 (1991); Kabat (1978) *Adv. Prot. Chem.* 32:1-75; Kabat, et al., (1977) *J. Biol. Chem.* 252: 6609-6616; Chothia, et al., (1987) *J Mol. Biol.* 196:901-917 or Chothia, et al., (1989) *Nature* 342:878-883; and for EU numbering, see Edelman, G. M. et al., *Proc. Natl. Acad. USA*, 63, 78-85 (1969).

The hypervariable region comprises amino acid residues from a "complementarity determining region" or "CDR" (i.e., CDRL1, CDRL2 and CDRL3 in the light chain variable domain and CDRH1, CDRH2 and CDRH3 in the heavy chain variable domain). A "CDR" refers to one of three hypervariable regions (H1, H2 or H3) within the non-framework region of the immunoglobulin (Ig or antibody) VH β-sheet framework, or one of three hypervariable regions (L1, L2 or L3) within the non-framework region of the antibody VL β-sheet framework. Accordingly, CDRs are variable region sequences interspersed within the framework region sequences. CDR regions are well known to those skilled in the art and have been defined by, for example, Kabat as the regions of most hypervariability within the antibody variable (V) domains (Kabat et al., 1997, J. Biol. Chem. 252:6609-16; Kabat, 1978, Adv. Prot. Chem. 32:1-75; Kabat et al. (1991) Sequences of Proteins of Immunological Interest, 5th Ed. Public Health Service, National Institutes of Health, Bethesda, Md. (defining the CDR regions of an antibody by sequence)). CDR region sequences also have been defined structurally by Chothia as those residues that are not part of the conserved β-sheet framework, and thus are able to adapt different conformations (Chothia and Lesk (1987) *J Mol. Biol.* 196: 901-917 (defining the CDR regions of an antibody by structure)). Both terminologies are well recognized in the art. CDR region sequences have also been defined by AbM, Contact, and IMGT. The positions of CDRs within a canonical antibody variable region have been determined by comparison of numerous structures (Al-Lazikani et al., 1997, J. Mol. Biol. 273:927-48; Morea et al., 2000, Methods 20:267-79). Because the number of residues within a hypervariable region varies in different antibodies, additional residues relative to the canonical positions are conventionally numbered with a, b, c and so forth next to the residue number in the canonical variable region numbering scheme (Al-Lazikani et al., supra). Such nomenclature is similarly well known to those skilled in the art.

The term "hypervariable region," "HVR," or "HV," when used herein refers to the regions of an antibody variable region that are hypervariable in sequence and/or form structurally defined loops. Generally, antibodies comprise six hypervariable regions, three in the VH (H1, H2, H3) and three in the VL (L1, L2, L3). A number of hypervariable region delineations are in use and are encompassed herein. The Kabat Complementarity Determining Regions (CDRs) are based on sequence variability and are the most commonly used (see, e.g., Kabat et al., supra). Chothia refers instead to the location of the structural loops (see, e.g., Chothia and Lesk, 1987, J. Mol. Biol. 196:901-17). The end of the Chothia CDR-H1 loop when numbered using the Kabat numbering convention varies between H32 and H34 depending on the length of the loop (this is because the Kabat numbering scheme places the insertions at H35A and H35B; if neither 35A nor 35B is present, the loop ends at 32; if only 35A is present, the loop ends at 33; if both 35A and 35B are present, the loop ends at 34). The AbM hypervariable regions represent a compromise between the Kabat CDRs and Chothia structural loops, and are used by Oxford Molecular's AbM antibody modeling software (see, e.g., *Antibody Engineering* Vol. 2 (Kontermann and Dübel eds., 2d ed. 2010)). The "contact" hypervariable regions are based on an analysis of the available complex crystal structures. The residues from each of these hypervariable regions or CDRs are noted below.

Recently, a universal numbering system has been developed and widely adopted, ImMunoGeneTics (IMGT) Information System® (Lafranc et al., 2003, Dev. Comp. Immunol. 27(1):55-77). IMGT is an integrated information system specializing in immunoglobulins (IG), T cell receptors (TCR), and major histocompatibility complex (MEW) of human and other vertebrates. Herein, the CDRs are referred to in terms of both the amino acid sequence and the location within the light or heavy chain. As the "location" of the CDRs within the structure of the immunoglobulin variable domain is conserved between species and present in structures called loops, by using numbering systems that align variable domain sequences according to structural features, CDR and framework residues are readily identified. This information can be used in grafting and replacement of CDR residues from immunoglobulins of one species into an acceptor framework from, typically, a human antibody. An additional numbering system (AHon) has been developed by Honegger and Plückthun, 2001, J. Mol. Biol. 309: 657-70. Correspondence between the numbering system, including, for example, the Kabat numbering and the IMGT unique numbering system, is well known to one skilled in the art (see, e.g., Kabat, supra; Chothia and Lesk, supra; Martin, supra; Lefranc et al., supra). In some embodiments, the CDRs are as defined by the IMGT numbering system. In other embodiments, the CDRs are as defined by the Kabat numbering system. In certain embodiments, the CDRs are as defined by the AbM numbering system. In other embodiments, the CDRs are as defined by the Chothia system. In yet other embodiments, the CDRs are as defined by the Contact numbering system.

|  | IMGT | Kabat | AbM | Chothia | Contact |
| --- | --- | --- | --- | --- | --- |
| $V_H$ CDR1 | 27-38 | 31-35 | 26-35 | 26-32 | 30-35 |
| $V_H$ CDR2 | 56-65 | 50-65 | 50-58 | 53-55 | 47-58 |
| $V_H$ CDR3 | 105-117 | 95-102 | 95-102 | 96-101 | 93-101 |
| $V_L$ CDR1 | 27-38 | 24-34 | 24-34 | 26-32 | 30-36 |
| $V_L$ CDR2 | 56-65 | 50-56 | 50-56 | 50-52 | 46-55 |
| $V_L$ CDR3 | 105-117 | 89-97 | 89-97 | 91-96 | 89-96 |

Hypervariable regions may comprise "extended hypervariable regions" as follows: 24-36 or 24-34 (L1), 46-56 or 50-56 (L2), and 89-97 or 89-96 (L3) in the VL, and 26-35 or 26-35A (H1), 50-65 or 49-65 (H2), and 93-102, 94-102, or 95-102 (H3) in the VH. As used herein, the terms "HVR" and "CDR" are used interchangeably.

As used herein, the term "framework" or "FR" refers to those variable region residues flanking the CDRs. FR residues are present, for example, in chimeric, humanized, human, domain antibodies, diabodies, linear antibodies, and bispecific antibodies. FR residues refers to those variable domain residues other than the hypervariable region residues defined herein as CDR residues.

An "Fc" region contains two heavy chain fragments comprising the $C_H3$ and $C_H2$ domains of an antibody. The two heavy chain fragments are held together by two or more disulfide bonds and by other interactions including hydrophobic interactions of the CH3 domains. Fc regions are defined as a C-terminal region of an immunoglobulin heavy chain, including, for example, native sequence Fc regions, recombinant Fc regions, and variant Fc regions. Although the boundaries of the Fc region of an immunoglobulin heavy chain might vary, the human IgG heavy chain Fc region is often defined to stretch from an amino acid residue at position Cys226, or from Pro230, to the carboxyl-terminus thereof. The C-terminal lysine (residue 447 according to the EU numbering system) of the Fc region may be removed, for example, during production or purification of the antibody, or by recombinantly engineering the nucleic acid encoding a heavy chain of the antibody. Accordingly, a composition of intact antibodies may comprise antibody populations with all K447 residues removed, antibody populations with no K447 residues removed, and antibody populations having a mixture of antibodies with and without the K447 residue.

The term "constant region" or "constant domain" refers to a carboxy terminal portion of the light and heavy chain which is not directly involved in binding of the antibody to antigen but exhibits various effector function, such as interaction with the Fc receptor. The term refers to the portion of an immunoglobulin molecule having a more conserved amino acid sequence relative to the other portion of the immunoglobulin, the variable region, which contains the antigen binding site. The constant region may contain the CH1, CH2, and CH3 regions of the heavy chain and the CL region of the light chain. An "IgG1 constant domain" includes all allotypes of the heavy chain IgG1 protein with or without the C-terminal lysine (K), including but not limited to G1m3, G1m17,1, G1m17, G1m17,1,2, G1m(f), G1m(z,a), and G1m(z,a,x). See Table 1 of Jefferis et al., mAbs 1:4, 1-7; 2009, and Lefranc G and Lefranc M P, IMGT®, the international ImMunoGeneTics® information system (world wide web: imgt.org/textes/IMGTrepertoire/Proteins/allotypes/human/IGH/IGHC/Hu_IGHCallotypes1.html). In one embodiment, the IgG1 constant domain without a C-terminal lysine is SEQ ID NO:124.

A "Kappa constant region" includes all allotypes of the light chain kappa protein, including but not limited to Km1, Km2 and Km3. See Jefferis et al., mAbs 1:4, 1-7; 2009. In one embodiment, the kappa constant domain is SEQ ID NO:125.

The term "single-chain Fv" or "scFv" antibody refers to antibody fragments comprising the $V_H$ and $V_L$ domains of an antibody, wherein these domains are present in a single polypeptide chain. Generally, the Fv polypeptide further comprises a polypeptide linker between the VH and VL domains which enables the scFv to form the desired structure for antigen-binding. For a review of scFv, see Pluckthun (1994) *The Pharmacology of Monoclonal Antibodies*, vol. 113, Rosenburg and Moore eds. Springer-Verlag, New York, pp. 269-315. See also, International Publ. No. WO 88/01649 and U.S. Pat. Nos. 4,946,778 and 5,260,203. In one embodiment, the scFv comprises from N to C terminal the VH region, the peptide linker and the VL region. In another embodiment, the scFv comprises from N to C terminal the VL region, the peptide linker and the VH region.

As used herein, the term "diabodies" refers to small antibody fragments with two antigen-binding sites, which fragments comprise a heavy chain variable domain (VH) connected to a light chain variable domain (VL) in the same polypeptide chain ($V_H$-$V_L$ or $V_L$-$V_H$). By using a linker that is too short to allow pairing between the two domains on the same chain, the domains are forced to pair with the complementary domains of another chain and create two antigen-binding sites. Diabodies are described more fully in, e.g., EP 404,097; WO 93/11161; and Holliger et al. (1993) *Proc. Natl. Acad. Sci. USA* 90: 6444-6448. For a review of engineered antibody variants generally see Holliger and Hudson (2005) *Nat. Biotechnol.* 23:1126-1136.

A "Fab" is comprised of the VH and CH1 regions of a heavy chain and the VL and CL regions of a light chain, which are typically joined together by disulfide bonds and have a single antigen binding site. The VH, CH1, VL and CL regions in a Fab can be arranged in various ways to confer an antigen binding capability according to the present disclosure. For example, the VH and CH1 regions can be on one polypeptide, and the VL and CL regions can be on a separate polypeptide. Alternatively, VH, CH1, VL and CL regions can all be on the same polypeptide, optionally arranged in different orders.

Figure 6:
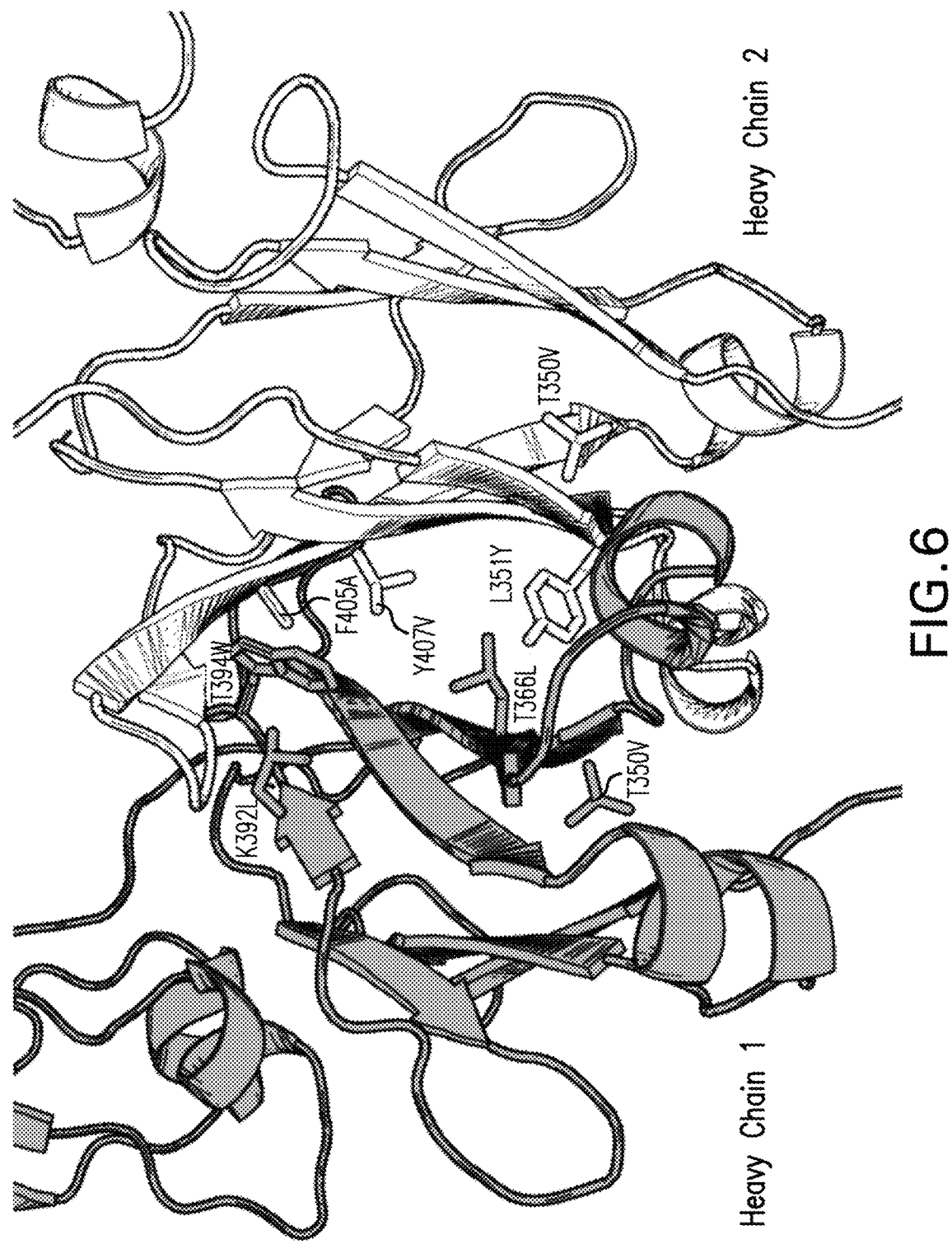
FIG. 6 depicts a 3D representation of the CH3 heterodimer interface formed in a bispecific antibody (18ASS and 90ASU) by heavy chain 1 (grey) and heavy chain 2 (white) upon introduction of the Azymetric™ mutations (sticks).

Also provided herein are anti-PD-1/LAG3 bispecific antibodies and methods of use thereof. An "anti-PD-1/LAG3 bispecific antibody" comprises an anti-PD-1 antigen-binding arm comprising a heavy chain variable region and a light chain variable region, and an anti-LAG3 antigen-binding arm comprising a heaving chain variable region and a light chain variable region. In a specific embodiment, the bispecific antibody is a heterodimer with an anti-PD-1 antigen-binding arm comprising a heavy and light chain, and an anti-LAG3 antigen-binding arm comprising a heavy and light chain. The two antigen-binding arms associate to form a heterodimer via the two heavy chain constant regions that have mutations in the CH3 region (see, for example, FIG. 6).

Also provided herein are anti-PD-1/LAG3 antigen-binding fragments and anti-PD-1 or LAG3 antigen-binding fragments and methods of use thereof. As used herein, unless otherwise indicated, "antibody fragment" or "antigen-binding fragment" refers to antigen-binding fragments of antibodies or bispecific antibodies, i.e. antibody fragments that retain the ability to bind specifically to the antigen bound by the full-length antibody, e.g. fragments that retain one or more CDR regions. Examples of antigen-binding fragments include, but are not limited to, Fab, Fab', F(ab')$_2$, and Fv fragments; diabodies; linear antibodies; single-chain antibody molecules, e.g., scFv; half bispecific molecule comprising the heavy and light chain of one antigen-binding arm.

Typically, an antibody, bispecific antibody or antigen-binding fragment provided herein which is modified in some way retains at least 10% of its binding activity (when compared to the parental antibody) when that activity is expressed on a molar basis. In certain embodiments, an antibody or bispecific antibody or antigen-binding fragment provided herein retains at least 20%, 50%, 70%, 80%, 90%, 95% or 100% or more of the PD-1 or LAG3 binding affinity as the parental antibody. It is also intended that an antibody, bispecific antibody or antigen-binding fragment provided herein can include conservative or non-conservative amino acid substitutions (referred to as "conservative variants" or "function conserved variants" of the antibody) that do not substantially alter its biologic activity.

In certain aspects, provided herein are isolated anti-PD-1/LAG3 bispecific antibodies and antigen-binding fragments thereof and methods of use thereof. "Isolated" antibodies or bispecific antibodies or antigen-binding fragments thereof are at least partially free of other biological molecules from the cells or cell cultures in which they are produced. Such biological molecules include nucleic acids, proteins, lipids, carbohydrates, or other material such as cellular debris and growth medium. An isolated antibody or antigen-binding fragment can further be at least partially free of expression system components such as biological molecules from a host cell or of the growth medium thereof. Generally, the term "isolated" is not intended to refer to a complete absence of such biological molecules or to an absence of water, buffers, or salts or to components of a pharmaceutical formulation that includes the antibodies or fragments.

"Isolated nucleic acid molecule" or "isolated polynucleotide" means a DNA or RNA of genomic, mRNA, cDNA, or synthetic origin or some combination thereof which is not associated with all or a portion of a polynucleotide in which the isolated polynucleotide is found in nature, or is linked to a polynucleotide to which it is not linked in nature. For purposes of this disclosure, it should be understood that "a nucleic acid molecule comprising" a particular nucleotide sequence does not encompass intact chromosomes. Isolated nucleic acid molecules "comprising" specified nucleic acid sequences can include, in addition to the specified sequences, coding sequences for up to ten or even up to twenty or more other proteins or portions or fragments thereof, or can include operably linked regulatory sequences that control expression of the coding region of the recited nucleic acid sequences, and/or can include vector sequences.

The phrase "control sequences" refers to DNA sequences necessary for the expression of an operably linked coding sequence in a particular host organism. The control sequences that are suitable for prokaryotes, for example, include a promoter, optionally an operator sequence, and a ribosome binding site. Eukaryotic cells are known to use promoters, polyadenylation signals, and enhancers.

A nucleic acid or polynucleotide is "operably linked" when it is placed into a functional relationship with another nucleic acid sequence. For example, DNA for a presequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, but not always, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

As used herein, the expressions "cell," "cell line," and "cell culture" are used interchangeably and all such designations include progeny. Thus, the words "transformants" and "transformed cells" include the primary subject cell and cultures derived therefrom without regard for the number of transfers. It is also understood that not all progeny will have precisely identical DNA content, due to deliberate or inadvertent mutations. Mutant progeny that have the same function or biological activity as screened for in the originally transformed cell are included. Where distinct designations are intended, it will be clear from the context.

As used herein, "germline sequence" refers to a sequence of unrearranged immunoglobulin DNA sequences. Any suitable source of unrearranged immunoglobulin sequences can be used. Human germline sequences can be obtained, for example, from JOINSOLVER germline databases on the website for the National Institute of Arthritis and Musculoskeletal and Skin Diseases of the United States National Institutes of Health. Mouse germline sequences can be obtained, for example, as described in Giudicelli et al. (2005) *Nucleic Acids Res.* 33:D256-D261.

5.2 Anti-PD-1/LAG3 Bispecific Antibodies and Antigen-Binding Fragments

In one aspect, provided herein is an anti-PD-1/LAG-3 bispecific antibody comprising an anti-PD-1 antigen binding fragment, and an anti-LAG3 antigen binding fragment.

In one embodiment, provided herein is an anti-PD-1/LAG-3 bispecific antibody comprising:
(A) an anti-PD-1 antigen-binding fragment comprising: (i) a heavy chain variable region CDR1 comprising the amino acid sequence of SEQ ID NO:8, (ii) a heavy chain variable region CDR2 comprising the amino acid sequence of SEQ ID NO:91, (iii) a heavy chain variable region CDR3 comprising the amino acid sequence of SEQ ID NO:10, (iv) a light chain variable region CDR1 comprising the amino acid sequence of SEQ ID NO:3, (v) a light chain variable region CDR2 comprising the amino acid sequence of SEQ ID NOs:15, 18, 21, 25, 29, 32, or 35, and (vi) light chain variable region CDR3 comprising the amino acid sequence of SEQ ID NO:5, 22, or 26, and
(B) an anti-LAG3 antigen-binding fragment comprising: (i) a heavy chain variable region CDR1 comprising the amino acid sequence of SEQ ID NO:112, (ii) a heavy chain variable region CDR2 comprising the amino acid sequence of SEQ ID NO:113, (iii) a heavy chain variable region CDR3 comprising the amino acid sequence of SEQ ID NO:114, (iv) a light chain variable region CDR1 comprising the amino acid sequence of SEQ ID NO:115, (v) a light chain variable region CDR2 comprising the amino acid sequence of SEQ ID NO:116, and (vi) a light chain variable region CDR3 comprising the amino acid sequence of SEQ ID NO:117.

In some embodiments, the light chain variable region CDR2 of the anti-PD-1 antigen-binding fragment comprises the amino acid sequence of SEQ ID NO:15, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:18, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:21, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:25, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:29, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:32, and the light chain variable region CDR3 of the anti-PD-1 antigen-binding fragment comprises the amino acid sequence of SEQ ID NO:5. In some embodiments, the light chain variable region CDR2 of the anti-PD-1 antigen-binding fragment comprises the amino acid sequence of SEQ ID NO:35, and the light chain variable region CDR3 of the anti-PD-1 antigen-binding fragment comprises the amino acid sequence of SEQ ID NO:5.

In some embodiments, the light chain variable region CDR2 of the anti-PD-1 antigen-binding fragment comprises the amino acid sequence of SEQ ID NO:15, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:18, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:21, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:25, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:29, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:32, and the light chain variable region CDR3 of the anti-PD-1 antigen-binding fragment comprises the amino acid sequence of SEQ ID NO:22. In some embodiments, the light chain variable region CDR2 of the anti-PD-1 antigen-binding fragment comprises the amino acid sequence of SEQ ID NO:35, and the light chain variable region CDR3 of the anti-PD-1 antigen-binding fragment comprises the amino acid sequence of SEQ ID NO:22.

In some embodiments, the light chain variable region CDR2 of the anti-PD-1 antigen-binding fragment comprises the amino acid sequence of SEQ ID NO:15, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:18, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:21, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:25, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:29, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:32, and the light chain variable region CDR3 of the anti-PD-1 antigen-binding fragment comprises the amino acid sequence of SEQ ID NO:26. In some embodiments, the light chain variable region CDR2 of the anti-PD-1 antigen-binding fragment comprises the amino acid sequence of SEQ ID NO:35, and the light chain variable region CDR3 of the anti-PD-1 antigen-binding fragment comprises the amino acid sequence of SEQ ID NO:26.

In one embodiment, the anti-PD-1 antigen-binding fragment comprises: (i) a heavy chain variable region CDR1 comprising the amino acid sequence of SEQ ID NO:8, (ii) a heavy chain variable region CDR2 comprising the amino acid sequence of SEQ ID NO:91, (iii) a heavy chain variable region CDR3 comprising the amino acid sequence of SEQ ID NO:10, (iv) a light chain variable region CDR1 comprising the amino acid sequence of SEQ ID NO:3, (v) a light chain variable region CDR2 comprising the amino acid sequence of SEQ ID NO:21, and (vi) a light chain variable region CDR3 comprising the amino acid sequence of SEQ ID NO:22.

In another embodiment, the anti-PD-1 heavy chain variable region CDR2 comprises the amino acid sequence of SEQ ID NO:86.

In a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NOs:14, 17, 20, 24, 28, 31, or 34; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:20; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:14; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:17; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:24; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:28; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:31; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99. In yet a further embodiment, the anti-PD-1 antigen-binding fragment comprises a heavy chain variable region comprising the amino acid sequence set forth in SEQ ID NO:92, and a light chain variable region comprising the amino acid sequence set forth in SEQ ID NO:34; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99.

In yet a further embodiment, the anti-PD-1 antigen-binding fragment comprises a heavy chain variable region comprising the amino acid sequence set forth in SEQ ID NO:85, and a light chain variable region comprising the amino acid sequence set forth in SEQ ID NO:20; and the anti-LAG3 antigen-binding fragment comprises an anti-LAG3 heavy chain variable region comprising the amino acid sequence of SEQ ID NO:97, and a light chain variable region comprising the amino acid sequence of SEQ ID NO:99.

In one embodiment, the anti-PD-1/LAG-3 bispecific antibody comprises: (A) an anti-PD1 antigen-binding fragment comprising a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:20 and a kappa constant region comprising $C_\kappa$ mutations 124R and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and CH3 mutations 350V, 366L, 392L, and 394W, and a light chain comprising a light chain variable region comprising the amino acid sequence of SEQ ID NO:99 and a kappa constant region comprising $C_\kappa$ mutations 124E, 131T, 178Y, and 180E (EU numbering).

In another embodiment, the anti-PD-1/LAG-3 bispecific antibody comprises: (A) an anti-PD-1 antigen-binding fragment comprising a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 366L, 392L, and 394W, and a light chain comprising a light chain variable region comprising the amino acid sequence set forth in SEQ ID NO:20 and a kappa constant region comprising $C_\kappa$ mutations 124R and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and CH3 mutations 350V, 351Y, 405A, and 407V, and a light chain comprising a light chain variable region comprising the amino acid sequence of SEQ ID NO:99 and a kappa constant region comprising $C_\kappa$ mutations 124E, 131T, 178Y, and 180E (EU numbering).

In a further embodiment, the anti-PD-1/LAG-3 bispecific antibody comprises: (A) an anti-PD-1 antigen-binding fragment comprising a heavy chain comprising a heavy chain variable region comprising the amino acid sequence set forth in SEQ ID NO:92 and an IgG1 constant region comprising CH1 mutations 145E, 147T, 175E, and 183L, and a light chain comprising a light chain variable region comprising the amino acid sequence set forth in SEQ ID NO:20 and a kappa constant region comprising $C_\kappa$ mutations 124R and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and a light chain comprising a light chain variable region comprising the amino acid sequence of SEQ ID NO:99 and a kappa constant region comprising $C_\kappa$ mutations 124E, 131T, 178Y, and 180E; wherein the IgG1 heavy chain constant regions of the anti-PD-1 and anti-LAG3 antigen-binding fragments further comprise pairs of CH3 mutations selected from the group consisting of: 351Y/405A/407V and 366I/392M/394W; 351Y/405A/407V and 366L/392L/394W; and 351Y/405A/407V and 366L/392M/394W (EU numbering). In some embodiments, the pair of CH3 mutations is 351Y/405A/407V and 366I/392M/394W. In some embodiments, the pair of CH3 mutations is 351Y/405A/407V and 366L/392L/394W. In some embodiments, the pair of CH3 mutations is 351Y/405A/407V, and 366L/392M/394W.

In one embodiment, the pairs of CH3 mutations are selected from the group consisting of: 350V/351Y/405A/407V, and 366I/392M/394W; 350V/351Y/405A/407V and 366L/392L/394W; and 350V/351Y/405A/407V and 366L/392M/394W. In some embodiments, the pair of CH3 mutations is 350V/351Y/405A/407V and 366I/392M/394W. In some embodiments, the pair of CH3 mutations is 350V/351Y/405A/407V and 366L/392L/394W. In some embodiments, the pair of CH3 mutations is 350V/351Y/405A/407V and 366L/392M/394W.

In yet a further embodiment, the anti-PD-1/LAG-3 bispecific antibody comprises: (A) an anti-PD-1 antigen-binding fragment comprising a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NOs:14, 17, 20, 24, 28, 31, or 34 and a kappa constant region comprising $C_\kappa$ mutations 124R and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and CH3 mutations 350V, 366L, 392L, and 394W, and a light chain comprising a light chain variable region comprising the amino acid sequence of SEQ ID NO:99 and a kappa constant region comprising $C_\kappa$ mutations 124E, 131T, 178Y, and 180E.

In one embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:14 and a kappa constant region comprising $C_K$ mutations 124R and 178R.

In one embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:17 and a kappa constant region comprising $C_K$ mutations 124R and 178R.

In another embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:20 and a kappa constant region comprising $C_K$ mutations 124R and 178R.

In another embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:24 and a kappa constant region comprising $C_K$ mutations 124R and 178R.

In yet another embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:28 and a kappa constant region comprising $C_K$ mutations 124R and 178R.

In yet another embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:31 and a kappa constant region comprising $C_K$ mutations 124R and 178R.

In yet another embodiment, the anti-PD-1 antigen-binding fragment comprises a heavy chain comprising a heavy chain variable region comprising the amino acid sequence set forth in SEQ ID NO:92 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:34 and a kappa constant region comprising $C_K$ mutations 124R and 178R.

In some specific embodiments, the anti-PD-1/LAG3 bispecific antibody comprises: an anti-PD-1 heavy chain comprising the amino acid sequence of SEQ ID NO:102 and a light chain comprising the amino acid sequence of SEQ ID NO:103, and an anti-LAG3 heavy chain comprising the amino acid sequence of SEQ ID NO:96 and a light chain comprising the amino acid sequence of SEQ ID NO:98.

In another aspect, provided herein is an anti-PD-1/LAG-3 bispecific antibody comprising:

(A) an anti-PD-1 antigen-binding fragment comprising: (i) a heavy chain variable region CDR1 comprising the amino acid sequence of SEQ ID NO:8, (ii) a heavy chain variable region CDR2 comprising the amino acid sequence of SEQ ID NO:91, (iii) a heavy chain variable region CDR3 comprising the amino acid sequence of SEQ ID NO:10, or 41, (iv) a light chain variable region CDR1 comprising the amino acid sequence of SEQ ID NO:3, (v) a light chain variable region CDR2 comprising the amino acid sequence of SEQ ID NO:4, and (vi) a light chain variable region CDR3 comprising the amino acid sequence of SEQ ID NO:5; and (B) an anti-LAG3 antigen-binding fragment comprising: (i) a heavy chain variable region CDR1 comprising the amino acid sequence of SEQ ID NO:112, (ii) a heavy chain variable region CDR2 comprising the amino acid sequence of SEQ ID NO:113, (iii) a heavy chain variable region CDR3 comprising the amino acid sequence of SEQ ID NO:114, (vi) a light chain variable region CDR1 comprising the amino acid sequence of SEQ ID NO:115, (v) a light chain variable region CDR2 comprising the amino acid sequence of SEQ ID NO:116, and (vi) a light chain variable region CDR3 comprising the amino acid sequence of SEQ ID NO:117.

In some embodiments, the heavy chain variable region CDR3 of the anti-PD-1 antigen-binding fragment comprises the amino acid sequence of SEQ ID NO:10. In other embodiments, the heavy chain variable region CDR3 of the anti-PD-1 antigen-binding fragment comprises the amino acid sequence of SEQ ID NO:41.

In one embodiment, the anti-PD-1 heavy chain variable region CDR2 comprises the amino acid sequence of SEQ ID NO:86.

In another embodiment, the anti-PD-1 antigen-binding fragment comprises a heavy chain variable region comprising the amino acid sequence set forth in SEQ ID NO:95 and a light chain variable region comprising the amino acid sequence set forth in SEQ ID NO:76; and wherein the anti-LAG3 antigen-binding fragment comprises an anti-LAG3 heavy chain variable region comprising the amino acid sequence of SEQ ID NO:97 and light chain variable region comprising the amino acid sequence of SEQ ID NO:99.

Also provided herein is an anti-PD-1/LAG-3 bispecific antibody comprising: (A) an anti-PD-1 antigen-binding fragment comprising a heavy chain comprising a heavy chain variable region comprising the amino acid sequence set forth in SEQ ID NO:93 and an IgG1 constant region comprising CH1 mutations 145E, 147T, 175E, and 183L, and CH3 mutations 350V, 351Y, 405A, and 407V, and a light chain comprising a light chain variable region comprising the amino acid sequence set forth in SEQ ID NO:76 and a kappa constant region comprising $C_K$ mutations Q124R, and T178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and CH3 mutations 350V, 366L, 392L, and 394W, and a light chain comprising a light chain variable region comprising the amino acid sequence of SEQ ID NO:99 and a kappa constant region comprising $C_K$ mutations 124E, 131T, 178Y, and 180E.

Also provided herein is an anti-PD-1/LAG-3 bispecific antibody comprising: (A) an anti-PD-1 antigen-binding fragment comprising a heavy chain comprising a heavy chain variable region comprising the amino acid sequence set forth in SEQ ID NO:93 and an IgG1 constant region comprising CH1 mutations 145E, 147T, 175E, and 183L, and CH3 mutations 350V, 366L, 392L, and 394W, and a light chain comprising a light chain variable region comprising the amino acid sequence set forth in SEQ ID NO:76 and a kappa constant region comprising $C_\kappa$ mutations 124R, and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and CH3 mutations 350V, 351Y, 405A, and 407V, and a light chain comprising a light chain variable region comprising the amino acid sequence of SEQ ID NO:99 and a kappa constant region comprising $C_\kappa$ mutations 124E, 131T, 178Y, and 180E.

Also provided herein is an anti-PD-1/LAG-3 bispecific antibody comprising: (A) an anti-PD-1 antigen-binding fragment comprising a heavy chain comprising a heavy chain variable region comprising the amino acid sequence set forth in SEQ ID NO:93 and an IgG1 constant region comprising CH1 mutations 145E, 147T, 175E, and 183L, and a light chain comprising a light chain variable region comprising the amino acid sequence set forth in SEQ ID NO:76 and a kappa constant region comprising $C_\kappa$ mutations 124R and 178R; and (B) an anti-LAG3 antigen-binding fragment comprising a heavy chain comprising a heavy chain variable region comprising the amino acid sequence of SEQ ID NO:97 and an IgG1 constant region comprising CH1 mutation 181K, and a light chain comprising a light chain variable region comprising the amino acid sequence of SEQ ID NO:99 and a kappa constant region comprising $C_\kappa$ mutations 124E, 131T, 178Y, and 180E; wherein the IgG1 heavy chain constant regions of the anti-PD-1 and anti-LAG3 antigen-binding fragments further comprise pairs of CH3 mutations selected from the group consisting of: 351Y/405A/407V and 366I/392M/394W; 351Y/405A/407V and 366L/392L/394W; and 351Y/405A/407V and 366L/392M/394W. In some embodiments, the pair of CH3 mutations is 351Y/405A/407V and 366I/392M/394W. In some embodiments, the pair of CH3 mutations is 351Y/405A/407V and 366L/392L/394W. In some embodiments, the pair of CH3 mutations is 351Y/405A/407V and 366L/392M/394W.

In one embodiment, the pairs of CH3 mutations are selected from the group consisting of: 350V/351Y/405A/407V and 366I/392M/394W; 350V/351Y/405A/407V and 366L/392L/394W; and 350V/351Y/405A/407V and 366L/392M/394W. In some embodiments, the pair of CH3 mutations is 350V/351Y/405A/407V and 366I/392M/394W. In some embodiments, the pair of CH3 mutations is 350V/351Y/405A/407V and 366L/392L/394W. In some embodiments, the pair of CH3 mutations is 350V/351Y/405A/407V and 366L/392M/394W.

In a specific embodiment, the anti-PD-1/LAG3 bispecific antibody comprises: (A) an anti-PD-1 heavy chain comprising: the amino acid sequence of SEQ ID NO:101 and a light chain comprising the amino acid sequence of SEQ ID NO:100, and (B) an anti-LAG3 heavy chain comprising the amino acid sequence of SEQ ID NO:96 and a light chain comprising the amino acid sequence of SEQ ID NO:98. In another embodiment, the anti-PD-1/LAG3 bispecific comprises: (A) an anti-PD-1 heavy chain variable region comprising the amino acid sequence of SEQ ID NO:109 and a light chain variable region comprising the amino acid sequence of SEQ ID NO:111, and (B) an anti-LAG3 heavy chain variable region comprising the amino acid sequence of SEQ ID NO:105 and light chain variable region comprising the amino acid sequence of SEQ ID NO:107. In a further embodiment, the anti-PD-1/LAG3 bispecific antibody comprises: (A) an anti-PD-1 heavy chain comprising the amino acid sequence of SEQ ID NO:108 and a light chain comprising the amino acid sequence of SEQ ID NO:110, and (B) anti-LAG3 heavy chain comprising the amino acid sequence of SEQ ID NO:104 and light chain comprising the amino acid sequence of SEQ ID NO:106.

In a further aspect, provided herein is an anti-PD-1/LAG-3 bispecific antibody comprising:
(A) an anti-PD-1 antigen-binding fragment comprising: (i) a heavy chain variable region CDR1 comprising the amino acid sequence of SEQ ID NO:40 or 53, (ii) a heavy chain variable region CDR2 comprising the amino acid sequence of SEQ ID NO:9 or 54, (iii) a heavy chain variable region CDR3 comprising the amino acid sequence of SEQ ID NO:41, (iv) a light chain variable region CDR1 comprising the amino acid sequence of SEQ ID NO:3, (v) a light chain variable region CDR2 comprising the amino acid sequence of SEQ ID NO:4, 42, 47, or 60, and (vi) a light chain variable region CDR3 comprising the amino acid sequence of SEQ ID NO:5, 48, or 55, and
(B) an anti-LAG3 antigen-binding fragment comprising: (i) a heavy chain variable region CDR1 comprising the amino acid sequence of SEQ ID NO:112, (ii) a heavy chain variable region CDR2 comprising the amino acid sequence of SEQ ID NO:113, (iii) a heavy chain variable region CDR3 comprising the amino acid sequence of SEQ ID NO:114, (iv) a light chain variable region CDR1 comprising the amino acid sequence of SEQ ID NO:115, (v) a light chain variable region CDR2 comprising the amino acid sequence of SEQ ID NO:116, and (vi) a light chain variable region CDR3 comprising the amino acid sequence of SEQ ID NO:117.

In one embodiment, the anti-PD-1 antigen-binding fragment comprises a heavy and light chain variable region, wherein the heavy and light chain CDRs are selected from the group consisting of: (a) a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:5; (b) a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:48; (c) a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:55; and (d) a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:40, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:9, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:4 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:42 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:47 and a light chain variable region CDR3 comprising the amino acid sequence of SEQ ID NO:55.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:5.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:48.

In one embodiment, the anti-PD-1 antigen-binding fragment comprises a heavy chain variable region CDR1 comprising the amino acid sequence of SEQ ID NO:53, a heavy chain variable region CDR2 comprising the amino acid sequence of SEQ ID NO:54, a heavy chain variable region CDR3 comprising the amino acid sequence of SEQ ID NO:41; and a light chain variable region CDR1 comprising the amino acid sequence of SEQ ID NO:3, a light chain variable region CDR2 comprising the amino acid sequence of SEQ ID NO:60 and a light chain variable region CDR3 comprising the amino acid sequence of SEQ ID NO:55.

In another embodiment, the anti-PD-1 antigen-binding fragment comprises a heavy chain variable region and a light chain variable region selected from the group consisting of: (a) a heavy chain variable region comprising the amino acid sequence set forth in SEQ ID NOs:37 or 119 and a light chain variable region comprising the amino acid sequence set forth in SEQ ID NO:39; (b) a heavy chain variable region comprising the amino acid sequence set forth in SEQ ID NOs:44 or 121 and a light chain variable region comprising the amino acid sequence set forth in SEQ ID NO:46; (c) a heavy chain variable region comprising the amino acid sequence set forth in SEQ ID NO:50 and a light chain variable region comprising the amino acid sequence set forth in SEQ ID NO:52; and (d) a heavy chain variable region comprising the amino acid sequence set forth in SEQ ID NOs:57 or 123 and a light chain variable region comprising the amino acid sequence set forth in SEQ ID NO:59; and wherein the anti-LAG3 antigen-binding fragment comprises an anti-LAG3 heavy chain variable region comprising the amino acid sequence of SEQ ID NO:97 and light chain variable region comprising the amino acid sequence of SEQ ID NO:99.

In one embodiment, the anti-PD-1 antigen-binding fragment comprises a heavy chain variable region comprising the amino acid sequence set forth in SEQ ID NO:37 and a light chain variable region comprising the amino acid sequence set forth in SEQ ID NO:39. In one embodiment, the anti-PD-1 antigen-binding fragment comprises a heavy chain variable region comprising the amino acid sequence set forth in SEQ ID NO:119 and a light chain variable region comprising the amino acid sequence set forth in SEQ ID NO:39. In one embodiment, the anti-PD-1 antigen-binding fragment comprises a heavy chain variable region comprising the amino acid sequence set forth in SEQ ID NO:44 and a light chain variable region comprising the amino acid sequence set forth in SEQ ID NO:46. In one embodiment, the anti-PD-1 antigen-binding fragment comprises a heavy chain variable region comprising the amino acid sequence set forth in SEQ ID NO:121 and a light chain variable region comprising the amino acid sequence set forth in SEQ ID NO:46. In one embodiment, the anti-PD-1 antigen-binding fragment comprises a heavy chain variable region comprising the amino acid sequence set forth in SEQ ID NO:50 and a light chain variable region comprising the amino acid sequence set forth in SEQ ID NO:52. In one embodiment, the anti-PD-1 antigen-binding fragment comprises a heavy chain variable region comprising the amino acid sequence set forth in SEQ ID NO:57 and a light chain variable region comprising the amino acid sequence set forth in SEQ ID NO:59. In one embodiment, the anti-PD-1 antigen-binding fragment comprises a heavy chain variable region comprising the amino acid sequence set forth in SEQ ID NO:123 and a light chain variable region comprising the amino acid sequence set forth in SEQ ID NO:59. In a specific embodiment, the bispecific antibody further comprises an anti-LAG3 antigen-binding fragment comprising an anti-LAG3 heavy chain variable region comprising the amino acid sequence of SEQ ID NO:97 and light chain variable region comprising the amino acid sequence of SEQ ID NO:99.

In one embodiment, the anti-PD-1 heavy chain variable region further comprises an IgG1 constant region comprising CH1 mutations 145E, 147T, 175E, and 183L, and CH3 mutations 350V, 351Y, 405A, and 407V, and the anti-PD-1 light chain variable region further comprises a kappa chain constant region comprising $C_\kappa$ mutations 124R, and 178R; and the anti-LAG3 heavy chain variable region further comprises an IgG1 constant region comprising CH1 mutation 181K, and CH3 mutations 350V, 366L, 392L, and 394W, and the anti-LAG3 light chain variable region further comprises a kappa constant region comprising $C_\kappa$ mutations 124E, 131T, 178Y, and 180E.

In another embodiment, the anti-PD-1 heavy chain variable region further comprises an IgG1 constant region comprising CH1 mutations 145E, 147T, 175E, and 183L, and CH3 mutations 350V, 366L, 392L, and 394W, and the anti-PD-1 light chain variable region further comprises a kappa chain constant region comprising $C_\kappa$ mutations 124R, and 178R; and the anti-LAG3 heavy chain variable region further comprises an IgG1 constant region comprising CH1 mutation 181K, and CH3 mutations 350V, 351Y, 405A, and 407V, and the anti-LAG3 light chain variable region further comprises a kappa constant region comprising $C_\kappa$ mutations 124E, 131T, 178Y, and 180E.

In another embodiment, the anti-PD-1 heavy chain variable region further comprises an IgG1 constant region comprising CH1 mutations 145E, 147T, 175E, and 183L, and the anti-PD-1 light chain variable region further comprises a kappa chain constant region comprising $C_\kappa$ mutations 124R, and 178R; and the anti-LAG3 heavy chain variable region further comprises an IgG1 constant region comprising CH1 mutation 181K, and the anti-LAG3 light chain variable region further comprises a kappa constant region comprising $C_\kappa$ mutations 124E, 131T, 178Y, and 180E, and the IgG1 heavy chain constant regions of the anti-PD-1 and anti-LAG3 antigen-binding fragments further comprise pairs of CH3 mutations selected from the group consisting of: 351Y/405A/407V and 366I/392M/394W; 351Y/405A/407V and 366L/392L/394W; and 351Y/405A/407V and 366L/392M/394W. In some embodiments, the pair of CH3 mutations is 351Y/405A/407V and 366I/392M/394W. In some embodiments, the pair of CH3 mutations is 351Y/405A/407V and 366L/392L/394W. In some embodiments, the pair of CH3 mutations is 351Y/405A/407V and 366L/392M/394W. In one embodiment, the pairs of CH3 mutations are selected from the group consisting of: 350V/351Y/405A/407V and 366I/392M/394W; 350V/351Y/405A/407V and 366L/392L/394W; and 350V/351Y/405A/407V and 366L/392M/394W. In some embodiments, the pair of CH3 mutations is 350V/351Y/405A/407V and 366I/392M/394W. In some embodiments, the pair of CH3 mutations is 350V/351Y/405A/407V and 366L/392L/394W. In some embodiments, the pair of CH3 mutations is 350V/351Y/405A/407V and 366L/392M/394W.

In one aspect of the foregoing embodiments, the anti-PD-1/LAG-3 bispecific antibody further comprises one or more of 234A or 234D; 235A or 235D; 265S or 265A; 237A; and 297A, 297Q or 297D (EU numbering) mutations in the CH2 region of the anti-LAG3 and/or anti-PD-1 heavy chain. In another embodiment, the IgG1 heavy chain constant region of the anti-LAG3 and/or anti-PD-1 heavy chain further comprises L234A, L235A, and D265S mutations in the CH2 region (EU numbering). In a further embodiment, the IgG1 heavy chain constant region of the anti-LAG3 and/or anti-PD-1 heavy chain further comprises L234A, L235A, and D265A mutations in the CH2 region (EU numbering). In yet a further embodiment, the IgG1 heavy chain constant region of the anti-LAG3 and/or anti-PD-1 heavy chain further comprises L234A, L235A, and G237A mutations in the CH2 region (EU numbering). In another embodiment, the IgG1 heavy chain constant region of the anti-LAG3 and/or anti-PD-1 heavy chain further comprises the mutation N297A, N297Q or N297D (EU numbering). In another aspect of the foregoing embodiments, the IgG1 constant domain of the anti-LAG3 and/or anti-PD-1 heavy chain further comprises M252Y, S254T and T256E mutations (EU numbering). In one embodiment, the antibody or antigen-binding fragment thereof comprises a glycosylation pattern characteristic of expression by a mammalian cell.

Also provided herein is an anti-PD-1 antibody or antigen-binding fragment thereof comprising the heavy and light chain CDRs or variable regions in any of the above anti-PD-1/LAG3 bispecific antibodies. In one embodiment, the anti-PD-1 antibody or antigen-binding fragment comprises: (i) a heavy chain variable region CDR1 comprising the amino acid sequence of SEQ ID NO:8, (ii) a heavy chain variable region CDR2 comprising the amino acid sequence of SEQ ID NO:91 or 86, (iii) a heavy chain variable region CDR3 comprising the amino acid sequence of SEQ ID NO:10, (iv) a light chain variable region CDR1 comprising the amino acid sequence of SEQ ID NO:3, (v) a light chain variable region CDR2 comprising the amino acid sequence of SEQ ID NO:21, and (vi) a light chain variable region CDR3 comprising the amino acid sequence of SEQ ID NO:22.

In some embodiments, the heavy chain variable region CDR2 comprises the amino acid sequence of SEQ ID NO:91. In some embodiments, the heavy chain variable region CDR2 comprises the amino acid sequence of SEQ ID NO:86.

In another embodiment, the anti-PD-1 antibody or antigen-binding fragment comprises a heavy chain variable region comprising the amino acid sequence set forth in SEQ ID NOs:92 or 85, and a light chain variable region comprising the amino acid sequence set forth in SEQ ID NO:20. In one embodiment, the anti-PD-1 antibody or antigen-binding fragment comprises a heavy chain variable region comprising the amino acid sequence set forth in SEQ ID NO:92, and a light chain variable region comprising the amino acid sequence set forth in SEQ ID NO:20. In one embodiment, the anti-PD-1 antibody or antigen-binding fragment comprises a heavy chain variable region comprising the amino acid sequence set forth in SEQ ID NO:85, and a light chain variable region comprising the amino acid sequence set forth in SEQ ID NO:20. In one embodiment, the anti-PD-1 antibody or antigen-binding fragment comprises a heavy chain variable region comprising the amino acid sequence set forth in SEQ ID NO:7, and a light chain variable region comprising the amino acid sequence set forth in SEQ ID NO:20. In one embodiment, the anti-PD-1 antibody or antigen-binding fragment comprises a heavy chain variable region comprising the amino acid sequence set forth in SEQ ID NO:88, and a light chain variable region comprising the amino acid sequence set forth in SEQ ID NO:76.

In a further embodiment, the anti-PD-1 antibody or antigen-binding fragment comprises: (i) a heavy chain variable region CDR1 comprising the amino acid sequence of SEQ ID NO:8, (ii) a heavy chain variable region CDR2 comprising the amino acid sequence of SEQ ID NO:91, 79 or 86, (iii) a heavy chain variable region CDR3 comprising the amino acid sequence of SEQ ID NO:10, or 41, (iv) a light chain variable region CDR1 comprising the amino acid sequence of SEQ ID NO:3, (v) a light chain variable region CDR2 comprising the amino acid sequence of SEQ ID NO:4, and (vi) a light chain variable region CDR3 comprising the amino acid sequence of SEQ ID NO:5.

In some embodiments, the heavy chain variable region CDR2 comprises the amino acid sequence of SEQ ID NO:91, and the heavy chain variable region CDR3 comprises the amino acid sequence of SEQ ID NO:10. In some embodiments, the heavy chain variable region CDR2 comprises the amino acid sequence of SEQ ID NO:86, and the heavy chain variable region CDR3 comprises the amino acid sequence of SEQ ID NO:10. In some embodiments, the heavy chain variable region CDR2 comprises the amino acid sequence of SEQ ID NO:91, and the heavy chain variable region CDR3 comprises the amino acid sequence of SEQ ID NO:41. In some embodiments, the heavy chain variable region CDR2 comprises the amino acid sequence of SEQ ID NO:86, and the heavy chain variable region CDR3 comprises the amino acid sequence of SEQ ID NO:41. In some embodiments, the heavy chain variable region CDR2 comprises the amino acid sequence of SEQ ID NO:79, and the heavy chain variable region CDR3 comprises the amino acid sequence of SEQ ID NO:41.

In yet further embodiment, the anti-PD-1 antibody or antigen-binding fragment comprises a heavy chain variable region comprising the amino acid sequence set forth in SEQ ID NOs:95 or 93, and a light chain variable region comprising the amino acid sequence set forth in SEQ ID NO:76. In one embodiment, the anti-PD-1 antibody or antigen-binding fragment comprises a heavy chain variable region comprising the amino acid sequence set forth in SEQ ID NO:95, and a light chain variable region comprising the amino acid sequence set forth in SEQ ID NO:76. In yet a further embodiment, the anti-PD-1 antibody or antigen-binding fragment comprises a heavy chain variable region comprising the amino acid sequence set forth in SEQ ID NO:93, and a light chain variable region comprising the amino acid sequence set forth in SEQ ID NO:76. In yet a further embodiment, the anti-PD-1 antibody or antigen-binding fragment comprises a heavy chain variable region comprising the amino acid sequence set forth in SEQ ID NO:75, and a light chain variable region comprising the amino acid sequence set forth in SEQ ID NO:76. In yet a further embodiment, the anti-PD-1 antibody or antigen-binding fragment comprises a heavy chain variable region comprising the amino acid sequence set forth in SEQ ID NO:78, and a light chain variable region comprising the amino acid sequence set forth in SEQ ID NO:76. In yet a further embodiment, the anti-PD-1 antibody or antigen-binding fragment comprises a heavy chain variable region comprising the amino acid sequence set forth in SEQ ID NO:81, and a light chain variable region comprising the amino acid sequence set forth in SEQ ID NO:76.

In yet a further aspect, provided herein is a composition comprising the foregoing antibody or antigen-binding fragment and a pharmaceutically acceptable carrier or diluent. In one embodiment, the composition further comprises an agent selected from the group consisting of: (i) an anti-LAG3 antibody or an antigen-binding fragment thereof; (ii) an anti-TIGIT antibody or an antigen-binding fragment thereof; (iii) an anti-VISTA antibody or an antigen-binding fragment thereof; (iv) an anti-BTLA antibody or an antigen-binding fragment thereof; (v) an anti-TIM3 antibody or an antigen-binding fragment thereof; (vi) an anti-CTLA4 antibody or an antigen-binding fragment thereof; (vii) an anti-HVEM antibody or an antigen-binding fragment thereof; (viii) an anti-CD70 antibody or an antigen-binding fragment thereof; (ix) an anti-OX40 antibody or an antigen-binding fragment thereof; (x) an anti-CD28 antibody or an antigen-binding fragment thereof; (xi) an anti-PDL1 antibody or an antigen-binding fragment thereof; (xii) an anti-PDL2 antibody or an antigen-binding fragment thereof; (xiii) an anti-GITR antibody or an antigen-binding fragment thereof; (xiv) an anti-ICOS antibody or an antigen-binding fragment thereof; (xv) an anti-SIRPα antibody or an antigen-binding fragment thereof; (xvi) an anti-ILT2 antibody or an antigen-binding fragment thereof; (xvii) an anti-ILT3 antibody or an antigen-binding fragment thereof; (xviii) an anti-ILT4 antibody or an antigen-binding fragment thereof; (xix) an anti-ILT5 antibody or an antigen-binding fragment thereof; (xx) an anti-4-1BB antibody or an antigen-binding fragment thereof; (xxi) an anti-NK2GA antibody or an antigen-binding fragment thereof; (xxii) an anti-NK2GC antibody or an antigen-binding fragment thereof; (xxiii) an anti-NK2GE antibody or an antigen-binding fragment thereof; (xxiv) an anti-TSLP antibody or an antigen-binding fragment thereof; (xxv) an anti-IL10 antibody or an antigen-binding fragment thereof; (xxvi) a STING agonist; (xxvii) a CXCR2 antagonist; and (xxviii) a PARP inhibitor.

In one embodiment, the agent is an anti-LAG3 antibody or antigen-binding fragment thereof. In one embodiment, the agent is an anti-TIGIT antibody or antigen-binding fragment thereof. In one embodiment, the agent is an anti-VISTA antibody or antigen-binding fragment thereof. In one embodiment, the agent is an anti-BTLA antibody or antigen-binding fragment thereof. In one embodiment, the agent is an anti-TIM3 antibody or antigen-binding fragment thereof. In one embodiment, the agent is an anti-CTLA4 antibody or antigen-binding fragment thereof. In one embodiment, the agent is an anti-HVEM antibody or antigen-binding fragment thereof. In one embodiment, the agent is an anti-CD70 antibody or antigen-binding fragment thereof. In one embodiment, the agent is an anti-OX40 antibody or antigen-binding fragment thereof. In one embodiment, the agent is an anti-CD28 antibody or antigen-binding fragment thereof. In one embodiment, the agent is an anti-PDL1 antibody or antigen-binding fragment thereof. In one embodiment, the agent is an anti-PDL2 antibody or antigen-binding fragment thereof. In one embodiment, the agent is an anti-GITR antibody or antigen-binding fragment thereof. In one embodiment, the agent is an anti-ICOS antibody or antigen-binding fragment thereof. In one embodiment, the agent is an anti-SIRPα antibody or antigen-binding fragment thereof. In one embodiment, the agent is an anti-ILT2 antibody or antigen-binding fragment thereof. In one embodiment, the agent is an anti-ILT3 antibody or antigen-binding fragment thereof. In one embodiment, the agent is an anti-ILT4 antibody or antigen-binding fragment thereof. In one embodiment, the agent is an anti-ILT5 antibody or antigen-binding fragment thereof. In one embodiment, the agent is an anti-4-1BB antibody or antigen-binding fragment thereof. In one embodiment, the agent is an anti-NK2GA antibody or antigen-binding fragment thereof. In one embodiment, the agent is an anti-NK2GE antibody or antigen-binding fragment thereof. In one embodiment, the agent is an anti-IL10 antibody or antigen-binding fragment thereof. In one embodiment, the agent is an anti-TSLP antibody or antigen-binding fragment thereof. In one embodiment, the agent is a STING agonist. In one embodiment, the agent is a CXCR2 antagonist. In one embodiment, the agent is a PARP inhibitor.

The present disclosure includes any antibody or antigen-binding fragment described in Table 8 below. In some embodiments, the antibody or antigen-binding fragment provided herein comprises a CDR sequence listed in Table 8. In some embodiments, the antibody or antigen-binding fragment provided herein comprises CDRs set forth in a VH sequence listed in Table 8 and CDRs set forth in a VL sequence listed in Table 8. In some embodiments, the antibody or antigen-binding fragment provided herein comprises a VH sequence listed in Table 8 and a VL sequence listed in Table 8.

5.3 Physical and Functional Properties of the Exemplary Antibodies

"Conservatively modified variants" or "conservative substitution" refers to substitutions of amino acids in a protein with other amino acids having similar characteristics (e.g. charge, side-chain size, hydrophobicity/hydrophilicity, backbone conformation and rigidity, etc.), such that the changes can frequently be made without altering the biological activity of the protein. Those of skill in this art recognize that, in general, single amino acid substitutions in non-essential regions of a polypeptide do not substantially alter biological activity (see, e.g., Watson et al. (1987) *Molecular Biology of the Gene*, The Benjamin/Cummings Pub. Co., p. 224 (4th Ed.)). In addition, substitutions of structurally or functionally similar amino acids are less likely to disrupt biological activity. Exemplary conservative substitutions are set forth in Table 1.

TABLE 1

Exemplary Conservative Amino Acid Substitutions

| Original residue | Conservative substitution |
|---|---|
| Ala (A) | Gly; Ser |
| Arg (R) | Lys; His |
| Asn (N) | Gln; His |
| Asp (D) | Glu; Asn |
| Cys (C) | Ser; Ala |
| Gln (Q) | Asn |
| Glu (E) | Asp; Gln |
| Gly (G) | Ala |
| His (H) | Asn; Gln |
| Ile (I) | Leu; Val |
| Leu (L) | Ile; Val |
| Lys (K) | Arg; His |
| Met (M) | Leu; Ile; Tyr |
| Phe (F) | Tyr; Met; Leu |
| Pro (P) | Ala |
| Ser (S) | Thr |
| Thr (T) | Ser |
| Trp (W) | Tyr; Phe |
| Tyr (Y) | Trp; Phe |
| Val (V) | Ile; Leu |

Function-conservative variants of the antibodies provided herein are also contemplated. "Function-conservative variants," as used herein, refers to antibodies or fragments in which one or more amino acid residues have been changed without altering a desired property, such as an antigen affinity and/or specificity. Such variants include, but are not limited to, replacement of an amino acid with one having similar properties, such as the conservative amino acid substitutions of Table 1. Also provided are isolated anti-PD-1/LAG3, anti-PD-1 antibodies or antigen-binding fragments having up to 0, 1, 2, 3, 4, 5, 6, 7, 8, 9, 10 or more amino acid substitutions, for example, in the framework region.

5.4 Polynucleotides and Polypeptides

Also provided herein are polynucleotides encoding any of the polypeptides or immunoglobulin chains of anti-PD-1/LAG3, anti-PD-1 or anti-LAG3 antigen-binding fragments thereof provided herein. For example, provided herein are polynucleotides encoding the amino acids described in any one of SEQ ID NOs: 1-117.

In one embodiment, an isolated polynucleotide, for example DNA, encoding the polypeptide chains of the isolated bispecific antibodies or antigen-binding fragments set forth herein is provided. In one embodiment, the isolated polynucleotide encodes an anti-PD-1 antigen-binding fragment thereof comprising one mature immunoglobulin light chain provided herein, and one mature immunoglobulin heavy chain provide herein. In one embodiment, the isolated polynucleotide further encodes an anti-LAG3 antigen-binding fragment thereof comprising one mature immunoglobulin light chain provided herein, and one mature immunoglobulin heavy chain provided herein. In some embodiments the isolated polynucleotide encodes both a light chain and a heavy chain on a single polynucleotide molecule. In other embodiments the light and heavy chains are encoded on separate polynucleotide molecules. In another embodiment, the polynucleotides further encodes a signal sequence.

Also provided herein are vectors, e.g., expression vectors, such as plasmids, comprising the isolated polynucleotides, wherein the polynucleotide is operably linked to control sequences that are recognized by a host cell when the host cell is transfected with the vector. Also provided are host cells comprising a vector and methods for producing the antibodies or antigen-binding fragment thereof or polypeptide disclosed herein comprising culturing a host cell harboring an expression vector or a nucleic acid encoding the immunoglobulin chains of the antibodies or antigen-binding fragment thereof in culture medium, and isolating the antibodies or antigen-binding fragment thereof from the host cell or culture medium.

5.5 Methods of Making Antibodies and Antigen-Binding Fragments Thereof

The antibodies disclosed herein can also be produced recombinantly (e.g., in an *E. coli*/T7 expression system, a mammalian cell expression system or a lower eukaryote expression system). In one embodiment, nucleic acids encoding the antibody molecules provided herein (e.g., scFv, VH or VL) can be inserted into a pET-based plasmid and expressed in the *E. coli*/T7 system. In some embodiments, provided herein are methods for expressing antibodies or antigen-binding fragments thereof or immunoglobulin chains thereof in a host cell (e.g., bacterial host cell such as *E. coli* such as BL21 or BL21DE3) comprising expressing T7 RNA polymerase in the cell, which also includes a polynucleotide encoding an immunoglobulin chain that is operably linked to a T7 promoter. In one embodiment, a bacterial host cell, such as a *E. coli*, includes a polynucleotide encoding the T7 RNA polymerase gene operably linked to a lac promoter, and expression of the polymerase and the chain is induced by incubation of the host cell with IPTG (isopropyl-beta-D-thiogalactopyranoside).

There are several methods by which to produce recombinant antibodies which are known in the art. One example of a method for recombinant production of antibodies is disclosed in U.S. Pat. No. 4,816,567.

Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, biolistic injection and direct microinjection of the DNA into nuclei. In addition, nucleic acid molecules can be introduced into mammalian cells by viral vectors. Methods of transforming cells are well known in the art. See, for example, U.S. Pat. Nos. 4,399,216; 4,912,040; 4,740,461 and 4,959,455.

Thus, also provided herein are recombinant methods for making antibodies or antigen-binding fragments thereof disclosed herein, or an immunoglobulin chain thereof, comprising introducing a polynucleotide encoding one or more immunoglobulin chains of the antibodies or fragments (e.g., heavy and/or light immunoglobulin chain, scFv); culturing the host cell (e.g., Chinese Hamster Ovary (CHO) or *Pichia* or *Pichia pastoris*) under conditions favorable to such expression. In certain embodiments, the method further comprises isolating the antibodies or fragments or immunoglobulin chains from the host cell and/or medium in which the host cell is grown.

Eukaryotic and prokaryotic host cells, including mammalian cells as hosts for expression of the antibodies or fragments or immunoglobulin chains disclosed herein are well known in the art and include many immortalized cell lines available from the American Type Culture Collection (ATCC). These include, inter alia, Chinese hamster ovary (CHO) cells, NSO, SP2 cells, HeLa cells, baby hamster kidney (BHK) cells, monkey kidney cells (COS), human hepatocellular carcinoma cells (e.g., Hep G2), A549 cells, 3T3 cells, HEK-293 cells and a number of other cell lines. Mammalian host cells include human, mouse, rat, dog, monkey, pig, goat, bovine, horse and hamster cells. Cell lines of particular preference are selected through determining which cell lines have high expression levels. Other cell lines that can be used are insect cell lines, such as Sf9 cells, amphibian cells, bacterial cells, plant cells and fungal cells. Fungal cells include yeast and filamentous fungus cells including, for example, *Pichia pastoris, Pichia finlandica, Pichia trehalophila, Pichia koclamae, Pichia membranaefaciens, Pichia minuta (Ogataea minuta, Pichia lindneri), Pichia opuntiae, Pichia thermotolerans, Pichia salictaria, Pichia guercuum, Pichia pijperi, Pichia stiptis, Pichia methanolica, Pichia sp., Saccharomyces cerevisiae, Saccharomyces sp., Hansenula polymorpha, Kluyveromyces sp., Kluyveromyces lactis, Candida albicans, Aspergillus nidulans, Aspergillus niger, Aspergillus oryzae, Trichoderma reesei, Chrysosporium lucknowense, Fusarium sp., Fusarium gramineum, Fusarium venenatum, Physcomitrella patens* and *Neurospora crassa. Pichia sp.*, any *Saccharomyces sp., Hansenula polymorpha*, any *Kluyveromyces sp., Candida albicans*, any *Aspergillus sp., Trichoderma reesei, Chrysosporium lucknowense*, any *Fusarium sp., Yarrowia lipolytica*, and *Neurospora crassa*. When recombinant expression vectors encoding the heavy chain or antigen-binding portion or fragment thereof, the light chain and/or antigen-binding fragment thereof, or scFv are introduced into mammalian host cells, the antibodies are produced by culturing the host cells for a period of time sufficient to allow for expression of the antibodies or fragments or chain in the host cells or secretion into the culture medium in which the host cells are grown.

Antibodies and antigen-binding fragments thereof and immunoglobulin chains can be recovered from the culture medium using standard protein purification methods. Further, expression of antibodies and antigen-binding fragments thereof and immunoglobulin chains (or other moieties therefrom) from production cell lines can be enhanced using a number of known techniques. For example, the glutamine synthetase gene expression system (the GS system) is a common approach for enhancing expression under certain conditions. The GS system is discussed in whole or part in connection with European Patent Nos. 0 216 846, 0 256 055, and 0 323 997 and European Patent Application No. 89303964.4. Thus, in an embodiment, the mammalian host cells (e.g., CHO) lack a glutamine synthetase gene and are grown in the absence of glutamine in the medium wherein, however, the polynucleotide encoding the immunoglobulin chain comprises a glutamine synthetase gene which complements the lack of the gene in the host cell.

In general, glycoproteins produced in a particular cell line or transgenic animal will have a set of glycosylation patterns that is characteristic for glycoproteins produced in the cell line or transgenic animal. Therefore, the particular glycosylation pattern of an antibody will depend on the particular cell line or transgenic animal used to produce the antibody. However, all antibodies comprising the amino acid sequences provided herein are contemplated, independent of the antibody glycosylation pattern. Similarly, in particular embodiments, antibodies with a glycosylation pattern comprising only non-fucosylated N-glycans can be advantageous, because these antibodies have been shown to typically exhibit more potent efficacy than their fucosylated counterparts both in vitro and in vivo (See for example, Shinkawa et al., *J. Biol. Chem.* 278: 3466-3473 (2003); U.S. Pat. Nos. 6,946,292 and 7,214,775). These antibodies with non-fucosylated N-glycans are not likely to be immunogenic because their carbohydrate structures are a normal component of the population that exists in human serum IgG.

Immunoglobulins can be assigned to different classes depending on the amino acid sequences of the constant domain of their heavy chains. In some embodiments, different constant domains can be appended to $V_L$, $V_H$ or $V_H$-$V_L$ regions. There are at least five major classes of immunoglobulins: IgA, IgD, IgE, IgG and IgM, and several of these can be further divided into subclasses (subtypes), e.g. IgG1, IgG2, IgG3 and IgG4; IgA1 and IgA2.

In one embodiment, the antibodies or antigen-binding fragments comprise a heavy chain constant region, e.g. a human constant region, such as γ1, γ2, γ3, or γ4 human heavy chain constant region or a variant thereof. In another embodiment, the antibody or antigen-binding fragment comprises a light chain constant region, e.g. a human light chain constant region, such as lambda or kappa human light chain region or variant thereof.

In one embodiment, the anti-PD-1 or anti-LAG3 antigen-binding fragment or anti-PD-1/LAG3 bispecific antibody comprises a heavy chain constant region of the IgG1 subtype. In another embodiment, the IgG1 heavy chain constant region of the anti-PD-1 and/or anti-LAG3 arm further comprises one or more of L234A or L234D; L235A or L235D; D265S or D265A; and G237A mutations in the CH2 region (EU numbering). In another embodiment, the IgG1 heavy chain constant region of the anti-PD-1 and/or anti-LAG3 arm further comprises the mutation N297A, N297D, or N297Q (EU numbering).

In other aspects of the anti-PD-1/LAG3 multispecific antibody, the IgG1 heavy chain constant region of the anti-PD-1 and anti-LAG3 arm further comprises pairs of CH3 mutations selected from the group consisting of: one or more mutations of L351Y/F405A/Y407V and one or more mutations of T366I/K392M/T394W; one or more mutations of T350V/L351Y/F405A/Y407V and one or more mutations of T350V/T366L/K392L/T394W; and one or more mutations of T350V/L351Y/F405A/Y407V and one or more mutations of T350V/T366L/K392M/T394W (EU numbering). In a further embodiment, the IgG1 heavy chain constant region of the anti-PD-1 arm further comprises CH3 mutations of T350V/L351Y/F405A/Y407V and the IgG1 heavy chain constant region of the anti-LAG3 arm further comprises CH3 mutations T350V/T366L/K392M/T394W. In a further embodiment, the IgG1 heavy chain constant region of the anti-LAG3 arm further comprises CH3 mutations of T350V/L351Y/F405A/Y407V and the IgG1 heavy chain constant region of the anti-PD-1 arm further comprises CH3 mutations T350V/T366L/K392M/T394W. In yet a further embodiment, the IgG1 heavy chain constant region of the anti-PD-1 arm further comprises CH3 mutations of L351Y/F405A/Y407V and the IgG1 heavy chain constant region of the anti-LAG3 arm further comprises CH3 mutations T366L/K392M/T394W. In yet a further embodiment, the IgG1 heavy chain constant region of the anti-LAG3 arm further comprises CH3 mutations of L351Y/F405A/Y407V and the IgG1 heavy chain constant region of the anti-PD-1 arm further comprises CH3 mutations T366L/K392M/T394W. These mutations in the heavy chain constant region of the anti-PD-1 arm and anti-LAG3 arm promote the heterodimer formation of the bispecific antibody. See WO2012058768 and WO2013063702. Other CH3 mutations to promote heterodimer formation of the bispecific antibodies includes those described in WO2012058768, WO2013063702, U.S. Pat. Nos. 5,731,168, 8,592,562, 9,828,619, 9,248,181 or WO2012131555, which are incorporated herein by reference in their entireties.

Figure 4:
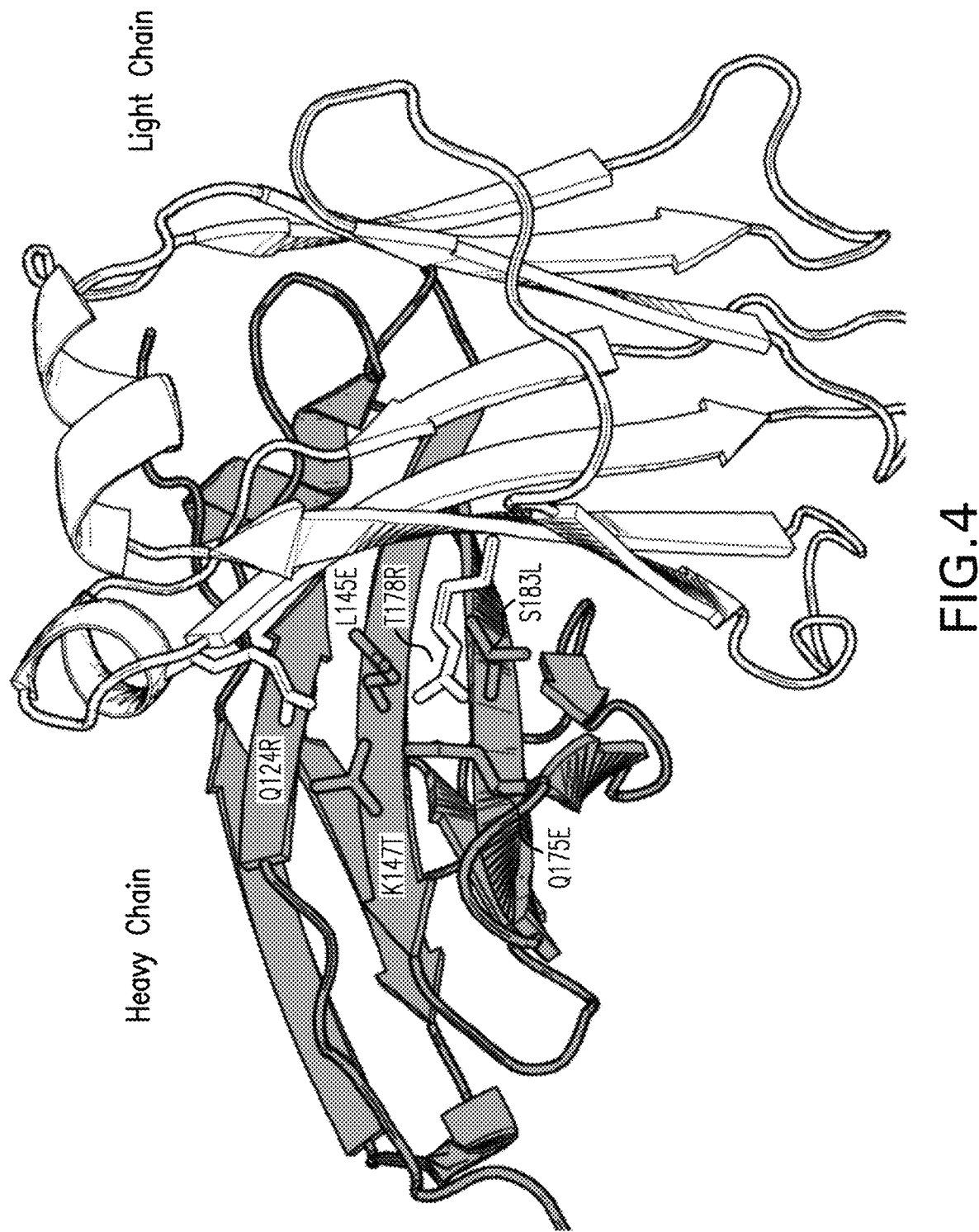
FIG. 4 depicts a 3D representation of the CH1 (grey) and CL (white) interface formed in the anti-PD1 arm of the 90ASU or 18ASS bispecific antibody upon introduction of the Azymetric™ mutations (sticks). A different set of mutations is introduced in the anti-LAG3 second arm to drive selective formation of the correctly paired interface and avoid heavy-light chain mispairing.
Figure 5:
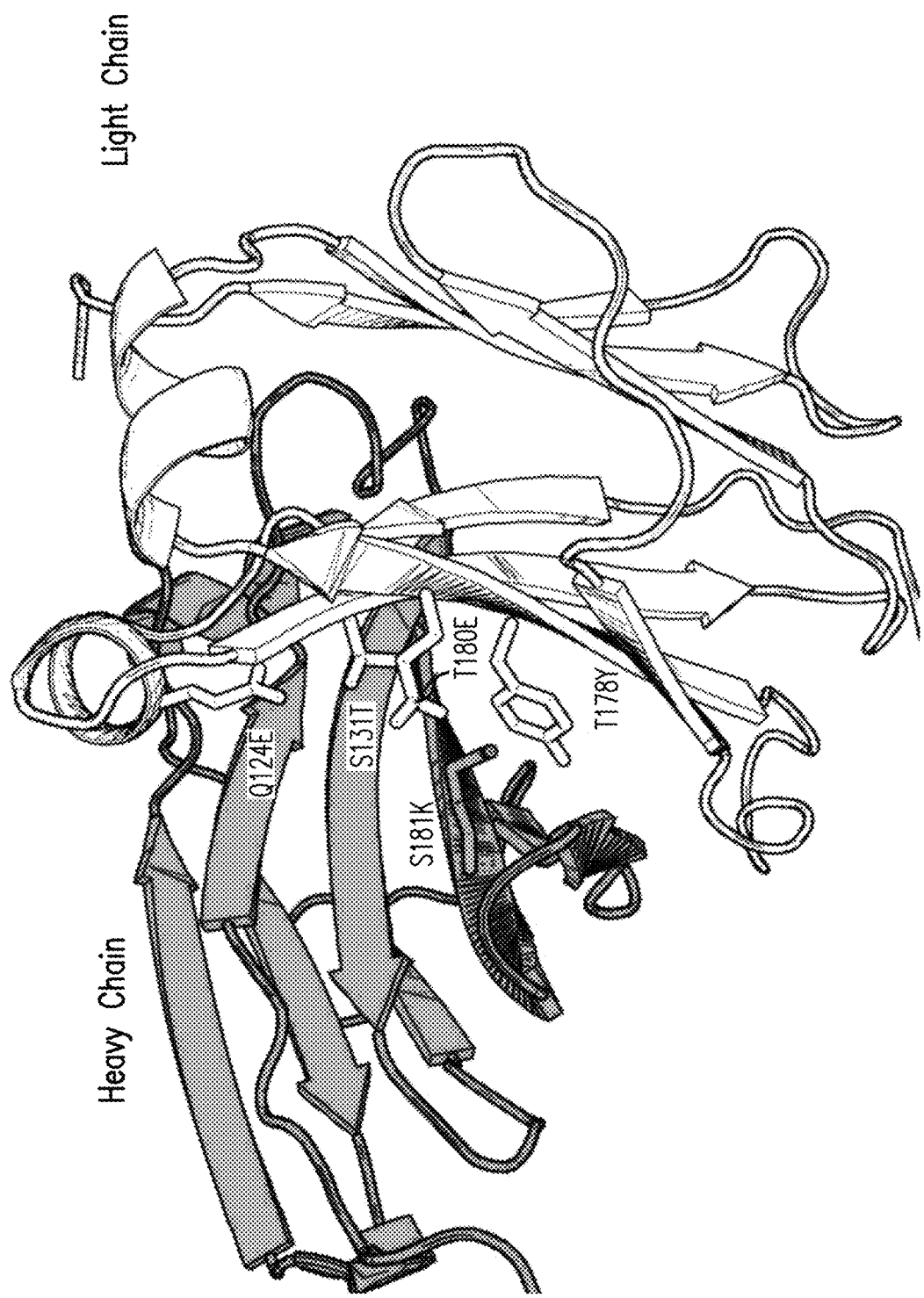
FIG. 5 depicts a 3D representation of the CH1 (grey) and CL (white) interface formed in the anti-LAG3 second arm of the 90ASU or 18ASS bispecific antibody upon introduction of the Azymetric™ mutations (sticks). A different set of mutations is introduced in the anti-PD-1 first arm to drive selective formation of the correctly paired interface and avoid heavy-light chain mispairing.

In another embodiment, the anti-PD-1 heavy chain further comprises CH1 mutations at L145E, K147T, Q175E, and S183L, and the anti-PD-1 light chain comprises $C_\kappa$ mutations at Q124R, T178R; and the anti-LAG3 heavy chain further comprises CH1 mutations at S181K, light chain $C_\kappa$ mutations at Q124E, S131T, T178Y, and T180E (EU numbering). In another embodiment, the anti-PD-1 heavy chain further comprises FR and CH1 mutations at Q39E, L145E, K147T, and Q175E, and the anti-PD-1 light chain comprises FR and $C_\kappa$ mutations at Q38R, Q124R, Q160K, and T178R; and the anti-LAG3 heavy chain further comprises FR and CH1 mutations at Q39R, H168R, Q175K, light chain FR and $C_\kappa$ mutations at Q38E, Q124E, Q160E, and T180E (EU numbering). These mutations assist in the correct pairing of the anti-PD-1 heavy and light chain, and anti-LAG3 heavy and light chain. See FIG. 4 and FIG. 5, and WO2015181805. Other CH1 and Ck mutations that promote correct light and heavy chain pairing include those described in WO2015181805, WO2016172485, WO2015173756, US20160039947, WO2014124326, US20140154254, or US20140370020, which are incorporated herein by reference in their entireties.

5.6 Antibody Engineering

Further included are embodiments in which the antibodies and antigen-binding fragments thereof are engineered antibodies to include modifications to framework residues within the variable domains of the sequences provided herein, e.g. to improve the properties of the antibody or fragment. Typically, such framework modifications are made to decrease the immunogenicity of the antibody or fragment. This is usually accomplished by replacing non-CDR residues in the variable domains (i.e. framework residues) in a parental (e.g. rodent) antibody or fragment with analogous residues from the immune repertoire of the species in which the antibody is to be used, e.g. human residues in the case of human therapeutics. Such an antibody or fragment is referred to as a "humanized" antibody or fragment. One approach is to mutate one or more framework residues to the corresponding germline sequence. More specifically, an antibody or fragment that has undergone somatic mutation can contain framework residues that differ from the germline sequence from which the antibody is derived. Such residues can be identified by comparing the antibody or fragment framework sequences to the germline sequences from which the antibody or fragment is derived. Another approach is to revert to the original parental (e.g., rodent) residue at one or more positions of the engineered (e.g. humanized) antibody, e.g. to restore binding affinity that may have been lost in the process of replacing the framework residues. (See, e.g., U.S. Pat. Nos. 5,693,762, 5,585,089 and 5,530,101.)

In certain embodiments, the antibodies and antigen-binding fragments thereof are engineered (e.g., humanized) to include modifications in the framework and/or CDRs to improve their properties. Such engineered changes can be based on molecular modelling. A molecular model for the variable region for the parental (non-human) antibody sequence can be constructed to understand the structural features of the antibody and used to identify potential regions on the antibody that can interact with the antigen. Conventional CDRs are based on alignment of immunoglobulin sequences and identifying variable regions. Kabat et al., (1991) *Sequences of Proteins of Immunological Interest*, Kabat, et al.; National Institutes of Health, Bethesda, Md.; 5*th* ed.; NIH Publ. No. 91-3242; Kabat (1978) *Adv. Prot. Chem.* 32:1-75; Kabat, et al., (1977) *J. Biol. Chem.* 252:6609-6616. Chothia and coworkers carefully examined conformations of the loops in crystal structures of antibodies and proposed hypervariable loops. Chothia, et al., (1987) *J Mol. Biol.* 196:901-917 or Chothia, et al., (1989) Nature 342:878-883. There are variations between regions classified as "CDRs" and "hypervariable loops". Later studies (Raghunathan et al, (2012) *J. Mol Recog.* 25, 3, 103-113) analyzed several antibody-antigen crystal complexes and observed that the antigen-binding regions in antibodies do not necessarily conform strictly to the "CDR" residues or "hypervarible" loops. The molecular model for the variable region of the non-human antibody can be used to guide the selection of regions that can potentially bind to the antigen. In practice the potential antigen-binding regions based on model differ from the conventional "CDR"s or "hypervariable" loops. Commercial scientific software such as MOE (Chemical Computing Group) can be used for molecular modeling. Human frameworks can be selected based on best matches with the non-human sequence both in the frameworks and in the CDRs. For FR4 (framework 4) in VH, VJ regions for the human germlines are compared with the corresponding non-human region. In the case of FR4 (framework 4) in VL, J-kappa and J-Lambda regions of human germline sequences are compared with the corresponding non-human region. Once suitable human frameworks are identified, the CDRs are grafted into the selected human frameworks. In some cases certain residues in the VL-VH interface can be retained as in the non-human (parental) sequence. Molecular models can also be used for identifying residues that can potentially alter the CDR conformations and hence binding to antigen. In some cases, these residues are retained as in the non-human (parental) sequence. Molecular models can also be used to identify solvent exposed amino acids that can result in unwanted effects such as glycosylation, deamidation and oxidation. Developability filters can be introduced early on in the design stage to eliminate/minimize these potential problems.

Another type of framework modification involves mutating one or more residues within the framework region, or even within one or more CDR regions, to remove T cell epitopes to thereby reduce the potential immunogenicity of the antibody. This approach is also referred to as "deimmunization" and is described in further detail in U.S. Pat. No. 7,125,689.

In particular embodiments, it will be desirable to change certain amino acids containing exposed side-chains to another amino acid residue in order to provide for greater chemical stability of the final antibody, so as to avoid deamidation or isomerization. The deamidation and/or isomerization of asparagine and glutamine can occur on DG, NG, NS, NA, NT, QG or QS sequences and result in the creation of an isoaspartic acid residue that introduces a kink into the polypeptide chain and decreases its stability (isoaspartic acid effect). Isomerization can occur at DG, DS, DA or DT sequences. In certain embodiments, the antibodies of the present disclosure do not contain deamidation or asparagine isomerism sites. In one embodiment, the anti-PD1 heavy chain CDRH2 comprises a G56A correction to remove a deamidation site.

For example, an asparagine (Asn) residue can be changed to Gln or Ala to reduce the potential for formation of isoaspartate at any Asn-Gly sequences, particularly within a CDR. A similar problem can occur at a Asp-Gly sequence. Reissner and Aswad (2003) *Cell. Mol. Life Sci.* 60:1281. Isoaspartate formation can debilitate or completely abrogate binding of an antibody to its target antigen. See, Presta (2005) *J. Allergy Clin. Immunol.* 116:731 at 734. In one embodiment, the asparagine is changed to glutamine (Gln). It can also be desirable to alter an amino acid adjacent to an asparagine (Asn) or glutamine (Gln) residue to reduce the likelihood of deamidation, which occurs at greater rates when small amino acids occur adjacent to asparagine or glutamine. See, Bischoff & Kolbe (1994) *J. Chromatog.* 662:261. In addition, any methionine residues (typically solvent exposed Met) in CDRs can be changed to Lys, Leu, Ala, or Phe or other amino acids in order to reduce the possibility that the methionine sulfur would oxidize, which could reduce antigen-binding affinity and also contribute to molecular heterogeneity in the final antibody preparation. Id. Additionally, in order to prevent or minimize potential scissile Asn-Pro peptide bonds, it can be desirable to alter any Asn-Pro combinations found in a CDR to Gln-Pro, Ala-Pro, or Asn-Ala. Antibodies with such substitutions are subsequently screened to ensure that the substitutions do not decrease the affinity or specificity of the antibody for PD-1 or LAG3, or other desired biological activity to unacceptable levels.

TABLE 2

Exemplary stabilizing CDR variants

| CDR Residue | Stabilizing Variant Sequence |
| --- | --- |
| Asn-Gly (N-G) | Gln-Gly, Ala-Gly, or Asn-Ala (Q-G), (A-G), or (N-A) |
| Asp-Gly (D-G) | Glu-Gly, Ala-Gly or Asp-Ala (E-G), (A-G), or (D-A) |
| Met (typically solvent exposed) (M) | Lys, Leu, Ala, or Phe (K), (L), (A), or (F) |
| Asn (N) | Gln or Ala (Q) or (A) |
| Asn-Pro (N-P) | Gln-Pro, Ala-Pro, or Asn-Ala (Q-P), (A-P), or (N-A) |

5.7 Antibody Engineering of the Fc Region

The antibodies and antigen-binding fragments thereof disclosed herein can also be engineered to include modifications within the Fc region, typically to alter one or more properties of the antibody, such as serum half-life, complement fixation, Fc receptor binding, and/or effector function (e.g., antigen-dependent cellular cytotoxicity). Furthermore, the antibodies and antigen-binding fragments thereof disclosed herein can be chemically modified (e.g., one or more chemical moieties can be attached to the antibody) or be modified to alter its glycosylation, again to alter one or more properties of the antibody or fragment. Each of these embodiments is described in further detail below. The numbering of residues in the Fc region is that of the EU index of Kabat.

The antibodies and antigen-binding fragments thereof disclosed herein also include antibodies and fragments with modified (or blocked) Fc regions to provide altered effector functions. See, e.g., U.S. Pat. No. 5,624,821; WO2003/086310; WO2005/120571; WO2006/0057702. Such modifications can be used to enhance or suppress various reactions of the immune system, with possible beneficial effects in diagnosis and therapy. Alterations of the Fc region include amino acid changes (substitutions, deletions and insertions), glycosylation or deglycosylation, and adding multiple Fc regions. Changes to the Fc can also alter the half-life of antibodies in therapeutic antibodies, enabling less frequent dosing and thus increased convenience and decreased use of material. See Presta (2005) J. Allergy Clin. Immunol. 116: 731 at 734-35.

In one embodiment, the antibody or antigen-binding fragment is an IgG4 isotype antibody or fragment comprising a Serine to Proline mutation at a position corresponding to position 228 (S228P; EU index) in the hinge region of the heavy chain constant region. This mutation has been reported to abolish the heterogeneity of inter-heavy chain disulfide bridges in the hinge region (Angal et al. supra; position 241 is based on the Kabat numbering system).

In one embodiment, the hinge region is modified such that the number of cysteine residues in the hinge region is increased or decreased. This approach is described further in U.S. Pat. No. 5,677,425. The number of cysteine residues in the hinge region of CH1 is altered, for example, to facilitate assembly of the light and heavy chains or to increase or decrease the stability of the antibody.

In another embodiment, the Fc hinge region of an antibody or antigen-binding fragment is mutated to decrease the biological half-life of the antibody or fragment. More specifically, one or more amino acid mutations are introduced into the CH2-CH3 domain interface region of the Fc-hinge fragment such that the antibody or fragment has impaired Staphylococcyl protein A (SpA) binding relative to native Fc-hinge domain SpA binding. This approach is described in further detail in U.S. Pat. No. 6,165,745.

In another embodiment, the antibody or antigen-binding fragment is modified to increase its biological half-life. Various approaches are possible. For example, one or more of the following mutations can be introduced: T252L, T254S, T256F, as described in U.S. Pat. No. 6,277,375. Alternatively, to increase the biological half-life, the antibody can be altered within the CH1 or CL region to contain a salvage receptor binding epitope taken from two loops of a CH2 domain of an Fc region of an IgG, as described in U.S. Pat. Nos. 5,869,046 and 6,121,022.

In yet other embodiments, the Fc region is altered by replacing at least one amino acid residue with a different amino acid residue to alter the effector function(s) of the antibody or antigen-binding fragment. For example, one or more amino acids selected from amino acid residues 234, 235, 236, 237, 297, 318, 320 and 322 can be replaced with a different amino acid residue such that the antibody has an altered affinity for an effector ligand and retains the antigen-binding ability of the parent antibody. The effector ligand to which affinity is altered can be, for example, an Fc receptor or the C1 component of complement. This approach is described in further detail in U.S. Pat. Nos. 5,624,821 and 5,648,260.

In another embodiment, one or more amino acids selected from amino acid residues 329, 331 and 322 can be replaced with a different amino acid residue such that the antibody has altered C1q binding and/or reduced or abolished complement-dependent cytotoxicity (CDC). This approach is described in further detail in U.S. Pat. No. 6,194,551.

In another embodiment, one or more amino acid residues within amino acid positions 231 and 239 are altered to thereby alter the ability of the antibody to fix complement. This approach is described further in PCT Publication WO 94/29351.

In yet another embodiment, the Fc region is modified to decrease the ability of the antibody or antigen-binding fragment to mediate antibody-dependent cellular cytotoxicity (ADCC) and/or to decrease the affinity of the antibody or fragment for an Fcγ receptor by modifying one or more amino acids at the following positions: 238, 239, 243, 248, 249, 252, 254, 255, 256, 258, 264, 265, 267, 268, 269, 270, 272, 276, 278, 280, 283, 285, 286, 289, 290, 292, 293, 294, 295, 296, 298, 301, 303, 305, 307, 309, 312, 315, 320, 322, 324, 326, 327, 329, 330, 331, 333, 334, 335, 337, 338, 340, 360, 373, 376, 378, 382, 388, 389, 398, 414, 416, 419, 430, 434, 435, 437, 438 or 439. This approach is described further in PCT Publication WO 00/42072. Moreover, the binding sites on human IgG1 for FcγR1, FcγRII, FcγRIII and FcRn have been mapped and variants with improved binding have been described (see Shields et al. (2001) J. Biol. Chem. 276:6591-6604).

In one embodiment, the Fc region is modified to decrease the ability of an antibody provided herein to mediate effector function and/or to increase anti-inflammatory properties by modifying residues 243 and 264. In one embodiment, the Fc region of the antibody or fragment is modified by changing the residues at positions 243 and 264 to alanine. In one embodiment, the Fc region is modified to decrease the ability of the antibody or fragment to mediate effector function and/or to increase anti-inflammatory properties by modifying residues 243, 264, 267 and 328.

5.8 Effector Function Regulation

The term "Effector Function" as used herein is meant to refer to one or more of Antibody Dependant Cell mediated Cytotoxic activity (ADCC), Complement-dependant cytotoxic activity (CDC) mediated responses, Fc-mediated phagocytosis or antibody dependant cellular phagocytosis (ADCP) and antibody recycling via the FcRn receptor.

The interaction between the constant region of an antigen-binding protein and various Fc receptors (FcR) including FcgammaRI (CD64), FcgammaRII (CD32) and FcgammaRIII (CD16) is believed to mediate the effector functions, such as ADCC and CDC, of the antigen-binding protein. The Fc receptor is also important for antibody cross-linking, which can be important for anti-tumor immunity.

Effector function can be measured in a number of ways including for example via binding of the FcgammaRIII to Natural Killer cells or via FcgammaRI to monocytes/macrophages to measure for ADCC effector function. In certain embodiments, an antigen-binding protein provided herein can be assessed for ADCC effector function in a natural killer (NK) cell assay. Examples of such assays can be found in Shields et al, 2001 *J. Biol. Chem.*, Vol. 276, p 6591-6604; Chappel et al, 1993 J. Biol. Chem., Vol 268, p 25124-25131; Lazar et al, 2006 PNAS, 103; 4005-4010.

The ADCC or CDC properties of antibodies provided herein, or their cross-linking properties, can be reduced in a number of ways. Human IgG1 constant regions containing specific mutations or altered glycosylation on residue Asn297 have been shown to reduce binding to Fc receptors. In other cases, these mutations have also been shown to enhance ADCC and CDC (Lazar et al., 2006, *PNAS*, 103; 4005-4010; Shields et al. J Biol Chem 2001, 276; 6591-6604; Nechansky et al., 2007, *Mol. Immunol.*, 44; 1815-1817). In addition, L234A or L235A, L236A, G237A mutations result in reductions in FcγRII recognition. Lund et al., 1991, *J of Immunol*, 147, 2657-2663. In one embodiment, such mutations are in one or more of positions selected from 239, 332 and 330 (IgG1), or the equivalent positions in other IgG isotypes. Examples of suitable mutations are S239D and I332E and A330L. In one embodiment, an antigen-binding protein provided herein is mutated at positions 239 and 332, for example S239D and I332E. In another embodiment an antigen-binding protein provided herein is mutated at three or more positions selected from 239 and 332 and 330, for example S239D and I332E and A330L. (EU index numbering).

5.9 Production of Antibodies with Modified Glycosylation

In still another embodiment, the bispecific antibodies or antigen-binding fragments provided herein comprise a particular glycosylation pattern. For example, an afucosylated or an aglycosylated antibody or fragment can be made (i.e., the antibody lacks fucose or glycosylation, respectively). The glycosylation pattern of an antibody or fragment can be altered to, for example, to increase the affinity or avidity of the antibody or fragment for a PD-1 or LAG3 antigen. Such modifications can be accomplished by, for example, altering one or more of the glycosylation sites within the antibody or fragment sequence. For example, one or more amino acid substitutions can be made that result in removal of one or more of the variable region framework glycosylation sites to thereby eliminate glycosylation at that site. Such aglycosylation can increase the affinity or avidity of the antibody or fragment for antigen. See, e.g., U.S. Pat. Nos. 5,714,350 and 6,350,861. In one embodiment, the anti-PD-1 CDRH2 region has a S61N glycosylation correction.

Antibodies and antigen-binding fragments disclosed herein can further include those produced in lower eukaryote host cells, in particular fungal host cells such as yeast and filamentous fungi that have been genetically engineered to produce glycoproteins that have mammalian- or human-like glycosylation patterns (See for example, Choi et al, (2003) *Proc. Natl. Acad. Sci.* 100: 5022-5027; Hamilton et al., (2003) *Science* 301: 1244-1246; Hamilton et al., (2006) *Science* 313: 1441-1443; Nett et al., *Yeast* 28(3):237-52 (2011); Hamilton et al., *Curr Opin Biotechnol*. October; 18(5):387-92 (2007)). A particular advantage of these genetically modified host cells over currently used mammalian cell lines is the ability to control the glycosylation profile of glycoproteins that are produced in the cells such that compositions of glycoproteins can be produced wherein a particular N-glycan structure predominates (see, e.g., U.S. Pat. Nos. 7,029,872 and 7,449,308). These genetically modified host cells have been used to produce antibodies that have predominantly particular N-glycan structures (See for example, Li et al., (2006) *Nat. Biotechnol.* 24: 210-215).

In particular embodiments, the antibodies and antigen-binding fragments thereof disclosed herein further include those produced in lower eukaryotic host cells and which comprise fucosylated and non-fucosylated hybrid and complex N-glycans, including bisected and multiantennary species, including but not limited to N-glycans such as $GlcNAc_{(1-4)}Man_3GlcNAc_2$; $Gal_{(1-4)}GlcNAc_{(1-4)}Man_3GlcNAc_2$; $NANA_{(1-4)}Gal_{(1-4)}GlcNAc_{(1-4)}Man_3GlcNAc_2$.

In particular embodiments, the antibodies and antigen-binding fragments thereof provided herein can comprise antibodies or fragments having at least one hybrid N-glycan selected from the group consisting of $GlcNAcMan_5GlcNAc_2$; $GalGlcNAcMan_5GlcNAc_2$; and $NANAGalGlcNAcMan_5GlcNAc_2$. In particular aspects, the hybrid N-glycan is the predominant N-glycan species in the composition.

In particular embodiments, the antibodies and antigen-binding fragments thereof provided herein comprise antibodies and fragments having at least one complex N-glycan selected from the group consisting of $GlcNAcMan_3GlcNAc_2$; $GalGlcNAcMan_3GlcNAc_2$; $NANAGalGlcNAcMan_3GlcNAc_2$; $GlcNAc_2Man_3GlcNAc_2$; $GalGlcNAc_2Man_3GlcNAc_2$; $Gal_2GlcNAc_2Man_3GlcNAc_2$; $NANAGal_2GlcNAc_2Man_3GlcNAc_2$; and $NANA_2Gal_2GlcNAc_2Man_3GlcNAc_2$. In particular aspects, the complex N-glycan are the predominant N-glycan species in the composition. In further aspects, the complex N-glycan is a particular N-glycan species that comprises about 30%, 40%, 50%, 60%, 70%, 80%, 90%, 95%, 97%, 98%, 99%, or 100% of the complex N-glycans in the composition. In one embodiment, the bispecific antibody and antigen-binding fragments thereof provided herein comprise complex N-glycans, wherein at least 50%, 60%, 70%, 80%, 90%, 95%, 97%, 98%, 99%, or 100% of the complex N-glycans comprise the structure $NANA_2Gal_2GlcNAc_2Man_3GlcNAc_2$, wherein such structure is afucosylated. Such structures can be produced, e.g., in engineered *Pichia pastoris* host cells.

In particular embodiments, the N-glycan is fucosylated. In general, the fucose is in an α1,3-linkage with the GlcNAc at the reducing end of the N-glycan, an α1,6-linkage with the GlcNAc at the reducing end of the N-glycan, an α1,2-linkage with the Gal at the non-reducing end of the N-glycan, an α1,3-linkage with the GlcNac at the non-reducing end of the N-glycan, or an α1,4-linkage with a GlcNAc at the non-reducing end of the N-glycan.

Therefore, in particular aspects of the above the glycoprotein compositions, the glycoform is in an α1,3-linkage or α1,6-linkage fucose to produce a glycoform selected from the group consisting of Man$_5$GlcNAc$_2$(Fuc), GlcNAcMan$_5$GlcNAc$_2$(Fuc), Man$_3$GlcNAc$_2$(Fuc), GlcNAcMan$_3$GlcNAc$_2$(Fuc), GlcNAc$_2$Man$_3$GlcNAc$_2$(Fuc), GalGlcNAc$_2$Man$_3$GlcNAc$_2$(Fuc), Gal$_2$GlcNAc$_2$Man$_3$GlcNAc$_2$(Fuc), NANAGal$_2$GlcNAc$_2$Man$_3$GlcNAc$_2$(Fuc), and NANA$_2$Gal$_2$GlcNAc$_2$Man$_3$GlcNAc$_2$(Fuc); in an α1,3-linkage or α1,4-linkage fucose to produce a glycoform selected from the group consisting of GlcNAc(Fuc)Man$_5$GlcNAc$_2$, GlcNAc(Fuc)Man$_3$GlcNAc$_2$, GlcNAc$_2$(Fuc$_{1-2}$)Man$_3$GlcNAc$_2$, GalGlcNAc$_2$(Fuc$_{1-2}$)Man$_3$GlcNAc$_2$, Gal$_2$GlcNAc$_2$(Fuc$_{1-2}$)Man$_3$GlcNAc$_2$, NANAGal$_2$GlcNAc$_2$(Fuc$_{1-2}$)Man$_3$GlcNAc$_2$, and NANA$_2$Gal$_2$GlcNAc$_2$(Fuc$_{1-2}$)Man$_3$GlcNAc$_2$; or in an α1,2-linkage fucose to produce a glycoform selected from the group consisting of Gal(Fuc)GlcNAc$_2$Man$_3$GlcNAc$_2$, Gal$_2$(Fuc$_{1-2}$)GlcNAc$_2$Man$_3$GlcNAc$_2$, NANAGal$_2$(Fuc$_{1-2}$)GlcNAc$_2$Man$_3$GlcNAc$_2$, and NANA$_2$Gal$_2$(Fuc$_{1-2}$)GlcNAc$_2$Man$_3$GlcNAc$_2$.

In further aspects, the antibodies or antigen-binding fragments thereof comprise high mannose N-glycans, including but not limited to, Man$_8$GlcNAc$_2$, Man$_7$GlcNAc$_2$, Man$_6$GlcNAc$_2$, Man$_5$GlcNAc$_2$, Man$_4$GlcNAc$_2$, or N-glycans that consist of the Man$_3$GlcNAc$_2$ N-glycan structure.

In further aspects of the above, the complex N-glycans further include fucosylated and non-fucosylated bisected and multiantennary species.

As used herein, the terms "N-glycan" and "glycoform" are used interchangeably and refer to an N-linked oligosaccharide, for example, one that is attached by an asparagine-N-acetylglucosamine linkage to an asparagine residue of a polypeptide. N-linked glycoproteins contain an N-acetylglucosamine residue linked to the amide nitrogen of an asparagine residue in the protein. The predominant sugars found on glycoproteins are glucose, galactose, mannose, fucose, N-acetylgalactosamine (GalNAc), N-acetylglucosamine (GlcNAc) and sialic acid (e.g., N-acetyl-neuraminic acid (NANA)). The processing of the sugar groups occurs co-translationally in the lumen of the ER and continues post-translationally in the Golgi apparatus for N-linked glycoproteins.

N-glycans have a common pentasaccharide core of Man$_3$GlcNAc$_2$ ("Man" refers to mannose; "Glc" refers to glucose; and "NAc" refers to N-acetyl; GlcNAc refers to N-acetylglucosamine). Usually, N-glycan structures are presented with the non-reducing end to the left and the reducing end to the right. The reducing end of the N-glycan is the end that is attached to the Asn residue comprising the glycosylation site on the protein. N-glycans differ with respect to the number of branches (antennae) comprising peripheral sugars (e.g., GlcNAc, galactose, fucose and sialic acid) that are added to the Man$_3$GlcNAc$_2$ ("Man$_3$") core structure which is also referred to as the "trimannose core", the "pentasaccharide core" or the "paucimannose core". N-glycans are classified according to their branched constituents (e.g., high mannose, complex or hybrid). A "high mannose" type N-glycan has five or more mannose residues. A "complex" type N-glycan typically has at least one GlcNAc attached to the 1,3 mannose arm and at least one GlcNAc attached to the 1,6 mannose arm of a "trimannose" core. Complex N-glycans can also have galactose ("Gal") or N-acetylgalactosamine ("GalNAc") residues that are optionally modified with sialic acid or derivatives (e.g., "NANA" or "NeuAc", where "Neu" refers to neuraminic acid and "Ac" refers to acetyl). Complex N-glycans can also have intrachain substitutions comprising "bisecting" GlcNAc and core fucose ("Fuc"). Complex N-glycans can also have multiple antennae on the "trimannose core," often referred to as "multiple antennary glycans." A "hybrid" N-glycan has at least one GlcNAc on the terminal of the 1,3 mannose arm of the trimannose core and zero or more mannoses on the 1,6 mannose arm of the trimannose core. The various N-glycans are also referred to as "glycoforms."

With respect to complex N-glycans, the terms "G-2", "G-1", "G0", "G1", "G2", "A1", and "A2" mean the following. "G-2" refers to an N-glycan structure that can be characterized as Man$_3$GlcNAc$_2$; the term "G-1" refers to an N-glycan structure that can be characterized as GlcNAcMan$_3$GlcNAc$_2$; the term "G0" refers to an N-glycan structure that can be characterized as GlcNAc$_2$Man$_3$GlcNAc$_2$; the term "G1" refers to an N-glycan structure that can be characterized as GalGlcNAc$_2$Man$_3$GlcNAc$_2$; the term "G2" refers to an N-glycan structure that can be characterized as Gal$_2$GlcNAc$_2$Man$_3$GlcNAc$_2$; the term "A1" refers to an N-glycan structure that can be characterized as NANAGal$_2$GlcNAc$_2$Man$_3$GlcNAc$_2$; and, the term "A2" refers to an N-glycan structure that can be characterized as NANA$_2$Gal$_2$GlcNAc$_2$Man$_3$GlcNAc$_2$. Unless otherwise indicated, the terms G-2", "G-1", "G0", "G1", "G2", "A1", and "A2" refer to N-glycan species that lack fucose attached to the GlcNAc residue at the reducing end of the N-glycan. When the term includes an "F", the "F" indicates that the N-glycan species contains a fucose residue on the GlcNAc residue at the reducing end of the N-glycan. For example, G0F, G1F, G2F, A1F, and A2F all indicate that the N-glycan further includes a fucose residue attached to the GlcNAc residue at the reducing end of the N-glycan. Lower eukaryotes such as yeast and filamentous fungi do not normally produce N-glycans that produce fucose.

With respect to multiantennary N-glycans, the term "multiantennary N-glycan" refers to N-glycans that further comprise a GlcNAc residue on the mannose residue comprising the non-reducing end of the 1,6 arm or the 1,3 arm of the N-glycan or a GlcNAc residue on each of the mannose residues comprising the non-reducing end of the 1,6 arm and the 1,3 arm of the N-glycan. Thus, multiantennary N-glycans can be characterized by the formulas GlcNAc$_{(2-4)}$Man$_3$GlcNAc$_2$, Gal$_{(1-4)}$GlcNAc$_{(2-4)}$Man$_3$GlcNAc$_2$, or NANA$_{(1-4)}$Gal$_{(1-4)}$GlcNAc$_{(2-4)}$Man$_3$GlcNAc$_2$. The term "1-4" refers to 1, 2, 3, or 4 residues.

With respect to bisected N-glycans, the term "bisected N-glycan" refers to N-glycans in which a GlcNAc residue is linked to the mannose residue at the reducing end of the N-glycan. A bisected N-glycan can be characterized by the formula GlcNAc$_3$Man$_3$GlcNAc$_2$ wherein each mannose residue is linked at its non-reducing end to a GlcNAc residue. In contrast, when a multiantennary N-glycan is characterized as GlcNAc$_3$Man$_3$GlcNAc$_2$, the formula indicates that two GlcNAc residues are linked to the mannose residue at the non-reducing end of one of the two arms of the N-glycans and one GlcNAc residue is linked to the mannose residue at the non-reducing end of the other arm of the N-glycan.

5.10 Antibody Physical Properties

The antibodies and antigen-binding fragments thereof disclosed herein can further contain one or more glycosylation sites in either the light or heavy chain immunoglobulin variable region. Such glycosylation sites can result in increased immunogenicity of the antibody or fragment or an alteration of the pK of the antibody due to altered antigen-binding (Marshall et al. (1972) *Annu Rev Biochem* 41:673-

702; Gala and Morrison (2004) *J Immunol* 172:5489-94; Wallick et al (1988) *J Exp Med* 168:1099-109; Spiro (2002) *Glycobiology* 12:43R-56R; Parekh et al (1985) *Nature* 316: 452-7; Mimura et al. (2000) *Mol Immunol* 37:697-706). Glycosylation has been known to occur at motifs containing an N-X-S/T sequence.

Each antibody or antigen-binding fragment will have a unique isoelectric point (pI), which generally falls in the pH range between 6 and 9.5. The pI for an IgG1 antibody typically falls within the pH range of 7-9.5 and the pI for an IgG4 antibody typically falls within the pH range of 6-8.

Each antibody or antigen-binding fragment will have a characteristic melting temperature, with a higher melting temperature indicating greater overall stability in vivo (Krishnamurthy R and Manning M C (2002) *Curr Pharm Biotechnol* 3:361-71). In general, the $T_{M1}$ (the temperature of initial unfolding) can be greater than 60° C., greater than 65° C., or greater than 70° C. The melting point of an antibody or fragment can be measured using differential scanning calorimetry (Chen et al (2003) *Pharm Res* 20:1952-60; Ghirlando et al (1999) *Immunol Lett* 68:47-52) or circular dichroism (Murray et al. (2002) *J. Chromatogr Sci* 40:343-9).

In a further embodiment, antibodies and antigen-binding fragments thereof are selected that do not degrade rapidly. Degradation of an antibody or fragment can be measured using capillary electrophoresis (CE) and MALDI-MS (Alexander A J and Hughes D E (1995) *Anal Chem* 67:3626-32).

In a further embodiment, antibodies and antigen-binding fragments thereof are selected that have minimal aggregation effects, which can lead to the triggering of an unwanted immune response and/or altered or unfavorable pharmacokinetic properties. Generally, antibodies and fragments are acceptable with aggregation of 25% or less, 20% or less, 15% or less, 10% or less, or 5% or less. Aggregation can be measured by several techniques, including size-exclusion column (SEC), high performance liquid chromatography (HPLC), and light scattering.

5.11 Antibody Conjugates

The antibodies and antigen-binding fragments thereof disclosed herein can also be conjugated to a chemical moiety. The chemical moiety can be, inter alia, a polymer, a radionuclide or a small molecule that binds to immunomodulators. In particular embodiments, the chemical moiety is a polymer which increases the half-life of the antibody or fragment in the body of a subject. Suitable polymers include, but are not limited to, hydrophilic polymers which include but are not limited to polyethylene glycol (PEG) (e.g., PEG with a molecular weight of 2 kDa, 5 kDa, 10 kDa, 12 kDa, 20 kDa, 30 kDa or 40 kDa), dextran and monomethoxypolyethylene glycol (mPEG). Lee, et al., (1999) (*Bioconj. Chem.* 10:973-981) discloses PEG conjugated single-chain antibodies. Wen, et al., (2001) (*Bioconj. Chem.* 12:545-553) disclose conjugating antibodies with PEG which is attached to a radiometal chelator (diethylenetriaminpentaacetic acid (DTPA)).

The antibodies and antigen-binding fragments thereof disclosed herein can also be conjugated with labels such as $^{99}Tc$, $^{90}Y$, $^{32}P$, $^{14}C$, $^{125}I$, $^{3}H$, $^{131}I$, $^{11}C$, $^{15}O$, $^{13}N$, $^{18}F$, $^{35}S$, $^{51}Cr$, $^{57}To$, $^{226}Ra$, $^{60}Co$, $^{59}Fe$, $^{57}Se$, $^{152}Eu$, $^{67}CU$, $^{217}Ci$, $^{211}At$, $^{212}Pb$, $^{47}Sc$, $^{109}Pd$, $^{234}Th$, $^{40}K$, $^{157}Gd$, $^{55}Mn$, $^{52}Tr$, and $^{56}Fe$.

The antibodies and antigen-binding fragments disclosed herein can also be PEGylated, for example to increase its biological (e.g., serum) half-life. To PEgylate an antibody or fragment, the antibody or fragment, typically is reacted with a reactive form of polyethylene glycol (PEG), such as a reactive ester or aldehyde derivative of PEG, under conditions in which one or more PEG groups become attached to the antibody or antibody fragment. In particular embodiments, the PEGylation is carried out via an acylation reaction or an alkylation reaction with a reactive PEG molecule (or an analogous reactive water-soluble polymer). As used herein, the term "polyethylene glycol" is intended to encompass any of the forms of PEG that have been used to derivatize other proteins, such as mono (C1-C10) alkoxy- or aryloxy-polyethylene glycol or polyethylene glycol-maleimide. In certain embodiments, the antibody or fragment to be PEGylated is an aglycosylated antibody or fragment. Methods for PEGylating proteins are known in the art and can be applied to the antibodies provided herein. See, e.g., EP0154316 and EP0401384.

The antibodies and antigen-binding fragments disclosed herein can also be conjugated with fluorescent or chemilluminescent labels, including fluorophores such as rare earth chelates, fluorescein and its derivatives, rhodamine and its derivatives, isothiocyanate, phycoerythrin, phycocyanin, allophycocyanin, o-phthaladehyde, fluorescamine, $^{152}Eu$, dansyl, umbelliferone, luciferin, luminal label, isoluminal label, an aromatic acridinium ester label, an imidazole label, an acridimium salt label, an oxalate ester label, an aequorin label, 2,3-dihydrophthalazinediones, biotin/avidin, spin labels and stable free radicals.

Any method known in the art for conjugating the antibodies and antigen-binding fragments thereof to the various moieties can be employed, including those methods described by Hunter et al., (1962) *Nature* 144:945; David et al., (1974) *Biochemistry* 13:1014; Pain et al., (1981) *J. Immunol. Meth.* 40:219; and Nygren, (1982) *Histochem. and Cytochem.* 30:407. Methods for conjugating antibodies and fragments are conventional and known in the art.

5.12 Therapeutic Uses of Antibodies

Further provided are methods for treating subjects, including human subjects, in need of treatment with the antibodies or antigen-binding fragments thereof disclosed herein. In one embodiment, such subject suffers from cancer or infectious disease.

A "subject" can be a mammal such as a human, dog, cat, horse, cow, mouse, rat, monkey (e.g., cynomolgous monkey, e.g., *Macaca fascicularis*) or rabbit. In certain embodiments, the subject is a human subject.

The term "in association with" indicates that the components administered in a method provided herein can be formulated into a single composition for simultaneous delivery or formulated separately into two or more compositions (e.g., a kit). Each component can be administered to a subject at a different time than when the other component is administered. In certain embodiments, each administration is given non-simultaneously (e.g., separately or sequentially) at several intervals over a given period of time. Moreover, the separate components can be administered to a subject by the same or by a different route.

Further provided are methods for treating subjects, including human subjects, in need of treatment with the isolated antibodies or antigen-binding fragments thereof disclosed herein. In one embodiment, such subject suffers from an infection or an infectious disease. In some embodiments, provided herein is an antibody or antigen-binding fragment for use in treatment of cancer. In other embodiments, provided herein is an antibody or antigen-binding fragment for use in the treatment of an infection or infectious disease. In some embodiments, provided herein is the use of the antibody or antigen-binding fragment for the manufacture of a medicament for treating cancer. In other embodiments, provided herein is the use of the antibody or antigen-binding fragment for the manufacture of a medicament for treating an infection or infectious disease. In one embodiment, provided herein is a method of treating cancer in a human subject, comprising administering to the subject an effective amount of an antibody or antigen-binding fragment provided herein. In one embodiment, provided herein is a method of treating cancer in a human subject, comprising administering to the subject an effective amount of an expression vector comprising a nucleic acid encoding an antibody or antigen-binding fragment provided herein. In certain embodiments, the methods provided herein further comprise or are otherwise associated with a further therapeutic agent or therapeutic procedure.

In one embodiment, the further therapeutic agent is selected from the group consisting of: (i) an anti-TIGIT antibody or an antigen-binding fragment thereof; (ii) an anti-VISTA antibody or an antigen-binding fragment thereof; (iii) an anti-BTLA antibody or an antigen-binding fragment thereof; (iv) an anti-TIM3 antibody or an antigen-binding fragment thereof; (v) an anti-CTLA4 antibody or an antigen-binding fragment thereof; (vi) an anti-HVEM antibody or an antigen-binding fragment thereof; (vii) an anti-CD70 antibody or an antigen-binding fragment thereof; (viii) an anti-OX40 antibody or an antigen-binding fragment thereof; (ix) an anti-CD28 antibody or an antigen-binding fragment thereof; (x) an anti-PDL1 antibody or an antigen-binding fragment thereof; (xi) an anti-PDL2 antibody or an antigen-binding fragment thereof; (xii) an anti-GITR antibody or an antigen-binding fragment thereof; (xiii) an anti-ICOS antibody or an antigen-binding fragment thereof; (xiv) an anti-SIRPα antibody or an antigen-binding fragment thereof; (xv) an anti-ILT2 antibody or an antigen-binding fragment thereof; (xvi) an anti-ILT3 antibody or an antigen-binding fragment thereof; (xvii) an anti-ILT4 antibody or an antigen-binding fragment thereof; (xviii) an anti-ILT5 antibody or an antigen-binding fragment thereof; (xix) an anti-4-1BB antibody or an antigen-binding fragment thereof; (xx) an anti-NK2GA antibody or an antigen-binding fragment thereof; (xxi) an anti-NK2GC antibody or an antigen-binding fragment thereof; (xxii) an anti-NK2GE antibody or an antigen-binding fragment thereof; (xxiii) an anti-TSLP antibody or an antigen-binding fragment thereof; (xxiv) an anti-IL10 antibody or an antigen-binding fragment thereof; (xxv) a STING agonist; (xxvi) a CXCR2 antagonist; and (xxvii) a PARP inhibitor.

In one embodiment, the agent is an anti-LAG3 antibody or antigen-binding fragment thereof. In one embodiment, the agent is an anti-TIGIT antibody or antigen-binding fragment thereof. In one embodiment, the agent is an anti-VISTA antibody or antigen-binding fragment thereof. In one embodiment, the agent is an anti-BTLA antibody or antigen-binding fragment thereof. In one embodiment, the agent is an anti-TIM3 antibody or antigen-binding fragment thereof. In one embodiment, the agent is an anti-CTLA4 antibody or antigen-binding fragment thereof. In one embodiment, the agent is an anti-HVEM antibody or antigen-binding fragment thereof. In one embodiment, the agent is an anti-CD70 antibody or antigen-binding fragment thereof. In one embodiment, the agent is an anti-OX40 antibody or antigen-binding fragment thereof. In one embodiment, the agent is an anti-CD28 antibody or antigen-binding fragment thereof. In one embodiment, the agent is an anti-PDL1 antibody or antigen-binding fragment thereof. In one embodiment, the agent is an anti-PDL2 antibody or antigen-binding fragment thereof. In one embodiment, the agent is an anti-GITR antibody or antigen-binding fragment thereof. In one embodiment, the agent is an anti-ICOS antibody or antigen-binding fragment thereof. In one embodiment, the agent is an anti-SIRPα antibody or antigen-binding fragment thereof. In one embodiment, the agent is an anti-ILT2 antibody or antigen-binding fragment thereof. In one embodiment, the agent is an anti-ILT3 antibody or antigen-binding fragment thereof. In one embodiment, the agent is an anti-ILT4 antibody or antigen-binding fragment thereof. In one embodiment, the agent is an anti-ILT5 antibody or antigen-binding fragment thereof. In one embodiment, the agent is an anti-4-1BB antibody or antigen-binding fragment thereof. In one embodiment, the agent is an anti-NK2GA antibody or antigen-binding fragment thereof. In one embodiment, the agent is an anti-NK2GE antibody or antigen-binding fragment thereof. In one embodiment, the agent is an anti-IL10 antibody or antigen-binding fragment thereof. In one embodiment, the agent is an anti-TSLP antibody or antigen-binding fragment thereof. In one embodiment, the agent is a STING agonist. In one embodiment, the agent is a CXCR2 antagonist. In one embodiment, the agent is a PARP inhibitor.

In another embodiment, the subject suffers from cancer. In one embodiment, the cancer is osteosarcoma, rhabdomyosarcoma, neuroblastoma, kidney cancer, leukemia, renal transitional cell cancer, bladder cancer, Wilm's cancer, ovarian cancer, pancreatic cancer, breast cancer, prostate cancer, bone cancer, lung cancer (e.g., non-small cell lung cancer), gastric cancer, colorectal cancer, cervical cancer, synovial sarcoma, head and neck cancer, squamous cell carcinoma, multiple myeloma, renal cell cancer, retinoblastoma, hepatoblastoma, hepatocellular carcinoma, melanoma, rhabdoid tumor of the kidney, Ewing's sarcoma, chondrosarcoma, brain cancer, glioblastoma, meningioma, pituitary adenoma, vestibular schwannoma, a primitive neuroectodermal tumor, medulloblastoma, astrocytoma, anaplastic astrocytoma, oligodendroglioma, ependymoma, choroid plexus papilloma, polycythemia vera, thrombocythemia, idiopathic myelfibrosis, soft tissue sarcoma, thyroid cancer, endometrial cancer, carcinoid cancer or liver cancer, breast cancer or gastric cancer. In an embodiment, the cancer is metastatic cancer, e.g., of the varieties described above.

Cancers that can be treated by the antibodies or antigen-binding fragments, compositions and methods provided herein include, but are not limited to: Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel (adenocarcinoma, lymphoma, carcinoid tumors, Karposi's sarcoma, leiomyoma, hemangioma, lipoma, neurofibroma, fibroma), large bowel (adenocarcinoma, tubular adenoma, villous adenoma, hamartoma, leiomyoma) colorectal; Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre tumor cervical dysplasia), ovaries (ovarian carcinoma [serous cystadenocarcinoma, mucinous cystadenocarcinoma, unclassified carcinoma], granulosa thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma]; Skin: malignant melanoma, basal cell carcinoma, squamous cell carcinoma, Karposi's sarcoma, moles dysplastic nevi, lipoma, angioma, dermatofibroma, keloids, psoriasis; and Adrenal glands: neuroblastoma. Thus, the term "cancerous cell" as provided herein, includes a cell afflicted by any one of the above-identified conditions.

In one embodiment, cancers that can be treated by the antibodies or antigen-binding fragments thereof, compositions, and methods provided herein include, but are not limited to: lung cancer, pancreatic cancer, colon cancer, colorectal cancer, myeloid leukemia, acute myelogenous leukemia, chronic myelogenous leukemia, chronic myelomonocytic leukemia, thyroid cancer, myelodysplastic syndrome, bladder carcinoma, epidermal carcinoma, melanoma, breast cancer, prostate cancer, head and neck cancers, ovarian cancer, brain cancers, cancers of mesenchymal origin, sarcomas, tetracarcinomas, neuroblastomas, kidney carcinomas, hepatomas, non-Hodgkin's lymphoma, multiple myeloma, and anaplastic thyroid carcinoma.

In an embodiment, provided are methods for treating subjects using an antibody or antigen-binding fragment thereof disclosed herein, wherein the subject suffers from a viral infection. In one embodiment, the viral infection is an infection with a virus selected from the group consisting of human immunodeficiency virus (HIV), hepatitis virus (A, B, or C), herpes virus (e.g., VZV, HSV-I, HAV-6, HSV-II, and CMV, Epstein Barr virus), adenovirus, influenza virus, flaviviruses, echovirus, rhinovirus, coxsackie virus, coronavirus, respiratory syncytial virus, mumps virus, rotavirus, measles virus, rubella virus, parvovirus, vaccinia virus, HTLV virus, dengue virus, papillomavirus, molluscum virus, poliovirus, rabies virus, JC virus or arboviral encephalitis virus.

In an embodiment, provided are methods for treating a subject using an antibody or antigen-binding fragment thereof disclosed herein, wherein the subject suffers from a bacterial infection. In one embodiment, the bacterial infection is infection with a bacteria selected from the group consisting of *Chlamydia*, rickettsial bacteria, mycobacteria, staphylococci, streptococci, pneumonococci, meningococci and gonococci, *klebsiella, proteus, serratia, pseudomonas, Legionella, Corynebacterium diphtherias, Salmonella*, bacilli, *Vibrio cholerae, Clostridium tetan, Clostridium botulinum, Bacillus anthricis, Yersinia pestis, Mycobacterium leprae, Mycobacterium lepromatosis*, and *Borriella*.

In an embodiment, provided herein is a method for treating a subject using an antibody or antigen-binding fragment thereof provided herein, wherein the subject suffers from a fungal infection. In one embodiment, the fungal infection is an infection with a fungus selected from the group consisting of *Candida (albicans, krusei, glabrata, tropicalis*, etc.), *Cryptococcus neoformans, Aspergillus (fumigatus, niger*, etc.), Genus *Mucorales (mucor, absidia, rhizopus), Sporothrix schenkii, Blastomyces dermatitidis, Paracoccidioides brasiliensis, Coccidioides immitis* and *Histoplasma capsulatum*.

In an embodiment, provided herein is a method for treating subjects using an antibody or antigen-binding fragment provided herein, wherein the subject suffers from a parasitic infection. In one embodiment, the parasitic infection is an infection with a parasite selected from the group consisting of *Entamoeba histolytica, Balantidium coli, Naegleria fowleri, Acanthamoeba, Giardia Zambia, Cryptosporidium, Pneumocystis carinii, Plasmodium vivax, Babesia microti, Trypanosoma brucei, Trypanosoma cruzi, Leishmania donovani, Toxoplasma gondii* and *Nippostrongylus brasiliensis*.

In particular embodiments, the antibodies or antigen-binding fragments thereof disclosed herein can be used alone, or in association with other, further therapeutic agents and/or therapeutic procedures, for treating or preventing any disease such as cancer, e.g., as discussed herein, in a subject in need of such treatment or prevention. Compositions, e.g., pharmaceutical compositions comprising a pharmaceutically acceptable carrier, comprising such antibodies and fragments in association with further therapeutic agents are also contemplated.

Therefore, provided herein is a method of treating cancer in a human subject, comprising administering to the subject an effective amount of the antibody or antigen-binding fragment disclosed herein. In certain embodiments, the administration is in association with a further therapeutic agent or therapeutic procedure.

Also provided herein is a method of treating an infection or infectious disease in a human subject, comprising administering to the subject an effective amount of the antibody or antigen-binding fragment disclosed herein. In certain embodiments, the administration is in association with a further therapeutic agent or therapeutic procedure.

In another embodiment, provided is an antibody or antigen-binding fragment thereof provided herein for use in the treatment of cancer; or treatment of an infection or infectious disease in combination with a further therapeutic agent. In one embodiment, the antibody or antigen-binding fragment thereof is for use in the treatment of cancer. In one embodiment, the antibody or antigen-binding fragment thereof is for use in the treatment of an infection. In one embodiment, the antibody or antigen-binding fragment thereof is for use in the treatment of an infectious disease. In certain embodiments, the treatment comprises a further therapeutic agent.

In a further embodiment, provided is the use of the antibody or antigen-binding fragment disclosed herein for the manufacture of a medicament for treating cancer; or treating an infection or infectious disease in combination with a further therapeutic agent. In another embodiment, provided is a combination of an antibody or antigen-binding fragment of the invention and a further therapeutic agent for the treatment of cancer; or treatment of an infection or infectious disease. In one embodiment, provided is an antibody or antigen-binding fragment thereof for the manufacture of a medicament for treating cancer. In one embodiment, provided is an antibody or antigen-binding fragment thereof for the manufacture of a medicament for treating an infection. In one embodiment, provided is an antibody or antigen-binding fragment thereof for the manufacture of a medicament for treating an infectious disease. In certain embodiments, the medicament is formulated with a further therapeutic agent.

In other embodiments, the provided is a method of treating cancer or treating an infection or infectious disease in a human subject, comprising administering to the subject an effective amount of an antibody or antigen-binding fragment disclosed herein, or an expression vector or a host cell disclosed herein, optionally in association with a further therapeutic agent or therapeutic procedure. In one embodiment, provided is a method of treating cancer in a human subject, comprising administering to the subject an effective amount of an antibody or antigen-binding fragment disclosed herein. In another embodiment, provided is a method of treating an infection in a human subject, comprising administering to the subject an effective amount of an antibody or antigen-binding fragment disclosed herein. In yet another embodiment, provided is a method of treating an infection disease in a human subject, comprising administering to the subject an effective amount of an antibody or antigen-binding fragment disclosed herein. In one embodiment, provided is a method of treating cancer in a human subject, comprising administering to the subject an effective amount of an expression vector comprising a polynucleotide encoding an antibody or antigen-binding fragment disclosed herein. In another embodiment, provided is a method of treating an infection in a human subject, comprising administering to the subject an effective amount of an expression vector comprising a polynucleotide encoding an antibody or antigen-binding fragment disclosed herein. In yet another embodiment, provided is a method of treating an infection disease in a human subject, comprising administering to the subject an effective amount of an expression vector comprising a polynucleotide encoding an antibody or antigen-binding fragment disclosed herein. In one embodiment, provided is a method of treating cancer in a human subject, comprising administering to the subject an effective amount of host cell comprising an expression vector comprising a polynucleotide encoding an antibody or antigen-binding fragment disclosed herein. In another embodiment, provided is a method of treating an infection in a human subject, comprising administering to the subject an effective amount of host cell comprising an expression vector comprising a polynucleotide encoding an antibody or antigen-binding fragment disclosed herein. In yet another embodiment, provided is a method of treating an infection disease in a human subject, comprising administering to the subject an effective amount of a host cell comprising an expression vector comprising a polynucleotide encoding an antibody or antigen-binding fragment disclosed herein. In certain embodiments, the method further comprises administration of an additional therapeutic agent. In other embodiments, the method further comprises an additional therapeutic procedure.

In particular embodiments, the antibodies or antigen-binding fragments thereof disclosed herein can be used alone, or in association with tumor vaccines. Examples of tumor vaccines include but are not limited to vaccines for Human Papillomavirus (HPV) infection caused cancer such as Gardasil®, Gardasil® and Cervarix®; vaccines that prevent hepatitis B virus caused liver cancer such as Engerix-B® and Recombivax HB®; oncolytic virus therapy that triggers immune response such as Imlygic®; DNA vaccines such as Synchotrope MA2M plasmid DNA vaccine and ZYC101; mammaglobin-a DNA vaccine (see Clinical Cancer Res. 2014 20(23):5964-75); vector based vaccines such as PSA-TRICOM (prostvac), PANVAC-VF, *Listeria monocytogenes*-based PSA vaccine (see Therapeutic Advances in Vaccines, 2014, 2(5) 137-148), *Listeria*-mesothelin Adeno-CEA; allogeneic vaccines such as GVAX, BLP-25 (anti-Ankara-mucin 1), Belagenpumatucel-L, TG4010, CIMAvax epidermal growth factor vaccine, NY-ESO, GM.CD40L-CCL21; autologous vaccines such as:Adeno-CD40L, BCG, INGN-225, Dendritic cell vaccines such as Provenge® (Sipuleucel-T), rF-CEA-MUC1-TRICOM (panvac-DC); antigen vaccines such as MUC-1 (stimuvax), NY-ESO-1, GP-100, MAGE-A3 (melanoma antigen encoding gene A3), INGN-225 (see Pharmacology & Therapeutics 153 (2015) 1-9).

In particular embodiments, the antibodies or antigen-binding fragments thereof disclosed herein can be used alone, or in association with chemotherapeutic agents.

In particular embodiments, the antibodies or antigen-binding fragments thereof disclosed herein can be used alone, or in association with radiation therapy.

In particular embodiments, the antibodies or antigen-binding fragments thereof disclosed herein can be used alone, or in association with targeted therapies. Examples of targeted therapies include: hormone therapies, signal transduction inhibitors (e.g., EGFR inhibitors, such as cetuximab (Erbitux®) and erlotinib (Tarceva®)); HER2 inhibitors (e.g., trastuzumab (Herceptin®) and pertuzumab (Perjeta®)); BCR-ABL inhibitors (such as imatinib (Gleevec®) and dasatinib (Sprycel®)); ALK inhibitors (such as crizotinib (Xalkori®) and ceritinib (Zykadia®)); BRAF inhibitors (such as vemurafenib (Zelboraf®) and dabrafenib (Tafinlar®)), gene expression modulators, apoptosis inducers (e.g., bortezomib (Velcade®) and carfilzomib (Kyprolis®)), angiogenesis inhibitors (e.g., bevacizumab (Avastin®) and ramucirumab (Cyramza®), monoclonal antibodies attached to toxins (e.g., brentuximab vedotin (Adcetris®) and ado-trastuzumab emtansine (Kadcyla®)).

In particular embodiments, the antibodies or antigen-binding fragments thereof provided herein are used in combination with an anti-cancer therapeutic agent. In other embodiments, the antibodies or antigen-binding fragments thereof provided herein are used in combination with an immunomodulatory drug. In some embodiments, the immunomodulatory drug is an immunomodulatory receptor inhibitor. In certain embodiments, the immunomodulatory drug is an antibody or antigen-binding fragment thereof that specifically binds to the receptor.

In an embodiment, an antibody or antigen-binding fragment thereof provided herein is used in association with one or more of: anti-PDL1 antibody, anti-TIGIT antibody, anti-CTLA4 antibody, anti-CS1 antibody (e.g., elotuzumab), anti-KIR2DL1/2/3 antibody (e.g., lirilumab), anti-CD137 antibody (e.g., urelumab), anti-GITR antibody (e.g., TRX518), anti-PD1 antibody (e.g., pembrolizumab, nivolumab, pidilizumab (CT-011)), anti-PD-L1 antibody (e.g., BMS-936559, Durvalumab, MSB0010718C or MPDL3280A), anti-PD-L2 antibody, anti-ILT1 antibody, anti-ILT2 antibody, anti-ILT3 antibody, anti-ILT4 antibody, anti-ILT5 antibody, anti-ILT6 antibody, anti-ILT7 antibody, anti-ILT8 antibody, anti-CD40 antibody, anti-OX40 antibody, anti-ICOS, anti-SIRPa, anti-KIR2DL1 antibody, anti-KIR2DL2/3 antibody, anti-KIR2DL4 antibody, anti-KIR2DL5A antibody, anti-KIR2DL5B antibody, anti-KIR3DL1 antibody, anti-KIR3DL2 antibody, anti-KIR3DL3 antibody, anti-NKG2A antibody, anti-NKG2C antibody, anti-NKG2E antibody, anti-4-1BB antibody (e.g., PF-05082566), anti-TSLP antibody, anti-IL-10 antibody, IL-10 or PEGylated IL-10, or any small organic molecule inhibitor of such targets.

In an embodiment, an antibody or antigen-binding fragment thereof is used in association with an anti-PDL1 antibody (e.g., BMS-936559, Durvalumab, MSB0010718C or MPDL3280A).

In an embodiment, an antibody or antigen-binding fragment thereof provided herein is used in association with an anti-CTLA4 antibody.

In an embodiment, an antibody or antigen-binding fragment thereof provided herein is used in association with an anti-CS1 antibody.

In an embodiment, an antibody or antigen-binding fragment thereof provided herein is used in association with an anti-KIR2DL1/2/3 antibody.

In an embodiment, an antibody or antigen-binding fragment thereof provided herein is used in association with an anti-CD137 (e.g., urelumab) antibody.

In an embodiment, an antibody or antigen-binding fragment thereof provided herein is used in association with an anti-GITR (e.g., TRX518) antibody.

In an embodiment, an antibody or antigen-binding fragment thereof provided herein is used in association with an anti-PD-L2 antibody.

In an embodiment, an antibody or antigen-binding fragment thereof provided herein is used in association with an anti-ITL1 antibody.

In an embodiment, an antibody or antigen-binding fragment thereof provided herein is used in association with an anti-ITL2 antibody.

In an embodiment, an antibody or antigen-binding fragment thereof provided herein is used in association with an anti-ITL3 antibody.

In an embodiment, an antibody or antigen-binding fragment thereof provided herein is used in association with an anti-ITL4 antibody.

In an embodiment, an antibody or antigen-binding fragment thereof provided herein is used in association with an anti-ITL5 antibody.

In an embodiment, an antibody or antigen-binding fragment thereof provided herein is used in association with an anti-ITL6 antibody.

In an embodiment, an antibody or antigen-binding fragment thereof provided herein is used in association with an anti-ITL7 antibody.

In an embodiment, an antibody or antigen-binding fragment thereof provided herein is used in association with an anti-ITL8 antibody.

In an embodiment, an antibody or antigen-binding fragment thereof provided herein is used in association with an anti-CD40 antibody.

In an embodiment, an antibody or antigen-binding fragment thereof provided herein is used in association with an anti-OX40 antibody.

In an embodiment, an antibody or antigen-binding fragment thereof provided herein is used in association with an anti-KIR2DL1 antibody.

In an embodiment, an antibody or antigen-binding fragment thereof provided herein is used in association with an anti-KIR2DL2/3 antibody.

In an embodiment, an antibody or antigen-binding fragment thereof provided herein is used in association with an anti-KIR2DL4 antibody.

In an embodiment, an antibody or antigen-binding fragment thereof provided herein is used in association with an anti-KIR2DL5A antibody.

In an embodiment, an antibody or antigen-binding fragment thereof provided herein is used in association with an anti-KIR2DL5B antibody.

In an embodiment, an antibody or antigen-binding fragment thereof provided herein is used in association with an anti-KIR3DL1 antibody.

In an embodiment, an antibody or antigen-binding fragment thereof provided herein is used in association with an anti-KIR3DL2 antibody.

In an embodiment, an antibody or antigen-binding fragment thereof provided herein is used in association with an anti-KIR3DL3 antibody.

In an embodiment, an antibody or antigen-binding fragment thereof provided herein is used in association with an anti-NKG2A antibody.

In an embodiment, an antibody or antigen-binding fragment thereof provided herein is used in association with an anti-NKG2C antibody.

In an embodiment, an antibody or antigen-binding fragment thereof provided herein is used in association with an anti-ICOS antibody.

In an embodiment, an antibody or antigen-binding fragment thereof provided herein is used in association with an anti-SIRPα antibody.

In an embodiment, an antibody or antigen-binding fragment thereof provided herein is used in association with an anti-4-1BB antibody.

In an embodiment, an antibody or antigen-binding fragment thereof provided herein is used in association with an anti-IL-10 antibody.

In an embodiment, an antibody or antigen-binding fragment thereof provided herein is used in association with an anti-TSLP antibody.

In an embodiment, an antibody or antigen-binding fragment thereof provided herein is used in association with IL-10 or PEGylated IL-10.

In an embodiment, an antibody or antigen-binding fragment thereof provided herein is used in association with one or more of an inhibitor (e.g., a small organic molecule or an antibody or antigen-binding fragment thereof) such as: an MTOR (mammalian target of rapamycin) inhibitor, a cytotoxic agent, a platinum agent, an EGFR inhibitor, a VEGF inhibitor, a microtubule stabilizer, a taxane, a CD20 inhibitor, a CD52 inhibitor, a CD30 inhibitor, a RANK (Receptor activator of nuclear factor kappa-B) inhibitor, a STING agonist, a CXCR2 antagonist, a RANKL (Receptor activator of nuclear factor kappa-B ligand) inhibitor, an ERK inhibitor, a MAP Kinase inhibitor, an AKT inhibitor, a MEK inhibitor, a PARP inhibitor, a PI3K inhibitor, a HER1 inhibitor, a HER2 inhibitor, a HER3 inhibitor, a HER4 inhibitor, a Bcl2 inhibitor, a CD22 inhibitor, a CD79b inhibitor, an ErbB2 inhibitor, or a farnesyl protein transferase inhibitor.

In an embodiment, an antibody or antigen-binding fragment thereof provided herein is used in association with any one or more of: 13-cis-retinoic acid, 3-[5-(methylsulfonylpiperadinemethyl)-indolyl]-quinolone, 4-hydroxytamoxifen, 5-deooxyuridine, 5'-deoxy-5-fluorouridine, 5-fluorouracil, 6-mecaptopurine, 7-hydroxystaurosporine, A-443654, abirateroneacetate, abraxane, ABT-578, acolbifene, ADS-100380, ALT-110, altretamine, amifostine, aminoglutethimide, amrubicin, Amsacrine, anagrelide, anastrozole, angiostatin, AP-23573, ARQ-197, arzoxifene, AS-252424, AS-605240, asparaginase, AT-9263, atrasentan, axitinib, AZD1152, *Bacillus* Calmette-Guerin (BCG) vaccine, batabulin, BC-210, besodutox, bevacizumab, bicalutamide, Bio111, BIO140, bleomycin, BMS-214662, BMS-247550, BMS-275291, BMS-310705, bortezimib, buserelin, busulfan, calcitriol, camptothecin, canertinib, capecitabine, carboplatin, carmustine, CC8490, cediranib, CG-1521, CG-781, chlamydocin, chlorambucil, chlorotoxin, cilengitide, cimitidine, cisplatin, cladribine, clodronate, COL-3, CP-724714, cyclophosphamide, cyproterone, cyproteroneacetate, cytarabine, cytosinearabinoside, dacarbazine, dacinostat, dactinomycin, dalotuzumab, danusertib, dasatanib, daunorubicin, decatanib, deguelin, denileukin, deoxycoformycin, depsipeptide, diarylpropionitrile, diethylstilbestrol, diftitox, docetaxel, dovitinib, doxorubicin, droloxifene, edotecarin, yttrium-90 labeled-edotreotide, edotreotide, EKB-569, EMD121974, endostatin, enzalutamide, enzastaurin, epirubicin, epithilone B, ERA-923, ERBITUX, erlotinib, estradiol, estramustine, etoposide, everolimus, exemestane, ficlatuzumab, finasteride, flavopiridol, floxuridine, fludarabine, fludrocortisone, fluoxymesterone, flutamide, FOLFOX regimen, Fulvestrant, galeterone, gefitinib, gemcitabine, gimatecan, goserelin, goserelin acetate, gossypol, GSK461364, GSK690693, HMR-3339, hydroxyprogesteronecaproate, hydroxyurea, IC87114, idarubicin, idoxyfene, ifosfamide, IM862, imatinib, IMC-1C11, INCB24360, IN01001, interferon (IFN), interleukin-12, ipilimumab, irinotecan, JNJ-16241199, ketoconazole, KRX-0402, lapatinib, lasofoxifene, letrozole, leucovorin, leuprolide, leuprolide acetate, levamisole, liposome entrapped paclitaxel, lomustine, lonafarnib, lucanthone, LY292223, LY292696, LY293646, LY293684, LY294002, LY317615, marimastat, mechlorethamine, medroxyprogesteroneacetate, megestrolacetate, melphalan, mercaptopurine, mesna, methotrexate, mithramycin, mitomycin, mitotane, mitoxantrone, tozasertib, MLN8054, neovastat, neratinib, neuradiab, nilotinib, nilutimide, nolatrexed, NVP-BEZ235, oblimersen, octreotide, ofatumumab, olaparib, oregovomab, orteronel, oxaliplatin, paclitaxel, palbociclib, pamidronate, panitumumab, pazopanib, PD0325901, PD184352, PEG-interferon, pemetrexed, pentostatin, perifosine, phenylalaninemustard, PI-103, pictilisib, PIK-75, pipendoxifene, PKI-166, plicamycin, porfimer, prednisone, procarbazine, progestins, PX-866, R-763, raloxifene, raltitrexed, razoxin, ridaforolimus, rituximab, romidepsin, RTA744, rubitecan, scriptaid, Sdx102, seliciclib, selumetinib, semaxanib, SF1126, sirolimus, SN36093, sorafenib, spironolactone, squalamine, SR13668, streptozocin, SU6668, suberoylanalide hydroxamic acid, sunitinib, synthetic estrogen, talampanel, talimogene laherparepvec, tamoxifen, temozolomide, temsirolimus, teniposide, tesmilifene, testosterone, tetrandrine, TGX-221, thalidomide, thioguanine, thiotepa, ticilimumab, tipifarnib, tivozanib, TKI-258, TLK286, topotecan, toremifene citrate, trabectedin, trastuzumab, tretinoin, trichostatin A, triciribinephosphate monohydrate, triptorelin pamoate, TSE-424, uracil mustard, valproic acid, valrubicin, vandetanib, vatalanib, VEGF trap, vinblastine, vincristine, vindesine, vinorelbine, vitaxin, vitespan, vorinostat, VX-745, wortmannin, Xr311, zanolimumab, ZK186619, ZK-304709, ZM336372, or ZSTK474.

Non-limiting examples of suitable anti-cancer agents to be used in combination with an antibody or antigen-binding fragment thereof provided herein include cytostatic agents, cytotoxic agents, targeted therapeutic agents (small molecules, biologics, siRNA and microRNA) against cancer and neoplastic diseases. In one embodiment, the agent is an anti-metabolites (such as methoxtrexate, 5-fluorouracil, gemcitabine, fludarabine, capecitabine). In one embodiment, the agent is an alkylating agents, such as temozolomide or cyclophosphamide. In one embodiment, the agent is a DNA interactive or DNA damaging agents, such as cisplatin, oxaliplatin, or doxorubicin. In one embodiment, the agent is ionizing irradiation, such as radiation therapy. In one embodiment, the agent is a topoisomerase II inhibitor, such as etoposide or doxorubicin/In one embodiment, the agent is a topoisomerase I inhibitor, such as irinotecan or topotecan In one embodiment, the agent is a tubulin interacting agent, such as paclitaxel, docetaxel, Abraxaner or epothilones. In one embodiment, the agent is a kinesin spindle protein inhibitor. In one embodiment, the agent is a spindle checkpoint inhibitor. In one embodiment, the agent is a Poly (ADP-ribose) polymerase (PARP) inhibitor, such as olaparib, niraparib or veliparib. In one embodiment, the agent is a matrix metalloprotease (MMP) inhibitor. In one embodiment, the agent is a rotease inhibitor, such as cathepsin D or cathepsin K inhibitors. In one embodiment, the agent is a proteosome or ubiquitination inhibitors, such as bortezomib. In one embodiment, the agent is an ctivator of mutant p53 to restore its wild-type p53 activity. In one embodiment, the agent is an adenoviral-p53. In one embodiment, the agent is aBcl-2 inhibitor, such as ABT-263. In one embodiment, the agent is a heat shock protein (HSP) modulators, such as geldanamycin and 17-AAG. In one embodiment, the agent is a istone deacetylase (HDAC) inhibitors, such as vorinostat (SAHA). In one embodiment, the agent is a sex hormone modulating agent. In one embodiment, the agent is an anti-estrogen, such as tamoxifen or fulvestrant. In one embodiment, the agent is a selective estrogen receptor modulators (SERM), such as raloxifene. In one embodiment, the agent is an anti-androgen, such as bicalutamide or flutamide. In one embodiment, the agent is a LHRH agonist, such as leuprolide. In one embodiment, the agent is a 5α-reductase inhibitors, such as finasteride. In one embodiment, the agent is a cytochrome P450 C17 lyase (CYP450c17, also called 17αC). In one embodiment, the agent is an aromatase inhibitor, such as letrozole, anastrozole or exemestane. In one embodiment, the agent is an EGFR kinase inhibitor, such as geftinib, erlotinib or laptinib. In one embodiment, the agent is a dual erbB1 and erbB2 inhibitors, such as lapatinib. In one embodiment, the agent is a multi-targeted kinase (serine/threonine and/or tyrosine kinase) inhibitor. In one embodiment, the agent is an ABL kinase inhibitors, such as imatinib and nilotinib or dasatinib. In one embodiment, the agent is a VEGFR-1, VEGFR-2, PDGFR, KDR, FLT, c-Kit, Tie2, Raf, MEK or ERK inhibitor, such as sunitinib, sorafenib, vandetanib, pazopanib, PLX-4032, Axitinib, PTK787 or GSK-1120212. In one embodiment, the agent is a polo-like kinase inhibitor. In one embodiment, the agent is an aurora kinase inhibitor. In one embodiment, the agent is a JAK inhibitor. In one embodiment, the agent is a c-MET kinase inhibitor. In one embodiment, the agent is a PI3K or mTOR inhibitors, such as GDC-0941, BEZ-235, BKM-120 or AZD-8055. In one embodiment, the agent is rapamycin or a rapamycin analog, such as temsirolimus, everolimus, or deforolimus. In one embodiment, the agent is a STING (Stimulator of Interferon Genes) agonist. In one embodiment, the agent is a CXCR (CXC Chemokine Receptor) inhibitor, CXCR2 antagonist.

Other anti-cancer (also known as anti-neoplastic) agents include but are not limited to ara-C, adriamycin, cytoxan, Carboplatin, Uracil mustard, Clormethine, Ifosfsmide, Melphalan, Chlorambucil, Pipobroman, Triethylenemelamine, Triethylenethiophoramine, Busulfan, Carmustine, Lomustine, Streptozocin, Dacarbazine, Floxuridine, Cytarabine, 6-Mercaptopurine, 6-Thioguanine, Fludarabine phosphate, Pentostatine, Vinblastine, Vincristine, Vindesine, Vinorelbine, Navelbine, Bleomycin, Dactinomycin, Daunorubicin, Doxorubicin, Epirubicin, teniposide, cytarabine, pemetrexed, Idarubicin, Mithramycin, Deoxycoformycin, Mitomycin-C, L-Asparaginase, Teniposide, Ethinylestradiol, Diethylstilbestrol, Testosterone, Prednisone, Fluoxymesterone, Dromostanolone propionate, Testolactone, Megestrolacetate, Methylprednisolone, Methyltestosterone, Prednisolone, Triamcinolone, Chlorotrianisene, Hydroxyprogesterone, Aminoglutethimide, Estramustine, Flutamide Medroxyprogesteroneacetate, Toremifene, goserelin, Carboplatin, Hydroxyurea, Amsacrine, Procarbazine, Mitotane, Mitoxantrone, Levamisole, Drolloxafine, Hexamethylmelamine, Bexxar®, Zevalin®, Trisenox®, Profimer, Thiotepa, Altretamine, Doxil, Ontak, Depocyt, Aranesp, Neupogen®, Neulasta®, or Kepivance®. In one embodiment, the agent is a farnesyl protein transferase inhibitor, such as SARASAR™ (4-[2-[4-[(11R)-3,10-dibromo-8-chloro-6, 11-dihydro-5H-benzo[5,6]cyclohepta[1,2-b]pyridin-11-yl-]-1-piperidinyl]-2-oxoethyl]-piperidinecarboxamide, tipifarnib. In one embodiment, the agent is an interferon, such as Intron A or Peg-Intron. In one embodiment, the agent is an anti-erbB1 antibody, such as cetuximab or panitumumab. In one embodiment, the agent is an anti-erbB2 antibody, such as trastuzumab. In one embodiment, the agent is an anti-CD52 antibody, such as alemtuzumab. In one embodiment, the agent is an anti-CD20 antibody, such as rituximab. In one embodiment, the agent is anti-CD33 antibody, such as gemtuzumab ozogamicin. In one embodiment, the agent is an anti-VEGF antibody, such as AVASTIN. In one embodiment, the agent is a TRIAL ligand, such as lexatumumab, mapatumumab, or AMG-655. In one embodiment, the agent is an anti-CTLA-4 antibody, such as ipilimumab. In one embodiment, the agent is an antibody against any of CTA1, CEA, CD5, CD19, CD22, CD30, CD44, CD44V6, CD55, CD56, EpCAM, FAP, MHCII, HGF, IL-6, MUC1, PSMA, TALE, TAG-72, TRAILR, VEGFR, IGF-2, or FGF. In one embodiment, the agent is an anti-IGF-1R antibodies, such as dalotuzumab (MK-0646) or robatumumab (SCH 717454).

"Estrogen receptor modulators" refers to compounds that interfere with or inhibit the binding of estrogen to the receptor, regardless of mechanism. Examples of estrogen receptor modulators include, but are not limited to, tamoxifen, raloxifene, idoxifene, LY353381, LY117081, toremifene, fulvestrant, 4-[7-(2,2-dimethyl-1-oxopropoxy-4-methyl-2-[4-[2-(1-piperidinyl)ethoxy]phenyl]-2H-1-benzopyran-3-yl]-phenyl-2,2-dimethylpropanoate, 4,4'-dihydroxybenzophenone-2,4-dinitrophenyl-hydrazone, and SH646.

"Androgen receptor modulators" refers to compounds which interfere or inhibit the binding of androgens to the receptor, regardless of mechanism. Examples of androgen receptor modulators include finasteride and other 5α-reductase inhibitors, nilutamide, flutamide, bicalutamide, liarozole, and abiraterone acetate.

"Retinoid receptor modulators" refers to compounds which interfere or inhibit the binding of retinoids to the receptor, regardless of mechanism. Examples of such retinoid receptor modulators include bexarotene, tretinoin, 13-cis-retinoic acid, 9-cis-retinoic acid, α-difluoromethylornithine, ILX23-7553, trans-N-(4'-hydroxyphenyl) retinamide, and N-4-carboxyphenyl retinamide.

"Cytotoxic/cytostatic agents" refer to compounds which cause cell death or inhibit cell proliferation primarily by interfering directly with the cell's functioning or inhibit or interfere with cell myosis, including alkylating agents, tumor necrosis factors, intercalators, hypoxia activatable compounds, microtubule inhibitors/microtubule-stabilizing agents, inhibitors of mitotic kinesins, histone deacetylase inhibitors, inhibitors of kinases involved in mitotic progression, inhibitors of kinases involved in growth factor and cytokine signal transduction pathways, antimetabolites, biological response modifiers, hormonal/anti-hormonal therapeutic agents, haematopoietic growth factors, monoclonal antibody targeted therapeutic agents, topoisomerase inhibitors, proteosome inhibitors, ubiquitin ligase inhibitors, and aurora kinase inhibitors.

Examples of cytotoxic/cytostatic agents include, but are not limited to, platinum coordinator compounds, sertenef, cachectin, ifosfamide, tasonermin, lonidamine, carboplatin, altretamine, prednimustine, dibromodulcitol, ranimustine, fotemustine, nedaplatin, oxaliplatin, temozolomide, heptaplatin, estramustine, improsulfan tosilate, trofosfamide, nimustine, dibrospidium chloride, pumitepa, lobaplatin, satraplatin, profiromycin, cisplatin, irofulven, dexifosfamide, cis-aminedichloro(2-methyl-pyridine)platinum, benzylguanine, glufosfamide, GPX100, (trans, trans, trans)-bis-mu-(hexane-1,6-diamine)-mu-[diamine-platinum(II)]bis [diamine(chloro)platinum (II)]tetrachloride, diarizidinylspermine, arsenic trioxide, 1-(11-dodecylamino-10-hydroxyundecyl)-3,7-dimethylxanthine, zorubicin, idarubicin, daunorubicin, bisantrene, mitoxantrone, pirarubicin, pinafide, valrubicin, amrubicin, antineoplaston, 3'-deamino-3'-morpholino-13-deoxo-10-hydroxycarminomycin, annamycin, galarubicin, elinafide, MEN10755, 4-demethoxy-3-deamino-3-aziridinyl-4-methylsulphonyl-daunorubicin (see WO 00/50032).

An example of a hypoxia activatable compound is tirapazamine.

Examples of proteosome inhibitors include but are not limited to lactacystin and MLN-341 (Velcade).

Examples of microtubule inhibitors/microtubule-stabilising agents include taxanes in general. Specific compounds include paclitaxel (Taxol®), vindesine sulfate, 3',4'-didehydro-4'-deoxy-8'-norvincaleukoblastine, docetaxol (Taxotere®), rhizoxin, dolastatin, mivobulin isethionate, auristatin, cemadotin, RPR109881, BMS184476, vinflunine, cryptophycin, 2,3,4,5,6-pentafluoro-N-(3-fluoro-4-methoxyphenyl) benzene sulfonamide, anhydrovinblastine, N,N-dimethyl-L-valyl-L-valyl-N-methyl-L-valyl-L-prolyl-L-proline-t-butylamide, ("L-valyl-L-valyl-N-methyl-L-valyl-L-prolyl-L-proline" disclosed as SEQ ID NO: 128), TDX258, the epothilones (see for example U.S. Pat. Nos. 6,284,781 and 6,288,237) and BMS188797.

Some examples of topoisomerase inhibitors are topotecan, hycaptamine, irinotecan, rubitecan, 6-ethoxypropionyl-3',4'-O-exo-benzylidene-chartreusin, 9-methoxy-N,N-dimethyl-5-nitropyrazolo[3,4,5-kl]acridine-2-(6H) propanamine, 1-amino-9-ethyl-5-fluoro-2,3-dihydro-9-hydroxy-4-methyl-1H,12H-benzo[de]pyrano[3',4':b,7]-indolizino[1,2b]quinoline-10,13(9H,15H)dione, lurtotecan, 7-[2-(N-isopropylamino)ethyl]-(20S)camptothecin, BNP1350, BNPI1100, BN80915, BN80942, etoposide phosphate, teniposide, sobuzoxane, 2'-dimethylamino-2'-deoxy-etoposide, GL331, N-[2-(dimethylamino)ethyl]-9-hydroxy-5,6-dimethyl-6H-pyrido[4,3-b]carbazole-1-carboxamide, asulacrine, (5a, 5aB, 8aa,9b)-9-[2-[N-[2-(dimethylamino)ethyl]-N-methylamino]ethyl]-5-[4-hydroxy-3,5-dimethoxyphenyl]-5,5a,6,8,8a,9-hexohydrofuro(3',4':6,7)naphtho(2,3-d)-1,3-dioxol-6-one, 2,3-(methylenedioxy)-5-methyl-7-hydroxy-8-methoxybenzo[c]-phenanthridinium, 6,9-bis[(2-aminoethyl)amino]benzo[g]isoquinoline-5,10-dione, 5-(3-aminopropylamino)-7,10-dihydroxy-2-(2-hydroxyethylaminomethyl)-6H-pyrazolo[4,5,1-de]acridin-6-one, N-[1-[2(diethylamino) ethylamino]-7-methoxy-9-oxo-9H-thioxanthen-4-ylmethyl] formamide, N-(2-(dimethylamino)ethyl)acridine-4-carboxamide, 6-[[2-(dimethylamino)ethyl]amino]-3-hydroxy-7H-indeno[2,1-c] quinolin-7-one, and dimesna.

Examples of inhibitors of mitotic kinesins, and in particular the human mitotic kinesin KSP, are described in Publications WO03/039460, WO03/050064, WO03/050122, WO03/049527, WO03/049679, WO03/049678, WO04/039774, WO03/079973, WO03/099211, WO03/105855, WO03/106417, WO04/037171, WO04/058148, WO04/058700, WO04/126699, WO05/018638, WO05/019206, WO05/019205, WO05/018547, WO05/017190, US2005/0176776. In an embodiment inhibitors of mitotic kinesins include, but are not limited to inhibitors of KSP, inhibitors of MKLP1, inhibitors of CENP-E, inhibitors of MCAK and inhibitors of Rab6-KIFL.

Examples of "histone deacetylase inhibitors" include, but are not limited to, SAHA, TSA, oxamflatin, PXD101, MG98 and scriptaid. Further reference to other histone deacetylase inhibitors can be found in the following manuscript; Miller, T. A. et al. *J. Med. Chem.* 46(24):5097-5116 (2003).

"Inhibitors of kinases involved in mitotic progression" include, but are not limited to, inhibitors of aurora kinase, inhibitors of Polo-like kinases (PLK; in particular inhibitors of PLK-1), inhibitors of bub-1 and inhibitors of bub-R1. An example of an "aurora kinase inhibitor" is VX-680.

"Antiproliferative agents" includes antisense RNA and DNA oligonucleotides such as G3139, ODN698, RVASK-RAS, GEM231, and INX3001, and antimetabolites such as enocitabine, carmofur, tegafur, pentostatin, doxifluridine, trimetrexate, fludarabine, capecitabine, galocitabine, cytarabine ocfosfate, fosteabine sodium hydrate, raltitrexed, paltitrexid, emitefur, tiazofurin, decitabine, nolatrexed, pemetrexed, nelzarabine, 2'-deoxy-2'-methylidenecytidine, 2'-fluoromethylene-2'-deoxycytidine, N-[5-(2,3-dihydrobenzofuryl)sulfonyl]-N'-(3,4-dichlorophenyl)urea, N6-[4-deoxy-4-[N2-[2(E),4(E)-tetradecadienoyl]glycylamino]-L-glycero-B-L-manno-heptopyranosyl]adenine, aplidine, ecteinascidin, troxacitabine, 4-[2-amino-4-oxo-4,6,7,8-tetrahydro-3H-pyrimidino[5,4-b][1,4]thiazin-6-yl-(S)-ethyl]-2,5-thienoyl-L-glutamic acid, aminopterin, 5-flurouracil, alanosine, 11-acetyl-8-(carbamoyloxymethyl)-4-formyl-6-methoxy-14-oxa-1,11-diazatetracyclo(7.4.1.0.0)-tetradeca-2,4,6-trien-9-yl acetic acid ester, swainsonine, lometrexol, dexrazoxane, methioninase, 2'-cyano-2'-deoxy-N4-palmitoyl-1-B-D-arabino furanosyl cytosine, 3-aminopyridine-2-carboxaldehyde thiosemicarbazone and trastuzumab.

Examples of monoclonal antibody targeted therapeutic agents include those therapeutic agents which have cytotoxic agents or radioisotopes attached to a cancer cell specific or target cell specific monoclonal antibody. Examples include Bexxar.

"Prenyl-protein transferase inhibitor" refers to a compound which inhibits any one or any combination of the prenyl-protein transferase enzymes, including farnesyl-protein transferase (FPTase), geranylgeranyl-protein transferase type I (GGPTase-I), and geranylgeranyl-protein transferase type-II (GGPTase-II, also called Rab GGPTase).

Examples of prenyl-protein transferase inhibitors can be found in the following publications and patents: WO 96/30343, WO 97/18813, WO 97/21701, WO 97/23478, WO 97/38665, WO 98/28980, WO 98/29119, WO 95/32987, U.S. Pat. Nos. 5,420,245, 5,523,430, 5,532,359, 5,510,510, 5,589,485, 5,602,098, European Patent Publ. 0 618 221, European Patent Publ. 0 675 112, European Patent Publ. 0 604 181, European Patent Publ. 0 696 593, WO 94/19357, WO 95/08542, WO 95/11917, WO 95/12612, WO 95/12572, WO 95/10514, U.S. Pat. No. 5,661,152, WO 95/10515, WO 95/10516, WO 95/24612, WO 95/34535, WO 95/25086, WO 96/05529, WO 96/06138, WO 96/06193, WO 96/16443, WO 96/21701, WO 96/21456, WO 96/22278, WO 96/24611, WO 96/24612, WO 96/05168, WO 96/05169, WO 96/00736, U.S. Pat. No. 5,571,792, WO 96/17861, WO 96/33159, WO 96/34850, WO 96/34851, WO 96/30017, WO 96/30018, WO 96/30362, WO 96/30363, WO 96/31111, WO 96/31477, WO 96/31478, WO 96/31501, WO 97/00252, WO 97/03047, WO 97/03050, WO 97/04785, WO 97/02920, WO 97/17070, WO 97/23478, WO 97/26246, WO 97/30053, WO 97/44350, WO 98/02436, and U.S. Pat. No. 5,532,359. For an example of the role of a prenyl-protein transferase inhibitor on angiogenesis see *European J. of Cancer, Vol.* 35, No. 9, pp. 1394-1401 (1999).

"Angiogenesis inhibitors" refers to compounds that inhibit the formation of new blood vessels, regardless of mechanism. Examples of angiogenesis inhibitors include, but are not limited to, tyrosine kinase inhibitors, such as inhibitors of the tyrosine kinase receptors Flt-1 (VEGFR1) and Flk-1/KDR (VEGFR2), inhibitors of epidermal-derived, fibroblast-derived, or platelet derived growth factors, MMP (matrix metalloprotease) inhibitors, integrin blockers, interferon-α, interleukin-12, pentosan polysulfate, cyclooxygenase inhibitors, including nonsteroidal anti-inflammatories (NSAIDs) like aspirin and ibuprofen as well as selective cyclooxy-genase-2 inhibitors like celecoxib and rofecoxib (*PNAS*, Vol. 89, p. 7384 (1992); *JNCI*, Vol. 69, p. 475 (1982); *Arch. Opthalmol.*, Vol. 108, p. 573 (1990); *Anat. Rec.*, Vol. 238, p. 68 (1994); *FEBS Letters*, Vol. 372, p. 83 (1995); *Clin, Orthop.* Vol. 313, p. 76 (1995); *J. Mol. Endocrinol.*, Vol. 16, p. 107 (1996); *Jpn. J Pharmacol.*, Vol. 75, p. 105 (1997); *Cancer Res.*, Vol. 57, p. 1625 (1997); *Cell,* Vol. 93, p. 705 (1998); *Intl. J. Mol. Med.*, Vol. 2, p. 715 (1998); *J. Biol. Chem.*, Vol. 274, p. 9116 (1999)), steroidal anti-inflammatories (such as corticosteroids, mineralocorticoids, dexamethasone, prednisone, prednisolone, methylpred, betamethasone), carboxyamidotriazole, combretastatin A-4, squalamine, 6-O-chloroacetyl-carbonyl)-fumagillol, thalidomide, angiostatin, troponin-1, angiotensin II antagonists (see Fernandez et al., *J. Lab. Clin. Med.* 105:141-145 (1985)), and antibodies to VEGF (see, *Nature Biotechnology*, Vol. 17, pp. 963-968 (October 1999); Kim et al., *Nature,* 362, 841-844 (1993); WO 00/44777; and WO 00/61186).

Other examples of angiogenesis inhibitors include, but are not limited to, endostatin, ukrain, ranpirnase, IM862, 5-methoxy-4-[2-methyl-3-(3-methyl-2-butenyl)oxiranyl]-1-oxaspiro[2,5]oct-6-yl(chloroacetyl)carbamate, acetyldinanaline, 5-amino-1-[[3,5-dichloro-4-(4-chlorobenzoyl) phenyl]methyl]-1H-1,2,3-triazole-4-carboxamide, CM101, squalamine, combretastatin, RPI4610, NX31838, sulfated mannopentaose phosphate, 7,7-(carbonyl-bis[imino-N-methyl-4,2-pyrrolocarbonylimino[N-methyl-4,2-pyrrole]-carbonylimino]-bis-(1,3-naphthalene disulfonate), and 3-[(2,4-dimethylpyrrol-5-yl)methylene]-2-indolinone (SU5416).

Other therapeutic agents that modulate or inhibit angiogenesis and can also be used in combination with the compounds provided herein include agents that modulate or inhibit the coagulation and fibrinolysis systems (see review in Clin. Chem. La. Med. 38:679-692 (2000)). Examples of such agents that modulate or inhibit the coagulation and fibrinolysis pathways include, but are not limited to, heparin (see Thromb. Haemost. 80:10-23 (1998)), low molecular weight heparins and carboxypeptidase U inhibitors (also known as inhibitors of active thrombin activatable fibrinolysis inhibitor [TAFIa]) (see Thrombosis Res. 101:329-354 (2001)). TAFIa inhibitors have been described in U.S. Ser. Nos. 60/310,927 (filed Aug. 8, 2001) and 60/349,925 (filed Jan. 18, 2002).

"Agents that interfere with receptor tyrosine kinases (RTKs)" refer to compounds that inhibit RTKs and therefore mechanisms involved in oncogenesis and tumor progression. Such agents include inhibitors of c-Kit, Eph, PDGF, Flt3 and c-Met. Further agents include inhibitors of RTKs as described by Bume-Jensen and Hunter, Nature, 411:355-365, 2001.

"Inhibitors of cell proliferation and survival signalling pathway" refer to compounds that inhibit signal transduction cascades downstream of cell surface receptors. Such agents include inhibitors of serine/threonine kinases (including but not limited to inhibitors of Akt such as described in WO 02/083064, WO 02/083139, WO 02/083140, US 2004-0116432, WO 02/083138, US 2004-0102360, WO 03/086404, WO 03/086279, WO 03/086394, WO 03/084473, WO 03/086403, WO 2004/041162, WO 2004/096131, WO 2004/096129, WO 2004/096135, WO 2004/096130, WO 2005/100356, WO 2005/100344, US 2005/029941, US 2005/44294, US 2005/43361, 60/734188, 60/652737, 60/670469), inhibitors of Raf kinase (for example PLX-4032), inhibitors of MEK (for example Array-162, RO-4987655 and GSK-1120212), inhibitors of mTOR (for example AZD-8055, BEZ-235 and everolimus), and inhibitors of PI3K (for example GDC-0941, BKM-120).

As used above, "integrin blockers" refers to compounds which selectively antagonize, inhibit or counteract binding of a physiological ligand to the $\alpha_v\beta_3$ integrin, to compounds which selectively antagonize, inhibit or counteract binding of a physiological ligand to the $\alpha v\beta 5$ integrin, to compounds which antagonize, inhibit or counteract binding of a physiological ligand to both the $\alpha v\beta 3$ integrin and the $\alpha v\beta 5$ integrin, and to compounds which antagonize, inhibit or counteract the activity of the particular integrin(s) expressed on capillary endothelial cells. The term also refers to antagonists of the $\alpha v\beta 6$, $\alpha v\beta 8$, $\alpha 1\beta 1$, $\alpha 2\beta 1$, $\alpha 5\beta 1$, $\alpha 6\beta 1$ and $\alpha 6\beta 4$ integrins. The term also refers to antagonists of any combination of $\alpha v\beta 3$, $\alpha v\beta 5$, $\alpha v\beta 6$, $\alpha v\beta 8$, $\alpha 1\beta 1$, $\alpha 2\beta 1$, $\alpha 5\beta 1$, $\alpha 6\beta 1$ and $\alpha 6\beta 4$ integrins.

Some specific examples of tyrosine kinase inhibitors include N-(trifluoromethylphenyl)-5-methylisoxazol-4-carboxamide, 3-[(2,4-dimethylpyrrol-5-yl)methylidenyl]indolin-2-one, 17-(allylamino)-17-demethoxygeldanamycin, 4-(3-chloro-4-fluorophenylamino)-7-methoxy-6-[3-(4-morpholinyl)propoxyl]quinazoline, N-(3-ethynylphenyl)-6,7-bis(2-methoxyethoxy)-4-quinazolinamine, BIBX1382, 2,3,9,10,11,12-hexahydro-10-(hydroxymethyl)-10-hydroxy-9-methyl-9,12-epoxy-1H-diindolo[1,2,3-fg:3',2',1'-kl]pyrrolo[3,4-i][1,6]benzodiazocin-1-one, SH268, genistein, STI571, CEP2563, 4-(3-chlorophenylamino)-5,6-dimethyl-7H-pyrrolo[2,3-d]pyrimidinemethane sulfonate, 4-(3-bromo-4-hydroxyphenyl)amino-6,7-dimethoxyquinazoline, 4-(4'-hydroxyphenyl)amino-6,7-dimethoxyquinazoline, SU6668, STI571A, N-4-chlorophenyl-4-(4-pyridylmethyl)-1-phthalazinamine, and EMD121974.

Combinations of the instantly claimed antibodies or antigen-binding fragments with PPAR-γ (i.e., PPAR-gamma) agonists and PPAR-δ (i.e., PPAR-delta) agonists can be useful in the treatment of certain malignancies. PPAR-γ and PPAR-δ are the nuclear peroxisome proliferator-activated receptors γ and δ. The expression of PPAR-γ on endothelial cells and its involvement in angiogenesis has been reported in the literature (see J. Cardiovasc. Pharmacol. 1998; 31:909-913; J. Biol. Chem. 1999; 274:9116-9121; Invest. Ophthalmol Vis. Sci. 2000; 41:2309-2317). More recently, PPAR-γ agonists have been shown to inhibit the angiogenic response to VEGF in vitro; both troglitazone and rosiglitazone maleate inhibit the development of retinal neovascularization in mice. (Arch. Ophthamol. 2001; 119:709-717). Examples of PPAR-γ agonists and PPAR-γ/α agonists include, but are not limited to, Lynparza®, Rucaparib®, Talazoparib®, niraparib, Veliparib®, thiazolidinediones (such as DRF2725, CS-011, troglitazone, rosiglitazone, and pioglitazone), fenofibrate, gemfibrozil, clofibrate, GW2570, SB219994, AR-H039242, JTT-501, MCC-555, GW2331, GW409544, NN2344, KRP297, NP0110, DRF4158, NN622, GI262570, PNU182716, DRF552926, 2-[(5,7-dipropyl-3-trifluoromethyl-1,2-benzisoxazol-6-yl)oxy]-2-methylpropionic acid, and 2(R)-7-(3-(2-chloro-4-(4-fluorophenoxy) phenoxy)propoxy)-2-ethylchromane-2-carboxylic acid.

The antibodies or antigen-binding fragments thereof provided herein can also be useful for treating or preventing breast cancer in combination with aromatase inhibitors. Examples of aromatase inhibitors include but are not limited to: anastrozole, letrozole and exemestane.

The antibodies or antigen-binding fragments thereof provided herein can also be useful for treating cancer in combination with the following chemotherapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexalen®); amifostine (Ethyol®); anastrozole (Arimidex®); arsenic trioxide (Trisenox®); asparaginase (Elspar®); azacitidine (Vidaza®); bendamustine hydrochloride (Treanda®); bevacuzimab (Avastin®); bexarotene capsules (Targretin®); bexarotene gel (Targretin®); bleomycin (Blenoxane®); bortezomib (Velcade®); brefeldin A; busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); dalteparin sodium injection (Fragmin®); Darbepoetin alfa (Aranesp®); dasatinib (Sprycel®); daunorubicin liposomal (DanuoXome®); daunorubicin, daunomycin (Daunorubicin®); daunorubicin, daunomycin (Cerubidine®); degarelix (Firmagon®); Denileukin diftitox (Ontak®); dexrazoxane (Zinecard®); dexrazoxane hydrochloride (Totect®);

didemnin B; 17-DMAG; docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); eculizumab injection (Soliris®); Elliott's B Solution (Elliott's B Solution®); eltrombopag (Promacta®); epirubicin (Ellence®); Epoetin alfa (Epogen®); erlotinib (Tarceva®); estramustine (Emcyt®); ethinyl estradiol; etoposide phosphate (Etopophos®); etoposide, VP-16 (Vepesid®); everolimus tablets (Afinitor®); exemestane (Aromasin®); ferumoxytol (Feraheme Injection®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); geldanamycin; gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); iobenguane I 123 injection (AdreView®); irinotecan (Camptosar®); ixabepilone (Ixempra®); lapatinib tablets (Tykerb®); lenalidomide (Revlimid®); letrozole (Femara®); leucovorin (Wellcovorin®, Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); 8-methoxypsoralen; mitomycin C (Mutamycin®); mitotane (Lysodren®); mitoxantrone (Novantrone®); mitramycin; nandrolone phenpropionate (Durabolin-50®); nelarabine (Arranon®); nilotinib (Tasigna®); Nofetumomab (Verluma®); ofatumumab (Arzerra®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); panitumumab (Vectibix®); pazopanib tablets (Votrienttm®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plerixafor (Mozobil®); plicamycin, mithramycin (Mithracin®); porfimer sodium (Photofrin®); pralatrexate injection (Folotyn®); procarbazine (Matulane®); quinacrine (Atabrine®); rapamycin; Rasburicase (Elitek®); raloxifene hydrochloride (Evista®); Rituximab (Rituxan®); romidepsin (Istodax®); romiplostim (Nplate®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); temsirolimus (Torisel®); teniposide, VM-26 (Vumon®); testolactone (Teslac®); thioguanine, 6-TG (Thioguanine®); thiopurine; thiotepa (Thioplex®); topotecan (Hycamtin®); toremifene (Fareston®); Tositumomab (Bexxar®); Tositumomab/I-131 tositumomab (Bexxar®); trans-retinoic acid; Trastuzumab (Herceptin®); tretinoin, ATRA (Vesanoid®); triethylenemelamine; Uracil Mustard (Uracil Mustard Capsules®); valrubicin (Valstar®); vinblastine (Velban®); vincristine (Oncovin®); vinorelbine (Navelbine®); vorinostat (Zolinza®); wortmannin; and zoledronate (Zometa®).

In an embodiment, an antibody or antigen-binding fragment thereof provided herein is used in association with one or more antiemetics including, but not limited to: casopitant (GlaxoSmithKline), Netupitant (MGI-Helsinn) and other NK-1 receptor antagonists, palonosetron (sold as Aloxi by MGI Pharma), aprepitant (sold as Emend by Merck and Co.; Rahway, N.J.), diphenhydramine (sold as Benadryl® by Pfizer; New York, N.Y.), hydroxyzine (sold as Atarax® by Pfizer; New York, N.Y.), metoclopramide (sold as Reglan® by AH Robins Co.; Richmond, Va.), lorazepam (sold as Ativan® by Wyeth; Madison, N.J.), alprazolam (sold as Xanax® by Pfizer; New York, N.Y.), haloperidol (sold as Haldol® by Ortho-McNeil; Raritan, N.J.), droperidol (Inapsine®), dronabinol (sold as Marinol® by Solvay Pharmaceuticals, Inc.; Marietta, Ga.), dexamethasone (sold as Decadron® by Merck and Co.; Rahway, N.J.), methylprednisolone (sold as Medrol® by Pfizer; New York, N.Y.), prochlorperazine (sold as Compazine® by Glaxosmithkline; Research Triangle Park, N.C.), granisetron (sold as Kytril® by Hoffmann-La Roche Inc.; Nutley, N.J.), ondansetron (sold as Zofran® by Glaxosmithkline; Research Triangle Park, N.C.), dolasetron (sold as Anzemet® by Sanofi-Aventis; New York, N.Y.), tropisetron (sold as Navoban® by Novartis; East Hanover, N.J.).

Other side effects of cancer treatment include red and white blood cell deficiency. Accordingly, in an embodiment, an antibody or antigen-binding fragment thereof is in association with an agent which treats or prevents such a deficiency, such as, e.g., filgrastim, PEG-filgrastim, erythropoietin, epoetin alfa or darbepoetin alfa.

In an embodiment, an antibody or antigen-binding fragment thereof provided herein is administered in association with anti-cancer radiation therapy. For example, in an embodiment, the radiation therapy is external beam therapy (EBT): a method for delivering a beam of high-energy X-rays to the location of the tumor. The beam is generated outside the patient (e.g., by a linear accelerator) and is targeted at the tumor site. These X-rays can destroy the cancer cells and careful treatment planning allows the surrounding normal tissues to be spared. No radioactive sources are placed inside the patient's body. In an embodiment, the radiation therapy is proton beam therapy: a type of conformal therapy that bombards the diseased tissue with protons instead of X-rays. In an embodiment, the radiation therapy is conformal external beam radiation therapy: a procedure that uses advanced technology to tailor the radiation therapy to an individual's body structures. In an embodiment, the radiation therapy is brachytherapy: the temporary placement of radioactive materials within the body, usually employed to give an extra dose—or boost—of radiation to an area.

In an embodiment, a surgical procedure is administered in association with an antibody or antigen-binding fragment thereof is surgical tumorectomy.

5.13 Pharmaceutical Compositions and Administration

To prepare pharmaceutical or sterile compositions of the antibodies and antigen-binding fragments provided herein, the antibody or antigen-binding fragment thereof can be admixed with a pharmaceutically acceptable carrier or excipient. See, e.g., *Remington's Pharmaceutical Sciences and U.S. Pharmacopeia: National Formulary*, Mack Publishing Company, Easton, Pa. (1984).

Formulations of therapeutic and diagnostic agents can be prepared by mixing with acceptable carriers, excipients, or stabilizers in the form of, e.g., lyophilized powders, slurries, aqueous solutions or suspensions (see, e.g., Hardman, et al. (2001) *Goodman and Gilman's The Pharmacological Basis of Therapeutics*, McGraw-Hill, New York, N.Y.; Gennaro (2000) *Remington: The Science and Practice of Pharmacy*, Lippincott, Williams, and Wilkins, New York, N.Y.; Avis, et al. (eds.) (1993) *Pharmaceutical Dosage Forms: Parenteral Medications*, Marcel Dekker, NY; Lieberman, et al. (eds.) (1990) *Pharmaceutical Dosage Forms: Tablets*, Marcel Dekker, NY; Lieberman, et al. (eds.) (1990) *Pharmaceutical Dosage Forms: Disperse Systems*, Marcel Dekker, NY; Weiner and Kotkoskie (2000) *Excipient Toxicity and Safety*, Marcel Dekker, Inc., New York, N.Y.).

Toxicity and therapeutic efficacy of the antibodies provided herein, administered alone or in combination with another therapeutic agent, can be determined by standard pharmaceutical procedures in cell cultures or experimental animals, e.g., for determining the $LD_{50}$ (the dose lethal to 50% of the population) and the $ED_{50}$ (the dose therapeutically effective in 50% of the population). The dose ratio between toxic and therapeutic effects is the therapeutic index ($LD_{50}/ED_{50}$). The data obtained from these cell culture assays and animal studies can be used in formulating a range of dosage for use in human. The dosage of such compounds lies preferably within a range of circulating concentrations that include the $ED_{50}$ with little or no toxicity. The dosage can vary within this range depending upon the dosage form employed and the route of administration.

In a further embodiment, a further therapeutic agent that is administered to a subject in association with an antibody or antigen-binding fragment thereof provided herein in accordance with the *Physicians' Desk Reference* 2003 (Thomson Healthcare; 57th edition (Nov. 1, 2002)).

The mode of administration can vary. Routes of administration include oral, rectal, transmucosal, intestinal, parenteral; intramuscular, subcutaneous, intradermal, intramedullary, intrathecal, direct intraventricular, intravenous, intraperitoneal, intranasal, intraocular, inhalation, insufflation, topical, cutaneous, transdermal, or intra-arterial.

In particular embodiments, the antibodies or antigen-binding fragments thereof provided herein can be administered by an invasive route such as by injection. In further embodiments, an antibody or antigen-binding fragment thereof, or pharmaceutical composition thereof, is administered intravenously, subcutaneously, intramuscularly, intraarterially, intratumorally, or by inhalation, aerosol delivery. Administration by non-invasive routes (e.g., orally; for example, in a pill, capsule or tablet) are also contemplated.

Also provided is a vessel (e.g., a plastic or glass vial, e.g., with a cap or a chromatography column, hollow bore needle or a syringe cylinder) comprising any of the antibodies or antigen-binding fragments provided herein, or a pharmaceutical composition thereof. Also provided is an injection device comprising any of the antibodies or antigen-binding fragments provided herein or a pharmaceutical composition thereof. An injection device is a device that introduces a substance into the body of a patient via a parenteral route, e.g., intramuscular, subcutaneous or intravenous. For example, an injection device can be a syringe (e.g., pre-filled with the pharmaceutical composition, such as an auto-injector) which, for example, includes a cylinder or barrel for holding fluid to be injected (e.g., antibody or fragment or a pharmaceutical composition thereof), a needle for piercing skin and/or blood vessels for injection of the fluid; and a plunger for pushing the fluid out of the cylinder and through the needle bore. In an embodiment, an injection device that comprises a bispecific antibody or antigen-binding fragment thereof provided herein, or a pharmaceutical composition thereof, is an intravenous (IV) injection device. Such a device includes the antibody or fragment or a pharmaceutical composition thereof in a cannula or trocar/needle which can be attached to a tube which can be attached to a bag or reservoir for holding fluid (e.g., saline; or lactated ringer solution comprising NaCl, sodium lactate, KCl, $CaCl_2$) and optionally including glucose) introduced into the body of the patient through the cannula or trocar/needle. In some embodiments, the antibody or fragment or a pharmaceutical composition thereof is introduced into the device once the trocar and cannula are inserted into the vein of a subject, and the trocar is removed from the inserted cannula. The IV device may, for example, be inserted into a peripheral vein (e.g., in the hand or arm); the superior vena cava or inferior vena cava, or within the right atrium of the heart (e.g., a central IV); or into a subclavian, internal jugular, or a femoral vein and, for example, advanced toward the heart until it reaches the superior vena cava or right atrium (e.g., a central venous line). In an embodiment, an injection device is an autoinjector; a jet injector or an external infusion pump. A jet injector uses a high-pressure narrow jet of liquid which penetrate the epidermis to introduce the antibody or fragment or a pharmaceutical composition thereof to a patient's body. External infusion pumps are medical devices that deliver the antibody or fragment or a pharmaceutical composition thereof into a patient's body in controlled amounts. External infusion pumps can be powered electrically or mechanically. Different pumps operate in different ways, for example, a syringe pump holds fluid in the reservoir of a syringe, and a moveable piston controls fluid delivery, an elastomeric pump holds fluid in a stretchable balloon reservoir, and pressure from the elastic walls of the balloon drives fluid delivery. In a peristaltic pump, a set of rollers pinches down on a length of flexible tubing, pushing fluid forward. In a multi-channel pump, fluids can be delivered from multiple reservoirs at multiple rates.

The pharmaceutical compositions disclosed herein can also be administered with a needleless hypodermic injection device; such as the devices disclosed in U.S. Pat. Nos. 6,620,135; 6,096,002; 5,399,163; 5,383,851; 5,312,335; 5,064,413; 4,941,880; 4,790,824 or 4,596,556. Such needle-less devices comprising the pharmaceutical composition are also contemplated. The pharmaceutical compositions disclosed herein can also be administered by infusion. Examples of well-known implants and modules for administering the pharmaceutical compositions include those disclosed in: U.S. Pat. No. 4,487,603, which discloses an implantable micro-infusion pump for dispensing medication at a controlled rate; U.S. Pat. No. 4,447,233, which discloses a medication infusion pump for delivering medication at a precise infusion rate; U.S. Pat. No. 4,447,224, which discloses a variable flow implantable infusion apparatus for continuous drug delivery; U.S. Pat. No. 4,439,196, which discloses an osmotic drug delivery system having multi-chamber compartments. Many other such implants, delivery systems, and modules are well known to those skilled in the art and those comprising the pharmaceutical compositions provided herein are also contemplated.

The administration regimen depends on several factors, including the serum or tissue turnover rate of the therapeutic antibody or antigen-binding fragment, the level of symptoms, the immunogenicity of the therapeutic antibody, and the accessibility of the target cells in the biological matrix. Preferably, the administration regimen delivers sufficient therapeutic antibody or fragment to effect improvement in the target disease state, while simultaneously minimizing undesired side effects. Accordingly, the amount of biologic delivered depends in part on the particular therapeutic antibody and the severity of the condition being treated.

Guidance in selecting appropriate doses of therapeutic antibodies or fragments is available (see, e.g., Wawrzynczak (1996) *Antibody Therapy*, Bios Scientific Pub. Ltd, Oxfordshire, UK; Kresina (ed.) (1991) *Monoclonal Antibodies, Cytokines and Arthritis*, Marcel Dekker, New York, N.Y.; Bach (ed.) (1993) *Monoclonal Antibodies and Peptide Therapy in Autoimmune Diseases*, Marcel Dekker, New York, N.Y.; Baert, et al. (2003) *New Engl. J. Med.* 348:601-608; Milgrom et al. (1999) *New Engl. J. Med.* 341:1966-1973; Slamon et al. (2001) *New Engl. J. Med.* 344:783-792; Beniaminovitz et al. (2000) *New Engl. J. Med.* 342:613-619; Ghosh et al. (2003) *New Engl. J. Med.* 348:24-32; Lipsky et al. (2000) *New Engl. J. Med.* 343:1594-1602).

Determination of the appropriate dose is made by the clinician, e.g., using parameters or factors known or suspected in the art to affect treatment. Generally, the dose begins with an amount somewhat less than the optimum dose and it is increased by small increments thereafter until the desired or optimum effect is achieved relative to any negative side effects. Important diagnostic measures include those of symptoms of, e.g., the inflammation or level of inflammatory cytokines produced. In general, it is desirable that a biologic that will be used is derived from the same species as the animal targeted for treatment, thereby minimizing any immune response to the reagent. In the case of human subjects, for example, humanized and fully human antibodies can be desirable.

As used herein, the term "effective amount" refers to an amount of a bispecific antibody or antigen-binding fragment thereof provided herein that, when administered alone or in combination with an additional therapeutic agent to a cell, tissue, or subject, is effective to cause a measurable improvement in one or more symptoms of disease. When applied to an individual active ingredient administered alone, an effective dose refers to that ingredient alone. When applied to a combination, an effective dose refers to combined amounts of the active ingredients that result in the therapeutic effect, whether administered in combination, serially or simultaneously. An effective amount of a therapeutic will result in an improvement of a diagnostic measure or parameter by at least 10%; usually by at least 20%; preferably at least about 30%; more preferably at least 40%, and most preferably by at least 50%. An effective amount can also result in an improvement in a subjective measure in cases where subjective measures are used to assess disease severity.

5.14 Kits

Further provided are kits comprising one or more components that include, but are not limited to, an anti-PD-1 antibody or antigen-binding fragment, an anti-PD-1/LAG3 bispecific antibody or antigen-binding fragment, in association with one or more additional components including, but not limited to a pharmaceutically acceptable carrier and/or a therapeutic agent, as discussed herein. The antibody or fragment and/or the therapeutic agent can be formulated as a pure composition or in combination with a pharmaceutically acceptable carrier, in a pharmaceutical composition.

In one embodiment, the kit includes an antibody or antigen-binding fragment thereof provided herein, or a pharmaceutical composition thereof, in one container (e.g., in a sterile glass or plastic vial), and a pharmaceutical composition thereof and/or a therapeutic agent in another container (e.g., in a sterile glass or plastic vial).

In another embodiment, the kit comprises a combination, including an antibody or antigen-binding fragment thereof provided herein along with a pharmaceutically acceptable carrier, optionally in combination with one or more therapeutic agents formulated together, optionally, in a pharmaceutical composition, in a single, common container.

If the kit includes a pharmaceutical composition for parenteral administration to a subject, the kit can include a device for performing such administration. For example, the kit can include one or more hypodermic needles or other injection devices as discussed above.

The kit can include a package insert including information concerning the pharmaceutical compositions and dosage forms in the kit. Generally, such information aids patients and physicians in using the enclosed pharmaceutical compositions and dosage forms effectively and safely. For example, the following information regarding a combination of agents provided herein can be supplied in the insert: pharmacokinetics, pharmacodynamics, clinical studies, efficacy parameters, indications and usage, contraindications, warnings, precautions, adverse reactions, overdosage, proper dosage and administration, how supplied, proper storage conditions, references, manufacturer/distributor information and patent information.

As a matter of convenience, an antibody or antigen-binding fragment thereof can be provided in a kit, i.e., a packaged combination of reagents in predetermined amounts with instructions for performing the diagnostic or detection assay. Where the antibody or fragment is labeled with an enzyme, the kit can include substrates and cofactors required by the enzyme (e.g., a substrate precursor which provides the detectable chromophore or fluorophore). In addition, other additives can be included such as stabilizers, buffers (e.g., a block buffer or lysis buffer) and the like. The relative amounts of the various reagents can be varied widely to provide for concentrations in solution of the reagents which substantially optimize the sensitivity of the assay. Particularly, the reagents can be provided as dry powders, usually lyophilized, including excipients which on dissolution will provide a reagent solution having the appropriate concentration.

Also provided are diagnostic or detection reagents and kits comprising one or more such reagents for use in a variety of detection assays, including for example, immunoassays, such as enzyme-linked immunosorbant assay (ELISA) (sandwich-type or competitive format). The kit's components can be pre-attached to a solid support, or can be applied to the surface of a solid support when the kit is used. In some embodiments, the signal generating means can come pre-associated with an antibody or fragment provided herein or can require combination with one or more components, e.g., buffers, antibody-enzyme conjugates, enzyme substrates, or the like, prior to use. Kits can also include additional reagents, e.g., blocking reagents for reducing nonspecific binding to the solid phase surface, washing reagents, enzyme substrates, and the like. The solid phase surface can be in the form of a tube, a bead, a microtiter plate, a microsphere, or other materials suitable for immobilizing proteins, peptides, or polypeptides. In particular aspects, an enzyme that catalyzes the formation of a chemilluminescent or chromogenic product or the reduction of a chemilluminescent or chromogenic substrate is a component of the signal generating means. Such enzymes are well known in the art. Kits can comprise any of the capture agents and detection reagents described herein. Optionally, the kit can also comprise instructions for carrying out the methods provided herein.

Also provided is a kit comprising an anti-PD-1/LAG3 bispecific antibody or antigen-binding fragment thereof packaged in a container, such as a vial or bottle, and further comprising a label attached to or packaged with the container, the label describing the contents of the container and providing indications and/or instructions regarding use of the contents of the container to treat one or more disease states as described herein.

As discussed above in the combination therapy section, concurrent administration of two therapeutic agents does not require that the agents be administered at the same time or by the same route, as long as there is an overlap in the time period during which the agents are exerting their therapeutic effect. Simultaneous or sequential administration is contemplated, as is administration on different days or weeks.

The therapeutic and detection kits disclosed herein can also be prepared that comprise at least one of the antibody, peptide, antigen-binding fragment, or polynucleotide disclosed herein and instructions for using the composition as a detection reagent or therapeutic agent. Containers for use in such kits can comprise at least one vial, test tube, flask, bottle, syringe or other suitable container, into which one or more of the detection and/or therapeutic composition(s) can be placed, and preferably suitably aliquoted. Where a second therapeutic agent is also provided, the kit can also contain a second distinct container into which this second detection and/or therapeutic composition can be placed. Alternatively, a plurality of compounds can be prepared in a single pharmaceutical composition, and can be packaged in a single container means, such as a vial, flask, syringe, bottle, or other suitable single container. The kits disclosed herein will also typically include a means for containing the vial(s) in close confinement for commercial sale, such as, e.g., injection or blow-molded plastic containers into which the desired vial(s) are retained. Where a radiolabel, chromogenic, fluorigenic, or other type of detectable label or detecting means is included within the kit, the labeling agent can be provided either in the same container as the detection or therapeutic composition itself, or can alternatively be placed in a second distinct container means into which this second composition can be placed and suitably aliquoted. Alternatively, the detection reagent and the label can be prepared in a single container means, and in most cases, the kit will also typically include a means for containing the vial(s) in close confinement for commercial sale and/or convenient packaging and delivery.

A device or apparatus for carrying out the detection or monitoring methods described herein is also provided. Such an apparatus can include a chamber or tube into which sample can be input, a fluid handling system optionally including valves or pumps to direct flow of the sample through the device, optionally filters to separate plasma or serum from blood, mixing chambers for the addition of capture agents or detection reagents, and optionally a detection device for detecting the amount of detectable label bound to the capture agent immunocomplex. The flow of sample can be passive (e.g., by capillary, hydrostatic, or other forces that do not require further manipulation of the device once sample is applied) or active (e.g., by application of force generated via mechanical pumps, electroosmotic pumps, centrifugal force, or increased air pressure), or by a combination of active and passive forces.

In further embodiments, also provided is a processor, a computer readable memory, and a routine stored on the computer readable memory and adapted to be executed on the processor to perform any of the methods described herein. Examples of suitable computing systems, environments, and/or configurations include personal computers, server computers, hand-held or laptop devices, multiprocessor systems, microprocessor-based systems, set top boxes, programmable consumer electronics, network PCs, minicomputers, mainframe computers, distributed computing environments that include any of the above systems or devices, or any other systems known in the art.

5.15 General Methodology

Standard methods in molecular biology are described Sambrook, Fritsch and Maniatis (1982 & 1989 $2^{nd}$ Edition, 2001 $3^{rd}$ Edition) *Molecular Cloning, A Laboratory Manual*, Cold Spring Harbor Laboratory Press, Cold Spring Harbor, N.Y.; Sambrook and Russell (2001) *Molecular Cloning, $3^{rd}$ ed.*, Cold Spring Harbor Laboratory Press, Cold Spring Harbor, N.Y.; Wu (1993) *Recombinant DNA*, Vol. 217, Academic Press, San Diego, Calif.). Standard methods also appear in Ausbel, et al. (2001) *Current Protocols in Molecular Biology*, Vols. 1-4, John Wiley and Sons, Inc. New York, N.Y., which describes cloning in bacterial cells and DNA mutagenesis (Vol. 1), cloning in mammalian cells and yeast (Vol. 2), glycoconjugates and protein expression (Vol. 3), and bioinformatics (Vol. 4).

Methods for protein purification including immunoprecipitation, chromatography, electrophoresis, centrifugation, and crystallization are described (Coligan, et al. (2000) *Current Protocols in Protein Science*, Vol. 1, John Wiley and Sons, Inc., New York). Chemical analysis, chemical modification, post-translational modification, production of fusion proteins, glycosylation of proteins are described (see, e.g., Coligan, et al. (2000) *Current Protocols in Protein Science*, Vol. 2, John Wiley and Sons, Inc., New York; Ausubel, et al. (2001) *Current Protocols in Molecular Biology*, Vol. 3, John Wiley and Sons, Inc., NY, N.Y., pp. 16.0.5-16.22.17; Sigma-Aldrich, Co. (2001) *Products for Life Science Research*, St. Louis, Mo.; pp. 45-89; Amersham Pharmacia Biotech (2001) *BioDirectory*, Piscataway, N.J., pp. 384-391). Production, purification, and fragmentation of polyclonal and monoclonal antibodies are described (Coligan, et al. (2001) *Current Protcols in Immunology, Vol. 1*, John Wiley and Sons, Inc., New York; Harlow and Lane (1999) *Using Antibodies*, Cold Spring Harbor Laboratory Press, Cold Spring Harbor, N.Y.; Harlow and Lane, supra). Standard techniques for characterizing ligand/receptor interactions are available (see, e.g., Coligan, et al. (2001) *Current Protocols in Immunology*, Vol. 4, John Wiley, Inc., New York).

Monoclonal, polyclonal, and humanized antibodies can be prepared (see, e.g., Sheperd and Dean (eds.) (2000) *Monoclonal Antibodies*, Oxford Univ. Press, New York, N.Y.; Kontermann and Dubel (eds.) (2001) *Antibody Engineering*, Springer-Verlag, New York; Harlow and Lane (1988) *Antibodies A Laboratory Manual*, Cold Spring Harbor Laboratory Press, Cold Spring Harbor, N.Y., pp. 139-243; Carpenter, et al. (2000) *J. Immunol.* 165:6205; He, et al. (1998) *J. Immunol.* 160:1029; Tang et al. (1999) *J. Biol. Chem.* 274:27371-27378; Baca et al. (1997) *J. Biol. Chem.* 272:10678-10684; Chothia et al. (1989) *Nature* 342:877-883; Foote and Winter (1992) *J. Mol. Biol.* 224:487-499; U.S. Pat. No. 6,329,511).

Single chain antibodies and diabodies are described (see, e.g., Malecki et al. (2002) *Proc. Natl. Acad. Sci. USA* 99:213-218; Conrath et al. (2001) *J. Biol. Chem.* 276:7346-7350; Desmyter et al. (2001) *J. Biol. Chem.* 276:26285-26290; Hudson and Kortt (1999) *J. Immunol. Methods* 231:177-189; and U.S. Pat. No. 4,946,778). Bifunctional antibodies are provided (see, e.g., Mack, et al. (1995) *Proc. Natl. Acad. Sci. USA* 92:7021-7025; Carter (2001) *J. Immunol. Methods* 248:7-15; Volkel, et al. (2001) *Protein Engi-* neering 14:815-823; Segal, et al. (2001) *J. Immunol. Methods* 248:1-6; Brennan, et al. (1985) *Science* 229:81-83; Raso, et al. (1997) *J. Biol. Chem.* 272:27623; Morrison (1985) *Science* 229:1202-1207; Traunecker, et al. (1991) *EMBO J.* 10:3655-3659; and U.S. Pat. Nos. 5,932,448, 5,532,210, and 6,129,914).

Bispecific antibodies are also provided (see, e.g., Azzoni et al. (1998) *J. Immunol.* 161:3493; Kita et al. (1999) *J. Immunol.* 162:6901; Merchant et al. (2000) *J. Biol. Chem.* 74:9115; Pandey et al. (2000) *J. Biol. Chem.* 275:38633; Zheng et al. (2001) *J. Biol Chem.* 276:12999; Propst et al. (2000) *J. Immunol.* 165:2214; Long (1999) *Ann. Rev. Immunol.* 17:875).

Purification of antigen is not necessary for the generation of antibodies. Animals can be immunized with cells bearing the antigen of interest. Splenocytes can then be isolated from the immunized animals, and the splenocytes can fused with a myeloma cell line to produce a hybridoma (see, e.g., Meyaard et al. (1997) *Immunity* 7:283-290; Wright et al. (2000) *Immunity* 13:233-242; Preston et al., supra; Kaithamana et al. (1999) *J. Immunol.* 163:5157-5164).

Antibodies can be conjugated, e.g., to small drug molecules, enzymes, liposomes, polyethylene glycol (PEG). Antibodies are useful for therapeutic, diagnostic, kit or other purposes, and include antibodies coupled, e.g., to dyes, radioisotopes, enzymes, or metals, e.g., colloidal gold (see, e.g., Le Doussal et al. (1991) *J. Immunol.* 146:169-175; Gibellini et al. (1998) *J. Immunol.* 160:3891-3898; Hsing and Bishop (1999) *J. Immunol.* 162:2804-2811; Everts et al. (2002) *J. Immunol.* 168:883-889).

Methods for flow cytometry, including fluorescence activated cell sorting (FACS), are available (see, e.g., Owens, et al. (1994) *Flow Cytometry Principles for Clinical Laboratory Practice*, John Wiley and Sons, Hoboken, N.J.; Givan (2001) *Flow Cytometry, $2^{nd\ ed}$.*; Wiley-Liss, Hoboken, N.J.; Shapiro (2003) *Practical Flow Cytometry*, John Wiley and Sons, Hoboken, N.J.). Fluorescent reagents suitable for modifying nucleic acids, including nucleic acid primers and probes, polypeptides, and antibodies, for use, e.g., as diagnostic reagents, are available (Molecular Probes (2003) *Catalogue*, Molecular Probes, Inc., Eugene, Oreg.; Sigma-Aldrich (2003) *Catalogue*, St. Louis, Mo.).

Standard methods of histology of the immune system are described (see, e.g., Muller-Harmelink (ed.) (1986) *Human Thymus: Histopathology and Pathology*, Springer Verlag, New York, N.Y.; Hiatt, et al. (2000) *Color Atlas of Histology*, Lippincott, Williams, and Wilkins, Phila, Pa.; Louis, et al. (2002) *Basic Histology: Text and Atlas*, McGraw-Hill, New York, N.Y.).

Software packages and databases for determining, e.g., antigenic fragments, leader sequences, protein folding, functional domains, glycosylation sites, and sequence alignments, are available (see, e.g., GenBank, Vector NTI® Suite (Informax, Inc, Bethesda, Md.); GCG Wisconsin Package (Accelrys, Inc., San Diego, Calif.); DeCypher® (TimeLogic Corp., Crystal Bay, Nev.); Menne, et al. (2000) *Bioinformatics* 16: 741-742; Menne, et al. (2000) *Bioinformatics Applications Note* 16:741-742; Wren, et al. (2002) *Comput. Methods Programs Biomed.* 68:177-181; von Heijne (1983) *Eur. J. Biochem.* 133:17-21; von Heijne (1986) *Nucleic Acids Res.* 14:4683-4690).

6. EXAMPLES

The examples in this section (i.e., Section 6) are offered by way of illustration, and not by way of limitation.

6.1 Example 1: Affinity Maturation of Humanized 08A Antibody and Binding Affinity Studies

6.1.1 Affinity Maturation of 08A by Single CDR Codon-Base Mutagenesis Library The CDRH3, CDRL1 and CDRL3 of humanized 08A (with S61N glycosylation site correction, sequential numbering according to SEQ ID) Fab001 (SEQ ID NOs: 1 and 2) were targeted for codon-based mutagenesis. The H3, L1 and L3 libraries were randomized at position H95-H100B, L27B-L32 and L90-L97, respectively. Sequencing of representative individual colonies from each library confirmed randomization in the expected CDR of targeted residues. Each library yielded more than $10^8$ individual colonies, suggesting that the size of library was sufficient to account for every possible combination of amino acids within the target area.

The libraries were subject to four rounds of affinity-based solution-phase phage display selection with decreasing concentration of antigen at each round. A relatively high antigen concentration (20 nM) was used for the first round. The antigen concentration was decreased 10-fold each of the subsequent three rounds to select for high affinity variants. Individual variants from the fourth round were tested for positive binding to antigen by ELISA screening.

To identify variant scFv with a lower KD than wt, apparent Koff was determined by OCTET RED96 (Fortebio, USA) on unpurified native scFv in bacterial PPE. A total of 156 scFv from the fourth round of selection were ranked by koff. Twenty (20) clones with koff improvement were selected for Fab conversion. The kon and koff were determined by BIACORE, and the KD was calculated using BIACORE T200 evaluation software. Only one Fab, Fab 004 or 3G9, showed a 2 fold improvement in KD over 08A.

6.1.2 Affinity Maturation of 08A by Random Mutagenesis Library and VH/VL Combinatorial Library To achieve improved KD, instead of focusing on H3, L1 and L3, we targeted all six VH and VL regions of CDR3 from 08A for randomized mutagenesis in order to build VH and VL combinatorial mutagenesis libraries. The sequences would have greater diversity relative to the wild type sequence, but panning using reduced concentrations of antigen should result in enrichment of clones of higher affinity that retain binding. Three VH/VL combinatorial libraries for panning were generated: (1) light chain shuffling using 08A VH+combinatorial VL library, (2) light chain shuffling using Fab 004 VH+combinatorial VL library, and (3) VH+VL combinatorial libraries.

In order to increase diversity across all 6 CDRs in VH and VL, we utilized a random mutagenesis strategy. Specifically, mutagenesis was carried out using NNK codon randomization to change the six CDRs to any one of the 20 amino acids. In order to obtain sequence libraries with random mutations at every residue within the CDR loop, a total of twelve libraries were constructed. The six VH libraries were randomized at positions H31-H35 (H1 library), H51-H54 (H2A library), H55-H59 (H2B library), H60-H64 (H2C library), H96-H100 (H3A library) and H96A-H102 (H3B library), respectively. The six VL libraries were randomized at positions L21-L27A (L1A library), L27B-L29 (L1B library), L30-L34 (L1C library), L51-L55 (L2 library), L89-L93 (L3A library) and L93-L97 (L3B library), respectively. Sequencing of representative individual colonies from each library confirmed randomization in the expected CDR of targeted residues. Each library yielded more than $10^8$ individual colonies, suggesting that the size of library was sufficient to account for every possible combination of amino acids within the target area.

All twelve libraries were subjected to three rounds of panning. The third round output plasmid DNA was prepared and used as template to amplify the mutated CDR fragments. The combinatorial VH mutagenesis scFv was generated by two step over-lapping PCR to combine the three CDRs together. The combinatorial VL mutagenesis scFv was generated in similar way. The heavy- and light-chain combinatorial libraries were generated by cloning the scFv into the phagemid vector as described above.

All twelve libraries separately were subjected to three rounds of off-rate phage display selection with decreasing concentration of antigen at each round. A relatively high antigen concentration (10 nM) was used for the first round. The antigen concentration was decreased 10-fold each of the subsequent two rounds. The combinatorial VH or VL mutagenesis libraries were generated by two step overlapping PCR of combining three CDRs together using the VH or VL pooled repertoires from the third round output. We also generated a chain shuffling library by combining the heavy chain of clone Fab 004 with combinatorial light chain using over-lapping PCR. These combinatorial libraries were subjected to two further rounds of off-rate selection in the presence of decreasing antigen concentration (100 pM and 10 am).

We prioritized panning and screening from the Fab 004 VH light chain shuffling library over the 08A VH light chain shuffling library due to the potential for greater enhancement in affinity by starting from Fab 004. Individual variants from the round two output of the Fab 004 VH light chain shuffling combinatorial library was tested for positive binding to antigen by ELISA screening. A total of 108 scFv were ranked by koff. Seven (7) clones with koff improvement were selected for Fab conversion. The kon and koff were determined by BIACORE, and the KD was calculated. All 7 Fabs showed 5- to 10-fold improvement in KD over 08A, which were greater improvements in KD than observed by previous methods using single mutagenesis libraries (Table 4). Fab098, Fab099, Fab100, Fab101, Fab102, Fab103 and Fab104 were isolated from second round selection of 3G9 heavy chain combined with combinatorial light chain library.

In order to generate the VH+VL combinatorial mutagenesis library, the VH and VL pooled repertoires from the first round output of VH and VL combinatorial libraries were recombined by overlapping PCR to generate a single library of recombined variants with mutations in both VH and VL chains. The VH and VL combinatorial libraries were subjected to two further rounds of off-rate selection with 10 pM antigen. Individual variants from the round two output of combinatorial libraries were tested for positive binding to antigen by ELISA. A total of 216 scFv were ranked by koff. Four (4) clones with koff improvement were selected for Fab conversion. The kon and koff were determined by BIACORE, and the KD was calculated. The 4 Fabs (Fab128, Fab133, Fab138 and Fab139) showed 5- to 18-fold improvement in KD over 08A (Table 4).

6.1.3 Sequences of Selected Clones

The variable regions of off-rate improved clones (VH and VL) were PCR-amplified (primers synthesized by Genewiz, Suzhou). The PCR reactions were conducted at 95° C. 2 minutes, 95° C. 30 seconds, 52° C. 1 minute, 72° C. 1 minute for 15 cycles, 72° C. 10 minutes followed by 4° C. The final PCR products were checked in 1% agarose gel and purified using Qiagen QIAQUICK purification kit.

The purified VL and VH PCR products were cloned into the pCP-hCk (VL) or into pCP-hCg4 (Fab vector), respectively. Positive clones were then sent to BioSune (Shanghai) for sequencing. Plasmid DNA was prepared using MN midi-prep kit (Macherey-Nagel, USA).

Fab98-104 affinity maturation mutation alignments are shown in Table 3.

TABLE 3

Fab98-104 affinity maturation mutation alignments

| Fab No. | VH CDR Region | | | | | | | VL CDR Region | | | | | |
|---|---|---|---|---|---|---|---|---|---|---|---|---|---|
| | H1 | H2A | H2B | H2C | H3A | H3B | | L1-A | L1-B | L1-C | L2 | L3-A | L3-B |
| Fab001 | SYYLY (SEQ ID NO: 8 & 129) | VNPSN (AA 1-5 OF SEQ ID NO: 130) | GGTNF (AA 6-10 OF SEQ ID NO: 130) | NEKFK (AA 7-15 OF SEQ ID NO: 130) | DSNYD (AA 1-5 OF SEQ ID NO: 131) | GGFDY (AA 6-10 OF SEQ ID NO: 131) | | RASKS (AA 1-5 OF SEQ ID NO: 132) | VSTSG (AA 6-10 OF SEQ ID NO: 132) | FSYLH (AA 11-15 OF SEQ ID NO: 132) | ASNLE (SEQ ID NO: 133) | QHSWE (AA 1-5 OF SEQ ID NO: 134) | LPLT (AA 6-9 OF SEQ ID NO: 134) |
| Fab098 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GKFRE (SEQ ID NO: 136) | QHSWE (AA 1-5 OF SEQ ID NO: 134) | LPLT (AA 6-9 OF SEQ ID NO: 134) |
| Fab099 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GTHRA (SEQ ID NO: 137) | QHSWE (AA 1-5 OF SEQ ID NO: 134) | LPLT (AA 6-9 OF SEQ ID NO: 134) |
| Fab100 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | SKYRS (SEQ ID NO: 138) | QHSWE (AA 1-5 OF SEQ ID NO: 139) | LPLT (AA 6-9 of SEQ ID NO: 139) |
| Fab101 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GKYGA (SEQ ID NO: 140) | AQATQ (AA 1-5 OF SEQ ID NO: 141) | LPLT (AA 6-9 OF SEQ ID NO: 141) |
| Fab102 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GHFAS (SEQ ID NO: 142) | QHSWE (AA 1-5 OF SEQ ID NO: 134) | LPLT (AA 6-9 OF SEQ ID NO: 134) |
| Fab103 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GRYLQ (SEQ ID NO: 143) | QHSWE (AA 1-5 OF SEQ ID NO: 134) | LPLT (AA 6-9 OF SEQ ID NO: 134) |
| Fab104 | | | | | LSHYD (SEQ ID NO: 135) | | | RASKS (AA 1-5 OF SEQ ID NO: 132) | VSTSG (AA 6-10 OF SEQ ID NO: 132) | FSYLH (AA 11-15 OF SEQ ID NO: 132) | GTHSV (SEQ ID NO: 144) | QHSWE (AA 1-5 OF SEQ ID NO: 134) | LPLT (AA 6-9 OF SEQ |

TABLE 3-continued

Fab98-104 affinity maturation mutation alignments

| Fab No. | VH CDR Region | | | | | | VL CDR Region | | | | | |
|---|---|---|---|---|---|---|---|---|---|---|---|---|
| | H1 | H2A | H2B | H2C | H3A | H3B | L1-A | L1-B | L1-C | L2 | L3-A | L3-B |
| Fab128 | QYYTY (SEQ ID NO: 145) | VNPSN (AA 1-5 OF SEQ ID NO: 130) | GGTNF (AA 6-10 OF SEQ ID NO: 130) | NEKFK (AA 11-15 OF SEQ ID NO: 130) | DSNYD (AA 1-5 OF SEQ ID NO: 131) | GGFDY (AA 6-10 OF SEQ ID NO: 131) | ID NO: 132) | | SEQ ID NO: 132) | GRHRA (SEQ ID NO: 146) | ID NO: 134) | ID NO: 134) |
| Fab133 | QYYTY (SEQ ID NO: 145) | VNPSN (AA 1-5 OF SEQ ID NO: 130) | GGTNF (AA 6-10 OF SEQ ID NO: 130) | N EKFK (AA 11-15 OF SEQ ID NO: 130) | DSNYD (AA 1-5 OF SEQ ID NO: 131) | GGFDY (AA 6-10 OF SEQ ID NO: 131) | RASKS (AA 1-5 OF SEQ ID NO: 132) | VSTSG (AA 6-10 OF SEQ ID NO: 132) | FSYLH (AA 11-15 OF SEQ ID NO: 132) | GFYRT (SEQ ID NO: 147) | QHSWE (AA 1-5 OF SEQ ID NO: 134) | LPLT (AA 6-9 OF SEQ ID NO: 134) |
| Fab138 | QYYTY (SEQ ID NO: 145) | IEPNR (AA 1-5 OF SEQ ID NO: 150) | GGTNF (AA 6-10 OF SEQ ID NO: 150) | N EKFK (AA 11-15 OF SEQ ID NO: 150) | DSNYD (AA 1-5 OF SEQ ID NO: 131) | GGFDY (AA 6-10 OF SEQ ID NO: 131) | RASKS (AA 1-5 OF SEQ ID NO: 132) | VSTSG (AA 6-10 OF SEQ ID NO: 132) | FSYLH (AA 11-15 OF SEQ ID NO: 132) | ASN LE (SEQ ID NO: 133) | SQMAD (AA 1-5 OF SEQ ID NO: 148) | LPLT (AA 6-9 OF SEQ ID NO: 148) |
| Fab139 | QYYTY (SEQ ID NO: 145) | VNPSN (AA 1-5 OF SEQ ID NO: 130) | GGTNF (AA 6-10 OF SEQ ID NO: 130) | N EKFK (AA 11-15 OF SEQ ID NO: 130) | DSNYD (AA 1-5 OF SEQ ID NO: 131) | GGFDY (AA 6-10 OF SEQ ID NO: 131) | RASKS (AA 1-5 OF SEQ ID NO: 132) | VSTSG (AA 6-10 OF SEQ ID NO: 132) | FSYLH (AA 11-15 OF SEQ ID NO: 132) | SKFRR (SEQ ID NO: 152) | AQTFE (AA 1-5 OF SEQ ID NO: 151) | LPLT (AA 6-9 OF SEQ ID NO: 151) |

6.1.4 Transient Transfection in 293 Cells

Approximately 24 hrs. before transfection, passed 293-F cells at $2.2 \times 10^6$ cells/ml in OPM-293 CD03 medium (OPM Biosciences, China), and incubated on a shaker at 120 rpm/min, 37° C. and 5% $CO_2$. On the day of transfection, the cell density was about $4 \times 10^6$ cells/ml. To ensure optimal transfection, viability of cells must be >95%.

150 μg plasmid DNA per 100 ml cell culture (Fd:LC=2:3) was prepared. DNA was diluted in OPTI-MEM expression medium (Gibco, USA) in a volume equivalent to one-twentieth of the culture to be transfected and 1 mg PEI (Polysciences, USA) was diluted in OPTI-MEM medium in an equivalent volume as that of the DNA solution.PEI solution was added into the diluted DNA solution; the DNA-PEI mixture was mixed gently and incubated for 15 min. at room temperature prior to transfection. The DNA-PEI mixture was added into cell culture while slowly swirling the flask cells, and the DNA-PEI mixture was incubated with cells for 4 hours. One-twentieth of culture medium volume of peptone (Fluka, USA) was added to the flask. Cells were then cultured at 125 rpm/min., 37° C., and 5% $CO_2$.

6.1.5 Purification of Fabs

Conditioned medium above on day 6 was loaded onto a 0.6 ml KAPPASELECT resin (GE Healthcare, USA) column, which was equilibrated by 25 mM Tris, 150 mM NaCl, pH 8.0. The column was then washed with equilibrating buffer to baseline after sample loading. After washing, the column was eluted with 50 mM sodium citrate, 150 mM NaCl, pH 3.0, followed with immediate addition of 1M arginine, 400 mM succinic acid, pH 9.0 to adjust pH value to 5.5. The final product was dialyzed against PBS solution. Protein purity was analyzed by SDS-PAGE and its concentration was determined by Bradford method.

6.1.6 Size Exclusion Chromatography Analysis of the Purified Fab

Size exclusion chromatography (SEC) for analyzing purified antibodies was carried out with a SEC SIZESEP-SIH column (Waters, 7.8-mm i.d., 30-cm length) using a HPLC system (E2695, Waters) at ambient temperature. Five times of PBS buffer, at a flow rate 1 mL/min was used as the mobile phase. The injection volume was 20 μl with detection at 280 nm.

6.1.7 Biacore Assay of the Purified Fabs

Immobilization of Recombinant Human or Cyno PD-1 onto CMS Chip:

A CMS sensor chip was activated in FC2 by 7-min. injection (10 μl/min.) of freshly prepared 1:1 50 mM NETS: 200 mM EDC. PD-1 at a concentration of 0.2 μg/ml in 10 mM sodium acetate buffer pH 5.0 was injected onto the activated chip at 5 μl/min. (HBS-EP running buffer: 10 mM HEPES, 150 mM NaCl, 3.4 mM EDTA, 0.005% surfactant P20, pH 7.4) for 120 seconds. The remaining active coupling sites were blocked with 7 min. injection of 1M ethanolamine at 10 μl/min.

Binding Kinetics Measurement:

Various concentrations of the Fabs were injected with a flow rate of 30 μl/min for 180 seconds(s) during the association phase. The dissociation of bound antibody was monitored by flowing HBS-EP buffer over the chip surface for 600 seconds. At the end of each cycle, the sensor surfaces were regenerated by injecting regeneration buffer (10 mM glycine buffer with pH 1.7) for 180 seconds. After sensograms were corrected for signals from a reference flow, kinetics were calculated with BIACORE T 200 evaluation software ver. 1.0 (Biacore, GE, USA).

TABLE 4

Affinity of Fabs isolated from combinatorial CDR mutagenesis library

| Fab No. | HC and LC SEQ ID Nos: | KD ($10^{-10}$ M) |
|---|---|---|
| Fab001 | 1, 2 | 2.80-2.90 |
| Fab 098 | 6, 13 | 0.31 |
| Fab 099 | 6, 16 | 0.34 |
| Fab 100 | 6, 19 | 0.24 |
| Fab 101 | 6, 23 | 0.29 |
| Fab 102 | 6, 27 | 0.42 |
| Fab 103 | 6, 30 | 0.28 |
| Fab 104 | 6, 33 | 0.52 |
| Fab 128 | 36, 38 | 0.15 |
| Fab 133 | 43, 45 | 0.31 |
| Fab 138 | 49, 51 | 0.66 |
| Fab 139 | 56, 58 | 0.14 |

6.2 Example 2: Affinities of Mouse and Humanized Anti-PD-1 mAbs Against Human PD1

6.2.1 Surface Kinetics by BIAcore

A surface plasmon resonance (SPR)-based assay utilizing capture mode was used to determine the binding kinetics and affinities of anti-PD-1 antibodies against polyhistidine-tagged human PD-1 (hPD1-His, 98AFK). Following manufacture instructions, a series S sensor chip CM5 (GE Healthcare, BR100530) was activated using an amine-coupling kit (GE Healthcare, BR100050). Either human capture kit (anti-human Fc, 25 μg/mL, GE Healthcare, BR100839) or mouse capture kit (anti-mouse Fc, 30 μg/mL, GE Healthcare, BR100838) antibody diluted in the supplied pH 5.0, 10 mM sodium acetate buffer was immobilized onto the activated surface for 7 minutes. After immobilization, surfaces were deactivated with 1M ethanolamine/HCl (pH 8.5) for 7 minutes. The final immoblization levels reached ~8,000 resonance units (RU) for mouse capture or ~12,000 RU for human capture in each of the four flow cells.

Binding kinetics were measured on a biacore T200 in HBS-EP+ (0.01 M HEPES pH 7.4, 0.15 M NaCl, 3 mM EDTA, 0.05% v/v Surfactant P20) running buffer at 25° C. Antibodies were captured either on mouse or human Fc capture surfaces at 10 μL/min flow rate. Antibodies were captured on flow cells 2, 3 and 4. Flow cell 1 was used as a reference with no antibody captured. A 6-point, 2-fold serial dilutions of the analyte 98AFK (hPD1-His), starting at 20 nM, were prepared in the running buffer (HBS-EP+). Two buffer blanks were included for double referencing. Titration series were injected for 3 minutes at 50 μl/min followed by 600 seconds of dissociation. After each cycle, surfaces were regenerated with a 30 second injection of 3M $MgCl_2$ at 10 μL/mL on the anti-human Fc chip or 180 seconds of 10 mM Glycine pH 1.7 at 10 μl/min on the anti-mouse Fc chip.

Sensorgram processing and data analysis were performed with Biacore T200 Evaluation Software Version 2.0.4 (GE Healthcare). Sensorgrams showing antibody binding were obtained after double referencing by subtracting signal in reference flow cell 1 and signals from blank injections. Processed curves were globally fitted to a 1:1 binding model to determine the association rate constant, $k_{on}$ ($M^{-1}s^{-1}$, where "M" equals molar and "s" equals seconds) and the dissociation rate constant, $k_{off}$ ($s^{-1}$). These rate constants were used to calculate the equilibrium dissociation constant, $K_D$ (M)=$k_{off}/k_{on}$.

6.2.2 Solution Affinity by BIAcore

A SPR-based assay utilizing solution mode was used to determine the solution affinities of anti-PD-1 humanized antibodies against polyhistidine tagged human PD-1 (hPD1-His, 98AFK). Following manufacture instructions, a series S sensor chip CM5 (GE Healthcare, BR100530) was activated using an amine-coupling kit (GE Healthcare, BR100050). Human PD1-His (98AFK, 40 µg/mL diluted in pH 5.0 10 mM sodium acetate buffer) was immobilized onto the activated surface for 7 minutes. After immobilization, surfaces were deactivated with 1M ethanolamine/HCl (pH 8.5) for 7 minutes. The final immoblization levels reached approximately 6,000 resonance units (RU) in the flow cell.

Solution affinities were determined by measuring the unbound fraction of antibody paratope in a series of titrations where the antibody concentration was held constant (either at 500 pM or 100 pM) and antigen, hPD1-His (98AFK) concentration was diluted 1:2 from 100 nM to 3 pM in a 16-point titration series. The titration series were incubated for 16-24 hours to reach equilibrium at room temperature. The unbound sites were measured using a BIAcore chip immobilized with antigen in a competition mode where SPR signal detected corresponded to unbound antibody.

Solution affinities were measured on a BIACORE T200 in HBS-EP+(0.01 M HEPES pH 7.4, 0.15 M NaCl, 3 mM EDTA, 0.05% v/v Surfactant P20) running buffer at 25° C. The titration series following >16 hr. incubation were injected over the sensor chip immobilized with hPD1-His (above). Free, unbound antibodies concentrations were measured as proportional to RU after 120 seconds (for 500 pM mAb series) or 400 seconds (for 100 pM mAb series) of injection at 10 µL/min. After each cycle, surfaces were regenerated with a 30 second injection of 1:1 mixture of 3M MgCl$_2$ and pH 2.0 10 mM glycine at 30 µL/min Data analyses were performed using KINEXA Pro Version 1.02 (Sapydyne) where RUs were normalized and plotted against concentrations. Normalized data from two titrations (using 100 pM and 500 pM fixed antibody concentrations) were fit using n-Curve Analysis Version 1.02 (Sapidyne) to obtain $K_D$ (M) values for each interaction.

In standard surface-based affinity measurement, the parental mouse 08A antibody showed 0.24 nM affinity. In contrast, parental mouse 08A antibody variants N59Q, N59E and N59A in VH CDR2 showed decreased affinity compared to parental mouse 08A antibody. Humanized 08A IgG4 antibody variants all showed tighter affinities relative to the parental mouse 08A antibody. Subsequent humanized 08A IgG4 antibody variants with G56A, S61N and G56A/S61N corrections in the CDHR2 showed trend towards improved affinity whereas N55E did not. The Humanized 08A affinity matured version Fab098 IgG4 antibody with G56A correction improved the affinity by about 3 fold. The humanized 08A affinity matured version Fab100 IgG4 antibody with S61N and G56A corrections improved the affinity by about 6-fold. (See Table 5)

TABLE 5

Standard surface-based affinities against human PD1-His(98AFK)

| mAb | Lot # | HC and LC SEQ ID NOs | $K_D$ (M) | $K_D$ (REF)/ $K_D$ |
|---|---|---|---|---|
| Mouse 09A | 03AFN | 67, 68 | 4.6E−10 | 0.5 |
| Mouse 08A (REF) | 09AFF | 65, 66 | 2.4E−10 | 1.0 |
| Mouse 08A N59Q | 38AFL | 69, 66 | 9.6E−09 | 0.04 |
| Mouse 08A N59E | 39AFL | 70, 66 | 5.9E−09 | 0.03 |
| Mouse 08A N59A | 80AFH | 71, 66 | 5.9E−10 | 0.4 |
| Humanized 08A IgG4 S61N N55E | 50AQK | 72, 2 | 3.0E−10 | 0.8 |
| Humanized 08A IgG4 | 73AGG | 73, 2 | 1.4E−10 | 1.7 |
| Humanized 08A IgG4 G56A | 89AVZ | 77, 2 | 1.0E−10 | 2.4 |
| Humanized 08A IgG4 Fab 098 G56A | 90AVZ | 89, 2 | 7.9E−11 | 3.0 |
| Humanized 08A IgG4 S61N | 67AGG | 82, 2 | 4.5E−11 | 5.2 |
| Humanized 08A IgG4 S61N | 98AIO | 74, 2 | 5.4E−11 | 4.4 |
| Humanized 08A IgG4 S61N G56A | 51AQK | 83, 2 | 5.7E−11 | 4.2 |
| Humanized 08A IgG4 Fab 100 S61N G56A | 25AVE | 90, 19 | 4.2E−11 | 5.7 |

In solution mode affinity determination, affinity matured humanized 08A IgG4 Fab 100 antibody with S61N and G56A corrections showed significant affinity improvement over humanized 08A IgG4 antibody with S61N correction (see Table 6).

TABLE 6

SPR Solution Affinities Against Human PD-1-His (98AFK)

| mAb | Lot # | $K_D$, (M) | $K_D$ Lower Limit | $K_D$ Upper Limit | $K_D$ (REF)/ $K_D$ |
|---|---|---|---|---|---|
| Humanized 08A IgG4 S61N (REF) | 98AIO | 3.3E−11 | 2.6E−11 | 4.0E−11 | 1.0 |
| Humanized 08A IgG4 S61N G56A | 51AQK | 3.3E−11 | 2.5E−11 | 4.0E−11 | 1.0 |
| Humanized 08A IgG4 G56A | 89AVZ | 5.6E−11 | 4.0E−11 | 7.5E−11 | 0.6 |
| Humanized 08A IgG4 Fab 098 G56A | 90AVZ | 1.9E−11 | 1.2E−11 | 2.7E−11 | 1.7 |
| Humanized 08A IgG4 Fab 100 S61N G56A | 25AVE | <2.5E−12 | <1.0E−12 | 2.5E−12 | ~>13 |

6.3 Example 3: Production of Anti-PD-1/LAG3 Bispecific Antibodies

Anti-PD-1/LAG-3 bispecific antibody (BsAb) 18ASS has an anti-PD-1 heavy chain with the heavy chain variable region of affinity matured Fab100 with CDRH2 S61N and G56A corrections and an IgG1 constant region with CH1 mutations L145E, K147T, Q175E, and S183L, CH2 mutations L234A, L235A, and D265S, CH3 mutations T350V, L351Y, F405A, Y407V (SEQ ID NO:102); an anti-PD-1 light chain with the light chain variable region of affinity matured Fab100 and kappa constant region with $C_K$ mutations Q124R, T178R (SEQ ID NO:103); an anti-LAG3 heavy chain with heavy chain variable region of humanized 22D2 antibody Ab6 of WO 2016028672 and IgG1 constant region with CH1 mutation S181K, CH2 mutations L234A, L235A, and D265S, CH3 mutations T350V, T366L, K392L, and T394W (SEQ ID NO:96); an anti-LAG3 light chain with light chain variable region of antibody Ab6 of WO 2016028672, and kappa constant region with $C_K$ mutations Q124E, S131T, T178Y, and T180E (SEQ ID NO:98).

Anti-PD-1/LAG3 bispecific antibody 90ASU has an anti-PD-1 heavy chain with humanized 08A heavy chain variable region with CDRH2 S61N and G56A corrections and an IgG1 constant region with CH1 mutations L145E, K147T, Q175E, and S183L, CH2 mutations L234A, L235A, and D265S, CH3 mutations T350V, L351Y, F405A, and Y407V (SEQ ID NO:101); an anti-PD-1 light chain with the light chain variable region of humanized 08A and kappa constant region with $C_K$ mutations Q124R, T178R (SEQ ID NO:100); an anti-LAG3 heavy chain with the heavy chain variable region of humanized 22D2 antibody Ab6 of WO 2016028672 and IgG1 constant region with CH1 mutation S181K, CH2 mutations L234A, L235A, and D265S, CH3 mutations T350V, T366L, K392L, and T394W (SEQ ID NO:96); anti-LAG3 light chain with light chain variable region of antibody Ab6 of WO 2016028672, and kappa constant region with $C_K$ mutations Q124E, S131T, T178Y, and T180E (SEQ ID NO:98).

Anti-PD-1/LAG3 bispecific antibody 33ARK has an anti-PD-1 heavy chain with humanized 08A heavy chain variable region with CDRH2 S61N and G56A corrections, and FR mutation Q39E and an IgG1 constant region with CH1 mutations L145E, K147T, and Q175E, CH2 mutations L234A, L235A, and D265S, CH3 mutations T350V, T366L, K392L, and T394W (SEQ ID NO:108); an anti-PD-1 light chain with the light chain variable region of humanized 08A with FR mutation Q38R and kappa constant region with $C_K$ mutations Q124R, Q160K, and T178R (SEQ ID NO:110); an anti-LAG3 heavy chain with heavy chain variable region of humanized 22D2 antibody Ab6 of WO 2016028672 with FR mutation Q39R, and IgG1 constant region with CH1 mutations H168R and Q175K, CH2 mutations L234A, L235A, and D265S, CH3 mutations T350V, L351Y, F405A and Y407V (SEQ ID NO:104); an anti-LAG3 light chain with light chain variable region of antibody Ab6 of WO2016028672 with Q38E FR mutation, and kappa constant region with $C_K$ mutations Q124E, Q160E, and T180E (SEQ ID NO:106).

The CH3 mutations (EU numbering) in each of the anti-PD-1 heavy chain and anti-LAG3 heavy chain promote heterodimer formation of the anti-PD-1 arm and anti-LAG3 arm. The CH1 and $C_K$ mutations (EU numbering) in the anti-PD-1 heavy and light chain as well as anti-LAG3 heavy and light chain promote the correct heavy and light chain pairing. In 33ARK, the FR mutations also promote the correct heavy and light chain pairing. The CH2 mutations (EU numbering) reduce effector function. The S61N correction removes a glycosylation site, and the G56A correction removes a deamidation site (sequential numbering in SEQ ID).

6.3.1 Transfection, Expression and Purification of 18ASS and 90ASU

18ASS and 90ASU were expressed recombinantly in Chinese hamster ovary cells (EXPIFECTAMINE; Thermo Fisher Scientific) via transient transfection using EXPIFECTAMINE transfection reagent. The genes encoding the two pairs of heavy and light antibody chains (90ASU: anti-PD-1: SEQ ID NOs:100 and 101; anti-LAG3: SEQ ID NOs:96 and 98) (18ASS: anti-PD-1: SEQ ID NOs:102 and 103; anti-LAG3: SEQ ID NOs:96 and 98) were constructed via gene synthesis using codons optimized for mammalian expression. The expression cassettes coding for the four chains were cloned in the pTT5 mammalian expression vector (from the National Research Council, Canada). Four plasmid DNAs encoding the different protein chains (2 Heavy Chains and 2 Light Chains) were transfected with a 1:1:1:1 plasmid DNA ratio and expressed for 7-days prior to harvest at a cell viability of 93%. Assembled, secreted antibody was captured from culture supernatant by overnight incubation with a Protein A chromatography resin (MAB SELECT SURE LX; GE Healthcare), and further purified via conventional protein purification methods. Final bispecific antibody purity was >98% as measured by capillary gel electrophoresis, analytical size exclusion chromatography, and mass spectrometry (intact mass).

6.3.2 Cloning, Transfection, Expression and Purification of 33ARK

Gene products for anti-PD-1/LAG3 bispecific antibody 33ARK were cloned into the mammalian expression vector pTT5 and transiently expressed in CHO cells (Raymond C. et al. Methods. 55(1):44-51 (2011)). CHO-3E7 cells were cultured at 37° C. in FreeStyle TM F17 medium (Invitrogen cat# A-1383501) supplemented with 4 mM glutamine and 0.1% Pluronic F-68 (Invitrogen cat#24040-032). Four plasmid DNAs encoding the two heavy chains and two light chains (anti-PD-1: SEQ ID Nos: 108 and 110) and (anti-LAG3: SEQ ID Nos:104 and 106) were transfected at 3L scale at a DNA ratio of 15:15:20:50 (anti-LAG3 HC: anti-PD-1 HC:anti-LAG3 LC: anti-PD-1 LC). Temperature was lowered to 32° C. 24 hr. after transfection and cell supernatants were collected after 10 days.

Antibody quantification in supernatants was performed using a 600/717/996 HPLC system (Waters Corporation, Milford, Mass.) with a protein A cartridge (POROSA20 column, Invitrogen, Grand Island, N.Y., Part#2-1001-00, 2.1 mmD×30 mmH, 104 µL). Samples were filtered by centrifugation at 8000-11000 g for 3 minutes using NANOSEP MF GHP 0.45 µm centrifugal devices (Pall Life Sciences, Part# ODGHPC35) prior to being injected on the column at a flow rate of 2 mL/min using PBS. Elution was performed with 0.15 M NaCl, pH 2.0. EMPOWER software (Waters Corporation, Milford, Mass.) was used to process data and curves were fit by linear regression.

2L and 3L cell culture broth were centrifuged and filtered before loading onto a 10 mL of MABSELECT SURE (GE Healthcare) protein A column at 10 ml/min. The 33ARK bispecific antibody was eluted with 100 mM citrate buffer at pH 3.0 and neutralized to pH 6-7 with TRIS buffer pH 11. Samples were mixed with either sample denaturing solution (for reducing conditions) or protein express sample buffer (for non-reducing conditions) and loaded on a BioRad hard-shell 96-well plate. Samples were then heated up at 70° C. for 15 min, centrifuged and mixed with water and gel-dye solution before running on LabChip GXII. The Protein A eluate were purified in a single injection on a Superdex 200 16/60 (GE Healthcare) via an AKTA Express FPLC at a flow-rate of 1 mL/min in PBS buffer at pH 7.4. Fractions with purity greater than 90% by CE-SDS were pooled together to form the final sample and buffer exchanged in 20 mM sodium acetate, pH 5.0, 7% sucrose to a concentration greater than 2 mg/mL.

6.4 Example 4: Engineered Jurkat.hPD-1.IL2luc+THP-1.PD-L1 Assay

Clone DT999A1 is a PD-1 transgene expressing Jurkat cell clone with an IL-2 mediated luciferase reporter (Jurkat.hPD-1.IL2luc). Jurkat.hPD-1.IL2luc cells were grown in RPMI media (Corning Cellgro 10-040-CV)+heat inactivated 10% FBS (Hyclone SH30910.03)+2 mM L-glutamine (Cellgro 25-005-CI)+2 µg/ml puromycin (Sigma P9620)+0.5 mg/ml Geneticin (Gibco 10131-027). Cells were split twice per week after seeding cells at $2\times10^5$ cells/ml and were split when the density exceeded $1\times10^6$ cells/ml. PD-L1 transgene expressing THP-1 cells (THP-1.PD-L1) were grown in RPMI media+heat inactivated 10% FBS+2 mM L-glutamine+0.5 ug/ml puromycin. Cells were split twice per week after seeding at $3\times10^5$ cells/ml and were split when they reach $1\times10^6$ cells/ml.

The bioassay was setup using Assay Media [Phenol red free RPMI media (Gibco 11835-030)+10% dialyzed FBS (Hyclone, 5H30079.03)]. Fifty microliters of 4-fold serial dilution of antibody with a starting concentration of 30 µg/ml was added to the white walled tissue culture treated plate. To the antibody titration, a 50 µl cell suspension containing $4\times10^6$ cells/ml THP-1.PD-L1+$1\times10^6$ cells/ml Jurkat.hPD-1.IL2luc cells and 2× stimulation conditions of 2 ng/ml LPS (Sigma L4391) and 100 ng/ml IFN-g (R&D systems 285-IF/CF) were added. At the end of the 22 hour incubation (37° C. in the incubator), 10 µl of 55 ng/ml anti-PD-1 antibody (BD Pharmingen 555336; 11× working solution) was added for an additional two hours. One hundred microliters of ONE-GLO reagent (Promega E6120) was added and plate read on the Perkin Elmer ENVISION with an integration time of 0.1 sec Raw data in relative light units (RLU) was plotted using the GRAPHPAD software and EC50 values calculated. See also FIG. 1.

TABLE 7

EC50 values for the test samples.

| Description | Lot # | AVG EC50 (nM) |
|---|---|---|
| Humanized x [PD-1_H] [LAG3_H] BsAb ((08A/HuPD1A-11 S61N CP-affinity matured Fab 100 VH H3G9 G56A ZWCH1-5 ZM856A/VL L28D1 ZWCL-4) and (22D2 ZWCH1-6 ZM857B/22D2 LC ZWCL-5) L234A L235A D265S) IgG1/Kappa (CX) | 18ASS (SEQ ID NOs: 96, 98, 102 and 103) | 0.55 ± 0.01 |
| Humanized x [PD-1_H] [LAG3_H] BsAb ((08A/Hu PD1A-11 S61N G56A ZWCH1-5 ZM856A/hum 08A LC ZWCL-4) and (22D2 ZWCH1-6 ZM857B/22D2 LC ZWCL-5) L234A L235A D265S) IgG1/Kappa (CX) | 90ASU (SEQ ID NOs: 96, 98, 100, 101) | 2.54 ± 0.47 |
| Humanized x [PD-1 H] FAb (08A/HuPD1A-11 S61N CP-affinity matured Fab 100 (VH H3G9 (D100L N102H)/VL L28D1 (A55S S56K N57Y L58R E59S Q93S H94Q S95A W96Y E97H))) IgG4 S228P/Kappa (PX) | 31ARL (SEQ ID NOs: 87 and 19) | 0.56 ± 0.03 |
| Humanized x [PD-1_H] FAb (08A/HuPD1A-11 S61N WT) IgG4/Kappa (PX) | 00APE (SEQ ID NOs: 80 and 2) | 3.32 ± 0.7 |
| Humanized x [PD-1_H] [LAG3_H] BsAb (08A/ Hu PD1 A-11 S61N Q39E ZW CH1-4 ZM857B and 22D2 Q39R ZW CH1-3 ZM856A) L234A, L235A, D265S IgG1/hum 08A LC Q42R ZW CL-3 and 22D2 Q39E LC ZWCL-2) Kappa (CE) | 33ARK (SEQ ID NOs: 104, 106, 108 and 110) | 3.12 ± 0.54 |

The bispecific antibody 18ASS with the affinity matured Fab100 sequence (with S61N and G56A corrections) is 5- to 6-fold more potent than the bispecific antibody 90ASU with the non-affinity matured humanized 08A sequence (with S61N and G56A corrections). Likewise, the Fab 31ARL with the affinity matured Fab100 sequence (with S61N correction) is 5- to 6-fold more potent than the Fab 00APE with the non-affinity matured humanized 08A sequence (with S61N correction). The bispecific antibody 18ASS with the affinity matured Fab100 sequence (with S61N and G56A corrections) is also 5- to 6-fold more potent than the bispecific antibody 33ARK with the non-affinity matured humanized 08A sequence (with S61N correction) and different CH1-CK and FR mutations for promoting correct light and heavy chain pairing.

6.5 Example 5: Mixed Lymphocyte Reaction (MLR) Assay

Human peripheral blood mononuclear cells (PBMCs) were purified from leukopacks and frozen down in the liquid nitrogen freezer. Frozen human PBMCs were thawed, diluted in Phosphate Buffered Saline (PBS) (ThermoFisher: 20012027), centrifuged at 450×g for 5 minutes, and the cell pellet was resuspended with cell separation buffer; PBS, fetal bovine serum (FBS) (ThermoFisher Scientific; Ser. No. 10/438,026), and ethylenediaminetetraacetic acid disodium salt solution (EDTA) (Sigma-Aldrich; E7889-100ML). Monocytes were enriched using Human Monocyte Enrichment kit (STEMCELL technologies; 19059). Cells were transferred to 6-well plates at $1\times10^6$ cells/ml (5 mL/well) in RPMI 1640 media (Gibco/ThermoFisher Scientific; 11875-119), FBS and Penicillin-Streptomycin (Pen/Strep) (ThermoFisher Scientific; Ser. No. 15/140,122) with 100 ng/mL GM-CSF (R&D Systems; 215-GM-110) and 50 ng/mL of human IL-4 (R&D Systems; 204-IL-010/CF). Monocytes were incubated at 37° C. for 5 days to allow for dendritic cell (DC) differentiation. Monocyte-derived dendritic cells (Mo-DC) were harvested on Day 6, counted, resuspended in RPMI 1640 media, human serum (Sigma-Aldrich; H4522-100ML) and Pen/Strep and used in MLR assay as stimulators.

On the day of experiment initiation, frozen human PBMCs were thawed and diluted in cell separation buffer. CD4 T cells from each donor were enriched using EASY-SEP Human CD4 T cell isolation kit (STEMCELL technologies; 17952). Isolated CD4 T cells were suspended at $1 \times 10^6$ cells/mL in RPMI 1640 media, human serum and Pen/Strep. Mo-DC were mixed at 1:10 ratio ($1 \times 10^4$ cells/mL) with CD4+ T-cells ($1 \times 10^5$ cells/mL) and cell mixture plated in a flat-bottom 96 well plate at 200 μL/well. Bispecific antibodies were serially diluted using a 6-fold dilution series and 5× working stocks were prepared. 50 μL of each dilution was added to the 200 μL cultures to give 1× final concentration of bispecific antibodies. Control wells were treated with an isotype control antibody or left untreated. Culture supernatants were collected at Day 2 post-experiment initiation for IL-2 quantitation using V-PLEX Human IL-2 kit (Meso Scale Discovery Cat# K151QQD-4).

Figure 2:
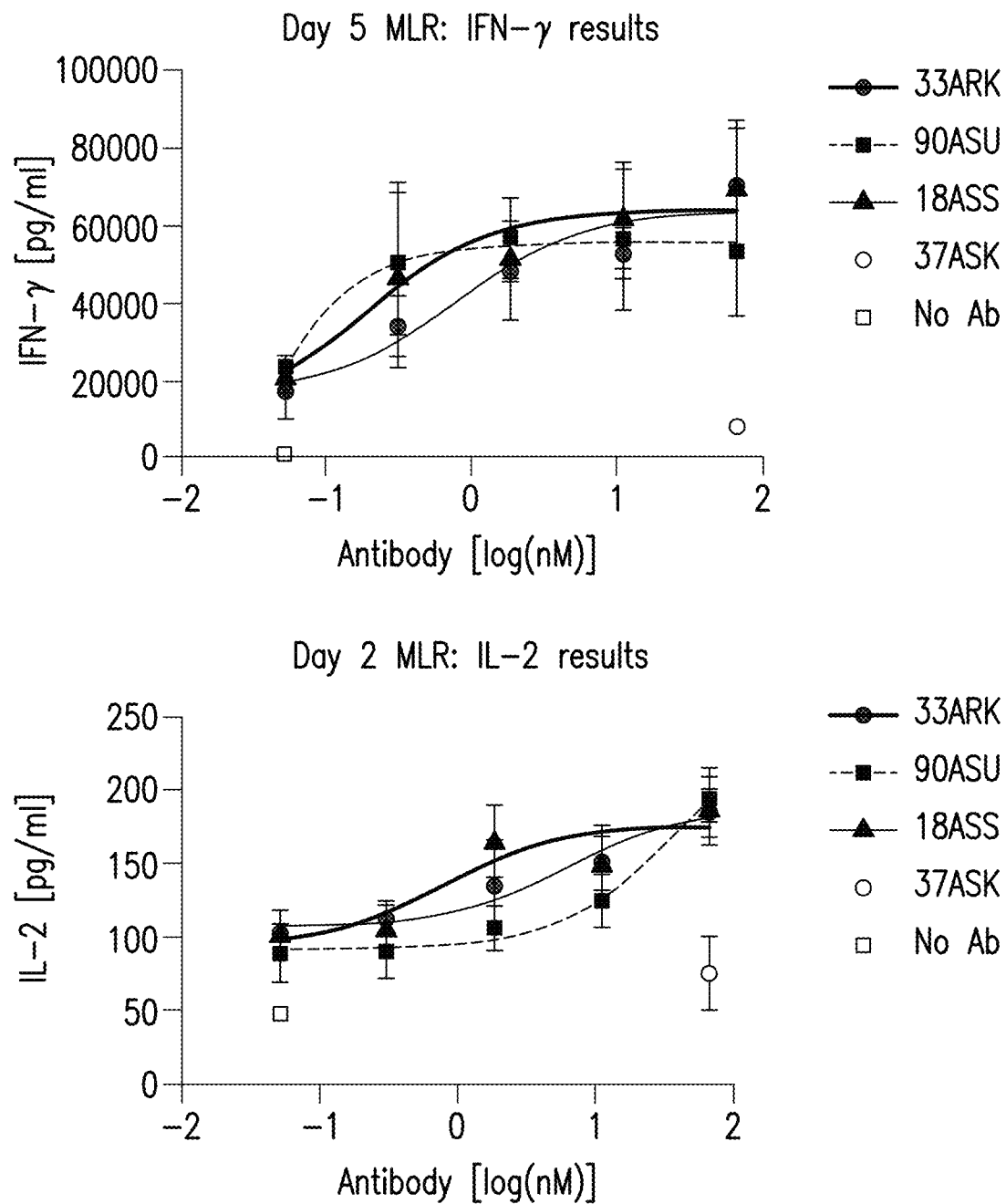
FIG. 2 depicts IL-2 (bottom panel) and IFN-γ (top panel) production induced by bispecific antibodies in Mixed Lymphocyte Reaction.

This Example demonstrated that the anti-human PD-1/LAG-3 bispecific antibodies 33ARK, 90ASU and 18ASS induce IFN-γ and IL-2 production by primary CD4 T-cells stimulated with allogeneic monocyte-derived dendritic cells (See FIG. 2). Isotype control antibody-treated (37ASK) and untreated (no Ab) MLR samples are shown as controls.

6.6 Example 6: Human T-Cell Clone+JY.hPD-L1 Assay

6.6.1 Generation and Culture of Human CD4+ T Cell Clone

MHC class II allo-antigen specific CD4+ T cell clone BC4-49 was generated by 2 rounds of mixed leukocyte reaction with the EBV-transformed B-cell line JY and cloned by limiting dilution. The clone was re-stimulated with allo-specific antigens at an interval of every 2 weeks and cultured in Yssel's medium (IMDM, Gibco 12440-053; human serum AB, Gemimi 100512; penicilin/streptomycin, Mediatech 30-002-CI; human albumin, Sigma A9080; ITS-X, Gibco 51500056; Transferin, Roche 10652202001; PA Bioxtra Sigma p5585; LA-OA-Albumin, Sigma L9655). Fresh PBMCs were isolated from two human buffy coats provided by Stanford Blood Center and pooled at 1:1 cell ratio. PBMCs were irradiated in a gamma irradiator at dose 4000 rads before use. Wildtype JY cells were prepared and irradiated at dose 5000 rads. T cell clones were cultured with feeders in 24-well plate at 1 mL per well with final concentrations of CD4+ T cells $0.2 \times 10^6$/mL, irradiated PBMCs $1 \times 10^6$/mL, irradiated JY $0.1 \times 10^6$/mL, and 100 ng/mL PHA (Sigma L9017). Recombinant human IL-2 (R&D Systems; 202-IL/CF) was added at final concentration of 100 ng/mL on day 3 after re-stimulation, and was replenished every 3-4 days throughout the expansion. Cells were passaged to an optimal concentration between $0.5-1.0 \times 10^6$/mL. On day 7 after re-stimulation, abundant level of LAG-3 and moderate level of PD-1 were expressed on T cell surface.

6.6.2 Human CD4+ T Cell Functional Assay

Figure 3:
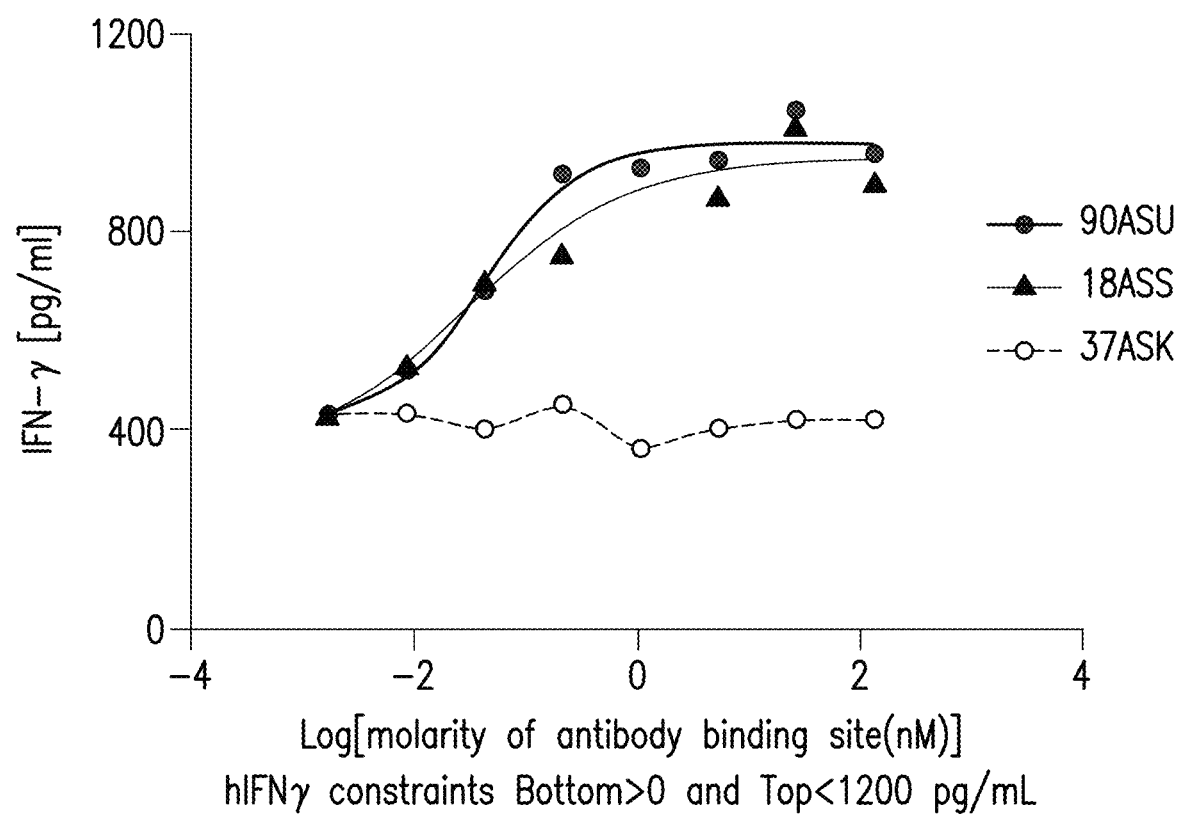
FIG. 3 depicts IFN-γ production of CD4+ T cell Clone 4-49 restimulated with PD-L1 transfected JY cells by bispecific antibodies.

Alloantigen-specific CD4+ T cells were harvested from 24 well culture plates on day 7 after antigen re-stimulation, then washed twice with 20 mL PBS (Hyclone, SH3002802) containing 2 mM EDTA (Invitrogen, 15575-38) by centrifugation. The pellets were resuspended into single cell suspension in Yssel's medium. Bispecific antibodies 90ASU, 18ASS were titrated by 5-fold serially dilutions in Yssel's medium starting from final highest concentration of 133 nM with total 7 dilutions in a volume of 100 μL in 96 well U-bottom culture plates (Falcon, 353077). The bispecific antibodies had hIgG1 Fc L234A/L235A/D265S mutation. Isotype control 37ASK (SEQ ID NOs: 126 and 127) was anti-RSV with the same mutation. Fifty microliters of T cell suspension at a density of $4 \times 10^5$ cells/mL was added into wells containing titrated antibodies. The antibody/T cell mixture was pre-incubated for 1 hour in an incubator at 37° C. with 5% $CO_2$. Human PD-L1 transgene expressing JY cells (JY.hPD-L1) were used in co-cultures to provide allo-specific antigens. JY.hPD-L1 cells cultured in T-75 flask (Thermo Scientific, 156499) in RPMI medium (Corning Cellgro, 10-040-CV) with 10% FCS were harvested and irradiated in a gamma irradiator at a dose of 5000 rads, then washed twice with PBS containing 2 mM EDTA by centrifugation. The pellet was resuspended with Yssel's medium, and filtered with 40 μm cell strainer before plating. Fifty μL/well of JY.hPD-L1 suspension at a concentration of $2 \times 10^5$ cells/mL was dispensed into pre-incubated antibody-T cells mixture, with T cell to JY.hPD-L1 cell ratio at 2:1. All conditions were run in duplicates. After approximately 3-day culture, 100 μL of supernatant per well was harvested for human IFNγ quantification. Human IFNγ ELISA was performed to assess IFNγ level on pooled supernatant from duplicates by using hIFNγ QUANTIKINE kit (R&D Systems, SIF50). Assays were run following the standard protocol provided by manufacturer. EC50 values were calculated using the GRAPHPAD prism software. The data from these experiments are set forth in FIG. 3.

This example demonstrated that the bispecific anti-human PD-1/LAG-3 antibody 90ASU (anti-PD-1 hu-08A with S61N and G56A, /anti-LAG3 hu-22D2 Ab6) and 18ASS (anti-PD-1 Fab100 affinity matured with S61N and G56A, /anti-LAG3 hu-22D2 Ab6) bound to both human PD-1 and human LAG-3 expressed by the T-cell clone, blocked PD-1's interaction with PD-L1, blocked LAG-3's interaction with MHC Class II; thereby, allowing the T-cell to respond to produce IFNγ to the allogeneic stimulation based on inhibiting the dual PD-L1-mediated and MHC Class II-mediated suppression. Additionally, this example showed that the bispecific anti-human PD-1/LAG-3 90ASU and 18ASS had comparable potency in promoting T cell IFNγ production. Isotype control antibody 37ASK did not enhance IFNγ production by the activated T cell clone.

REFERENCES

1. Sharpe et al. The function of programmed cell death 1 and its ligands in regulating autoimmunity and infection. *Nat. Immunol.* (2007) 8:239-245.
2. Dong et al. Tumor-associated B7-H1 promotes T-cell apoptosis: a potential mechanism of immune evasion. *Nat. Med.* (2002) 8:793-800.

3. Yang et al. PD-1 interaction contributes to the functional suppression of T-cell responses to human uveal melanoma cells in vitro. *Invest Ophthalmol Vis Sci.* (2008) 49:2518-2525.
4. Ghebeh et al. The B7-H1 (PD-L1) T lymphocyte-inhibitory molecule is expressed in breast cancer patients with infiltrating ductal carcinoma: correlation with important high-risk prognostic factors. *Neoplasia* (2006) 8:190-198.
5. Hamanishi et al. Programmed cell death 1 ligand 1 and tumor-infiltrating CD8+ T lymphocytes are prognostic factors of human ovarian cancer. *Proc. Natl. Acad Sci. USA* (2007) 104:3360-3365.
6. Thompson et al. Significance of B7-H1 overexpression in kidney cancer. *Clinical Genitourin Cancer* (2006) 5:206-211.
7. Nomi et al. Clinical significance and therapeutic potential of the programmed death-1 ligand/programmed death-1 pathway in human pancreatic cancer. *Clin. Cancer Res.* (2007) 13:2151-2157.
8. Ohigashi et al. Clinical significance of programmed death-1 ligand-1 and programmed death-1 ligand 2 expression in human esophageal cancer. *Clin. Cancer Res.* (2005) 11:2947-2953.
9. Inman et al. PD-L1 (B7-H1) expression by urothelial carcinoma of the bladder and BCG-induced granulomata: associations with localized stage progression. *Cancer* (2007) 109:1499-1505.
10. Shimauchi et al. Augmented expression of programmed death-1 in both neoplasmatic and nonneoplastic CD4+ T-cells in adult T-cell Leukemia/Lymphoma. *Int. J. Cancer* (2007) 121:2585-2590.
11. Gao et al. Overexpression of PD-L1 significantly associates with tumor aggressiveness and postoperative recurrence in human hepatocellular carcinoma. *Clin. Cancer Res.* (2009) 15:971-979.
12. Nakanishi et al. Overexpression of B7-H1 (PD-L1) significantly associates with tumor grade and postoperative prognosis in human urothelial cancers. *Cancer Immunol. Immunother.* (2007) 56:1173-1182.
13. Hino et al. Tumor cell expression of programmed cell death-1 is a prognostic factor for malignant melanoma. *Cancer* (2010) 116:1757-1766.
14. Ghebeh et al. Foxp3+ tregs and B7-H1+/PD-1+ T lymphocytes co-infiltrate the tumor tissues of high-risk breast cancer patients: implication for immunotherapy. *BMC Cancer* (2008) 8:57.
15. Ahmadzadeh et al. Tumor antigen-specific CD8 T cells infiltrating the tumor express high levels of PD-1 and are functionally impaired. *Blood* (2009) 114:1537-1544.
16. Thompson et al. PD-1 is expressed by tumor infiltrating cells and is associated with poor outcome for patients with renal carcinoma. *Clinical Cancer Research* (2007) 15:1757-1761.

All references cited herein are incorporated by reference to the same extent as if each individual publication, database entry (e.g., Genbank sequences or GeneID entries), patent application, or patent, was specifically and individually indicated to be incorporated by reference. This statement of incorporation by reference is intended by Applicants, pursuant to 37 C.F.R. § 1.57(b)(1), to relate to each and every individual publication, database entry (e.g., Genbank sequences or GeneID entries), patent application, or patent, each of which is clearly identified in compliance with 37 C.F.R. § 1.57(b)(2), even if such citation is not immediately adjacent to a dedicated statement of incorporation by reference. The inclusion of dedicated statements of incorporation by reference, if any, within the specification does not in any way weaken this general statement of incorporation by reference. Citation of the references herein is not intended as an admission that the reference is pertinent prior art, nor does it constitute any admission as to the contents or date of these publications or documents.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

The foregoing written specification is considered to be sufficient to enable one skilled in the art to practice the invention. Various modifications of the invention in addition to those shown and described herein will become apparent to those skilled in the art from the foregoing description and fall within the scope of the appended claims.

TABLE 8

Sequence Information

```
Name, Sequence
Fab001 heavy chain Fab region (Humanized 08A (Hu08A) Fab heavy chain region with S61N
correction):
EVQLVQSGAEVKKPGASVKVSCKASGYTFTSYYLYWVRQAPGQGLEWIGGVNPSNGGTNFN
EKFKSRVTLTVDTSISTAYMELSRLRSDDTAVYYCTRRDSNYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVE (SEQ ID NO: 1)

Fab004 or Fab001 light chain (Humanized 08A Fab light chain region)
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Fab004, Fab001 or Hu08A light chain CDRL regions
CDRL1: RASKSVSTSGFSYLH (SEQ ID NO: 3)

CDRL2: LASNLES (SEQ ID NO: 4)

CDRL3: QHSWELPLT (SEQ ID NO: 5)

Fab 004, 98, 99, 100, 101, 102, 103 or 104 heavy chain Fab region (H3G9) with CDRH2 S61N
correction, and CDRH3 affinity maturation mutations (in bold, italics)
EVQLVQSGAEVKKPGASVKVSCKASGYTFTSYYLYWVRQAPGQGLEWIGGVNPSNGGTNFN
```

TABLE 8-continued

Sequence Information

EKFKSRVTLTVDTSISTAYMELSRLRSDDTAVYYCTR<u>R*LS*H*YDGGFDY*</u>WGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVE (SEQ ID NO: 6)

Fab 004, 98, 99, 100, 101, 102, 103 and 104 heavy chain variable region
EVQLVQSGAEVKKPGASVKVSCKASGYTFT<u>SYYLY</u>WVRQAPGQGLEWIGG<u>VNPSNGGTNFN
EKFKS</u>RVTLTVDTSISTAYMELSRLRSDDTAVYYCTR<u>R*LS*H*YDGGFDY*</u>WGQGTTVTVSS
(SEQ ID NO: 7) [Note that the CDRH3 affinity maturation mutations are in bold, italics.]

Fab 004, 98, 99, 100, 101, 102, 103 and 104 CDRH regions
CDRH1: SYYLY (SEQ ID NO: 8)

CDRH2: GVNPSNGGTNFNEKFKS (SEQ ID NO: 9)

CDRH3: R*LS*H*YDGGFDY* (SEQ ID NO: 10) [Note that the CDRH3 affinity maturation mutations are in bold, italics.]

Fab 098, 099, 100, 101, 102, 103 and 104 light chain CDRL regions (including consensus sequences)
CDRL1: RASKSVSTSGFSYLH (SEQ ID NO: 3)

CDRL2: LY$_1$Y$_2$Y$_3$Y$_4$Y$_5$S; wherein Y$_1$ is G or S, Y$_2$ is K, T, H, or R, Y$_3$ is F, H, or Y, Y$_4$ is R, G, A, L or S, and Y$_5$ is E, A, S, Q or V. (SEQ ID NO: 11)

CDRL3: Y$_6$Y$_7$Y$_8$Y$_9$Y$_{10}$LPLT; wherein Y$_6$ is Q, S, or A, Y$_7$ is H or Q, Y$_8$ is S or A, Y$_9$ is W, Y or T, and Y$_{10}$ is E, H, or Q. (SEQ ID NO: 12)

Fab098 light chain (L28B6) with CDRL2 affinity maturation mutations (in bold, italics)
DIVMTQTPLSLSVTPGQPASISC<u>RASKSVSTSGFSYLH</u>WYLQKPGQPPQLLIFL*GKFRE*SGVPD
RFSGSGSGTDFTLKISRVEAEDVGVYYC<u>QHSWELPLT</u>FGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 13)

Fab098 light chain (L28B6) variable region [Note that the CDRL2 affinity maturation mutations are in bold, italics.]
DIVMTQTPLSLSVTPGQPASISC<u>RASKSVSTSGFSYLH</u>WYLQKPGQPPQLLIFL*GKFRE*SGVPD
RFSGSGSGTDFTLKISRVEAEDVGVYYC<u>QHSWELPLT</u>FGQGTKLEIK (SEQ ID NO: 14)

Fab098 light chain CDRL regions
CDRL1: RASKSVSTSGFSYLH (SEQ ID NO: 3)

CDRL2: L*GKFR*ES (SEQ ID NO:15) [Note that the CDRL2 affinity maturation mutations are in bold, italics.]

CDRL3: QHSWELPLT (SEQ ID NO: 5)

Fab099 light chain (L28C3) with CDRL2 affinity maturation mutations
DIVMTQTPLSLSVTPGQPASISC<u>RASKSVSTSGFSYLH</u>WYLQKPGQPPQLLIFL*GTHRA*SGVPD
RFSGSGSGTDFTLKISRVEAEDVGVYYC<u>QHSWELPLT</u>FGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 16) [Note that the CDRL2 affinity maturation mutations are in bold, italics.]

Fab099 light chain (L28C3) variable region [Note that the CDRL2 affinity maturation mutations are in bold, italics.]
DIVMTQTPLSLSVTPGQPASISC<u>RASKSVSTSGFSYLH</u>WYLQKPGQPPQLLIFL*GTHRA*SGVPD
RFSGSGSGTDFTLKISRVEAEDVGVYYC<u>QHSWELPLT</u>FGQGTKLEIK (SEQ ID NO: 17)

Fab099 light chain (L28C3) CDRL regions
CDRL1: RASKSVSTSGFSYLH (SEQ ID NO: 3)

CDRL2: L*GTHRA*S (SEQ ID NO: 18) [Note that the CDRL2 affinity maturation mutations are in bold, italics.]

CDRL3: QHSWELPLT (SEQ ID NO: 5)

Fab100 light chain (L28D1) with CDRL2 and CDRL3 affinity maturation mutations (in bold, italics)
DIVMTQTPLSLSVTPGQPASISC<u>RASKSVSTSGFSYLH</u>WYLQKPGQPPQLLIFL*SKYRS*SGVPDR
FSGSGSGTDFTLKISRVEAEDVGVYYC*SQAYH*LPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 19)

Fab100 light chain (L28D1) variable region [Note that the CDRL2 and CDRL3 affinity maturation mutations are in bold, italics.]
DIVMTQTPLSLSVTPGQPASISC<u>RASKSVSTSGFSYLH</u>WYLQKPGQPPQLLIFL*SKYRS*SGVPDR
FSGSGSGTDFTLKISRVEAEDVGVYYC*SQAYH*LPLTFGQGTKLEIK (SEQ ID NO: 20)

TABLE 8-continued

Sequence Information

Fab100 light chain (L28D1) CDRL regions [Note that the CDRL2 and CDRL3 affinity maturation mutations are in bold, italics.]
CDRL1: RASKSVSTSGFSYLH (SEQ ID NO: 3)

CDRL2: LSKYRSS (SEQ ID NO: 21)

CDRL3: SQAYHLPLT (SEQ ID NO: 22)

Fab101 light chain L28G1) with CDRL2 and CDRL3 affinity maturation mutations (in bold, italics)
DIVMTQTPLSLSVTPGQPASISCRASKSVSTSGFSYLHWYLQKPGQPPQLLIFLGKYGASGVPD
RFSGSGSGTDFTLKISRVEAEDVGVYYCAQATQLPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 23)

Fab101 light chain (L28G1) variable region [Note that the CDRL2 and CDRL3 affinity maturation mutations are in bold, italics.]
DIVMTQTPLSLSVTPGQPASISCRASKSVSTSGFSYLHWYLQKPGQPPQLLIFLGKYGASGVPD
RFSGSGSGTDFTLKISRVEAEDVGVYYCAQATQLPLTFGQGTKLEIK (SEQ ID NO: 24)

Fab101 light chain (L28G1) CDRL regions [Note that the CDRL2 and CDRL3 affinity maturation mutations are in bold, italics.]
CDRL1: RASKSVSTSGFSYLH (SEQ ID NO: 3)

CDRL2: LGKYGAS (SEQ ID NO: 25)

CDRL3: AQATQLPLT (SEQ ID NO: 26)

Fab102 light chain (L28G8) with CDRL2 affinity maturation mutations (in bold, italics)
DIVMTQTPLSLSVTPGQPASISCRASKSVSTSGFSYLHWYLQKPGQPPQLLIFLGHFASSGVPD
RFSGSGSGTDFTLKISRVEAEDVGVYYCQHSWELPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 27)

Fab102 light chain (L28G8) variable region [Note that the CDRL2 affinity maturation mutations are in bold, italics.]
DIVMTQTPLSLSVTPGQPASISCRASKSVSTSGFSYLHWYLQKPGQPPQLLIFLGHFASSGVPD
RFSGSGSGTDFTLKISRVEAEDVGVYYCQHSWELPLTFGQGTKLEIK (SEQ ID NO: 28)

Fab102 light chain (L28G8) CDRL regions
CDRL1: RASKSVSTSGFSYLH (SEQ ID NO: 3)

CDRL2: LGHFASS (SEQ ID NO: 29) [Note that the CDRL2 affinity maturation mutations are in bold, italics.]

CDRL3: QHSWELPLT (SEQ ID NO: 5)

Fab103 light chain (L28H3) with CDRL2 affinity maturation mutations (in bold, italics)
DIVMTQTPLSLSVTPGQPASISCRASKSVSTSGFSYLHWYLQKPGQPPQLLIFLGRYLQSGVPD
RFSGSGSGTDFTLKISRVEAEDVGVYYCQHSWELPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 30)

Fab103 light chain (L28H3) variable region [Note that the CDRL2 affinity maturation mutations are in bold, italics.]
DIVMTQTPLSLSVTPGQPASISCRASKSVSTSGFSYLHWYLQKPGQPPQLLIFLGRYLQSGVPD
RFSGSGSGTDFTLKISRVEAEDVGVYYCQHSWELPLTFGQGTKLEIK (SEQ ID NO: 31)

Fab103 light chain (L28H3) CDRL regions
CDRL1: RASKSVSTSGFSYLH (SEQ ID NO: 3)

CDRL2: LGRYLQS (SEQ ID NO: 32) [Note that the CDRL2 affinity maturation mutations are in bold, italics.]

CDRL3: QHSWELPLT (SEQ ID NO: 5)

Fab104 light chain (L28H10) with CDRL2 affinity maturation mutations (in bold, italics)
DIVMTQTPLSLSVTPGQPASISCRASKSVSTSGFSYLHWYLQKPGQPPQLLIFLGTHSVSGVPD
RFSGSGSGTDFTLKISRVEAEDVGVYYCQHSWELPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 33)

Fab104 light chain (L28H10) variable region [Note that the CDRL2 affinity maturation mutations are in bold, italics.]
DIVMTQTPLSLSVTPGQPASISCRASKSVSTSGFSYLHWYLQKPGQPPQLLIFLGTHSVSGVPD
RFSGSGSGTDFTLKISRVEAEDVGVYYCQHSWELPLTFGQGTKLEIK (SEQ ID NO: 34)

TABLE 8-continued

Sequence Information

Fab104 light chain (L28H10) CDRL regions
CDRL1: RASKSVSTSGFSYLH (SEQ ID NO: 3)

CDRL2: L*GTHSV*S (SEQ ID NO: 35) [Note that the CDRL2 affinity maturation mutations are in bold, italics.]

CDRL3: QHSWELPLT (SEQ ID NO: 5)

Fab128 heavy chain Fab region (H34B7) with CDRH1 affinity maturation mutations (in bold, italics) and CDRH2 S61N correction, A92S FR mutation
EVQLVQSGAEVKKPGASVKVSCKASGYTFTQYYYYWVRQAPGQGLEWIGGVNPSNGGTNF
NEKFKSRVTLTVDTSISTAYMELSRLSDDTSVYYCTRRDSNYDGGFDYWGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 36)

Fab128 heavy chain (H34B7) variable region with CDRH1 affinity maturation mutations (in bold, italics) and CDRH2 S61N correction, A92S FR mutation
EVQLVQSGAEVKKPGASVKVSCKASGYTFTQYYYYWVRQAPGQGLEWIGGVNPSNGGTNF
NEKFKSRVTLTVDTSISTAYMELSRLSDDTSVYYCTRRDSNYDGGFDYWGQGTTVTVSS
(SEQ ID NO: 37)

Fab128 heavy chain (H34B7) with CDRH1 affinity maturation mutations (in bold, italics) and CDRH2 S61N correction
EVQLVQSGAEVKKPGASVKVSCKASGYTFTQYYYYWVRQAPGQGLEWIGGVNPSNGGTNF
NEKFKSRVTLTVDTSISTAYMELSRLSDDTAVYYCTRRDSNYDGGFDYWGQGTTVTVSSAS
TKGPSVFPLAPCSRSTSESTAALGCLVKDYFPEPVTVSWNSGALTSGVHTFPAVLQSSGLYSLS
SVVTVPSSSLGTKTYTCNVDHKPSNTKVDKRVE (SEQ ID NO: 118)

Fab128 heavy chain (H34B7) variable region with CDRH1 affinity maturation mutations (in bold, italics) and CDRH2 S61N correction
EVQLVQSGAEVKKPGASVKVSCKASGYTFTQYYYYWVRQAPGQGLEWIGGVNPSNGGTNF
NEKFKSRVTLTVDTSISTAYMELSRLSDDTAVYYCTRRDSNYDGGFDYWGQGTTVTVSS
(SEQ ID NO: 119)

Fab128 light chain (L34B7) with CDRL2 affinity maturation mutations (in bold, italics)
DIVMTQTPLSLSVTPGQPASISCRASKSVSTSGFSYLHWYLQKPGQPPQLLIFLGRHRAS
GVPDRFSGSGSGTDFTLKISRVEAEDVGVYYCQHSWELPLTFGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 38)

Fab128 light chain (L34B7) variable region [Note that the CDRL2 affinity maturation mutations are in bold, italics.]
DIVMTQTPLSLSVTPGQPASISCRASKSVSTSGFSYLHWYLQKPGQPPQLLIFLGRHRAS
GVPDRFSGSGSGTDFTLKISRVEAEDVGVYYCQHSWELPLTFGQGTKLEIK (SEQ ID NO: 39)

Fab128 (L34B7) CDRH and CDRL regions
CDRH1: QYYYY (SEQ ID NO: 40)

CDRH2: GVNPSNGGTNFNEKFKS (SEQ ID NO: 9)

CDRH3: RDSNYDGGFDY (SEQ ID NO: 41)

CDRL1: RASKSVSTSGFSYLH (SEQ ID NO: 3)

CDRL2: LGRHRAS (SEQ ID NO: 42)

CDRL3: QHSWELPLT (SEQ ID NO: 5)

Fab 133 heavy chain Fab region (H33F5) with CDRH1 affinity maturation mutations (in bold, italics) and CDRH2 S61N correction, and FR mutation A92S
EVQLVQSGAEVKKPGASVKVSCKASGYTFTQYYYWVRQAPGQGLEWIGGVNPSNGGTNF
NEKFKSRVTLTVDTSISTAYMELSRLSDDTSVYYCTRRDSNYDGGFDYWGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 43)

Fab 133 heavy chain (H33F5) variable region with CDRH1 affinity maturation mutations (in bold, italics) and CDRH2 S61N correction, and FR mutation A92S
EVQLVQSGAEVKKPGASVKVSCKASGYTFTQYYYWVRQAPGQGLEWIGGVNPSNGGTNF
NEKFKSRVTLTVDTSISTAYMELSRLSDDTSVYYCTRRDSNYDGGFDYWGQGTTVTVSS
(SEQ ID NO: 44)

Fab 133 heavy chain Fab region (H33F5) with CDRH1 affinity maturation mutations (in bold, italics) and CDRH2 S61N correction
EVQLVQSGAEVKKPGASVKVSCKASGYTFTQYYYWVRQAPGQGLEWIGGVNPSNGGTNF
NEKFKSRVTLTVDTSISTAYMELSRLSDDTAVYYCTRRDSNYDGGFDYWGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 120)

TABLE 8-continued

Sequence Information

Fab 133 heavy chain (H33F5) variable region with CDRH1 affinity maturation mutations (in bold, italics) and CDRH2 S61N correction
EVQLVQSGAEVKKPGASVKVSCKASGYTFTQYYYYWVRQAPGQGLEWIGG<u>VNPSNGGTNF
NEKFKS</u>RVTLTVDTSISTAYMELSRLRSDDTAVYYCTR<u>RDSNYDGGFDY</u>WGQGTTVTVSS
(SEQ ID NO: 121)

Fab133 light chain (L33F5) with CDRL2 and CDRL3 affinity maturation mutations (in bold, italics)
DIVMTQTPLSLSVTPGQPASISC<u>RASKSVSTSGFSYLH</u>WYLQKPGQPPQLLIFL*GFYRT*S
GVPDRFSGSGSGTDFTLKISRVEAEDVGVYYC*SQMAD*LPLTFGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 45)

Fab133 light chain (L33F5) variable region [Note that the CDRL2 and CDRL3 affinity maturation mutations are in bold, italics.]
DIVMTQTPLSLSVTPGQPASISC<u>RASKSVSTSGFSYLH</u>WYLQKPGQPPQLLIFL*GFYRT*S
GVPDRFSGSGSGTDFTLKISRVEAEDVGVYYC*SQMAD*LPLTFGQGTKLEIK (SEQ ID NO: 46)

Fab133 (L33F5) CDRH and CDRL regions
CDRH1: QYYYY (SEQ ID NO: 40)

CDRH2: GVNPSNGGTNFNEKFKS (SEQ ID NO: 9)

CDRH3: RDSNYDGGFDY (SEQ ID NO: 41)

CDRL1: RASKSVSTSGFSYLH (SEQ ID NO: 3)

CDRL2: LGFYRTS (SEQ ID NO: 47)

CDRL3: SQMADLPLT (SEQ ID NO: 48)

Fab 138 heavy chain (H34F11) Fab region with CDRH1 and CDRH2 affinity maturation mutations (in bold, italics) and CDRH2 S61N correction
EVQLVQSGAEVKKPGASVKVSCKASGYTFTQYYTYWVRQAPGQGLEWIGG*IEPNR*GGTNF
NEKFKSRVTLTVDTSISTAYMELSRLRSDDTAVYYCTR<u>RDSNYDGGFDY</u>WGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 49)

Fab 138 heavy chain (H34F11) variable region [Note that the CDRH1 and CDRH2 affinity maturation mutations are in bold, italics.]
EVQLVQSGAEVKKPGASVKVSCKASGYTFTQYYTYWVRQAPGQGLEWIGG*IEPNR*GGTNF
NEKFKSRVTLTVDTSISTAYMELSRLRSDDTAVYYCTR<u>RDSNYDGGFDY</u>WGQGTTVTVSS
(SEQ ID NO: 50)

Fab138 light chain (L34F11) with CDRL3 affinity maturation mutations (in bold, italics)
DIVMTQTPLSLSVTPGQPASISC<u>RASKSVSTSGFSYLH</u>WYLQKPGQPPQLLIF<u>LASNLES</u>
GVPDRFSGSGSGTDFTLKISRVEAEDVGVYYC*AQTFE*LPLTFGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 51)

Fab138 light chain (L34F11) variable region [Note that the CDRL3 affinity maturation mutations are in bold, italics.]
DIVMTQTPLSLSVTPGQPASISC<u>RASKSVSTSGFSYLH</u>WYLQKPGQPPQLLIF<u>LASNLES</u>
GVPDRFSGSGSGTDFTLKISRVEAEDVGVYYC*AQTFE*LPLTFGQGTKLEIK (SEQ ID NO: 52)

Fab138 CDRH and CDRL regions
CDRH1: QYYTY (SEQ ID NO: 53)

CDRH2: GIEPNRGGTNFNEKFKS (SEQ ID NO: 54)

CDRH3: RDSNYDGGFDY (SEQ ID NO: 41)

CDRL1: RASKSVSTSGFSYLH (SEQ ID NO: 3)

CDRL2: LASNLES (SEQ ID NO: 4)

CDRL3: AQTFELPLT (SEQ ID NO: 55)

Fab139 heavy chain Fab region (H34G8) with CDRH1 affinity maturation mutations (in bold, italics) and CDRH2 S61N correction, and A92S FR mutation
EVQLVQSGAEVKKPGASVKVSCKASGYTFTQYYYYWVRQAPGQGLEWIGG<u>VNPSNGGTNF
NEKFKS</u>RVTLTVDTSISTAYMELSRLRSDDTSVYYCTR<u>RDSNYDGGFDY</u>WGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 56)

Fab139 heavy chain (H34G8) variable region with CDRH1 affinity maturation mutations (in bold, italics) and CDRH2 S61N correction, and A92S FR mutation TABLE 8-continued Sequence Information EVQLVQSGAEVKKPGASVKVSCKASGYTFT*QYY*YWVRQAPGQGLEWIGG<u>VNPSNGGTNF</u>
<u>NEKFKS</u>RVTLTVDTSISTAYMELSRLRSDDTSVYYCTR<u>RDSNYDGGFDY</u>WGQGTTVTVSS
(SEQ ID NO: 57)

Fab139 heavy chain Fab region (H34G8) with CDRH1 affinity maturation mutations (in bold, italics) and CDRH2 S61N correction
EVQLVQSGAEVKKPGASVKVSCKASGYTFT*QYY*YWVRQAPGQGLEWIGG<u>VNPSNGGTNF</u>
<u>NEKFKS</u>RVTLTVDTSISTAYMELSRLRSDDTAVYYCTR<u>RDSNYDGGFDY</u>WGQGTTVTVSS
ASTKGPSVFPLAPCSRSTSESTAALGCLVKDYFPEPVTVSWNSGALTSGVHTFPAVLQSS
GLYSLSSVVTVPSSSLGTKTYTCNVDHKPSNTKVDKRVE (SEQ ID NO: 122)

Fab139 heavy chain (H34G8) variable region with CDRH1 affinity maturation mutations (in bold, italics) and CDRH2 S61N correction
EVQLVQSGAEVKKPGASVKVSCKASGYTFT*QYY*YWVRQAPGQGLEWIGG<u>VNPSNGGTNF</u>
<u>NEKFKS</u>RVTLTVDTSISTAYMELSRLRSDDTAVYYCTR<u>RDSNYDGGFDY</u>WGQGTTVTVSS
(SEQ ID NO: 123)

Fab139 light chain (L34G8) with CDRL2 affinity maturation mutations (in bold, italics)
DIVMTQTPLSLSVTPGQPASISC<u>RASKSVSTSGFSYLH</u>WYLQKPGQPPQLLIFL*SKFRR*S
GVPDRFSGSGSGTDFTLKISRVEAEDVGVYYC<u>QHSWELPLT</u>FGQGTKLEIKRTVAAPSVF
IFPPSDEQLKSGTASVVCLLNNFYPREAKVQWKVDNALQSGNSQESVTEQDSKDSTYSLS
STLTLSKADYEKHKVYACEVTHQGLSSPVTKSFNRGEC (SEQ ID NO: 58)

Fab139 light chain (L34G8) variable region [Note that the CDRL2 affinity maturation mutations are in bold, italics.]
DIVMTQTPLSLSVTPGQPASISC<u>RASKSVSTSGFSYLH</u>WYLQKPGQPPQLLIFL*SKFRR*S
GVPDRFSGSGSGTDFTLKISRVEAEDVGVYYC<u>QHSWELPLT</u>FGQGTKLEIK (SEQ ID NO: 59)

Fab139 CDRH an CDRL regions
CDRH1: QYYYY (SEQ ID NO: 40)

CDRH2: GVNPSNGGTNFNEKFKS (SEQ ID NO: 9)

CDRH3: RDSNYDGGFDY (SEQ ID NO: 41)

CDRL1: RASKSVSTSGFSYLH (SEQ ID NO: 3)

CDRL2: LSKFRRS (SEQ ID NO: 60)

CDRL3: QHSWELPLT (SEQ ID NO: 5)

Fab128, 133, 138 and 139 CDRH and CDRL sequences, including consensus sequences (with or without S61N or G56A correction, or both)
CDRH1: QYYZ$_1$Y; wherein Z$_1$ is T or Y (SEQ ID NO: 61)

CDRH2: GZ$_2$Z$_3$PZ$_4$Z$_5$Z$_6$GTNFZ$_7$EKFKS; wherein Z$_2$ is V or I, Z$_3$ is E or N, Z$_4$ is N or S, Z$_5$ is R or N, Z$_6$ is G or A, and Z$_7$ is S or N (SEQ ID NO: 62)

CDRH3: RDSNYDGGFDY (SEQ ID NO: 41)

CDRL1: RASKSVSTSGFSYLH (SEQ ID NO: 3)

CDRL2: LZ$_8$Z$_9$Z$_{10}$Z$_{11}$Z$_{12}$S; wherein Z$_8$ is G, A or S, Z$_9$ is R, F, S or K, Z$_{10}$ is H, Y, N or F, Z$_{11}$ is R or L, and Z$_{12}$ is A, T, E or R (SEQ ID NO: 63)

CDRL3: Z$_{13}$Z$_{14}$Z$_{15}$Z$_{16}$Z$_{17}$LPLT; wherein Z$_{13}$ is Q, S or A, Z$_{14}$ is Q or H, Z$_{15}$ is S, M, or T, Z$_{16}$ is W, A, or F, and Z$_{17}$ is E or D. (SEQ ID NO: 64)

Mouse x [PD-1_H] mAb (Clone 08A) IgG1/Kappa (CE) (09AFF)
Mouse-08A mAb Heavy Chain:
QVQLQQPGAELVKPGASVKLSCKASGYTFT<u>SYYLY</u>WMKQRPGQGLEWIGG<u>VNPSNGGTNFS</u>
<u>EKFKS</u>KATLTVDKSSSTAYMQLSSLTSEDSAVYYCTR<u>RDSNYDGGFDY</u>WGQGTTLTVSSAKT
TPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTIT
LTPKVTCVVVAISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHTEKS
LSHSPGK (SEQ ID NO: 65)

Mouse-08A mAb Light Chain:
DIVLTQSPTSLAVSLGQRATISC<u>RASKSVSTSGFSYLH</u>WYQQKPGQPPKLLIF<u>LASNLES</u>GVPA
RFSGSGSGTDFTLNIHPVEEEDAATYYC<u>QHSWELPLT</u>FGAGTKLELKRADAAPTVSIFPPSSEQ
LTSGGASVVCFLNNFYPKDINVKWKIDGSERQNGVLNSWTDQDSKDSTYSMSSTLTLTKDEY
ERHNSYTCEATHKTSTSPIVKSFNRNEC (SEQ ID NO: 66)

Mouse x [PD-1_H] mAb (clone 09A) IgG1/Kappa (CE) (03AFN)
Mouse-09A mAb Heavy Chain TABLE 8-continued Sequence Information

```
QVQLQQPGAELVKPGTSVKLSCKASGYTFTNYYMYWVKQRPGQGLEWIGGINPSNGGTNFN
EKFKNKATLTVDSSSSTTYMQLSSLTSEDSAVYYCTRRDYRFDMGFDYWGQGTTLTVSSAKT
TPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTIT
LTPKVTCVVVDISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHTEKS
LSHSPGK (SEQ ID NO: 67)

Mouse-09A mAb Light Chain
DIVLTQSPASLAVSLGQRAAISCRASKGVSTSGYSYLHWYQQKPGQSPKLLIYLASYLESGVP
ARFSGSGSGTDFTLNIHPVEEEDAATYYCQHSRDLPLTFGTGTKLELKRADAAPTVSIFPPSSE
QLTSGGASVVCFLNNFYPKDINVKWKIDGSERQNGVLNSWTDQDSKDSTYSMSSTLTLTKDE
YERHNSYTCEATHKTSTSPIVKSFNRNEC (SEQ ID NO: 68)

Mouse x [PD-1_H] mAb (Clone 1.08 N59Q) IgG1/Kappa (CE) (38AFL)
Mouse-08A mAb Heavy Chain with CDRH2 N59Q mutation
QVQLQQPGAELVKPGASVKLSCKASGYTFTSYYLYWMKQRPGQGLEWIGGVNPSNGGTQFS
EKFKSKATLTVDKSSSTAYMQLSSLTSEDSAVYYCTRRDSNYDGGFDYWGQGTTLTVSSAKT
TPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTIT
LTPKVTCVVVAISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHTEKS
LSHSPGK (SEQ ID NO: 69)

Mouse-08A mAb Light Chain
DIVLTQSPTSLAVSLGQRATISCRASKSVSTSGFSYLHWYQQKPGQPPKLLIFLASNLESGVPA
RFSGSGSGTDFTLNIHPVEEEDAATYYCQHSWELPLTFGAGTKLELKRADAAPTVSIFPPSSEQ
LTSGGASVVCFLNNFYPKDINVKWKIDGSERQNGVLNSWTDQDSKDSTYSMSSTLTLTKDEY
ERHNSYTCEATHKTSTSPIVKSFNRNEC (SEQ ID NO: 66)

Mouse x [PD-1_H] mAb (Clone 1.08 N59E) IgG1/Kappa (CE) (39AFL)
Mouse-08A mAb Heavy Chain with CDRH2 N59E mutation
QVQLQQPGAELVKPGASVKLSCKASGYTFTSYYLYWMKQRPGQGLEWIGGVNPSNGGTEFS
EKFKSKATLTVDKSSSTAYMQLSSLTSEDSAVYYCTRRDSNYDGGFDYWGQGTTLTVSSAKT
TPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTIT
LTPKVTCVVVAISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHHTEKS
LSHSPGK (SEQ ID NO: 70)

Mouse-08A mAb Light Chain
DIVLTQSPTSLAVSLGQRATISCRASKSVSTSGFSYLHWYQQKPGQPPKLLIFLASNLESGVPA
RFSGSGSGTDFTLNIHPVEEEDAATYYCQHSWELPLTFGAGTKLELKRADAAPTVSIFPPSSEQ
LTSGGASVVCFLNNFYPKDINVKWKIDGSERQNGVLNSWTDQDSKDSTYSMSSTLTLTKDEY
ERHNSYTCEATHKTSTSPIVKSFNRNEC (SEQ ID NO: 66)

Mouse x [PD-1_H] mAb (Clone 1.08 N59A) IgG1/Kappa (CE) (80AFH)
Mouse-08A mAb Heavy Chain with CDRH2 N59A mutation
QVQLQQPGAELVKPGASVKLSCKASGYTFTSYYLYWMKQRPGQGLEWIGGVNPSNGGTAFS
EKFKSKATLTVDKSSSTAYMQLSSLTSEDSAVYYCTRRDSNYDGGFDYWGQGTTLTVSSAKT
TPPSVYPLAPGSAAQTNSMVTLGCLVKGYFPEPVTVTWNSGSLSSGVHTFPAVLQSDLYTLSS
SVTVPSSTWPSETVTCNVAHPASSTKVDKKIVPRDCGCKPCICTVPEVSSVFIFPPKPKDVLTIT
LTPKVTCVVVAISKDDPEVQFSWFVDDVEVHTAQTQPREEQFNSTFRSVSELPIMHQDWLNG
KEFKCRVNSAAFPAPIEKTISKTKGRPKAPQVYTIPPPKEQMAKDKVSLTCMITDFFPEDITVE
WQWNGQPAENYKNTQPIMDTDGSYFVYSKLNVQKSNWEAGNTFTCSVLHEGLHNHEITEKS
LSHSPGK (SEQ ID NO: 71)

Mouse-08A mAb Light Chain
DIVLTQSPTSLAVSLGQRATISCRASKSVSTSGFSYLHWYQQKPGQPPKLLIFLASNLESGVPA
RFSGSGSGTDFTLNIHPVEEEDAATYYCQHSWELPLTFGAGTKLELKRADAAPTVSIFPPSSEQ
LTSGGASVVCFLNNFYPKDINVKWKIDGSERQNGVLNSWTDQDSKDSTYSMSSTLTLTKDEY
ERHNSYTCEATHKTSTSPIVKSFNRNEC (SEQ ID NO: 66)

Humanized x [PD-1_H] mAb (08A/HuPD1A-11 N55E S228P) IgG4/Kappa (50AQK)
50AQK mAb Heavy Chain (Hu08A Fab with CDRH2 N55E mutation) with S228P correction
EVQLVQSGAEVKKPGASVKVSCKASGYTFTSYYLYWVRQAPGQGLEWIGGVNPSEGGTNFN
EKFKSRVTLTVDTSISTAYMELSRLRSDDTAVYYCTRRDSNYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 72)
```

TABLE 8-continued

Sequence Information

50AQK mAb Light Chain
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Humanized x [PD-1_H] mAb (08A/HuPD1A-11 S228P) IgG4/Kappa (PK) (lot 73AGG)
73AGG mAb Heavy Chain with S228P correction (Hu08A Fab)
EVQLVQSGAEVKKPGASVKVSCKASGYTFTSYYLYWVRQAPGQGLEWIGGVNPSNGGTNFS
EKFKSRVTLTVDTSISTAYMELSRLRSDDTAVYYCTRRDSNYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 73)

73AGG mAb Light Chain
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Humanized x [PD-1_H] mAb (08A/HuPD1A-11 S61N S228P corrected) IgG4/Kappa (CE)
(98AIO)
98AIO mAb Heavy Chain (Hu08A Fab with S61N correction to remove N-glycosylation site) with
S228P correction
EVQLVQSGAEVKKPGASVKVSCKASGYTFT<u>SYYLY</u>WVRQAPGQGLEWIGG<u>VNPSNGGTNFN</u>
<u>EKFKS</u>RVTLTVDTSISTAYMELSRLRSDDTAVYYCTR<u>RDSNYDGGFDY</u>WGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 74)

Hu08A Heavy Chain Variable Region with S61N correction to remove N-glycosylation site
EVQLVQSGAEVKKPGASVKVSCKASGYTFT<u>SYYLY</u>WVRQAPGQGLEWIGG<u>VNPSNGGTNFN</u>
<u>EKFKS</u>RVTLTVDTSISTAYMELSRLRSDDTAVYYCTR<u>RDSNYDGGFDY</u>WGQGTTVTVSS
(SEQ ID NO: 75)

98AIO mAb Light Chain
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Hu08A Light Chain Variable Region:
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIK (SEQ ID NO: 76)

Hu08A Heavy Chain CDRH regions with S61N correction and Light Chain CDRL regions
CDRH1: SYYLY (SEQ ID NO: 8)

CDRH2: GVNPSNGGTNFNEKFKS (SEQ ID NO: 9)

CDRH3: RDSNYDGGFDY (SEQ ID NO: 41)

CDRL1: RASKSVSTSGFSYLH (SEQ ID NO: 3)

CDRL2: LASNLES (SEQ ID NO: 4)

CDRL3: QHSWELPLT (SEQ ID NO: 5)

Humanized x [PD-1_H] mAb (08A/HuPD1A-11 G56A) IgG4 S228P/Kappa (CX) (lot 89AVZ)
89AVZ mAb Heavy Chain (Hu08A Fab with G56A correction) with S228P correction
EVQLVQSGAEVKKPGASVKVSCKASGYTFT<u>SYYLY</u>WVRQAPGQGLEWIGG<u>VNPSNAGTNFS</u>
<u>EKFKS</u>RVTLTVDTSISTAYMELSRLRSDDTAVYYCTR<u>RDSNYDGGFDY</u>WGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 77)

TABLE 8-continued

Sequence Information

Hu08A Heavy Chain Variable Region with G56A correction
EVQLVQSGAEVKKPGASVKVSCKASGYTFT<u>SYYLY</u>WVRQAPGQGLEWIGG<u>VNPSNAGTNFS
EKFKS</u>RVTLTVDTSISTAYMELSRLRSDDTAVYYCTR<u>RDSNYDGGFDY</u>WGQGTTVTVSS
(SEQ ID NO: 78)

89AVZ mAb Light Chain
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Hu08A Light Chain Variable Region
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIK (SEQ ID NO: 76)

Hu08A Heavy Chain CDRH regions with G56A correction and Light Chain CDRL regions
CDRH1: SYYLY (SEQ ID NO: 8)

CDRH2: GVNPSNAGTNFSEKFKS (SEQ ID NO: 79)

CDRH3: RDSNYDGGFDY (SEQ ID NO: 41)

CDRL1: RASKSVSTSGFSYLH (SEQ ID NO: 3)

CDRL2: LASNLES (SEQ ID NO: 4)

CDRL3: QHSWELPLT (SEQ ID NO: 5)

Humanized x [PD-1_H] Fab (08A/HuPD1A-11 S61N WT) IgG4/Kappa (PX) (00APE)-
humanized 08A Fab with N-glycosylation correction (S61N)
Hu08A Heavy Chain Fab region with S61N correction:
EVQLVQSGAEVKKPGASVKVSCKASGYTFT<u>SYYLY</u>WVRQAPGQGLEWIGG<u>VNPSNGGTNFN
EKFKS</u>RVTLTVDTSISTAYMELSRLRSDDTAVYYCTR<u>RDSNYDGGFDY</u>WGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPP (SEQ ID NO: 80)

Hu08A Light Chain
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Humanized x [PD-1_H] mAb (08A/HuPD1A-11 S61N WT) S228P IgG4/Kappa (PX) (67AGG)-
humanized 08A mAb with N-glycosylation correction (S61N) and HFR4 mutation
67AGG mAb Heavy Chain (Hu08A Fab with CDRH2 S61N correction, HFR4 mutation), with IgG4
S228P mutation
EVQLVQSGAEVKKPGASVKVSCKASGYTFT<u>SYYLY</u>WVRQAPGQGLEWIGG<u>VNPSNGGTNFN
EKFKS</u>RVTLTVDTSISTAYMELSRLRSDDTAVYYCTR<u>RDSNYDGGFDY</u>WGQGTTLTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 82)

Hu08A Heavy Chain variable region with CDRH2 S61N correction, and HFR4 mutation
EVQLVQSGAEVKKPGASVKVSCKASGYTFT<u>SYYLY</u>WVRQAPGQGLEWIGG<u>VNPSNGGTNFN
EKFKS</u>RVTLTVDTSISTAYMELSRLRSDDTAVYYCTR<u>RDSNYDGGFDY</u>WGQGTTLTVSS
(SEQ ID NO: 81)

67AGG mAb Light Chain
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Hu08A Light Chain Variable region
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIK (SEQ ID NO: 76)

Humanized x [PD-1_H] mAb (08A/HuPD1A-11 S61N VH G56A/VL) IgG4 S228P/Kappa
(PX) (51AQK)
51AQK mAb Heavy Chain (Hu08A Fab with S61N and G56A corrections in CDRH2), with IgG4
S228P correction
EVQLVQSGAEVKKPGASVKVSCKASGYTFT<u>SYYLY</u>WVRQAPGQGLEWIGG<u>VNPSNAGTNFN
EKFKS</u>RVTLTVDTSISTAYMELSRLRSDDTAVYYCTR<u>RDSNYDGGFDY</u>WGQGTTVTVSSAST
KGPSVFPLAPCSRSTSESTAALGCLVKDYFPEPVTVSWNSGALTSGVHTFPAVLQSSGLYSLSS TABLE 8-continued Sequence Information VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 83)

51AQK mAb Light Chain
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Humanized x [PD-1_H] Fab (08A/HuPD1A-11 S61N G56A CP-affinity matured Fab 100 (VH
H3G9 (D100L N102H affinity maturation mutations)/VL L28D1 (A55S S56K N57Y L58R
E59S Q93S H94Q S95A W96Y E97H affinity maturation mutations) IgG4 S228P/Kappa (PX)
(Fab100 with S61N and G56A corrections in VH-CDR2)
Fab100 Heavy Chain Fab region with S61N, G56A corrections, and D100L N102H affinity
maturation mutations
EVQLVQSGAEVKKPGASVKVSCKASGYTFTSYYLYWVRQAPGQGLEWIGGVNPSNAGTNFN
EKFKSRVTLTVDTSISTAYMELSRLRSDDTAVYYCTRRLSHYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVE (SEQ ID NO: 84)

Fab100 Heavy Chain Variable Region with S61N, G56A corrections, and D100L N102H affinity
maturation mutations
EVQLVQSGAEVKKPGASVKVSCKASGYTFTSYYLYWVRQAPGQGLEWIGGVNPSNAGTNFN
EKFKSRVTLTVDTSISTAYMELSRLRSDDTAVYYCTRRLSHYDGGFDYWGQGTTVTVSS
(SEQ ID NO: 85)

Fab100 Light Chain with A55S S56K N57Y L58R E59S Q93S H94Q S95A W96Y E97H affinity
maturation mutations
DIVMTQTPLSLSVTPGQPASISCRASKSVSTSGFSYLHWYLQKPGQPPQLLIFLSKYRSSGVPD
RFSGSGSGTDFTLKISRVEAEDVGVYYCSQAYHLPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 19)

Fab100 Light Chain Variable Region with A55S S56K N57Y L58R E59S Q93S H94Q S95A W96Y
E97H affinity maturation mutations
DIVMTQTPLSLSVTPGQPASISCRASKSVSTSGFSYLHWYLQKPGQPPQLLIFLSKYRSSGVPD
RFSGSGSGTDFTLKISRVEAEDVGVYYCSQAYHLPLTFGQGTKLEIK (SEQ ID NO: 20)

Fab100 CDRH and CDRL regions with S61N and G56A corrections
CDRH1: SYYLY (SEQ ID NO: 8)

CDRH2: GVNPSNAGTNFNEKFKS (SEQ ID NO: 86)

CDRH3: RLSHYDGGFDY (SEQ ID NO: 10)

CDRL1: RASKSVSTSGFSYLH (SEQ ID NO: 3)

CDRL2: LSKYRSS (SEQ ID NO: 21)

CDRL3: SQAYHLPLT (SEQ ID NO: 22)

Humanized x [PD-1_H] Fab (08A/HuPD1A-11 S61N CP-affinity matured Fab 100 (VH H3G9
(D100L N102H affinity maturation mutations)/VL L28D1 (A55S S56K N57Y L58R E59S Q93S
H94Q S95A W96Y E97H affinity maturation mutations) IgG4 S228P/Kappa (PX) (31ARL)
Fab100 Heavy Chain Fab region with S61N correction, and D100L N102H affinity maturation
mutations
EVQLVQSGAEVKKPGASVKVSCKASGYTFTSYYLYWVRQAPGQGLEWIGGVNPSNGGTNFN
EKFKSRVTLTVDTSISTAYMELSRLRSDDTAVYYCTRRLSHYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVE (SEQ ID NO: 87)

Fab100 Heavy Chain Variable Region with S61N correction, and D100L N102H affinity
maturation mutations
EVQLVQSGAEVKKPGASVKVSCKASGYTFTSYYLYWVRQAPGQGLEWIGGVNPSNGGTNFN
EKFKSRVTLTVDTSISTAYMELSRLRSDDTAVYYCTRRLSHYDGGFDYWGQGTTVTVSS
(SEQ ID NO: 7)

Fab100 Light Chain with A55S S56K N57Y L58R E59S Q93S H94Q S95A W96Y E97H affinity
maturation mutations
DIVMTQTPLSLSVTPGQPASISCRASKSVSTSGFSYLHWYLQKPGQPPQLLIFLSKYRSSGVPD
RFSGSGSGTDFTLKISRVEAEDVGVYYCSQAYHLPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 19)

TABLE 8-continued

Sequence Information

Fab100 Light Chain Variable Region with A55S S56K N57Y L58R E59S Q93S H94Q S95A W96Y
E97H affinity maturation mutations
DIVMTQTPLSLSVTPGQPASISCRASKSVSTSGFSYLHWYLQKPGQPPQLLIFLSKYRSSGVPD
RFSGSGSGTDFTLKISRVEAEDVGVYYCSQAYHLPLTFGQGTKLEIK (SEQ ID NO: 20)

Fab100 CDRH and CDRL regions with S61N correction
CDRH1: SYYLY (SEQ ID NO: 8)

CDRH2: GVNPSNGGTNFNEKFKS (SEQ ID NO: 9)

CDRH3: RLSHYDGGFDY (SEQ ID NO: 10)

CDRL1: RASKSVSTSGFSYLH (SEQ ID NO: 3)

CDRL2: LSKYRSS (SEQ ID NO: 21)

CDRL3: SQAYHLPLT (SEQ ID NO: 22)

Humanized x [PD-1_H] mAb (08A/HuPD1A-11 CP-affinity matured Fab 098 VH H3G9 (D100L
N102H) G56A) IgG4 S228P/Kappa (CX) (90AVZ)
90AVZ mAb Heavy Chain (Fab098 with G56A correction, and D100L N102H affinity maturation
mutations), with IgG4 S228P mutation
EVQLVQSGAEVKKPGASVKVSCKASGYTFTSYYLYWVRQAPGQGLEWIGGVNPSNAGTNFS
EKFKSRVTLTVDTSISTAYMELSRLRSDDTAVYYCTRRLSHYDGGFDYWGQGTTVTVSSAST
KGPSVFPLAPCSRSTSESTAALGCLVKDYFPEPVTVSWNSGALTSGVHTFPAVLQSSGLYSLSS
VVTVPSSSLGTKTYTCNVDHKPSNTKVDKRVESKYGPPCPPCPAPEFLGGPSVFLFPPKPKDTL
MISRTPEVTCVVVDVSQEDPEVQFNWYVDGVEVHNAKTKPREEQFNSTYRVVSVLTVLHQD
WLNGKEYKCKVSNKGLPSSIEKTISKAKGQPREPQVYTLPPSQEEMTKNQVSLTCLVKGFYPS
DIAVEWESNGQPENNYKTTPPVLDSDGSFFLYSRLTVDKSRWQEGNVFSCSVMHEALHNHYT
QKSLSLSLGK (SEQ ID NO: 89)

Fab098 Heavy Chain Variable Region with G56A correction, and D100L N102H affinity
maturation mutations
EVQLVQSGAEVKKPGASVKVSCKASGYTFTSYYLYWVRQAPGQGLEWIGGVNPSNAGTNFS
EKFKSRVTLTVDTSISTAYMELSRLRSDDTAVYYCTRRLSHYDGGFDYWGQGTTVTVSS
(SEQ ID NO: 88)

Fab098 Light Chain Variable Region
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIK (SEQ ID NO: 76)

90AVZ mAb Light Chain
DIVMTQTPLSLSVTPGQPASISCRASKSVSTSGFSYLHWYLQKPGQPPQLLIFLASNLESGVPDR
FSGSGSGTDFTLKISRVEAEDVGVYYCQHSWELPLTFGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Fab098 CDRH and CDRL regions with CDRH2 G56A correction, and CDRH3 D100L and N102H
affinity maturation mutations
CDRH1: SYYLY (SEQ ID NO: 8)

CDRH2: GVNPSNAGTNFSEKFKS (SEQ ID NO: 79)

CDRH3: RLSHYDGGFDY (SEQ ID NO: 10)

CDRL1: RASKSVSTSGFSYLH (SEQ ID NO: 3)

CDRL2: LASNLES (SEQ ID NO: 4)

CDRL3: QHSWELPLT (SEQ ID NO: 5)

Humanized x [PD-1_H] mAb (08A/HuPD1A-11 S61N CP-affinity matured Fab 100 (VH H3G9
(D100L N102H) G56A/VL L28D1 (A55S S56K N57Y L58R E59S Q93S H94Q S95A W96Y
E97H)) L234A L235A D265S) IgG1/Kappa (CX) (25AVE)
25AVE mAb Heavy Chain (Fab100 with S61N and G56A corrections, and D100L N102H affinity
maturation mutations), with L234A L23 5A D265S mutations
EVQLVQSGAEVKKPGASVKVSCKASGYTFTSYYLYWVRQAPGQGLEWIGGVNPSNAGTNFN
EKFKSRVTLTVDTSISTAYMELSRLRSDDTAVYYCTRRLSHYDGGFDYWGQGTTVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGK (SEQ ID NO: 90)

25AVE mAb Light Chain (Fab100 with A55S S56K N57Y L58R E59S Q93S H94Q S95A W96Y
E97H affinity maturation mutations)

TABLE 8-continued

Sequence Information

DIVMTQTPLSLSVTPGQPASISC<u>RASKSVSTSGFSYLH</u>WYLQKPGQPPQLLIF<u>LSKYRS</u>SGVPD
RFSGSGSGTDFTLKISRVEAEDVGVYYCSQAYHLPLTFGQGTKLEIKRTVAAPSVFIFPPSDEQ
LKSGTASVVCLLNNFYPREAKVQWKVDNALQSGNSQESVTEQDSKDSTYSLSSTLTLSKADY
EKHKVYACEVTHQGLSSPVTKSFNRGEC (SEQ ID NO: 19)

Fab100 anti-PD-1 CDRH and CDRL regions with or without G56A, S61N correction, or both
CDRH1: SYYLY (SEQ ID NO: 8)

CDRH2: GVNPSNX₁GTNFX₂EKFKS; wherein X₁ = G or A, and X₂ = S or N (SEQ ID NO: 91)

CDRI3: RLSHYDGGFDY (SEQ ID NO: 10)

CDRL1: RASKSVSTSGFSYLH (SEQ ID NO: 3)

CDRL2: LSKYRSS (SEQ ID NO: 21)

CDRL3: SQAYHLPLT (SEQ ID NO: 22)

Fab100 anti-PD-1 heavy chain variable region with or without G56A, S61N correction, or both
EVQLVQSGAEVKKPGASVKVSCKASGYTFT<u>SYYLY</u>WVRQAPGQGLEWIGGVNPSNX₁GTNF
X₂EKFKSRVTLTVDTSISTAYMELSRLRSDDTAVYYCTR<u>RLSHYDGGFDY</u>WGQGTTVTVSS;
wherein X₁ = G or A, and X₂ = S or N (SEQ ID NO: 92)

Hu08A anti-PD-1 heavy chain variable region with or without G56A, S61N correction, or both
EVQLVQSGAEVKKPGASVKVSCKASGYTFT<u>SYYLY</u>WVRQAPGQGLEWIGGVNPSNX₁GTNF
X₂EKFKSRVTLTVDTSISTAYMELSRLRSDDTAVYYCTR<u>RDSNYDGGFDY</u>WGQGTTVTVSS;
wherein X₁ = G or A, and X₂ = S or N (SEQ ID NO: 93)

Humanized x [PD-1_H] mAb (08A/HuPD1A-11 S61N VH G56A/VL) IgG1 L234A L235A
D265S/Kappa (CX) (71ATV/55AFL)-humanized 08A with N-glyc correction and deamidation
correction
55AFL mAb Heavy Chain (Hu08A Fab with S61N and G56A corrections) with IgG1 L234A L235A
D265S mutations
EVQLVQSGAEVKKPGASVKVSCKASGYTFT<u>SYYLY</u>WVRQAPGQGLEWIGG<u>VNPSNAGTNFN
EKFKS</u>RVTLTVDTSISTAYMELSRLRSDDTAVYYCTR<u>RDSNYDGGFDY</u>WGQGTTVTVSSAST
KGPSVFPLAPSSKSTSGGTAALGCLVKDYFPEPVTVSWNSGALTSGVHTFPAVLQSSGLYSLS
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGK (SEQ ID NO: 94)

Hu08A Heavy Chain Variable Region with S61N and G56A corrections:
EVQLVQSGAEVKKPGASVKVSCKASGYTFT<u>SYYLY</u>WVRQAPGQGLEWIGG<u>VNPSNAGTNFN
EKFKS</u>RVTLTVDTSISTAYMELSRLRSDDTAVYYCTR<u>RDSNYDGGFDY</u>WGQGTTVTVSS
(SEQ ID NO: 95)

55AFL mAb Light Chain:
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDEQL
KSGTASVVCLLNNFYPREAKVQWKVDNALQSGNSQESVTEQDSKDSTYSLSSTLTLSKADYE
KHKVYACEVTHQGLSSPVTKSFNRGEC (SEQ ID NO: 2)

Hu08A Light Chain Variable Region:
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIK (SEQ ID NO: 76)

Hu08A CDRH regions with S61N and G56A corrections and CDRL regions
CDRH1: SYYLY (SEQ ID NO: 8)

CDRH2: GVNPSNAGTNFNEKFKS (SEQ ID NO: 86)

CDRH3: RDSNYDGGFDY (SEQ ID NO: 41)

CDRL1: RASKSVSTSGFSYLH (SEQ ID NO: 3)

CDRL2: LASNLES (SEQ ID NO: 4)

CDRL3: QHSWELPLT (SEQ ID NO: 5)

Hu08A CDRH and CDRL regions with or without G56A, S61N correction, or both
CDRH1: SYYLY (SEQ ID NO: 8)

CDRH2: GVNPSNX₁GTNFX₂EKFKS; wherein X₁ = G or A, and X₂ = S or N (SEQ ID NO: 91)

CDRH3: RDSNYDGGFDY (SEQ ID NO: 41)

CDRL1: RASKSVSTSGFSYLH (SEQ ID NO: 3)

TABLE 8-continued

Sequence Information

CDRL2: LASNLES (SEQ ID NO: 4)

CDRL3: QHSWELPLT (SEQ ID NO: 5)

Anti-PD1/LAG3 BsAb (08A/Hu PD1A-11 S61N G56A ZWCH1-5 ZM856A/hum 08A LC
ZWCL-4) and (22D2 ZWCH1-6 ZM857B/22D2 LC ZWCL-5) L234A L235A D265S) IgG1/
Kappa (CX)-11ARW (22D2 HC), 13ARW (22D2 LC), 12ARW (08A LC),14ARW (08A HC) (lot
90ASU)
Anti-LAG3 humanized 22D2 Heavy Chain with CH1 mutation (S181K), L234A, L235A, D265S
mutations in CH2, ZW 857B mutations in CH3 (T350V, T366L, K392L, T394W)
QMQLVQSGPEVKKPGTSVKVSCKASGYTFT<u>DYNVD</u>WVRQARGQRLEWIG<u>DINPNDGGTIYA</u>
<u>QKFQE</u>RVTITVDKSTSTAYMELSSLRSEDTAVYYCAR<u>NYRWFGAMDH</u>WGQGTTVTVSSAST
KGPSVFPLAPSSKSTSGGTAALGCLVKDYFPEPVTVSWNSGALTSGVHTFPAVLQSSGLYKLS
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYVLPPSRDELTKNQVSLLCLVK
GFYPSDIAVEWESNGQPENNYLTWPPVLDSDGSFFLYSKLTVDKSRWQQGNVFSCSVMHEA
LHNHYTQKSLSLSPG (SEQ ID NO: 96)

Anti-LAG3 humanized 22D2 Heavy Chain Variable Region
QMQLVQSGPEVKKPGTSVKVSCKASGYTFT<u>DYNVD</u>WVRQARGQRLEWIG<u>DINPNDGGTIYA</u>
<u>QKFQE</u>RVTITVDKSTSTAYMELSSLRSEDTAVYYCAR<u>NYRWFGAMDH</u>WGQGTTVTVSS
(SEQ ID NO: 97)

Anti-LAG3 humanized 22D2 Light Chain with Ck mutations (Q124E, S131T, T178Y, T180E)
DIVMTQTPLSLSVTPGQPASISC<u>KASQSLDYEGDSDMN</u>WYLQKPGQPPQLLIY<u>GASNLES</u>GVP
DRFSGSGSGTDFTLKISRVEAEDVGVYYC<u>QQSTEDPRT</u>FGGGTKVEIKRTVAAPSVFIFPPSDE
ELKSGTATVVCLLNNFYPREAKVQWKVDNALQSGNSQESVTEQDSKDSTYSLSSYLELSKA
DYEKHKVYACEVTHQGLSSPVTKSFNRGEC (SEQ ID NO: 98)

Anti-LAG3 humanized 22D2 Light Chain Variable Region
DIVMTQTPLSLSVTPGQPASISC<u>KASQSLDYEGDSDMN</u>WYLQKPGQPPQLLIY<u>GASNLES</u>GVP
DRFSGSGSGTDFTLKISRVEAEDVGVYYC<u>QQSTEDPRT</u>FGGGTKVEIK (SEQ ID NO: 99)

Anti-PD1 humanized 08A Light Chain with CL mutations (Q124R, T178R)
DIVMTQTPLSLSVTPGQPASISC<u>RASKSVSTSGFSYLH</u>WYLQKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDERL
KSGTASVVCLLNNFYPREAKVQWKVDNALQSGNSQESVTEQDSKDSTYSLSSRLTLSKADYE
KHKVYACEVTHQGLSSPVTKSFNRGEC (SEQ ID NO: 100)

Anti-PD1 humanized 08A Heavy Chain with S61N and G56A corrections, CH1 mutations (L145E,
K147T, Q175E, S183L), L234A, L235A, D265S mutations in CH2, ZW 856A mutations in CH3
(T350V, L351Y, F405A, Y407V)
EVQLVQSGAEVKKPGASVKVSCKASGYTFT<u>SYYLY</u>WVRQAPGQGLEWIGG<u>VNPSNAGTNFN</u>
<u>EKFKS</u>RVTLTVDTSISTAYMELSRLRSDDTAVYYCTRR<u>DSNYDGGFD</u>YWGQGTTVTVSSAST
KGPSVFPLAPSSKSTSGGTAALGCEVTDYFPEPVTVSWNSGALTSGVHTFPAVLESSGLYSLL
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVVYPPSRDELTKNQVSLTCLVK
GFYPSDIAVEWESNGQPENNYKTTPPVLDSDGSFALVSKLTVDKSRWQQGNVFSCSVMHEAL
HNHYTQKSLSLSPG (SEQ ID NO: 101)

Humanized x [PD-1_H] [LAG3_H] BsAb ((08A/HuPD1A-11 S61N CP-affinity matured Fab 100
VH H3G9 G56A ZWCH1-5 ZM856A/VL L28D1 ZWCL-4) and (22D2 ZWCH1-6 ZM857B/
22D2 LC ZWCL-5) L234A L235A D265S) IgG1/Kappa (CX)-(lot 35ASI or 18ASS)
Anti-LAG3 humanized 22D2 Heavy Chain with CH1 mutation (S181K), L234A, L235A, D265S
mutations in CH2, ZW 857B mutations in CH3 (T350V, T366L, K392L, T394W)
QMQLVQSGPEVKKPGTSVKVSCKASGYTFT<u>DYNVD</u>WVRQARGQRLEWIG<u>DINPNDGGTIYA</u>
<u>QKFQE</u>RVTITVDKSTSTAYMELSSLRSEDTAVYYCAR<u>NYRWFGAMDH</u>WGQGTTVTVSSAST
KGPSVFPLAPSSKSTSGGTAALGCLVKDYFPEPVTVSWNSGALTSGVHTFPAVLQSSGLYKLS
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYVLPPSRDELTKNQVSLLCLVK
GFYPSDIAVEWESNGQPENNYLTWPPVLDSDGSFFLYSKLTVDKSRWQQGNVFSCSVMHEA
LHNHYTQKSLSLSPG (SEQ ID NO: 96)

Anti-LAG3 humanized 22D2 Light Chain with Ck mutations (Q124E, S131T, T178Y, T180E)
DIVMTQTPLSLSVTPGQPASISC<u>KASQSLDYEGDSDMN</u>WYLQKPGQPPQLLIY<u>GASNLES</u>GVP
DRFSGSGSGTDFTLKISRVEAEDVGVYYC<u>QQSTEDPRT</u>FGGGTKVEIKRTVAAPSVFIFPPSDE
ELKSGTATVVCLLNNFYPREAKVQWKVDNALQSGNSQESVTEQDSKDSTYSLSSYLELSKA
DYEKHKVYACEVTHQGLSSPVTKSFNRGEC (SEQ ID NO: 98)

Anti-PD1 Fab100 Heavy Chain with S61N and G56A corrections, CH1 mutations (L145E, K147T,
Q175E, S183L), L234A, L235A, D265S mutations in CH2, ZW 856A mutations in CH3 (T350V,
L351Y, F405A, Y407V)
EVQLVQSGAEVKKPGASVKVSCKASGYTFT<u>SYYLY</u>WVRQAPGQGLEWIGG<u>VNPSNAGTNFN</u>
<u>EKFKS</u>RVTLTVDTSISTAYMELSRLRSDDTAVYYCTRR<u>LSHYDGGFD</u>YWGQGTTVTVSSAST TABLE 8-continued Sequence Information KGPSVFPLAPSSKSTSGGTAALGCEVTDYFPEPVTVSWNSGALTSGVHTFPAVLESSGLYSLL
SVVTVPSSSLGTQTYICNVNHKPSNTKVDKKVEPKSCDKTHTCPPCPAPEAAGGPSVFPFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYVYPPSRDELTKNQVSLTCLVK
GFYPSDIAVEWESNGQPENNYKTTPPVLDSDGSFALVSKLTVDKSRWQQGNVFSCSVMHEAL
HNHYTQKSLSLSPG (SEQ ID NO: 102)

Anti-PD1 Fab100 Light Chain with CL mutations (Q124R, T178R)
DIVMTQTPLSLSVTPGQPASISC<u>RASKSVSTSGFSYLH</u>WYLQKPGQPPQLLIF<u>LSKYRS</u>GVPD
RFSGSGSGTDFTLKISRVEAEDVGVYYC<u>SQAYHLPLT</u>FGQGTKLEIKRTVAAPSVFIFPPSDER
LKSGTASVVCLLNNFYPREAKVQWKVDNALQSGNSQESVTEQDSKDSTYSLSSRLTLSKADY
EKHKVYACEVTHQGLSSPVTKSFNRGEC (SEQ ID NO: 103)

Humanized x [PD-1_H] [LAG3_H] BsAb (08A/Hu PD1A-11 S61N Q39E ZW CH1-4 ZM857B
and 22D2 Q39R ZW CH1-3 ZM856A) L234A, L235A, D265S IgG1/hum 08A LC Q42R ZW CL-
3 and 22D2 Q39E LC ZWCL-2) Kappa (CE) (lot 33ARK)
Anti-LAG3 humanized 22D2 Heavy Chain with FR mutation (Q39R), CH1 mutations (H168R.
Q175K), L234A, L235A, D265S mutations in CH2, ZW 857B mutations in CH3 (T350V, L351Y,
F405A, Y407V)
QMQLVQSGPEVKKPGTSVKVSCKASGYTFT<u>DYNVD</u>WVRRARGQRLEWIG<u>DINPNDGGTIYA
QKFQE</u>RVTITVDKSTSTAYMELSSLRSEDTAVYYCAR<u>NYRWFGAMDH</u>WGQGTTVTVSSAST
KGPSVFPLAPSSKSTSGGTAALGCLVKDYFPEPVTVSWNSGALTSGVRTFPAVLKSSGLYSLS
SVVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYVVYPPSRDELTKNQVSLTCLVK
GFYPSDIAVEWESNGQPENNYKTTPPVLDSDGSFALVSKLTVDKSRWQQGNVFSCSVMHEAL
HNHYTQKSLSLSPG (SEQ ID NO: 104)

Anti-LAG3 humanized 22D2 Heavy Chain Variable Region with FR mutation Q39R
QMQLVQSGPEVKKPGTSVKVSCKASGYTFT<u>DYNVD</u>WVRRARGQRLEWIG<u>DINPNDGGTIYA
QKFQE</u>RVTITVDKSTSTAYMELSSLRSEDTAVYYCAR<u>NYRWFGAMDH</u>WGQGTTVTVSS
(SEQ ID NO: 105)

Anti-LAG3 humanized 22D2 Light Chain with FR and Ck mutations (Q38E, Q124E, Q160E, T180E)
DIVMTQTPLSLSVTPGQPASISC<u>KASQSLDYEGDSDMN</u>WYLEKPGQPPQLLIY<u>GASNLES</u>GVP
DRFSGSGSGTDFTLKISRVEAEDVGVYYC<u>QQSTEDPRT</u>FGGGTKVEIKRTVAAPSVFIFPPSDE
ELKSGTASVVCLLNNFYPREAKVQWKVDNALQSGNSEESVTEQDSKDSTYSLSSTLELSKAD
YEKHKVYACEVTHQGLSSPVTKSFNRGEC (SEQ ID NO: 106)

Anti-LAG3 humanized 22D2 Light Chain Variable Region with FR mutation Q38E
DIVMTQTPLSLSVTPGQPASISC<u>KASQSLDYEGDSDMN</u>WYLEKPGQPPQLLIY<u>GASNLES</u>GVP
DRFSGSGSGTDFTLKISRVEAEDVGVYYC<u>QQSTEDPRT</u>FGGGTKVEIK (SEQ ID NO: 107)

Anti-PD1 humanized 08A Heavy Chain with S61N correction, FR mutation (Q39E), CH1 mutations
(L145E, K147T, Q175E), L234A, L235A, D265S mutations in CH2, ZW mutations in CH3 (T350V,
T366L, K392L, T394W)
EVQLVQSGAEVKKPGASVKVSCKASGYTFT<u>SYYLYW</u>VREAPGQGLEWIGG<u>VNPSNGGTNFN
EKFKS</u>RVTLTVDTSISTAYMELSRLRSDDTAVYYCTRR<u>DSNYDGGFDY</u>WGQGTTVTVSSAST
KGPSVFPLAPSSKSTSGGTAALGCEVTDYFPEPVTVSWNSGALTSGVHTFPAVLESSGLYSLSS
VVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYVLPPSRDELTKNQVSLLCLVK
GFYPSDIAVEWESNGQPENNYLTWPPVLDSDGSFFLYSKLTVDKSRWQQGNVFSCSVMHEA
LHNHYTQKSLSLSPG (SEQ ID NO: 108)

Anti-PD1 humanized 08A Heavy Chain Variable Region with S61N correction, FR mutation Q39E
EVQLVQSGAEVKKPGASVKVSCKASGYTFT<u>SYYLYW</u>VREAPGQGLEWIGG<u>VNPSNGGTNFN
EKFKS</u>RVTLTVDTSISTAYMELSRLRSDDTAVYYCTRR<u>DSNYDGGFDY</u>WGQGTTVTVSS
(SEQ ID NO: 109)

Anti-PD1 humanized 08A Light Chain with FR and Ck mutations (Q38R, Q124R, Q160K, T178R)
DIVMTQTPLSLSVTPGQPASISC<u>RASKSVSTSGFSYLH</u>WYLRKPGQPPQLLIF<u>LASNLES</u>GVPDR
FSGSGSGTDFTLKISRVEAEDVGVYYC<u>QHSWELPLT</u>FGQGTKLEIKRTVAAPSVFIFPPSDERL
KSGTASVVCLLNNFYPREAKVQWKVDNALQSGNSKESVTEQDSKDSTYSLSSRLTLSKADYE
KHKVYACEVTHQGLSSPVTKSFNRGEC (SEQ ID NO: 110)

Anti-PD1 humanized 08A Light Chain Variable Region with FR mutation Q38R
DIVMTQTPLSLSVTPGQPASISC<u>RASKSVSTSGFSYLH</u>WYLRKPGQPPQLLIF<u>LASNLES</u>GVPDR
FSGSGSGTDFTLKISRVEAEDVGVYYC<u>QHSWELPLT</u>FGQGTKLEIK (SEQ ID NO: 111)

Anti-LAG3 22D2 CDRH and CDRL regions
CDRH1: DYNVD (SEQ ID NO: 112)

CDRH2: DINPNDGGTIYAQKFQE (SEQ ID NO: 113)

CDRH3: NYRWFGAMDH (SEQ ID NO: 114)

CDRL1: KASQSLDYEGDSDMN (SEQ ID NO: 115)

TABLE 8-continued

Sequence Information

CDRL2: GASNLES (SEQ ID NO: 116)

CDRL3: QQSTEDPRT (SEQ ID NO: 117)

Heavy Chain IgG1 constant domain
ASTKGPSVFPLAPSSKSTSGGTAALGCLVKDYFPEPVTVSWNSGALTSGVHTFPAVLQSSGLY
SLSSVVTVPSSSLGTQTYICNVNHKPSNTKVDKKVEPKSCDKTHTCPPCPAPELLGGPSVFLFP
PKPKDTLMISRTPEVTCVVVDVSHEDPEVKFNWYVDGVEVHNAKTKPREEQYNSTYRVVSV
LTVLHQDWLNGKEYKCKVSNKALPAPIEKTISKAKGQPREPQVYTLPPSRDELTKNQVSLTCL
VKGFYPSDIAVEWESNGQPENNYKTTPPVLDSDGSFFLYSKLTVDKSRWQQGNVFSCSVMHE
ALHNHYTQKSLSLSPG (SEQ ID NO: 124)

Light Chain kappa constant domain
RTVAAPSVFIFPPSDEQLKSGTASVVCLLNNFYPREAKVQWKVDNALQSGNSQESVTEQDSK
DSTYSLSSTLTLSKADYEKHKVYACEVTHQGLSSPVTKSFNRGEC (SEQ ID NO: 125)

Anti-RSV Mab isotype control heavy chain (37ASK)
VTLRESGPALVKPTQTLTLTCTFSGFSLSTSGMSVGWIRQPPGKALEWLADIWWDDKKDYNP
SLKSRLTISKDTSKNQVVLKVTNMDPADTATYYCARSMITNWYFDVWGAGTTVTVSSASTK
GPSVFPLAPSSKSTSGGTAALGCLVKDYFPEPVTVSWNSGALTSGVHTFPAVLQSSGLYSLSS
VVTVPSSSLGTQTYICNVNHKPSNTKVDKKVEPKSCDKTHTCPPCPAPEAAGGPSVFLFPPKP
KDTLMISRTPEVTCVVVSVSHEDPEVKFNWYVDGVEVHNAKTKPREEQYNSTYRVVSVLTV
LHQDWLNGKEYKCKVSNKALPAPIEKTISKAKGQPREPQVYTLPPSRDELTKNQVSLTCLVK
GFYPSDIAVEWESNGQPENNYKTTPPVLDSDGSFFLYSKLTVDKSRWQQGNVFSCSVMHEAL
HNHYTQKSLSLSPGK (SEQ ID NO: 126)

Anti-RSV Mab isotype control light chain (37ASK)
DIQMTQSPSTLSASVGDRVTITCKCQLSVGYMHWYQQKPGKAPKLLIYDTSKLASGVPSRFSG
SGSGTEFTLTISSLQPDDFATYYCFQGSGYPFTFGGGTKLEIKRTVAAPSVFIFPPSDEQLKSGT
ASVVCLLNNFYPREAKVQWKVDNALQSGNSQESVTEQDSKDSTYSLSSTLTLSKADYEKHK
VYACEVTHQGLSSPVTKSFNRGEC (SEQ ID NO: 127)

Mutations in bold (mutations in variable region use sequential numbering, mutations in constant region use EU numbering), underlining highlights CDR regions (Kabat)

What is claimed is:

1. An anti-PD-1/LAG-3 bispecific antibody comprising:
   (A) an anti-PD-1 antigen-binding fragment comprising:
      (i) a heavy chain variable region CDR1 comprising the amino acid sequence of SEQ ID NO:8,
      (ii) a heavy chain variable region CDR2 comprising the amino acid sequence of SEQ ID NO:91,
      (iii) a heavy chain variable region CDR3 comprising the amino acid sequence of SEQ ID NO:10,
      (iv) a light chain variable region CDR1 comprising the amino acid sequence of SEQ ID NO:3,
      (v) a light chain variable region CDR2 comprising the amino acid sequence of SEQ ID NO:21, and
      (vi) a light chain variable region CDR3 comprising the amino acid sequence of SEQ ID NO:22; and
   (B) an anti-LAG3 antigen-binding fragment comprising:
      (i) a heavy chain variable region CDR1 comprising the amino acid sequence of SEQ ID NO:112,
      (ii) a heavy chain variable region CDR2 comprising the amino acid sequence of SEQ ID NO:113,
      (iii) a heavy chain variable region CDR3 comprising the amino acid sequence of SEQ ID NO:114,
      (iv) a light chain variable region CDR1 comprising the amino acid sequence of SEQ ID NO:115,
      (v) a light chain variable region CDR2 comprising the amino acid sequence of SEQ ID NO:116, and
      (vi) a light chain variable region CDR3 comprising the amino acid sequence of SEQ ID NO:117.

2. The anti-PD-1/LAG-3 bispecific antibody of claim 1, wherein the anti-PD-1 heavy chain variable region CDR2 comprises the amino acid sequence of SEQ ID NO:86.

3. An anti-PD-1/LAG-3 bispecific antibody comprising
   (A) an anti-PD-1 antigen-binding fragment comprising a heavy chain variable region comprising the amino acid sequence set forth in SEQ ID NO:92, and a light chain variable region comprising the amino acid sequence set forth in SEQ ID NO:14, 17, 20, 24, 28, 31, or 34; and
   (B) an anti-LAG3 antigen-binding fragment comprising an anti-LAG3 heavy chain variable region comprising the amino acid sequence of SEQ ID NO:97, and a light chain variable region comprising the amino acid sequence of SEQ ID NO:99.

4. The anti-PD-1/LAG-3 bispecific antibody of claim 3, wherein the anti-PD-1 antigen-binding fragment comprises a heavy chain variable region comprising the amino acid sequence set forth in SEQ ID NO:92, and a light chain variable region comprising the amino acid sequence set forth in SEQ ID NO:20.

5. The anti-PD-1/LAG-3 bispecific antibody of claim 3, wherein the anti-PD-1 antigen-binding fragment comprises a heavy chain variable region comprising the amino acid sequence set forth in SEQ ID NO:85, and a light chain variable region comprising the amino acid sequence set forth in SEQ ID NO:20.

6. The anti-PD-1/LAG-3 bispecific antibody of claim 4, comprising:
   (A) an anti-PD-1 antigen-binding fragment comprising (i) a heavy chain comprising a heavy chain variable region comprising the amino acid sequence set forth in SEQ ID NO:92, and an IgG1 constant region comprising CH1 mutations 145E, 147T, 175E, and 183L, and CH3 mutations 350V, 351Y, 405A, and 407V, and (ii) a light chain comprising a light chain variable region comprising the amino acid sequence set forth in SEQ ID NO:20, and a kappa constant region comprising $C_\kappa$ mutations 124R and 178R; and
   (B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and CH3 mutations 350V, 366L, 392L, and 394W, and (ii) a light chain comprising a light chain variable region comprising the amino acid sequence of SEQ ID NO:99, and a kappa constant region comprising $C_\kappa$ mutations 124E, 131T, 178Y, and 180E,
   wherein the mutations are in EU numbering.

7. The anti-PD-1/LAG-3 bispecific antibody of claim 4, comprising:
   (A) an anti-PD-1 antigen-binding fragment comprising (i) a heavy chain comprising a heavy chain variable region comprising the amino acid sequence set forth in SEQ ID NO:92, and an IgG1 constant region comprising CH1 mutations 145E, 147T, 175E, and 183L, and CH3 mutations 350V, 366L, 392L, and 394W, and (ii) a light chain comprising a light chain variable region comprising the amino acid sequence set forth in SEQ ID NO:20, and a kappa constant region comprising $C_\kappa$ mutations 124R and 178R; and (B) an anti-LAG3 antigen-binding fragment comprising (i) a heavy chain comprising a heavy chain variable region comprising the amino acid sequence of SEQ ID NO:97 and an IgG1 constant region comprising CH1 mutation 181K, and CH3 mutations 350V, 351Y, 405A, and 407V, and (ii) a light chain comprising a light chain variable region comprising the amino acid sequence of SEQ ID NO:99, and a kappa constant region comprising $C_\kappa$ mutations 124E, 131T, 178Y, and 180E;

wherein the mutations are in EU numbering.

8. The anti-PD-1/LAG-3 bispecific antibody of claim 4, comprising:

(A) an anti-PD-1 antigen-binding fragment comprising (i) a heavy chain comprising a heavy chain variable region comprising the amino acid sequence set forth in SEQ ID NO:92, and an IgG1 constant region comprising CH1 mutations 145E, 147T, 175E, and 183L, and (ii) a light chain comprising a light chain variable region comprising the amino acid sequence set forth in SEQ ID NO:20, and a kappa constant region comprising $C_\kappa$ mutations 124R and 178R; and (B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and (ii) a light chain comprising a light chain variable region comprising the amino acid sequence of SEQ ID NO:99, and a kappa constant region comprising $C_\kappa$ mutations 124E, 131T, 178Y, and 180E;

wherein the IgG1 heavy chain constant regions of the anti-PD-1 and anti-LAG3 antigen-binding fragments further comprise pairs of CH3 mutations selected from the group consisting of: 351Y/405A/407V and 366I/392M/394W; 351Y/405A/407V and 366L/392L/394W; 351Y/405A/407V and 366L/392M/394W, and wherein the mutations are in EU numbering.

9. The anti-PD-1/LAG-3 bispecific antibody of claim 3, comprising:

(A) an anti-PD-1 antigen-binding fragment comprising (i) a heavy chain comprising a heavy chain variable region comprising the amino acid sequence set forth in SEQ ID NO:92, and an IgG1 constant region comprising CH1 mutations 145E, 147T, 175E, and 183L, and CH3 mutations 350V, 351Y, 405A, and 407V, and (ii) a light chain comprising a light chain variable region comprising the amino acid sequence set forth in SEQ ID NO:14, 17, 20, 24, 28, 31, or 34, and a kappa constant region comprising $C_\kappa$ mutations 124R and 178R; and (B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and CH3 mutations 350V, 366L, 392L, and 394W, and (ii) a light chain comprising a light chain variable region comprising the amino acid sequence of SEQ ID NO:99, and a kappa constant region comprising $C_\kappa$ mutations 124E, 131T, 178Y, and 180E, wherein the mutations are in EU numbering.

10. An anti-PD-1/LAG3 bispecific antibody, comprising:

(A) an anti-PD-1 heavy chain comprising the amino acid sequence of SEQ ID NO:102, and a light chain comprising the amino acid sequence of SEQ ID NO:103, and (B) an anti-LAG3 heavy chain comprising the amino acid sequence of SEQ ID NO:96, and a light chain comprising the amino acid sequence of SEQ ID NO:98.

11. An anti-PD-1/LAG-3 bispecific antibody comprising:

(A) an anti-PD-1 antigen-binding fragment comprising:
 (i) a heavy chain variable region CDR1 comprising the amino acid sequence of SEQ ID NO:8,
 (ii) a heavy chain variable region CDR2 comprising the amino acid sequence of SEQ ID NO:86,
 (iii) a heavy chain variable region CDR3 comprising the amino acid sequence of SEQ ID NO:10 or 41,
 (iv) a light chain variable region CDR1 comprising the amino acid sequence of SEQ ID NO:3,
 (v) a light chain variable region CDR2 comprising the amino acid sequence of SEQ ID NO:4, and
 (vi) a light chain variable region CDR3 comprising the amino acid sequence of SEQ ID NO:5; and (B) an anti-LAG3 antigen-binding fragment comprising:
 (i) a heavy chain variable region CDR1 comprising the amino acid sequence of SEQ ID NO:112,
 (ii) a heavy chain variable region CDR2 comprising the amino acid sequence of SEQ ID NO:113,
 (iii) a heavy chain variable region CDR3 comprising the amino acid sequence of SEQ ID NO:114,
 (iv) a light chain variable region CDR1 comprising the amino acid sequence of SEQ ID NO:115,
 (v) a light chain variable region CDR2 comprising the amino acid sequence of SEQ ID NO:116, and
 (vi) a light chain variable region CDR3 comprising the amino acid sequence of SEQ ID NO:117.

12. The anti-PD-1/LAG-3 bispecific antibody of claim 11, wherein (A) the anti-PD-1 antigen-binding fragment comprises a heavy chain variable region comprising the amino acid sequence set forth in SEQ ID NO:95, and a light chain variable region comprising the amino acid sequence set forth in SEQ ID NO:76; and (B) the anti-LAG3 antigen-binding fragment comprises an anti-LAG3 heavy chain variable region comprising the amino acid sequence of SEQ ID NO:97, and light chain variable region comprising the amino acid sequence of SEQ ID NO:99.

13. An anti-PD-1/LAG-3 bispecific antibody comprising:

(A) an anti-PD-1 antigen-binding fragment comprising (i) a heavy chain comprising a heavy chain variable region comprising the amino acid sequence set forth in SEQ ID NO:93, and an IgG1 constant region comprising CH1 mutations 145E, 147T, 175E, and 183L, and CH3 mutations 350V, 351Y, 405A, and 407V, and (ii) a light chain comprising a light chain variable region comprising the amino acid sequence set forth in SEQ ID NO:76, and a kappa constant region comprising $C_\kappa$ mutations Q124R and T178R; and (B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and CH3 mutations 350V, 366L, 392L, and 394W, and (ii) a light chain comprising a light chain variable region comprising the amino acid sequence of SEQ ID NO:99, and a kappa constant region comprising C<sub>κ</sub> mutations 124E, 131T, 178Y, and 180E, wherein the mutations are in EU numbering.

14. An anti-PD-1/LAG-3 bispecific antibody comprising:
(A) an anti-PD-1 antigen-binding fragment comprising (i) a heavy chain comprising a heavy chain variable region comprising the amino acid sequence set forth in SEQ ID NO:93, and an IgG1 constant region comprising CH1 mutations 145E, 147T, 175E, and 183L, and CH3 mutations 350V, 366L, 392L, and 394W, and (ii) a light chain comprising a light chain variable region comprising the amino acid sequence set forth in SEQ ID NO:76, and a kappa constant region comprising $C_\kappa$ mutations 124R and 178R; and
(B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and CH3 mutations 350V, 351Y, 405A, and 407V, and (ii) a light chain comprising a light chain variable region comprising the amino acid sequence of SEQ ID NO:99, and a kappa constant region comprising $C_\kappa$ mutations 124E, 131T, 178Y, and 180E,
wherein the mutations are in EU numbering.

15. An anti-PD-1/LAG-3 bispecific antibody comprising:
(A) an anti-PD-1 antigen-binding fragment comprising (i) a heavy chain comprising a heavy chain variable region comprising the amino acid sequence set forth in SEQ ID NO:93, and an IgG1 constant region comprising CH1 mutations 145E, 147T, 175E, and 183L, and (ii) a light chain comprising a light chain variable region comprising the amino acid sequence set forth in SEQ ID NO:76, and a kappa constant region comprising $C_\kappa$ mutations 124R and 178R; and
(B) an anti-LAG3 antigen-binding fragment comprising (i) a heavy chain comprising a heavy chain variable region comprising the amino acid sequence of SEQ ID NO:97, and an IgG1 constant region comprising CH1 mutation 181K, and (ii) a light chain comprising a light chain variable region comprising the amino acid sequence of SEQ ID NO:99, and a kappa constant region comprising $C_\kappa$ mutations 124E, 131T, 178Y, and 180E;
wherein the IgG1 heavy chain constant regions of the anti-PD-1 and anti-LAG3 antigen-binding fragments further comprise pairs of CH3 mutations selected from the group consisting of: 351Y/405A/407V and 366I/392M/394W; 351Y/405A/407V and 366L/392L/394W; and 351Y/405A/407V and 366L/392M/394W, and wherein the mutations are in EU numbering.

16. An anti-PD-1/LAG3 bispecific antibody comprising:
(A) an anti-PD-1 heavy chain comprising the amino acid sequence of SEQ ID NO:101, and a light chain comprising the amino acid sequence of SEQ ID NO:100, and
(B) an anti-LAG3 heavy chain comprising the amino acid sequence of SEQ ID NO:96, and a light chain comprising the amino acid sequence of SEQ ID NO:98.

17. An anti-PD1/LAG3 bispecific antibody comprising:
(A) an anti-PD-1 heavy chain variable region comprising the amino acid sequence of SEQ ID NO:109, and a light chain variable region comprising the amino acid sequence of SEQ ID NO:111, and
(B) an anti-LAG3 heavy chain variable region comprising the amino acid sequence of SEQ ID NO:105, and a light chain variable region comprising the amino acid sequence of SEQ ID NO:107.

18. The anti-PD-1/LAG3 bispecific antibody of claim 17, comprising:
(A) an anti-PD-1 heavy chain comprising the amino acid sequence of SEQ ID NO:108, and a light chain comprising the amino acid sequence of SEQ ID NO:110, and
(B) an anti-LAG3 heavy chain comprising the amino acid sequence of SEQ ID NO:104, and a light chain comprising the amino acid sequence of SEQ ID NO:106.

19. The bispecific antibody or antigen-binding fragment of claim 10, wherein the antibody or antigen-binding fragment thereof comprises a glycosylation pattern characteristic of expression by a CHO cell.

* * * * *